(12) United States Patent
Gordon et al.

(10) Patent No.: US 9,487,578 B2
(45) Date of Patent: Nov. 8, 2016

(54) METHODS AND COMPOSITIONS FOR TARGETING POLYUBIQUITIN

(71) Applicant: Genentech, Inc., South San Francisco, CA (US)

(72) Inventors: Nathaniel C. Gordon, Campbell, CA (US); Robert F. Kelley, San Bruno, CA (US); Anh Pham, Alhambra, CA (US)

(73) Assignee: Genentech, Inc., South San Francisco, CA (US)

( * ) Notice: Subject to any disclaimer, the term of this patent is extended or adjusted under 35 U.S.C. 154(b) by 143 days.

(21) Appl. No.: 14/079,727

(22) Filed: Nov. 14, 2013

(65) Prior Publication Data

US 2014/0179905 A1    Jun. 26, 2014

Related U.S. Application Data

(62) Division of application No. 12/766,772, filed on Apr. 23, 2010, now Pat. No. 8,603,475, which is a division of application No. 11/611,058, filed on Dec. 14, 2006, now Pat. No. 7,763,245.

(60) Provisional application No. 60/793,980, filed on Apr. 21, 2006, provisional application No. 60/751,081, filed on Dec. 15, 2005.

(51) Int. Cl.
*C07H 21/04* (2006.01)
*C07K 16/18* (2006.01)

(52) U.S. Cl.
CPC ........... *C07K 16/18* (2013.01); *C07K 2317/32* (2013.01); *C07K 2317/55* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| 7,763,245 B2 | 7/2010 | Gordon et al. |
| 7,985,840 B2 | 7/2011 | Fuh et al. |
| 8,133,488 B2 | 3/2012 | Kelley et al. |
| 2005/0106667 A1 | 5/2005 | Fellhouse et al. |
| 2007/0166778 A1 | 7/2007 | Rain et al. |
| 2007/0218079 A1 | 9/2007 | Patzel |
| 2009/0191209 A1 | 7/2009 | Kelley et al. |
| 2011/0256133 A1 | 10/2011 | Dixit et al. |
| 2013/0058955 A1 | 3/2013 | Kelley et al. |

FOREIGN PATENT DOCUMENTS

| JP | 07238096 | 9/1995 |
| WO | 2004003019 | 1/2004 |
| WO | 2007025216 | 3/2007 |
| WO | 2007120334 | 10/2007 |
| WO | 2008121813 | 10/2008 |
| WO | 2009126350 | 10/2009 |

OTHER PUBLICATIONS

Boone et al., "The ubiquitin-modifying enzyme A20 is required for termination of toll-like receptor responses," Nature Immunol., 2004, 5(10):1052-1060.
Brorson, "Mutational analysis fo avidity and fine specificity of anti-levan antibodies," J Immunol, 1999, 163:6694-6701.
Brummell, et al., "Probing the combining site of an anti-carbohydrate antibody by saturation-mutagenesis: role of the heavy-chain CDR3 residues," Biochemistry, 1993, 32(4):1180-1187.
Burks et al., "In vitro scanning saturation mutagenesis of an antibody binding pocket," PNAS, 1997, 94:412-417.
Chen et al., "Structural basis for scaffolding-mediated assembly and maturation of a dsDNA virus," PNAS, 2011, 108(4):1355-1360.
Clark et al, "Affinity enhancement of an in vivo matured therapeutic antibody using structure-based computational design," Prot. Sci., 2006, 15:949-960.
Coleman et al., "Effects of amino acid sequence changes on antibody-antigen interactions," Res Immunol, 1994, 145:33-36.
Cook et al., "Structure of a diubiquitin conjugate and a model for interaction with ubiquitin conjugating enzyme (E2)," Journal of Biological Chemistry, 1992, 267(23):16467-16471.
Crosas et al., "Ubiquitin chains are remodeled at the proteasome by opposing ubiquitin ligase and deubiquitinating activities," Cell, 2006, 127:1401-1413.
Dufner et al., "Harnessing phage and ribosome display for antibody optimisation," Trends in Biotechnology, 2006, 24(11):523-529.
Fellouse et al., "High-throughput generation of synthetic antibodies for highly functional minimalist phage-displayed libraries," J Mol Biol., 2007, 373(4):924-940.
Gallop et al., "Applications of combinatorial technologies to drug discovery. 1. background and peptide combinatorial libraries," J Med Chem., 1994, 37(9):1233-1251.
Garnett et al., "IJBE2S elongates ubiquitin chains on APC/C substrates to promote mitotic exit," Nat Cell Biol., 2009, 11(11)1363-1369.
Gorman et al., "Transient Production of Proteins Using an Adenovirus Transformed Cell Line," DNA Prot Eng Tech., 1990, 2(1):3-10.
Jang et al., "The structural basis for DNA binding by an anti-DNA autoantibody," Mol Immunol, 1998, 35(18):1207-1217.
Jin et al., "Mechanism of ubquitin-chain formation by the human anaphase-promoting complex," Cell, 2008, 133(4):653-665.
Kim et al., "Certain pairs of ubiquitin-conjugating enzymes (E2s) and ubiquitin-protein ligases (E3s) synthesize nondegradable forked ubiquing chains containing all possible isopeptide lingages," J Biol Chem., 2007, 282(24):17375-17386.
Kirkpatrick et al., "Quantitative analysis of in vitro ubiquitinated cyclin B1 reveals complex chain topology," Nature Cell Biol, 2006, 8(7):700-710.
Kobayashi et al., "Tryptophan H33 plays an important role in pyrimidin (6-4) pyrimidone photoproduct binding by a high-affinity antibody," Protein Engineering, 1999, 12(10):879-884.

(Continued)

*Primary Examiner* — Laura B Goddard
*Assistant Examiner* — Meera Natarajan
(74) *Attorney, Agent, or Firm* — McNeill Baur PLLC

(57) ABSTRACT

Anti-polyubiquitin monoclonal antibodies, and methods for using the antibodies, are provided.

21 Claims, 45 Drawing Sheets

(56) References Cited

OTHER PUBLICATIONS

Kumar et al., "Molecular cloning and expression of the fabs of human autoantibodies in *Escherichia coli*," J. Biol Chem., 2000, 275(45):35129-35136.
Kunkel, "Rapid and Efficient Site-Specific Mutagenesis Without Phenotypic Selection," PNAS, 1985, 82:488-492.
Lee et al., "High-affinity human antibodies from phage-displayed synthetic Fab libraries with a single framework scaffold," J Mol Biol., 2004, 340(5):1073-1093.
Matsumoto et al., "K11-linked polyubiquitination in cell cycle control revealed by a K11 linkage-specific antibody," Mol Cell, 2010, 39(3):477-484.
Smith-Gill et al., "Contributions of immunoglobulin heavy and light chains to antibody specificity for lysozyme and two haptens," J Immunol., 1987, 139(12):4135-4144.
Song et al., "Light chain of natural antibody plays a dominant role in protein antigen binding," Biochem Biophys Res Commun., 2000, 268(2):390-394.
Varadan et al., "Structural properties of polyubiquitin chains in solution," J Mol Biol, 2002, 324(4):637-647.
Ward et al., "Binding activities of a repertoire of single immunoglobulin variable domains secreted from *Escherichia coli*," Nature, 1989, 341(6242):544-546.
Williamson et al., "Identification of a physiological E2 module for the human anaphase-promoting complex," PNAS, 2009, 106(43):18213-8.
Yamin and Miller, "The interleukin-1 receptor-associated kinase is degraded by proteasomes following its phosphorylation,"J Biol Chem., 1997, 272(34):21540-21547.
International Search Report and Written Opinion for International Patent Application No. PCT/US2011/032466, mailed Jun. 3, 2011, 15 pages.
File History for U.S. Appl. No. 12/355,531, filed Jan. 16, 2009.
File History for U.S. Appl. No. 13/086,941, filed Apr. 14, 2011.
File History for U.S. Appl. No. 13/567,919, filed Aug. 6, 2012.
Alves-Rodrigues et al., "Ubiquitin, cellular inclusions and their role in neurodegeneration" Trends Neurosci 21(12):516-520 ( 1998).
Bodine et al., "Identification of ubiquitin ligases required for skeletal muscle atrophy" Science 294(5547):1704-1708 (Nov. 23, 2001).
Beckmann et al., "On ubiquitin ligases and cancer" Hum Mutat 25(6):507-512 ( 2005).
Cammarata et al., "Ubiquitin-reactive neurites in cerebral cortex of subjects with Huntington's chorea: a pathological correlate of dementia?" Neurosci Lett 156(1-2):96-98 ( 1993).
Campbell, "Monoclonal Antibody Technology "1"" The Netherlands:Elsevier Science Publishers B.V.:1-32 ( 1984).
Carrion-Vazquez et al., "The mechanical stability of ubiquitin is linkage dependent" Nat Struct Biol (Epub Aug. 17, 2003), 10(9):738-743 (Sep. 2003).
Casset et al., "A peptide mimetic of an anti-CD4 monoclonal antibody by rational design" Biochem Bioph Res Co 307:198-205 ( 2003).
Chau et al., "A multiubiquitin chain is confined to specific lysine in a targeted short-lived protein" Science 243(4898):1576-1583 (Mar. 24, 1989).
Chen et al., "Selection and analysis of an optimized anti-VEGF antibody: crystal structure of an affinity-matured Fab in complex with antibody" J Mol Biol 293:151-162 ( 1999).
Chung et al., "The role of the ubiquitin-proteasomal pathway in Parkinson's disease and other neurodegenerative disorders" Trends Neurosci 24(11 SUPPL Suppl):S7-14 (Nov. 2001).
Ciechanover, "The ubiquitin-proteasome pathway: on protein death and cell life" EMBO J 17(24):7151-7160 ( 1998).
De Pascalis et al., "Grafting of 'abbreviated' complementarity determining regions containing specificity determining residues essential for ligand contact to engineer a less immunogenic humanized monoclonal antibody", J Immunol 169:3076-3084 ( 2002).

Deng et al., "Activation of the IkappaB kinase complex by TRAF6 requires a dimeric ubiquitin-conjugating enzyme complex and a unique polyubiquitin chain" Cell 103(2):351-361 (Oct. 13, 2000).
Finley et al., "Inhibition of proteolysis and cell cycle progression in a multiubiquitination-deficient yeast mutant" Mol Cell Biol 14(8):5501-5509 (Aug. 1994).
Flick et al., "Proteolysis-independent regulation of the transcription factor Met4 by a single Lys 48-linked ubiquitin chain" Nat Cell Biol (epub Jun. 20, 2004), 6(7):634-641 (Jul. 2004).
Fujimuro and Yokosawa "Production of antipolyubiquitin monoclonal antibodies and their use for characterization and isolation of polyubiquitinated proteins" Method Enzymol 399:75-86 (Dec. 15, 2005).
Fujimuro et al., "Production and characterization of monoclonal antibodies specific to multi-ubiquitin chains of polyubiquitinated proteins" FEBS Lett 349(2):173-180 ( 1994).
Ghosh and Karin et al., "Missing pieces in the NF-kappaB puzzle" Cell 109(Suppl):S81-S96 (Apr. 2002).
Guterman and Glickman et al., "Deubiquitinating enzymes are IN/(trinsic to proteasome function)" Curr Protein Pept Sci 5(3):201-211 ( 2004).
Hashizume et al., "The RING heterodimer BRCA1-BARD1 is a ubiquitin ligase inactivated by a breast cancer-derived mutation" J Biol Chem 276(18):14537-14540 (May 4, 2001).
Hicke and Dunn et al., "Regulation of membrane protein transport by ubiquitin and ubiquitin-binding proteins" Annu Rev Cell Dev Biol (epub Jun. 20, 2003), 19:141-172 ( 2003).
Hicke, L., "Protein regulation by monoubiquitin" Nature Reviews Mol Cell Biol 2:195-201 (Mar. 2001).
Hoege et al., "RAD6-dependent DNA repair is linked to modification of PCNA by ubiquitin and SUMO" Nature 419(6903):135-141 (Sep. 12, 2002).
Hofmann et al., "In vitro assembly and recognition of Lys-63 polyubiquitin chains" J Biol Chem 276(30):27936-27943 (Jul. 27, 2001).
Hofmann et al., "Noncanonical MMS2-encoded ubiquitin-conjugating enzyme functions in assembly of novel polyubiquitin chains for DNA repair" Cell 96(5):545-653 (Mar. 5, 1999).
Holm et al., "Functional mapping and single chain construction of the anti-cytokeratin 8 monoclonal antibody TS1" Mol Immunol 44:1075-1084 ( 2007).
Holmberg et al., "Spinocerebellar ataxia type 7 (SCA7): a neurodegenerative disorder with neuronal intranuclear inclusions" Hum Mol Genet 7(5):913-918 ( 1998).
Johnson, "Ubiquitin branches out" Nat Cell Biol 4(12):E295-E298 (Dec. 2002).
Kalchman et al., "Huntingtin is ubiquitinated and interacts with a specific ubiquitin-conjugating enzyme" J Biol Chem 271(32):19385-19394 (Aug. 9, 1996).
Kishino et al., "UBE3A/E6-AP mutations cause Angelman syndrome" Nat Genet 15(1):70-73 (Jan. 1997).
Kuzuhara et al., "Lewy bodies are ubiquitinated. A light and electron microscopic immunocytochemical study" Acta Neuropathology 75(4):345-353 ( 1988).
Lam et al., "Inhibition of the ubiquitin-proteasome system in Alzheimer's disease" P Natl Acad Sci USA 97(18):9902-9906 (Aug. 29, 2000).
Leigh et al., "New aspects of the pathology of neurodegenerative disorders as revealed by ubiquitin antibodies" Acta Neuropathol 79(1):61-72 ( 1989).
Leroy et al., "The ubiquitin pathway in Parkinson's disease" Nature 395(6701):451-452 (Oct. 1, 1998).
Lim et al., "Parkin mediates nonclassical, proteasomal-independent ubiquitination of synphilin-1: implications for Lewy body formation" J Neurosci 25(8):2002-2009 (Feb. 23, 2005).
MacCullum et al., "Antibody-antigen interactions: contact analysis and binding site topography" J Mol Biol 262:732-745 ( 1996).
Majetschak et al., "Extracellular ubiquitin inhibits the TNF-alpha response to endotoxin in peripheral blood mononuclear cells and regulates endotoxin hyporesponsiveness in critical illness" Blood 101(5):1882-1890 (Mar. 1, 2003).
McNaught et al., "Failure of the ubiquitin-proteasome system in Parkinson's disease" Nat Rev Neurosci 2(8):589-594 (Aug. 2001).

(56) References Cited

OTHER PUBLICATIONS

Mitch et al., "Mechanisms of muscle wasting. The role of the ubiquitin-proteasome pathway" New Engl J Med 335(25):1897-1905 (Dec. 19, 1996).
Mori et al., "Ubiquitin is a component of paired helical filaments in Alzheimer's disease" Science 235(4796):1641-1644 (Mar. 27, 1987).
Naze "Mutation analysis and association studies of the ubiquitin carboxy-terminal hydrolase L1 gene in Huntington's disease" Neurosci Lett 328(1):1-4 ( 2002).
Nemes et al., "Cross-linking of ubiquitin, HSP27, parkin and ?-synuclein by /147-glutamyl-?-lysine bonds in Alzheimer's nurofibrillary tangles" FASEB J 18(10):1135-7 (May 2004).
Newton et al., "Ubiquitin chain editing revealed by polyubiquitin linkage-specific antibodies" Cell 134:668-678 (Aug. 22, 2008).
Palombella et al., "The ubiquitin-proteasome pathway is required for processing the NF-kappa B1 precursor protein and the activation of NF-kappa B" Cell 78(5):773-785 (Sep. 9, 1994).
Peng et al., "A proteomics approach to understanding protein ubiquitination" Nat Biotechnol 21(8):921-926 (Aug. 2003).
Pickart and Fushman "Polyubiquitin chains: polymeric protein signals" Curr Opin Chem Biol. (epub Oct. 28, 2004), 8(6):610-616 (Dec. 2004).
Pickart "Mechanisms underlying ubiquitination" Annu Rev Biochem 70:503-533 ( 2001).
Pickart "Ubiquitin enters the new millennium" Mol Cell 8(3):499-504 (Sep. 2001).
Rudikoff et al., "Single amino acid substitution altering antigen binding specificity" P Natl Acad Sci USA 79:1979-1983 (Mar. 1982).
Salghetti et al., "Destruction of Myc by ubiquitin-mediated proteolysis: cancer-associated and transforming mutations stabilize Myc" EMBO J 18(3):717-726 ( 1999).
Seibenhener et al., "Sequestosome 1/p62 is a polyubiquitin chain binding protein involved in ubiquitin proteasome degradation" Mol Cell Biol 24(18):8055-8068 (Sep. 2004).
Shimura et al., "Familial Parkinson disease gene product, parkin, is a ubiquitin-protein ligase" Nat Genet 25(3):302-305 (Jul. 2000).
Spataro et al., "The ubiquitin-proteasome pathway in cancer" Brit J Cancer 77(3):448-455 ( 1998).
Spence et al., "A ubiquitin mutant with specific defects in DNA repair and multiubiquitination" Mol Cell Biol 15(3):1265-1273 (Mar. 1995).
Spence et al., "Cell cycle-regulated modification of the ribosome by a variant multiubiquitin chain" Cell 102(1):67-76 (Jul. 7, 2000).
Staub et al., "Regulation of stability and function of the epithelial Na+ channel (ENaC) by ubiquitination" EMBO J 16(21):6325-6336 ( 1997).
Stelter and Ulrich et al., "Control of spontaneous and damage-induced mutagenesis by SUMO and ubiquitin conjugation" Nature 425(6954):188-191 (Sep. 11, 2003).
Sun and Chen et al., "The novel functions of ubiquitination in signaling" Curr Opin Cell Biol 16(2):119-126 ( 2004).
Takeda et al., "Serum concentrations of free ubiquitin and multiubiquitin chains" Clin Chem 43(7):1188-1195 ( 1997).
Tan et al., "Lysine 63-linked ubiquitination promotes the formation and autophagic clearance of protein inclusions associated with neurodegenerative diseases" Human Mol Genetics 17(3):431-439 (Mar. 2008).
Tenno et al., "Structural basis for distinct roles of Lys63- and Lys48-linked polyubiquitin chains" Genes Cells 9(10):865-875 ( 2004).
Treier et al., "Ubiquitin-dependent c-Jun degradation in vivo is mediated by the delta domain" Cell 78(5):787-798 (Sep. 9, 1994).
Ulrich, "Degradation or maintenance: actions of the ubiquitin system on eukaryotic chromatin" Eukaryot Cell 1(1):1-10 (Feb. 2002).
Vajdos et al., "Comprehensive functional maps of the antigen-binding site of an anti-ErbB2 antibody obtained with shotgun scanning mutagenesis" J. Mol. Biol. 320:415-428 (2002).
Ward et al., "Degradation of CFTR by the ubiquitin-proteasome pathway" Cell 83(1):121-127 (Oct. 6, 1995).
Wertz et al., "De-ubiquitination and ubiquitin ligase domains of A20 downregulate NF-kappaB signalling" Nature 430:694-699 (Aug. 5, 2004).
Wilkinson, "Ubiquitination and deubiquitination: targeting of proteins for degradation by the proteasome" Semin Cell Dev Biol 11(3):141-148 ( 2000).
"Product information sheet for BIOMOL catalogue No. PW8805" pp. 1-2 (Jan. 25, 2004).
International Search Report for PCT/US2006/062115, dated May 29, 2008 (7 pgs).
International Search Report for PCT/US2009/031310 dated Dec. 3, 2009 (11 pgs).
Wong et al., "Drug discovery in the ubiquitin regulatory pathway" Drug Discov Today 8(16):746-754 (Aug. 2003).
Wu et al., "Humanization of a Murine Monoclonal Antibody by Simultaneous Optimization of Framework and CDR Residues" J Mol Biol 294:151-162 ( 1999).
Yedida et al., "Proteasomes and ubiquitin are involved in the turnover of the wild-type prion protein" EMBO J 20(19):5383-5391 ( 2001).
Zhang et al., "Parkin functions as an E2-dependent ubiquitin-protein ligase and promotes the degradation of the synaptic vesicle-associated protein, CDCrel-1" P Natl Acad Sci USA 97(24):13354-13359 (Nov. 21, 2000).

```
1   MET GLN ILE PHE VAL LYS THR LEU THR GLY LYS THR ILE THR
15  LEU GLU VAL GLU PRO SER ASP THR ILE GLU ASN VAL LYS ALA
29  LYS ILE GLN ASP LYS GLU GLY ILE PRO PRO ASP GLN GLN ARG
43  LEU ILE PHE ALA GLY LYS GLN LEU GLU ASP GLY ARG THR LEU
57  SER ASP TYR ASN ILE GLN LYS GLU SER THR LEU HIS LEU VAL
71  LEU ARG LEU ARG GLY GLY
```
*FIG. 1A*
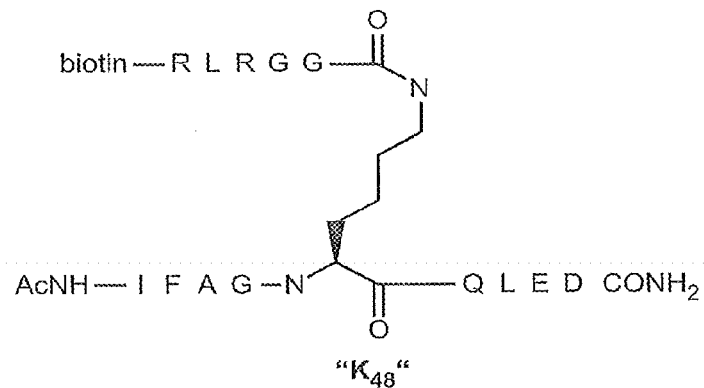
"K₄₈"
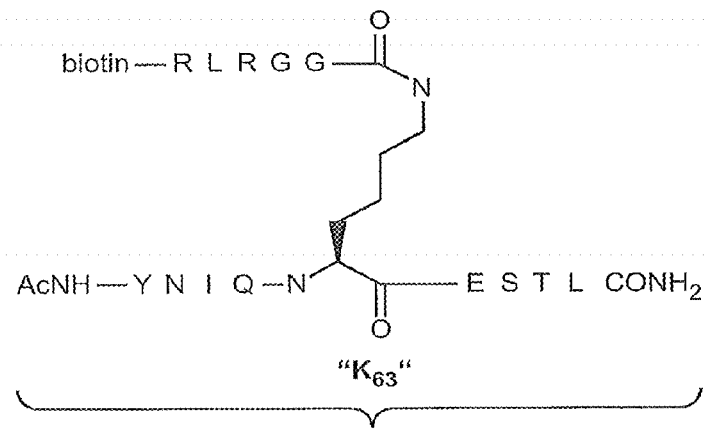
"K₆₃"
*FIG. 1B*

HVR-H1

| Clone # | SEQ ID NO: | 26 | 27 | 28 | 29 | 30 | 31 | 32 | 33 | 34 | 35 | Binds to |
|---|---|---|---|---|---|---|---|---|---|---|---|---|
| 48-1 | 1 | G | F | N | L | S | Y | S | S | M | H | 48 |
| 48-2 | 2 | G | F | N | V | S | Y | S | S | I | H | 48 |
| 48-3 | 3 | G | F | N | I | Y | Y | S | S | I | H | 48 |
| 48-4 | 4 | G | F | N | I | S | Y | Y | Y | I | H | 48 |
| 48-5 | 5 | G | F | N | V | S | Y | Y | Y | M | H | 48 |
| 48-6 | 6 | G | F | N | F | Y | S | S | Y | M | H | 48 |
| 48-7 | 7 | G | F | N | L | Y | Y | S | Y | M | H | 48 |
| 48-8 | 8 | G | F | N | V | Y | Y | S | S | I | H | 48 |
| 48-9 | 9 | G | F | N | I | S | Y | S | Y | M | H | 48 |
| 48-10 | 10 | G | F | N | V | Y | Y | S | S | I | H | 48 |
| 48-11 | 11 | G | F | N | V | S | Y | S | Y | M | H | 48 |
| 48-12 | 12 | G | F | N | L | Y | Y | S | Y | M | H | 48 |
| 48-13 | 13 | G | F | N | V | Y | Y | S | S | I | H | 48 |
| 48-14 | 14 | G | F | N | I | S | Y | S | S | M | H | 48 |
| 48-15 | 15 | G | F | N | V | S | Y | S | S | I | H | 48/BOTH |
| 48-16 | 16 | G | F | N | F | Y | Y | Y | Y | I | H | 48/BOTH |
| 48-17 | 17 | G | F | N | V | S | S | Y | S | I | H | 48 |
| 48-18 | 18 | G | F | N | V | S | S | Y | S | M | H | 48/BOTH |
| 48-19 | 19 | G | F | N | L | S | Y | Y | S | I | H | 48/BOTH |
| 48-20 | 20 | G | F | N | L | S | Y | Y | S | I | H | ALL |
| 48-21 | 21 | G | F | N | V | S | Y | S | Y | M | H | BOTH |
| 48-22 | 22 | G | F | N | V | S | Y | Y | S | I | H | BOTH |
| 48-23 | 23 | G | F | N | L | S | Y | S | S | I | H | BOTH |
| 48-24 | 24 | G | F | N | V | S | Y | S | S | I | H | BOTH |
| 48-25 | 25 | G | F | N | L | S | Y | S | S | M | H | NONE/BOTH |
| Consensus | 26 | G | F | N | L/V/I/F | S/Y | Y/S | S/Y | S/Y | M/I | H | |

FIG. 2A

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 | Binds to |
|---|---|---|---|---|---|---|---|---|---|---|---|---|---|---|---|---|---|---|---|
| 48-1 | 27 | S | I | Y | P | Y | Y | S | Y | T | S | Y | A | D | S | V | K | G | 48 |
| 48-2 | 28 | S | I | S | P | Y | Y | G | Y | T | S | Y | A | D | S | V | K | G | 48 |
| 48-3 | 29 | S | I | Y | S | Y | Y | S | Y | T | S | Y | A | D | S | V | K | G | 48 |
| 48-4 | 30 | S | I | S | S | Y | Y | G | Y | T | S | Y | A | D | S | V | K | G | 48 |
| 48-5 | 31 | S | I | S | S | Y | Y | G | Y | T | S | Y | A | D | S | V | K | G | 48 |
| 48-6 | 32 | S | I | S | P | Y | Y | G | Y | T | S | Y | A | D | S | V | K | G | 48 |
| 48-7 | 33 | S | I | Y | S | Y | Y | S | Y | T | S | Y | A | D | S | V | K | G | 48 |
| 48-8 | 34 | S | I | S | S | Y | Y | G | Y | T | S | Y | A | D | S | V | K | G | 48 |
| 48-9 | 35 | S | I | S | P | Y | Y | S | Y | T | S | Y | A | D | S | V | K | G | 48 |
| 48-10 | 36 | S | I | S | S | Y | Y | S | Y | T | S | Y | A | D | S | V | K | G | 48 |
| 48-11 | 37 | S | I | S | P | Y | Y | S | Y | T | S | Y | A | D | S | V | K | G | 48 |
| 48-12 | 38 | S | I | Y | S | Y | Y | S | Y | T | S | Y | A | D | S | V | K | G | 48 |
| 48-13 | 39 | S | I | Y | P | Y | Y | S | Y | T | S | Y | A | D | S | V | K | G | 48 |
| 48-14 | 40 | S | I | Y | S | Y | Y | S | Y | T | S | Y | A | D | S | V | K | G | 48 |
| 48-15 | 41 | S | I | S | S | Y | Y | S | Y | T | S | Y | A | D | S | V | K | G | 48/BOTH |
| 48-16 | 42 | S | I | S | P | S | S | S | S | T | S | Y | A | D | S | V | K | G | 48/BOTH |
| 48-17 | 43 | S | I | S | S | S | Y | S | S | T | S | Y | A | D | S | V | K | G | 48 |
| 48-18 | 44 | S | I | Y | S | Y | Y | S | Y | T | Y | Y | A | D | S | V | K | G | 48/BOTH |
| 48-19 | 45 | S | I | Y | S | Y | Y | G | Y | T | S | Y | A | D | S | V | K | G | 48/BOTH |
| 48-20 | 46 | S | I | S | S | Y | Y | S | Y | T | S | Y | A | D | S | V | K | G | ALL |
| 48-21 | 47 | S | I | Y | P | Y | Y | S | Y | T | S | Y | A | D | S | V | K | G | BOTH |
| 48-22 | 48 | S | I | S | S | Y | Y | G | Y | T | S | Y | A | D | S | V | K | G | BOTH |
| 48-23 | 49 | S | I | Y | P | Y | Y | S | Y | T | S | Y | A | D | S | V | K | G | BOTH |
| 48-24 | 50 | S | I | Y | P | Y | Y | S | Y | T | S | Y | A | D | S | V | K | G | BOTH |
| 48-25 | 51 | S | I | Y | P | Y | Y | S | Y/S | T | S/Y | Y | A | D | S | V | K | G | NONE/BOTH |
| Consensus | 52 | S | I | Y/S | P/S | Y/S | Y/S | S/G | Y/S | T | S/Y | Y | A | D | S | V | K | G | |

HVR-H3

| Clone # | SEQ ID NO: | 95 | 96 | 97 | 98 | 99 | 100 | 100a | 100b | 100c | 100d | 100e | 100f | 100g | 100h | 100i | 100j | 100k | 100l | 100m | 101 | 102 | Binds to |
|---|---|---|---|---|---|---|---|---|---|---|---|---|---|---|---|---|---|---|---|---|---|---|---|
| 48-1 | 53 | G | Y | E | G | G | M | A | M | | | | | | | | | | | | D | Y | 48 |
| 48-2 | 54 | D | G | Y | A | M | D | A | L | | | | | | | | | | | | D | Y | 48 |
| 48-3 | 55 | L | Y | H | N | T | L | G | M | | | | | | | | | | | | D | Y | 48 |
| 48-4 | 56 | P | Y | S | Y | S | E | A | M | | | | | | | | | | | | D | Y | 48 |
| 48-5 | 57 | E | Y | Y | M | Y | D | A | L | | | | | | | | | | | | D | Y | 48 |
| 48-6 | 58 | D | Y | Y | Y | S | S | A | I | | | | | | | | | | | | D | Y | 48 |
| 48-7 | 59 | S | Y | S | Y | S | S | A | L | | | | | | | | | | | | D | Y | 48 |
| 48-8 | 60 | G | Y | K | Y | W | S | A | F | | | | | | | | | | | | D | Y | 48 |
| 48-9 | 61 | S | Y | S | S | Y | G | G | I | | | | | | | | | | | | D | Y | 48 |
| 48-10 | 62 | E | G | Y | Y | Q | G | G | F | | | | | | | | | | | | D | Y | 48 |
| 48-11 | 63 | S | Y | G | F | Y | V | A | F | | | | | | | | | | | | D | Y | 48 |
| 48-12 | 64 | D | Y | K | Y | Q | Y | A | I | | | | | | | | | | | | D | Y | 48 |
| 48-13 | 65 | E | G | Y | Y | Q | G | G | F | | | | | | | | | | | | D | Y | 48 |
| 48-14 | 66 | S | Y | S | Y | Y | S | A | M | | | | | | | | | | | | D | Y | 48 |
| 48-15 | 67 | G | Y | M | W | Y | G | G | I | | | | | | | | | | | | D | Y | 48/BOTH |
| 48-16 | 68 | E | Y | - | S | S | L | A | Y | I | T | | | | | | | | | | D | Y | 48/BOTH |
| 48-17 | 69 | H | T | - | Y | V | Y | L | G | T | Y | W | | | | | | | | | D | Y | 48 |
| 48-18 | 70 | S | S | M | W | E | W | Y | Y | S | W | Y | E | D | S | M | D | Y | | L | D | Y | 48/BOTH |
| 48-19 | 71 | E | S | - | Y | S | Y | Y | G | | | | | | | W | E | S | G | I | D | Y | 48/BOTH |
| 48-20 | 72 | S | S | I | W | Y | Y | A | M | | | | | | | | | | | | D | Y | ALL |
| 48-21 | 73 | S | Y | S | Y | S | S | G | I | | | | | | | | | | | | D | Y | BOTH |
| 48-22 | 74 | S | Y | S | Y | S | Y | G | L | | | | | | | | | | | | D | Y | BOTH |
| 48-23 | 75 | G | Y | I | H | W | E | A | L | | | | | | | | | | | | D | Y | BOTH |
| 48-24 | 76 | S | Y | S | Y | S | S | G | L | | | | | | | | | | | | D | Y | BOTH |
| 48-25 | 77 | S | Y | S | Y | S | Y | G | M | | | | | | | | | | | | D | Y | NONE/BOTH |
| Consensus | 78 | G/D/L/P/E/S/H | Y/G/T/S | E/Y/H/S/K/G/M/I | G/A/N/Y/M/S/F/W/H | G/M/T/S/Y/N/W/Q/V/E | M/D/L/E/S/G/V/Y/W | A/G/L/Y | M/L/F/I/A/Y/G | I/T/S | Y/W | W/Y | E/Y | D/F | S/W | M/E | D/S | Y/S | | L/ | D | Y | |

HVR-H1

| Clone # | SEQ ID NO: | 26 | 27 | 28 | 29 | 30 | 31 | 32 | 33 | 34 | 35 | Binds to |
|---|---|---|---|---|---|---|---|---|---|---|---|---|
| 63-1 | 81 | G | F | N | I | S | S | S | Y | I | H | 63/BOTH |
| 63-2 | 82 | G | F | N | F | S | Y | S | Y | I | H | ALL |
| 63-3 | 83 | G | F | N | L | S | Y | Y | Y | I | H | BOTH |
| 63-4 | 84 | G | F | N | F | Y | S | S | S | I | H | 63/BOTH |
| 63-5 | 85 | G | F | N | F | Y | S | S | S | I | H | BOTH |
| 63-6 | 86 | G | F | N | I | S | Y | S | S | I | H | ALL |
| 63-7 | 87 | G | F | N | F | Y | Y | S | S | I | H | BOTH |
| 63-8 | 88 | G | F | N | F | S | S | Y | S | I | H | ALL |
| 63-9 | 89 | G | F | N | V | S | S | Y | S | I | H | ALL |
| Consensus | 90 | G | F | N | I/F/L/V | S/Y | S/Y | S/Y | Y/S | I | H | |

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 | Binds to |
|---|---|---|---|---|---|---|---|---|---|---|---|---|---|---|---|---|---|---|---|
| 63-1 | 91 | Y | I | S | P | Y | Y | G | S | T | S | Y | A | D | S | V | K | G | 63/BOTH |
| 63-2 | 92 | S | I | S | S | S | Y | G | Y | T | S | Y | A | D | S | V | K | G | ALL |
| 63-3 | 93 | S | I | S | S | Y | Y | G | Y | T | S | Y | A | D | S | V | K | G | BOTH |
| 63-4 | 94 | S | I | S | S | S | Y | G | S | T | S | Y | A | D | S | V | K | G | 63/BOTH |
| 63-5 | 95 | S | I | S | P | S | Y | G | S | T | S | Y | A | D | S | V | K | G | BOTH |
| 63-6 | 96 | S | I | S | S | S | Y | S | Y | T | S | Y | A | D | S | V | K | G | ALL |
| 63-7 | 97 | S | I | Y | S | S | Y | G | S | T | S | Y | A | D | S | V | K | G | BOTH |
| 63-8 | 98 | S | I | Y | P | S | S | S | S | T | Y | Y | A | D | S | V | K | G | ALL |
| 63-9 | 99 | S | I | Y | S | S | S | G | S | T | S/Y | Y | A | D | S | V | K | G | ALL |
| Consensus | 100 | Y/S | I | S/Y | P/S | Y/S | Y/S | G/S | S/Y | T | S/Y | Y | A | D | S | V | K | G | |

| HVR-H3 Clone # | SEQ ID NO: | 95 | 96 | 97 | 98 | 99 | 100 | 100a | 100b | 100c | 100d | 100e | 100f | 100g | 100h | 100i | 100j | 100k | 100l | 100m | 101 | 102 | Binds to |
|---|---|---|---|---|---|---|---|---|---|---|---|---|---|---|---|---|---|---|---|---|---|---|---|
| 63-1 | 101 | E | Y | Y | R | W | Y | T | A | I | | | | | | | | | | | D | Y | 63/BOTH |
| 63-2 | 102 | E | K | M | Y | Y | S | Y | G | F | | | | | | | | | | | D | Y | ALL |
| 63-3 | 103 | E | S | Y | S | I | H | F | G | F | | | | | | | | | | | D | Y | BOTH |
| 63-4 | 104 | M | Y | Y | S | Y | Y | W | R | P | Y | G | N | A | I | | | | | | D | Y | 63/BOTH |
| 63-5 | 105 | G | S | I | P | S | Y | Y | S | A | D | W | M | Y | Y | Y | G | | | | D | Y | BOTH |
| 63-6 | 106 | Y | K | Y | N | Y | Y | K | F | E | S | G | S | A | | | | L | | | D | Y | ALL |
| 63-7 | 107 | E | Y | Y | W | W | Y | W | E | A | W | Y | D | Y | G | M | A | | | | D | Y | BOTH |
| 63-8 | 108 | G | I | M | F | S | S | G | W | W | Y | Y | Y | Y | S | D | A | L | G | M | D | Y | ALL |
| 63-9 | 109 | S | G | Y | Y | Y | Q | G | Y | W | W | Y | Y | Y | T | G | Y | Y | G | M | D | Y | ALL |
| Consensus | 110 | E/M/G/Y/S | Y/K/S/I/G | Y/M/I | R/Y/S/P/N/W/F | W/Y/I/S | Y/S/H/Q | T/Y/F/W/K/G | A/G/R/S/F/E/W/Y | I/F/P/A/M/S/E/W/Y | Y/D/S/W/n.p. | G/W/Y/n.p. | N/Y/M/S/D/n.p. | A/Y/n.p. | I/Y/G/S/T/n.p. | Y/M/D/G/n.p. | G/A/Y/n.p. | L/Y/n.p. | G/n.p. | M/n.p. | D | Y | |

|   | | | | |
|---|---|---|---|---|
| I | A | QVQLVQSGAEVKKPGASVKVSCKASGYTFT | -H1- | WVRQAPGQGLEWMG | -H2- | RVTIT |
|   | B | QVQLVQSGAEVKKPGASVKVSCKAS | -H1- | WVRQAPGQGLEWM | -H2- | RVTIT |
|   | C | QVQLVQSGAEVKKPGASVKVSCKAS | -H1- | WVRQAPGQGLEWM | -H2- | RVTIT |
|   | D | QVQLVQSGAEVKKPGASVKVSCKAS | -H1- | WVRQAPGQGLEWM | -H2- | RVTIT |
| II | A | QVQLQESGPGLVKPSQTLSLTCTVSGGSVS | -H1- | WIRQPPGKGLEWIG | -H2- | RVTIS |
|   | B | QVQLQESGPGLVKPSQTLSLTCTVS | -H1- | WIRQPPGKGLEWI | -H2- | RVTIS |
|   | C | QVQLQESGPGLVKPSQTLSLTCTVS | -H1- | WIRQPPGKGLEWI | -H2- | RVTIS |
|   | D | QVQLQESGPGLVKPSQTLSLTCTVS | -H1- | WIRQPPGKGLEWI | -H2- | RVTIS |
| III | A | EVQLVESGGGLVQPGGSLRLSCAASGFTFS | -H1- | WVRQAPGKGLEWVS | -H2- | RFTIS |
|   | B | EVQLVESGGGLVQPGGSLRLSCAAS | -H1- | WVRQAPGKGLEWV | -H2- | RFTIS |
|   | C | EVQLVESGGGLVQPGGSLRLSCAAS | -H1- | WVRQAPGKGLEWV | -H2- | RFTIS |
|   | D | EVQLVESGGGLVQPGGSLRLSCAAS | -H1- | WVRQAPGKGLEWV | -H2- | RFTIS |
| Acceptor | A | EVQLVESGGGLVQPGGSLRLSCAASGFNIK | -H1- | WVRQAPGKGLEWVS | -H2- | RFTIS |
|   | B | EVQLVESGGGLVQPGGSLRLSCAAS | -H1- | WVRQAPGKGLEWV | -H2- | RFTIS |
|   | C | EVQLVESGGGLVQPGGSLRLSCAAS | -H1- | WVRQAPGKGLEWV | -H2- | RFTIS |
| Second Acceptor | A | EVQLVESGGGLVQPGGSLRLSCAASGFNIK | -H1- | WVRQAPGKGLEWVS | -H2- | RFTIS |
|   | B | EVQLVESGGGLVQPGGSLRLSCAAS | -H1- | WVRQAPGKGLEWV | -H2- | RFTIS |
|   | C | EVQLVESGGGLVQPGGSLRLSCAAS | -H1- | WVRQAPGKGLEWV | -H2- | RFTIS |
|   | D | EVQLVESGGGLVQPGGSLRLSCAAS | -H1- | WVRQAPGKGLEWV | -H2- | RFTIS |

FIG. 4A

| | | | |
|---|---|---|---|
| I | | | |
| A | ADTSTSTAYMELSSLRSEDTAVYYCAR | WGQGTLVTVSS | SEQ ID NO: 111, 839, 858 & 877 |
| B | ADTSTSTAYMELSSLRSEDTAVYYCAR | WGQGTLVTVSS | SEQ ID NO: 112, 840, 859 & 878 |
| C | ADTSTSTAYMELSSLRSEDTAVYYCAR | WGQGTLVTVSS | SEQ ID NO: 113, 841, 860 & 879 |
| D | ADTSTSTAYMELSSLRSEDTAVYYC | WGQGTLVTVSS | SEQ ID NO: 114, 842, 861 & 880 |
| II | | | |
| A | VDTSKNQFSLKLSSVTAADTAVYYCAR | WGQGTLVTVSS | SEQ ID NO: 115, 843, 862 & 881 |
| B | VDTSKNQFSLKLSSVTAADTAVYYCAR | WGQGTLVTVSS | SEQ ID NO: 116, 844, 863 & 882 |
| C | VDTSKNQFSLKLSSVTAADTAVYYCA | WGQGTLVTVSS | SEQ ID NO: 117, 845, 864 & 883 |
| D | VDTSKNQFSLKLSSVTAADTAVYYC | WGQGTLVTVSS | SEQ ID NO: 118, 846, 865 & 884 |
| III | | | |
| A | RDNSKNTLYLQMNSLRAEDTAVYYCAR | WGQGTLVTVSS | SEQ ID NO: 119, 847, 866 & 885 |
| B | RDNSKNTLYLQMNSLRAEDTAVYYCAR | WGQGTLVTVSS | SEQ ID NO: 120, 848, 867 & 886 |
| C | RDNSKNTLYLQMNSLRAEDTAVYYCA | WGQGTLVTVSS | SEQ ID NO: 121, 849, 868 & 887 |
| D | RDNSKNTLYLQMNSLRAEDTAVYYC | WGQGTLVTVSS | SEQ ID NO: 122, 850, 869 & 888 |
| Acceptor | | | |
| A | ADTSKNTAYLQMNSLRAEDTAVYYCSR | WGQGTLVTVSS | SEQ ID NO: 123, 851, 870 & 889 |
| B | ADTSKNTAYLQMNSLRAEDTAVYYCSR | WGQGTLVTVSS | SEQ ID NO: 124, 852, 871 & 890 |
| C | ADTSKNTAYLQMNSLRAEDTAVYYCS | WGQGTLVTVSS | SEQ ID NO: 125, 853, 872 & 891 |
| Second Acceptor | | | |
| A | ADTSKNTAYLQMNSLRAEDTAVYYCAR | WGQGTLVTVSS | SEQ ID NO: 126, 854, 873 & 892 |
| B | ADTSKNTAYLQMNSLRAEDTAVYYCAR | WGQGTLVTVSS | SEQ ID NO: 127, 855, 874 & 893 |
| C | ADTSKNTAYLQMNSLRAEDTAVYYCA | WGQGTLVTVSS | SEQ ID NO: 128, 856, 875 & 894 |
| D | ADTSKNTAYLQMNSLRAEDTAVYYC | WGQGTLVTVSS | SEQ ID NO: 129, 857, 876 & 895 |

FIG. 4B

Framework Sequences of huMAb4D5-8 Light Chain

LC-FR1    $^1$Asp Ile Gln Met Thr Gln Ser Pro Ser Ser Leu Ser Ala Ser Val Gly Asp Arg Val Thr Ile Thr Cys$^{23}$ (SEQ ID NO: 134)

LC-FR2    $^{35}$Trp Tyr Gln Gln Lys Pro Gly Lys Ala Pro Lys Leu Leu Ile Tyr$^{49}$ (SEQ ID NO: 135)

LC-FR3    $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 136)

LC-FR4    $^{98}$Phe Gly Gln Gly Thr Lys Val Glu Ile Lys$^{107}$ (SEQ ID NO: 137)

Framework Sequences of huMAb4D5-8 Heavy Chain

HC-FR1    $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 138)

HC-FR2    $^{36}$Trp Val Arg Gln Ala Pro Gly Lys Gly Leu Glu Trp Val$^{48}$ (SEQ ID NO: 139)

HC-FR3    $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO: 140)

HC-FR4    $^{103}$Trp Gly Gln Gly Thr Leu Val Thr Val Ser Ser$^{113}$ (SEQ ID NO: 141)

*FIG. 6*

Framework Sequences of huMAb4D5-8 Light Chain Modified at Position 66 and 99 (Underlined)

LC-FR1    $^1$Asp Ile Gln Met Thr Gln Ser Pro Ser Ser Leu Ser Ala Ser Val Gly Asp Arg Val Thr Ile Thr Cys$^{23}$ (SEQ ID NO: 142)

LC-FR2    $^{35}$Trp Tyr Gln Gln Lys Pro Gly Lys Ala Pro Lys Leu Leu Ile Tyr$^{49}$ (SEQ ID NO: 143)

LC-FR3    $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO: 144)

LC-FR4    $^{98}$Phe <u>Arg</u> Gln Gly Thr Lys Val Glu Ile Lys$^{107}$ (SEQ ID NO: 145)

Framework Sequences of huMAb4D5-8 Heavy Chain Modified at Postions 71, 73 and 78 (Underlined)

HC-FR1    $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 146)

HC-FR2    $^{36}$Trp Val Arg Gln Ala Pro Gly Lys Gly Leu Glu Trp Val$^{48}$ (SEQ ID NO: 147)

HC-FR3    $^{66}$Arg Phe Thr Ile Ser <u>Arg</u> Asp <u>Asn</u> Ser Lys Asn Thr <u>Leu</u> Tyr Leu Gln Met Asn83 Ser83a Leu83b Arg83c Ala Glu Asp Thr Ala Val Tyr Tyr Cys$^{92}$ (SEQ ID NO: 148)

HC-FR4    $^{103}$Trp Gly Gln Gly Thr Leu Val Thr Val Ser Ser$^{113}$ (SEQ ID NO: 149)

*FIG. 7*

HVR-H1

| Clone # | SEQ ID NO: | 26 | 27 | 28 | 29 | 30 | 31 | 32 | 33 | 34 | 35 |
|---|---|---|---|---|---|---|---|---|---|---|---|
| 48-26 | 151 | G | F | N | V | Y | Y | S | S | I | H |
| 48-27 | 152 | G | F | N | V | S | Y | S | Y | M | H |
| 48-28 | 153 | G | F | N | F | S | Y | Y | S | M | H |
| 48-29 | 154 | G | F | N | L | S | Y | Y | S | I | H |
| 48-30 | 155 | G | F | N | I | S | Y | S | S | M | H |
| 48-31 | 156 | G | F | N | V | Y | Y | S | S | I | H |
| 48-32 | 157 | G | F | N | L | S | Y | S | Y | I | H |
| 48-33 | 158 | G | F | N | F | Y | Y | Y | Y | I | H |
| 48-34 | 159 | G | F | N | L | S | Y | S | S | I | H |
| 48-35 | 160 | G | F | N | V | S | Y | S | S | I | H |
| 48-36 | 161 | G | F | N | V | S | Y | S | S | I | H |
| 48-37 | 162 | G | F | N | V | Y | Y | S | S | I | H |
| 48-38 | 163 | G | F | N | V | S | Y | Y | Y | I | H |
| 48-39 | 164 | G | F | N | L | S | Y | S | S | I | H |
| 48-40 | 165 | G | F | N | I | S | Y | S | Y | M | H |
| 48-41 | 166 | G | F | N | L | Y | Y | S | Y | M | H |
| 48-42 | 167 | G | F | N | V | S | Y | Y | Y | M | H |
| 48-43 | 168 | G | F | N | I | S | Y | S | Y | M | H |
| 48-44 | 169 | G | F | N | I | S | Y | S | S | I | H |
| 48-45 | 170 | G | F | N | V | S | Y | S | S | M | H |
| 48-46 | 171 | G | F | N | L | S | Y | Y | S | I | H |
| 48-47 | 172 | G | F | N | V | S | Y | Y | S | I | H |
| 48-48 | 173 | G | F | N | I | S | Y | S | S | I | H |
| 48-49 | 174 | G | F | N | F | S | Y | Y | S | I | H |
| 48-50 | 175 | G | F | N | L | S | Y | S | S | M | H |
| Consensus | 176 | G | F | N | V/F/L/I | Y/S | Y | S/Y | S/Y | I/M | H |

FIG. 8A

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| 48-26 | 177 | S | I | S | P | Y | Y | S | Y | T | S | Y | A | D | S | V | K | G |
| 48-27 | 178 | S | I | S | S | Y | Y | S | Y | T | S | Y | A | D | S | V | K | G |
| 48-28 | 179 | S | I | Y | P | Y | Y | G | Y | T | Y | Y | A | D | S | V | K | G |
| 48-29 | 180 | S | I | Y | P | Y | Y | G | Y | T | S | Y | A | D | S | V | K | G |
| 48-30 | 181 | S | I | Y | S | Y | Y | S | Y | T | S | Y | A | D | S | V | K | G |
| 48-31 | 182 | S | I | Y | P | Y | Y | G | Y | T | S | Y | A | D | S | V | K | G |
| 48-32 | 183 | S | I | S | S | Y | Y | G | S | T | S | Y | A | D | S | V | K | G |
| 48-33 | 184 | S | I | S | P | Y | Y | S | Y | T | S | Y | A | D | S | V | K | G |
| 48-34 | 185 | S | I | Y | P | Y | Y | S | Y | T | S | Y | A | D | S | V | K | G |
| 48-35 | 186 | S | I | Y | P | Y | Y | S | Y | T | S | Y | A | D | S | V | K | G |
| 48-36 | 187 | S | I | Y | S | Y | Y | S | Y | T | S | Y | A | D | S | V | K | G |
| 48-37 | 188 | S | I | Y | P | Y | Y | G | Y | T | S | Y | A | D | S | V | K | G |
| 48-38 | 189 | S | I | S | S | Y | Y | G | Y | T | S | Y | A | D | S | V | K | G |
| 48-39 | 190 | S | I | Y | S | Y | Y | G | Y | T | S | Y | A | D | S | V | K | G |
| 48-40 | 191 | S | I | S | P | Y | Y | G | Y | T | S | Y | A | D | S | V | K | G |
| 48-41 | 192 | S | I | S | S | Y | Y | S | Y | T | S | Y | A | D | S | V | K | G |
| 48-42 | 193 | S | I | S | S | Y | Y | S | Y | T | S | Y | A | D | S | V | K | G |
| 48-43 | 194 | S | I | S | S | Y | Y | S | Y | T | S | Y | A | D | S | V | K | G |
| 48-44 | 195 | S | I | S | S | S | Y | S | S | T | Y | Y | A | D | S | V | K | G |
| 48-45 | 196 | S | I | S | P | Y | Y | G | Y | T | S | Y | A | D | S | V | K | G |
| 48-46 | 197 | S | I | Y | S | S | Y | S | S | T | Y | Y | A | D | S | V | K | G |
| 48-47 | 198 | S | I | Y | P | Y | Y | S | Y | T | S | Y | A | D | S | V | K | G |
| 48-48 | 199 | S | I | Y | P | Y | Y | S | Y | T | S | Y | A | D | S | V | K | G |
| 48-49 | 200 | S | I | Y | P | Y | Y | S | Y | T | Y | Y | A | D | S | V | K | G |
| 48-50 | 201 | S | I | Y | P | Y | Y | S | Y | T | S | Y | A | D | S | V | K | G |
| Consensus | 202 | S | I | S/Y | P/S | Y/S | Y | S/G | Y/S | T | S/Y | Y | A | D | S | V | K | G |

FIG. 8B

HVR-H3

| Clone # | SEQ ID NO: | 95 | 96 | 97 | 98 | 99 | 100 | 100a | 100b | 100c | 101 | 102 |
|---|---|---|---|---|---|---|---|---|---|---|---|---|
| 48-26 | 203 | E | G | Y | S | Q | G | G | F |  | D | Y |
| 48-27 | 204 | S | Y | S | Y | Y | S | A | I |  | D | Y |
| 48-28 | 205 | S | Y | S | Y | S | Y | G | M |  | D | Y |
| 48-29 | 206 | S | Y | S | Y | S | Y | G | I |  | D | Y |
| 48-30 | 207 | S | Y | S | Y | Y | S | A | M |  | D | Y |
| 48-31 | 208 | G | Y | K | Y | W | S | A | F |  | D | Y |
| 48-32 | 209 | E | S | F | Y | Y | S | P | A | F | D | Y |
| 48-33 | 210 | E | Y | Y | S | Y | L | G | A | I | D | Y |
| 48-34 | 211 | G | Y | E | G | G | M | A | M |  | D | Y |
| 48-35 | 212 | S | Y | S | Y | S | S | G | L |  | D | Y |
| 48-36 | 213 | G | Y | M | W | Y | G | G | I |  | D | Y |
| 48-37 | 214 | D | C | Y | Y | x | A | A | F |  | D | Y |
| 48-38 | 215 | E | N | Y | W | W | A | I |  |  | D | Y |
| 48-39 | 216 | S | Y | S | Y | Y | S | A | F |  | D | Y |
| 48-40 | 217 | D | Y | Y | F | F | S | A | I |  | D | Y |
| 48-41 | 218 | S | Y | S | Y | S | S | A | L |  | D | Y |
| 48-42 | 219 | E | G | Y | I | S | G | D | A | I | D | Y |
| 48-43 | 220 | S | Y | S | S | Y | S | A | I |  | D | Y |
| 48-44 | 221 | G | Y | F | E | G | W | Y | G | L | D | Y |
| 48-45 | 222 | E | Y | S | Y | Y | G | G | F |  | D | Y |
| 48-46 | 223 | E | S | Y | W | S | Y | A | M |  | D | Y |
| 48-47 | 224 | S | Y | S | Y | S | Y | G | L |  | D | Y |
| 48-48 | 225 | Y | Y | S | Y | S | S | G | L |  | D | Y |
| 48-49 | 226 | S | Y | S | Y | S | Y | G | L |  | D | Y |
| 48-50 | 227 | S | Y | S | Y | S | Y | G | M |  | D | Y |
| Con-sensus | 228 | E/S/G/D/Y | G/Y/S/C/N | Y/S/K/F/E/M | S/Y/G/W/F/I/E | Q/Y/S/W/G/X/F | G/S/Y/L/M/G/A/W | G/A/P/I/D/Y | F/I/M/A/L/G/n.p. | F/I/L/n.p. | D | Y |

*FIG. 8C*

HVR-H1

| Clone # | SEQ ID NO: | 26 | 27 | 28 | 29 | 30 | 31 | 32 | 33 | 34 | 35 |
|---|---|---|---|---|---|---|---|---|---|---|---|
| 63-10 | 229 | G | F | N | I | S | S | S | Y | I | H |
| 63-11 | 230 | G | F | N | V | S | S | Y | S | I | H |
| 63-12 | 231 | G | F | N | F | S | Y | S | S | I | H |
| 63-13 | 232 | G | F | N | F | Y | S | S | S | I | H |
| 63-14 | 233 | G | F | N | F | Y | Y | S | S | I | H |
| 63-15 | 234 | G | F | N | V | Y | Y | S | Y | I | H |
| 63-16 | 235 | G | F | N | F | S | S | S | Y | I | H |
| 63-17 | 236 | G | F | N | F | Y | Y | S | S | I | H |
| 63-18 | 237 | G | F | N | F | Y | S | S | Y | I | H |
| 63-19 | 238 | G | F | N | V | S | S | Y | S | M | H |
| 63-20 | 239 | G | F | N | V | S | S | S | Y | I | H |
| Consensus | 240 | G | F | N | I/V/F | S/Y | S/Y | S/Y | Y/S | I/M | H |

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| 63-10 | 241 | Y | I | S | P | Y | Y | G | S | T | S | Y | A | D | S | V | K | G |
| 63-11 | 242 | S | I | Y | P | Y | S | S | S | T | Y | Y | A | D | S | V | K | G |
| 63-12 | 243 | S | I | Y | S | S | Y | G | Y | T | S | Y | A | D | S | V | K | G |
| 63-13 | 244 | S | I | S | S | S | Y | S | Y | T | S | Y | A | D | S | V | K | G |
| 63-14 | 245 | S | I | Y | S | S | Y | G | S | T | Y | Y | A | D | S | V | K | G |
| 63-15 | 246 | S | I | S | P | S | S | S | S | T | S | Y | A | D | S | V | K | G |
| 63-16 | 247 | S | I | S | P | S | Y | G | Y | T | Y | Y | A | D | S | V | K | G |
| 63-17 | 248 | S | I | Y | S | S | S | S | Y | T | V | Y | A | D | S | V | K | G |
| 63-18 | 249 | Y | I | S | P | Y | S | G | S | T | S | Y | A | D | S | V | K | G |
| 63-19 | 250 | S | I | Y | P | S | S | G | Y | T | Y | Y | A | D | S | V | K | G |
| 63-20 | 251 | S | I | S | S | Y | S | S | S | T | V | Y | A | D | S | V | K | G |
| Consensus | 252 | Y/S | I | S/Y | P/S | Y/S | Y/S | G/S | S/Y | T | S/Y | Y | A | D | S | V | K | G |

FIG. 9A

HVR-H3

| Clone # | SEQ ID NO: | 95 | 96 | 97 | 98 | 99 | 100 | 100a | 100b | 100c | 100d | 100e | 100f | 100g | 100h | 100i | 100j | 100k | 100l | 100m | 101 | 102 |
|---|---|---|---|---|---|---|---|---|---|---|---|---|---|---|---|---|---|---|---|---|---|---|
| 63-10 | 253 | E | Y | Y | R | W | Y | T | A | | | Y | Y | Y | T | G | Y | Y | G | M | D | Y |
| 63-11 | 254 | S | G | Y | Y | Y | Q | G | Y | I | W | Y | Y | Y | S | D | Y | | | | D | Y |
| 63-12 | 255 | G | I | M | F | S | S | W | W | W | Y | W | D | Y | Y | Y | A | L | | | D | Y |
| 63-13 | 256 | G | S | I | P | S | Y | W | S | A | D | Y | Y | Y | Y | M | G | L | G | | D | Y |
| 63-14 | 257 | E | Y | Y | W | W | Y | K | E | A | W | S | S | A | G | | Y | | | L | D | Y |
| 63-15 | 258 | W | Q | G | Y | G | F | K | Y | Y | Y | G | Y | Y | V | S | Y | G | G | | D | Y |
| 63-16 | 259 | S | Y | S | Y | S | Y | Y | S | S | Y | F | F | | | | | | | | D | Y |
| 63-17 | 260 | E | S | Y | A | G | V | P | P | Y | G | Y | | | | | | | | | D | Y |
| 63-18 | 261 | G | I | M | F | S | S | W | W | W | Y | Y | D | Y | S | D | A | L | | | D | Y |
| 63-19 | 262 | G | I | M | F | S | S | W | W | W | Y | Y | D | Y | S | D | A | L | | | D | Y |
| 63-20 | 263 | E | Y | Y | W | W | Y | K | E | A | W | Y | S | A | G | M | | | | | D | Y |
| Consensus | 264 | E/S/ G/W | Y/ G/I/ S/G | Y/M/ I/Y/ G/S | R/Y/ F/P/W | W/Y/ S/G | Y/Q/ S/F/V | T/G/ W/K/ Y/P | A/Y/ W/S/ E/P | I/W/ A/Y/ S | W/Y/ D/G | Y/W/ S/G F | Y/D/ S/F/ n.p. | Y/A/ n.p. | T/S/ Y/G/ V/ n.p. | G/D/ Y/M/ S/ n.p. | Y/A/ G/ n.p. | Y/L/ G/ n.p. | G/ n.p. | M/L/ n.p. | D | Y |

FIG. 9B

HVR-H1

| Clone # | SEQ ID NO: | 26 | 27 | 28 | 29 | 30 | 31 | 32 | 33 | 34 | 35 |
|---|---|---|---|---|---|---|---|---|---|---|---|
| apu01 | 265 | G | F | N | V | Y | Y | S | S | I | H |
| apu02 | 266 | G | F | N | V | S | Y | S | Y | M | H |
| apu03 | 267 | G | F | N | F | S | Y | Y | S | M | H |
| apu04 | 268 | G | F | N | L | S | Y | Y | S | I | H |
| apu05 | 269 | G | F | N | I | S | Y | S | S | M | H |
| apu06 | 270 | G | F | N | V | Y | Y | S | S | I | H |
| apu07 | 271 | G | F | N | L | S | Y | S | Y | I | H |
| apu08 | 272 | G | F | N | L | S | Y | S | S | M | H |
| apu09 | 273 | G | F | N | V | S | Y | S | S | I | H |
| apu10 | 274 | G | F | N | V | S | Y | S | S | I | H |
| apu11 | 275 | G | F | N | V | S | Y | Y | Y | I | H |
| apu12 | 276 | G | F | N | L | Y | Y | S | Y | M | H |
| apu13 | 277 | G | F | N | V | S | Y | Y | S | I | H |
| apu14 | 278 | G | F | N | I | S | Y | S | S | I | H |
| apu15 | 279 | G | F | N | F | S | Y | S | Y | I | H |
| Consensus | 280 | G | F | N | V/F/L/I | Y/S | Y | S/Y | S/Y | I/M | H |

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| apu01 | 281 | S | I | S | P | Y | Y | S | Y | T | S | Y | A | D | S | V | K | G |
| apu02 | 282 | S | I | S | S | Y | Y | S | Y | T | S | Y | A | D | S | V | K | G |
| apu03 | 283 | S | I | Y | P | Y | Y | G | Y | T | Y | Y | A | D | S | V | K | G |
| apu04 | 284 | S | I | Y | P | Y | Y | G | Y | T | S | Y | A | D | S | V | K | G |
| apu05 | 285 | S | I | Y | S | Y | Y | S | Y | T | S | Y | A | D | S | V | K | G |
| apu06 | 286 | S | I | Y | P | Y | Y | G | Y | T | S | Y | A | D | S | V | K | G |
| apu07 | 287 | S | I | S | S | Y | Y | G | S | T | S | Y | A | D | S | V | K | G |
| apu08 | 288 | S | I | Y | P | Y | Y | S | Y | T | S | Y | A | D | S | V | K | G |
| apu09 | 289 | S | I | Y | P | Y | Y | S | Y | T | S | Y | A | D | S | V | K | G |
| apu10 | 290 | S | I | Y | P | Y | Y | S | Y | T | S | Y | A | D | S | V | K | G |
| apu11 | 291 | S | I | S | S | Y | Y | G | Y | T | S | Y | A | D | S | V | K | G |
| apu12 | 292 | S | I | S | S | Y | Y | S | Y | T | S | Y | A | D | S | V | K | G |
| apu13 | 293 | S | I | Y | P | Y | Y | S | Y | T | S | Y | A | D | S | V | K | G |
| apu14 | 294 | S | I | Y | P | Y | Y | S | Y | T | Y | Y | A | D | S | V | K | G |
| apu15 | 295 | S | I | Y | P | Y | Y | S | Y | T | Y | Y | A | D | S | V | K | G |
| Consensus | 296 | S | I | S/Y | P/S | Y | Y | S/G | Y/S | T | S/Y | Y | A | D | S | V | K | G |

FIG. 10A

HVR-H3

| Clone # | SEQ ID NO: | 95 | 96 | 97 | 98 | 99 | 100 | 100a | 100b | 100c | 101 | 102 |
|---|---|---|---|---|---|---|---|---|---|---|---|---|
| apu01 | 297 | E | G | Y | S | Q | G | G | F | | D | Y |
| apu02 | 298 | S | Y | S | Y | Y | S | A | I | | D | Y |
| apu03 | 299 | S | Y | S | Y | S | Y | G | M | | D | Y |
| apu04 | 300 | S | Y | S | Y | S | Y | G | I | | D | Y |
| apu05 | 301 | S | Y | S | Y | Y | S | A | M | | D | Y |
| apu06 | 302 | G | Y | K | Y | W | S | A | F | | D | Y |
| apu07 | 303 | E | S | F | Y | Y | S | P | A | F | D | Y |
| apu08 | 304 | G | Y | E | G | G | M | A | M | | D | Y |
| apu09 | 305 | S | Y | S | Y | S | S | G | L | | D | Y |
| apu10 | 306 | G | Y | M | W | Y | G | G | I | | D | Y |
| apu11 | 307 | E | N | Y | W | W | A | I | | | D | Y |
| apu12 | 308 | S | Y | S | Y | S | S | A | L | | D | Y |
| apu13 | 309 | S | Y | S | Y | S | Y | G | L | | D | Y |
| apu14 | 310 | Y | Y | S | Y | S | S | G | L | | D | Y |
| apu15 | 311 | S | Y | S | Y | S | Y | G | L | | D | Y |
| Consensus | 312 | E/S/G/Y | G/Y/S/N | Y/S/K/F/E | S/Y/G/W | Q/Y/S/G | G/S/Y/M/A | G/A/P/I | F/I/M/A/L/n.p. | F/n.p. | D | Y |

FIG. 10B

HVR-L3

| Clone # | SEQ ID NO: | 89 | 90 | 91 | 92 | 93 | 94 | 95 | 95a | 95b | 96 | 97 |
|---|---|---|---|---|---|---|---|---|---|---|---|---|
| apu01 | 313 | Q | Q | S | S | Y | S | S | L | | F | T |
| apu02 | 314 | Q | Q | S | S | Y | S | S | L | | F | T |
| apu03 | 315 | Q | Q | Y | S | S | Y | S | S | P | I | T |
| apu04 | 316 | Q | Q | Y | S | S | Y | Y | S | P | V | T |
| apu05 | 317 | Q | Q | S | S | Y | S | S | L | | I | T |
| apu06 | 318 | Q | Q | S | S | Y | S | S | L | | V | T |
| apu07 | 319 | Q | Q | S | Y | Y | Y | S | L | | F | T |
| apu08 | 320 | Q | Q | S | S | Y | S | S | L | | V | T |
| apu09 | 321 | Q | Q | S | S | Y | S | S | L | | F | T |
| apu10 | 322 | Q | Q | Y | S | Y | S | S | L | | F | T |
| apu11 | 323 | Q | Q | S | Y | Y | Y | Y | P | | I | T |
| apu12 | 324 | Q | Q | S | S | Y | S | S | L | | V | T |
| apu13 | 325 | Q | Q | Y | S | S | S | Y | Y | P | F | T |
| apu14 | 326 | Q | Q | S | S | Y | S | S | L | | L | T |
| apu15 | 327 | Q | Q | Y | Y | Y | Y | Y | Y | P | I | T |
| Consensus | 328 | Q | Q | S/Y | S/Y | Y/S | S/Y | S/Y | L/S/P/Y | P/n.p. | F/I/V/L | T |

FIG. 10C

HVR-H1

| Clone # | SEQ ID NO: | 26 | 27 | 28 | 29 | 30 | 31 | 32 | 33 | 34 | 35 |
|---|---|---|---|---|---|---|---|---|---|---|---|
| apu17 | 329 | G | F | N | V | S | S | Y | S | I | H |
| apu18 | 330 | G | F | N | I | S | S | S | S | I | H |
| apu19 | 331 | G | F | N | F | S | Y | S | S | I | H |
| apu20 | 332 | G | F | N | V | Y | Y | S | S | I | H |
| apu21 | 333 | G | F | N | F | S | S | S | S | I | H |
| apu22 | 334 | G | F | N | V | Y | S | S | Y | I | H |
| apu23 | 335 | G | F | N | F | Y | S | S | Y | M | H |
| apu24 | 336 | G | F | N | F | Y | S | S | S | I | H |
| Consensus | 337 | G | F | N | V/I/F | S/Y | S/Y | V/S | S/Y | I/M | H |

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| apu17 | 338 | S | I | Y | P | S | S | G | S | T | Y | Y | A | D | S | V | K | G |
| apu18 | 339 | Y | I | S | P | Y | Y | G | S | T | S | Y | A | D | S | V | K | G |
| apu19 | 340 | S | I | Y | S | S | Y | G | Y | T | S | Y | A | D | S | V | K | G |
| apu20 | 341 | S | I | S | P | S | Y | G | Y | T | S | Y | A | D | S | V | K | G |
| apu21 | 342 | S | I | Y | S | S | Y | S | Y | T | S | Y | A | D | S | V | K | G |
| apu22 | 343 | S | I | S | S | Y | S | G | Y | T | S | Y | A | D | S | V | K | G |
| apu23 | 344 | Y | I | S | S | Y | S | G | Y | T | S | Y | A | D | S | V | K | G |
| apu24 | 345 | S | I | S | S | S | S | G | S | T | S | Y | A | D | S | V | K | G |
| Consensus | 346 | S/Y | I | Y/S | P/S | S/Y | S/Y | G/S | S/Y | T | Y/S | Y | A | D | S | V | K | G |

HVR-H3

| Clone # | SEQ ID NO: | 95 | 96 | 97 | 98 | 99 | 100 | 100a | 100b | 100c | 100d | 100e | 100f | 100g | 100h | 100i | 100j | 100k | 100l | 100m | 101 | 102 |
|---|---|---|---|---|---|---|---|---|---|---|---|---|---|---|---|---|---|---|---|---|---|---|
| apu17 | 347 | S | G | Y | Y | Y | Q | G | Y | W | W | Y | Y | Y | T | G | Y | Y | G | M | D | Y |
| apu18 | 348 | E | Y | Y | R | W | Y | T | A | I | Y | Y | | | | | | | | | D | Y |
| apu19 | 349 | G | | M | F | S | S | W | W | W | Y | D | Y | Y | S | D | A | L | | | D | Y |
| apu20 | 350 | W | Q | G | Y | G | F | K | Y | Y | W | S | Y | Y | V | S | Y | G | G | L | D | Y |
| apu21 | 351 | E | Y | Y | W | W | Y | K | E | A | W | Y | S | A | G | M | | | | | D | Y |
| apu22 | 352 | E | S | Y | A | G | V | P | P | Y | G | F | D | Y | | D | A | L | | | D | Y |
| apu23 | 353 | G | I | M | F | S | S | W | W | W | Y | Y | Y | Y | S | D | G | L | | | D | Y |
| apu24 | 354 | G | S | I | P | S | Y | W | S | A | D | W | W | Y | Y | Y | Y | Y | | | D | Y |
| Consensus | 355 | S/E/ G/W | G/ Y/I/ Q/S | Y/W/ G/I | Y/R/ F/W/ A/P | Y/W/ S/G | Q/Y/ S/F/V | G/T/ W/K/ P | Y/A/ W/E/ P/S | W/I/ Y/A | W/Y/ G/D/ Y/A | Y/S/ F/W/ S/ | Y/D/ S/ | Y/A/ n.p. | T/S/ V/G/ Y/ n.p. | G/D/ S/M/ Y/ n.p. | Y/A/ G/ n.p. | Y/L/ G/ n.p. | G/ n.p. | M/L/ n.p. | D | Y |

FIG. 11C

HVR-L3

| Clone # | SEQ ID NO: | 89 | 90 | 91 | 92 | 93 | 94 | 95 | 95a | 95b | 96 | 97 |
|---|---|---|---|---|---|---|---|---|---|---|---|---|
| apu17 | 356 | Q | Q | Y | S | Y | Y | P | | | F | R |
| apu18 | 357 | Q | Q | Y | S | S | Y | S | S | L | F | T |
| apu19 | 358 | Q | Q | Y | S | S | S | L | | | V | T |
| apu20 | 359 | Q | Q | Y | S | S | S | S | P | F | T | T |
| apu21 | 360 | Q | Q | S | S | Y | S | P | | | I | F |
| apu22 | 361 | Q | Q | Y | Y | Y | S | S | Y | | | T |
| apu23 | 362 | Q | Q | S | Y | Y | S | P | | L | F | T |
| apu24 | 363 | Q | Q | Y | Y | S | S | L | | | V | T |
| Consensus | 364 | Q | Q | Y/S | S/Y | Y/S | Y/S | P/S/ L | S/P/ Y/n.p. | L/F n.p. | F/V/ T/I | R/T/ F |

HVR-H1

| Clone # | SEQ ID NO: | 26 | 27 | 28 | 29 | 30 | 31 | 32 | 33 | 34 | 35 |
|---|---|---|---|---|---|---|---|---|---|---|---|
| 48-51 | 392 | G | F | N | I | S | Y | S | S | M | H |
| 48-52 | 393 | G | F | N | I | S | Y | S | S | M | H |
| 48-53 | 394 | G | F | N | I | S | Y | S | S | M | H |
| 48-54 | 395 | G | F | N | I | S | Y | S | S | M | H |
| 48-55 | 396 | G | F | N | I | G | Y | S | F | M | H |
| 48-56 | 397 | G | F | N | V | D | Y | S | Y | M | H |
| 48-57 | 398 | G | F | N | V | D | Y | S | Y | M | H |
| 48-58 | 399 | G | F | N | F | S | Y | S | F | M | H |
| 48-59 | 400 | G | F | N | I | V | Y | S | F | M | H |
| 48-60 | 401 | G | F | N | I | I | Y | S | F | M | H |
| 48-61 | 402 | G | F | N | I | V | Y | S | F | I | H |
| 48-62 | 403 | G | F | N | L | S | Y | S | F | M | H |
| 48-63 | 404 | G | F | N | V | D | Y | S | F | M | H |
| 48-64 | 405 | G | F | N | V | I | Y | S | F | M | H |
| 48-65 | 406 | G | F | N | V | A | Y | S | L | M | H |
| 48-66 | 407 | G | F | N | I | S | Y | S | W | M | H |
| 48-67 | 408 | G | F | N | L | D | Y | S | F | M | H |
| 48-68 | 409 | G | F | N | F | L | Y | S | G | I | H |
| 48-69 | 410 | G | F | N | I | S | Y | S | S | M | H |
| 48-70 | 411 | G | F | N | I | S | Y | S | S | M | H |
| 48-71 | 412 | G | F | N | I | S | Y | S | S | M | H |
| 48-72 | 413 | G | F | N | I | S | Y | S | S | M | H |
| 48-73 | 414 | G | F | N | I | S | Y | S | S | M | H |
| 48-74 | 415 | G | F | N | I | L | Y | S | G | I | H |
| 48-75 | 416 | G | F | N | I | S | Y | S | S | M | H |
| 48-76 | 417 | G | F | N | I | S | Y | S | S | M | H |
| 48-77 | 418 | G | F | N | I | S | Y | S | S | M | H |
| 48-78 | 419 | G | F | N | I | S | Y | S | S | M | H |
| 48-79 | 420 | G | F | N | I | S | Y | S | S | M | H |
| 48-80 | 421 | G | F | N | I | S | Y | S | S | M | H |
| 48-81 | 422 | G | F | N | I | S | Y | S | S | M | H |
| 48-82 | 423 | G | F | N | I | S | Y | S | S | M | H |
| 48-83 | 424 | G | F | N | I | S | Y | S | S | M | H |
| 48-84 | 425 | G | F | N | I | S | Y | S | S | M | H |
| 48-85 | 426 | G | F | N | I | S | Y | S | S | M | H |
| 48-86 | 427 | G | F | N | I | F | Y | S | G | I | H |
| 48-87 | 428 | G | F | N | I | S | Y | S | S | M | H |
| 48-88 | 429 | G | F | N | I | S | Y | S | S | M | H |
| 48-89 | 430 | G | F | N | I | S | Y | S | S | M | H |
| 48-90 | 431 | G | F | N | I | S | Y | S | S | M | H |
| 48-91 | 432 | G | F | N | I | S | Y | S | S | M | H |
| 48-92 | 433 | G | F | N | I | S | Y | S | S | M | H |
| 48-93 | 434 | G | F | N | I | S | Y | S | S | M | H |
| 48-94 | 435 | G | F | N | I | S | Y | S | S | M | H |
| 48-95 | 436 | G | F | N | I | S | Y | S | S | M | H |
| 48-96 | 437 | G | F | N | I | S | Y | S | S | M | H |

*FIG. 14A*

HVR-H1 (Con't.)

| Clone # | SEQ ID NO: | 26 | 27 | 28 | 29 | 30 | 31 | 32 | 33 | 34 | 35 |
|---|---|---|---|---|---|---|---|---|---|---|---|
| 48-97 | 438 | G | F | N | I | S | Y | S | S | M | H |
| 48-98 | 439 | G | F | N | I | S | Y | S | S | M | H |
| 48-99 | 440 | G | F | N | I | S | Y | S | S | M | H |
| 48-100 | 441 | G | F | N | I | S | Y | S | S | M | H |
| 48-101 | 442 | G | F | N | I | S | Y | S | S | M | H |
| 48-102 | 443 | G | F | N | I | S | Y | S | S | M | H |
| 48-103 | 444 | G | F | N | I | S | Y | S | S | M | H |
| 48-104 | 445 | G | F | N | I | S | Y | S | S | M | H |
| 48-105 | 446 | G | F | N | I | S | Y | S | S | M | H |
| 48-106 | 447 | G | F | N | I | S | Y | S | S | M | H |
| 48-107 | 448 | G | F | N | I | S | Y | S | S | M | H |
| 48-108 | 449 | G | F | N | I | S | Y | S | S | M | H |
| 48-109 | 450 | G | F | N | I | S | Y | S | S | M | H |
| 48-110 | 451 | G | F | N | I | S | Y | S | S | M | H |
| 48-111 | 452 | G | F | N | I | S | Y | S | S | M | H |
| 48-112 | 453 | G | F | N | L | S | Y | S | G | M | H |
| 48-113 | 454 | G | F | N | L | L | Y | S | G | M | H |
| 48-114 | 455 | G | F | N | V | A | Y | S | G | I | H |
| 48-115 | 456 | G | F | N | V | D | Y | S | G | M | H |
| 48-116 | 457 | G | F | N | V | D | Y | S | G | M | H |
| 48-117 | 458 | G | F | N | V | S | Y | S | S | I | H |
| 48-118 | 459 | G | F | N | V | V | Y | S | G | I | H |
| Consensus | 460 | G | F | N | I/V/F/L | S/G/D/V/I/L/F/A | Y | S | S/F/Y/L/W/G | M/I | H |

*FIG. 14B*

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| 48-51 | 461 | S | I | Y | S | Y | Y | S | Y | T | S | Y | A | D | S | V | K | G |
| 48-52 | 462 | S | I | Y | S | Y | Y | S | Y | T | S | Y | A | D | S | V | K | G |
| 48-53 | 463 | S | I | Y | S | Y | Y | S | Y | T | S | Y | A | D | S | V | K | G |
| 48-54 | 464 | S | I | Y | S | Y | Y | S | Y | T | S | Y | A | D | S | V | K | G |
| 48-55 | 465 | S | I | A | S | Y | Y | S | Y | T | S | Y | A | D | S | V | K | G |
| 48-56 | 466 | S | I | A | P | Y | Y | S | Y | T | S | Y | A | D | S | V | K | G |
| 48-57 | 467 | S | I | A | P | Y | Y | S | Y | T | S | Y | A | D | S | V | K | G |
| 48-58 | 468 | S | I | S | S | Y | Y | S | Y | T | S | Y | A | D | S | V | K | G |
| 48-59 | 469 | S | I | S | P | Y | Y | S | Y | T | S | Y | A | D | S | V | K | G |
| 48-60 | 470 | S | I | S | S | Y | Y | S | Y | T | S | Y | A | D | S | V | K | G |
| 48-61 | 471 | S | I | S | S | Y | Y | S | Y | T | S | Y | A | D | S | V | K | G |
| 48-62 | 472 | S | I | S | S | Y | Y | S | Y | T | S | Y | A | D | S | V | K | G |
| 48-63 | 473 | S | I | S | S | Y | Y | S | Y | T | S | Y | A | D | S | V | K | G |
| 48-64 | 474 | S | I | S | S | Y | Y | S | Y | T | S | Y | A | D | S | V | K | G |
| 48-65 | 475 | S | I | S | S | Y | Y | S | Y | T | S | Y | A | D | S | V | K | G |
| 48-66 | 476 | S | I | T | S | Y | Y | S | Y | T | S | Y | A | D | S | V | K | G |
| 48-67 | 477 | S | I | T | P | Y | Y | S | Y | T | S | Y | A | D | S | V | K | G |
| 48-68 | 478 | S | I | Y | S | Y | Y | S | Y | T | S | Y | A | D | S | V | K | G |
| 48-69 | 479 | S | I | Y | S | Y | Y | S | Y | T | S | Y | A | D | S | V | K | G |
| 48-70 | 480 | S | I | Y | S | Y | Y | S | Y | T | S | Y | A | D | S | V | K | G |
| 48-71 | 481 | S | I | Y | S | Y | Y | S | Y | T | S | Y | A | D | S | V | K | G |
| 48-72 | 482 | S | I | Y | S | Y | Y | S | Y | T | S | Y | A | D | S | V | K | G |
| 48-73 | 483 | S | I | Y | P | Y | Y | S | Y | T | S | Y | A | D | S | V | K | G |
| 48-74 | 484 | S | I | Y | S | Y | Y | S | Y | T | S | Y | A | D | S | V | K | G |
| 48-75 | 485 | S | I | Y | S | Y | Y | S | Y | T | S | Y | A | D | S | V | K | G |
| 48-76 | 486 | S | I | Y | S | Y | Y | S | Y | T | S | Y | A | D | S | V | K | G |
| 48-77 | 487 | S | I | Y | S | Y | Y | S | Y | T | S | Y | A | D | S | V | K | G |
| 48-78 | 488 | S | I | Y | S | Y | Y | S | Y | T | S | Y | A | D | S | V | K | G |
| 48-79 | 489 | S | I | Y | S | Y | Y | S | Y | T | S | Y | A | D | S | V | K | G |
| 48-80 | 490 | S | I | Y | S | Y | Y | S | Y | T | S | Y | A | D | S | V | K | G |
| 48-81 | 491 | S | I | Y | S | Y | Y | S | Y | T | S | Y | A | D | S | V | K | G |
| 48-82 | 492 | S | I | Y | S | Y | Y | S | Y | T | S | Y | A | D | S | V | K | G |
| 48-83 | 493 | S | I | Y | S | Y | Y | S | Y | T | S | Y | A | D | S | V | K | G |
| 48-84 | 494 | S | I | Y | S | Y | Y | S | Y | T | S | Y | A | D | S | V | K | G |
| 48-85 | 495 | S | I | Y | S | Y | Y | S | Y | T | S | Y | A | D | S | V | K | G |
| 48-86 | 496 | S | I | Y | S | Y | Y | S | Y | T | S | Y | A | D | S | V | K | G |
| 48-87 | 497 | S | I | Y | S | Y | Y | S | Y | T | S | Y | A | D | S | V | K | G |
| 48-88 | 498 | S | I | Y | S | Y | Y | S | Y | T | S | Y | A | D | S | V | K | G |
| 48-89 | 499 | S | I | Y | S | Y | Y | S | Y | T | S | Y | A | D | S | V | K | G |
| 48-90 | 500 | S | I | Y | S | Y | Y | S | Y | T | S | Y | A | D | S | V | K | G |
| 48-91 | 501 | S | I | Y | S | Y | Y | S | Y | T | S | Y | A | D | S | V | K | G |
| 48-92 | 502 | S | I | Y | S | Y | Y | S | Y | T | S | Y | A | D | S | V | K | G |
| 48-93 | 503 | S | I | Y | S | Y | Y | S | Y | T | S | Y | A | D | S | V | K | G |

FIG. 14C

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| 48-94 | 504 | S | I | Y | S | Y | Y | S | Y | T | S | Y | A | D | S | V | K | G |
| 48-95 | 505 | S | I | Y | S | Y | Y | S | Y | T | S | Y | A | D | S | V | K | G |
| 48-96 | 506 | S | I | Y | S | Y | Y | S | Y | T | S | Y | A | D | S | V | K | G |
| 48-97 | 507 | S | I | Y | S | Y | Y | S | Y | T | S | Y | A | D | S | V | K | G |
| 48-98 | 508 | S | I | Y | S | Y | Y | S | Y | T | S | Y | A | D | S | V | K | G |
| 48-99 | 509 | S | I | Y | P | Y | Y | S | Y | T | S | Y | A | D | S | V | K | G |
| 48-100 | 510 | S | I | Y | S | Y | Y | S | Y | T | S | Y | A | D | S | V | K | G |
| 48-101 | 511 | S | I | Y | S | Y | Y | S | Y | T | S | Y | A | D | S | V | K | G |
| 48-102 | 512 | S | I | Y | S | Y | Y | S | Y | T | S | Y | A | D | S | V | K | G |
| 48-103 | 513 | S | I | Y | S | Y | Y | S | Y | T | S | Y | A | D | S | V | K | G |
| 48-104 | 514 | S | I | Y | S | Y | Y | S | Y | T | S | Y | A | D | S | V | K | G |
| 48-105 | 515 | S | I | Y | S | Y | Y | S | Y | T | S | Y | A | D | S | V | K | G |
| 48-106 | 516 | S | I | Y | S | Y | Y | S | Y | T | S | Y | A | D | S | V | K | G |
| 48-107 | 517 | S | I | Y | S | Y | Y | S | Y | T | S | Y | A | D | S | V | K | G |
| 48-108 | 518 | S | I | Y | S | Y | Y | S | Y | T | S | Y | A | D | S | V | K | G |
| 48-109 | 519 | S | I | Y | S | Y | Y | S | Y | T | S | Y | A | D | S | V | K | G |
| 48-110 | 520 | S | I | Y | S | Y | Y | S | Y | T | S | Y | A | D | S | V | K | G |
| 48-111 | 521 | S | I | Y | S | Y | Y | S | Y | T | S | Y | A | D | S | V | K | G |
| 48-112 | 522 | S | I | Y | S | Y | Y | S | Y | T | S | Y | A | D | S | V | K | G |
| 48-113 | 523 | S | I | Y | S | Y | Y | S | Y | T | S | Y | A | D | S | V | K | G |
| 48-114 | 524 | S | I | Y | S | Y | Y | S | Y | T | S | Y | A | D | S | V | K | G |
| 48-115 | 525 | S | I | Y | S | Y | Y | S | Y | T | S | Y | A | D | S | V | K | G |
| 48-116 | 526 | S | I | Y | S | Y | Y | T | Y | T | S | Y | A | D | S | V | K | G |
| 48-117 | 527 | S | I | Y | S | Y | Y | S | Y | T | S | Y | A | D | S | V | K | G |
| 48-118 | 528 | S | I | Y | S | Y | Y | S | Y | T | S | Y | A | D | S | V | K | G |
| Consensus | 529 | S | I | Y/A/S/T | S/P | Y | Y | S/T | Y | T | S | Y | A | D | S | V | K | G |

*FIG. 14D*

HVR-H3

| Clone # | SEQ ID NO: | 95 | 96 | 97 | 98 | 99 | 100 | 100a | 100b | 101 | 102 |
|---|---|---|---|---|---|---|---|---|---|---|---|
| 48-51 | 530 | S | Y | N | N | T | T | S | I | D | Y |
| 48-52 | 531 | G | Y | S | W | Y | N | A | M | D | Y |
| 48-53 | 532 | G | Y | S | W | F | N | A | I | D | Y |
| 48-54 | 533 | G | Y | Y | W | F | D | A | M | D | Y |
| 48-55 | 534 | S | Y | S | Y | Y | S | A | M | D | Y |
| 48-56 | 535 | S | Y | S | Y | R | E | T | M | D | Y |
| 48-57 | 536 | S | Y | S | Y | R | E | T | M | D | Y |
| 48-58 | 537 | S | Y | S | Y | Y | S | A | M | D | Y |
| 48-59 | 538 | S | Y | S | Y | Y | S | A | M | D | Y |
| 48-60 | 539 | S | Y | S | Y | Y | S | A | M | D | Y |
| 48-61 | 540 | S | Y | S | Y | Y | S | A | M | D | Y |
| 48-62 | 541 | S | Y | S | Y | Y | S | A | M | D | Y |
| 48-63 | 542 | S | Y | S | Y | Y | S | A | M | D | Y |
| 48-64 | 543 | S | Y | S | Y | Y | S | A | M | D | Y |
| 48-65 | 544 | S | Y | S | Y | Y | S | A | M | D | Y |
| 48-66 | 545 | S | Y | S | Y | Y | S | A | M | D | Y |
| 48-67 | 546 | S | Y | S | Y | Y | S | A | M | D | Y |
| 48-68 | 547 | S | Y | S | Y | Y | S | A | M | D | Y |
| 48-69 | 548 | S | Y | S | Y | Y | S | A | M | D | Y |
| 48-70 | 549 | S | Y | S | Y | S | F | G | M | D | Y |
| 48-71 | 550 | S | Y | S | Y | F | M | G | M | D | Y |
| 48-72 | 551 | S | Y | S | Y | H | V | A | F | D | Y |
| 48-73 | 552 | S | Y | S | Y | Y | S | A | M | D | Y |
| 48-74 | 553 | S | Y | S | Y | Y | S | A | M | D | Y |
| 48-75 | 554 | S | Y | S | Y | H | L | A | F | D | Y |
| 48-76 | 555 | S | Y | S | Y | S | L | A | F | D | Y |
| 48-77 | 556 | S | Y | S | Y | Y | I | A | M | D | Y |
| 48-78 | 557 | S | Y | S | Y | Y | M | G | M | D | Y |
| 48-79 | 558 | S | Y | S | Y | S | M | G | M | D | Y |
| 48-80 | 559 | S | Y | S | Y | H | V | A | M | D | Y |
| 48-81 | 560 | S | Y | S | Y | H | M | G | M | D | Y |
| 48-82 | 561 | S | Y | S | Y | H | L | G | M | D | Y |
| 48-83 | 562 | S | Y | S | Y | Y | Q | G | F | D | Y |
| 48-84 | 563 | S | Y | S | Y | S | M | G | M | D | Y |
| 48-85 | 564 | S | Y | S | Y | F | L | A | M | D | Y |
| 48-86 | 565 | S | Y | S | Y | Y | S | A | M | D | Y |
| 48-87 | 566 | S | Y | S | Y | S | E | A | L | D | Y |
| 48-88 | 567 | S | Y | S | Y | S | L | G | M | D | Y |
| 48-89 | 568 | S | Y | S | Y | Y | S | A | M | D | Y |
| 48-90 | 569 | S | Y | S | Y | F | M | G | M | D | Y |
| 48-91 | 570 | S | Y | S | Y | F | L | A | M | D | Y |
| 48-92 | 571 | S | Y | S | Y | F | L | A | M | D | Y |
| 48-93 | 572 | S | Y | S | Y | Y | L | A | M | D | Y |
| 48-94 | 573 | S | Y | S | Y | F | I | G | M | D | Y |
| 48-95 | 574 | S | Y | S | Y | H | L | G | M | D | Y |

FIG. 14E

| Clone # | SEQ ID NO: | 95 | 96 | 97 | 98 | 99 | 100 | 100a | 100b | 101 | 102 |
|---|---|---|---|---|---|---|---|---|---|---|---|
| 48-96 | 575 | S | Y | S | Y | T | E | A | F | D | Y |
| 48-97 | 576 | S | Y | S | Y | Y | S | A | M | D | Y |
| 48-98 | 577 | S | Y | S | Y | T | Y | G | L | D | Y |
| 48-99 | 578 | S | Y | S | Y | Y | S | A | M | D | Y |
| 48-100 | 579 | S | Y | S | Y | S | L | G | M | D | Y |
| 48-101 | 580 | S | Y | S | Y | W | V | G | M | D | Y |
| 48-102 | 581 | S | Y | S | Y | T | L | A | M | D | Y |
| 48-103 | 582 | S | Y | S | Y | T | M | G | L | D | Y |
| 48-104 | 583 | S | Y | S | Y | F | L | G | M | D | Y |
| 48-105 | 584 | S | Y | S | Y | H | M | G | F | D | Y |
| 48-106 | 585 | S | Y | S | Y | S | L | G | M | D | Y |
| 48-107 | 586 | S | Y | S | Y | Y | E | A | F | D | Y |
| 48-108 | 587 | S | Y | S | Y | R | M | A | F | D | Y |
| 48-109 | 588 | S | Y | S | Y | H | I | A | F | D | Y |
| 48-110 | 589 | S | Y | S | Y | S | V | G | M | D | Y |
| 48-111 | 590 | S | Y | S | Y | T | L | G | M | D | Y |
| 48-112 | 591 | S | Y | S | Y | Y | S | A | M | D | Y |
| 48-113 | 592 | S | Y | S | Y | Y | S | A | M | D | Y |
| 48-114 | 593 | S | Y | S | Y | Y | S | A | M | D | Y |
| 48-115 | 594 | S | Y | S | Y | Y | S | A | M | D | Y |
| 48-116 | 595 | S | Y | S | Y | Y | S | A | M | D | Y |
| 48-117 | 596 | S | Y | S | Y | Y | S | A | M | D | Y |
| 48-118 | 597 | S | Y | S | Y | Y | S | A | M | D | Y |
| Consensus | 598 | S/G | Y | S/N/Y | Y/N/W | T/Y/F/R/S/H/W | T/N/D/S/E/F/M/Y/L/I/Y | S/A/T/G | I/M/F/L | D | Y |

FIG. 14F

HVR-H1

| Clone # | SEQ ID NO: | 26 | 27 | 28 | 29 | 30 | 31 | 32 | 33 | 34 | 35 |
|---|---|---|---|---|---|---|---|---|---|---|---|
| 63-21 | 599 | G | F | N | I | S | S | S | Y | I | H |
| 63-22 | 600 | G | F | N | I | S | S | S | Y | I | H |
| 63-23 | 601 | G | F | N | I | S | S | S | Y | I | H |
| 63-24 | 602 | G | F | N | I | S | S | S | Y | I | H |
| 63-25 | 603 | G | F | N | I | S | S | S | Y | I | H |
| 63-26 | 604 | G | F | N | I | S | S | S | Y | I | H |
| 63-27 | 605 | G | F | N | I | S | S | S | Y | I | H |
| 63-28 | 606 | G | F | N | I | S | S | S | Y | I | H |
| 63-29 | 607 | G | F | N | I | S | S | S | Y | I | H |
| 63-30 | 608 | G | F | N | I | S | S | S | Y | I | H |
| 63-31 | 609 | G | F | N | I | S | S | S | Y | I | H |
| 63-32 | 610 | G | F | N | I | S | S | S | Y | I | H |
| 63-33 | 611 | G | F | N | I | S | S | S | Y | I | H |
| 63-34 | 612 | G | F | N | I | S | S | S | Y | I | H |
| 63-35 | 613 | G | F | N | F | S | S | S | Y | I | H |
| 63-36 | 614 | G | F | N | I | K | G | S | L | I | H |
| 63-37 | 615 | G | F | N | I | K | G | S | I | M | H |
| 63-38 | 616 | G | F | N | I | K | S | S | I | M | H |
| 63-39 | 617 | G | F | N | I | S | S | S | Y | I | H |
| 63-40 | 618 | G | F | N | I | S | S | S | Y | I | H |
| 63-41 | 619 | G | F | N | I | S | S | S | Y | I | H |
| 63-42 | 620 | G | F | N | I | S | S | S | Y | I | H |
| 63-43 | 621 | G | F | N | I | S | S | S | Y | I | H |
| 63-44 | 622 | G | F | N | I | S | S | S | Y | I | H |
| 63-45 | 623 | G | F | N | I | S | S | S | Y | I | H |
| 63-46 | 624 | G | F | N | I | S | S | S | Y | I | H |
| 63-47 | 625 | G | F | N | L | A | S | S | F | M | H |
| 63-48 | 626 | G | F | N | L | V | S | S | L | M | H |
| 63-49 | 627 | G | F | N | V | K | T | G | L | I | H |
| 63-50 | 628 | G | F | N | V | K | W | N | Y | I | H |
| 63-51 | 629 | G | F | N | V | V | S | S | F | I | H |
| Consensus | 630 | G | F | N | I/F/L/V | S/K/A/V | S/G/T/W | S/G/N | Y/L/I/F | I/M | H |

FIG. 15A

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| 63-21 | 631 | A | I | A | P | Y | L | G | S | T | S | Y | A | D | S | V | K | G |
| 63-22 | 632 | A | I | P | P | F | Y | G | W | T | S | Y | A | D | S | V | K | G |
| 63-23 | 633 | A | I | Q | P | Y | F | G | W | T | I | Y | A | D | S | V | K | G |
| 63-24 | 634 | A | I | S | P | Y | L | G | S | T | S | Y | A | D | S | V | K | G |
| 63-25 | 635 | D | I | A | P | Y | L | G | T | T | K | Y | A | D | S | V | K | G |
| 63-26 | 636 | D | I | S | P | W | Y | G | G | T | S | Y | A | D | S | V | K | G |
| 63-27 | 637 | D | I | S | S | Y | T | G | S | T | D | Y | A | D | S | V | K | G |
| 63-28 | 638 | F | I | Q | P | Y | Y | G | S | T | I | Y | A | D | S | V | K | G |
| 63-29 | 639 | F | I | S | P | Y | L | G | S | T | N | Y | A | D | S | V | K | G |
| 63-30 | 640 | G | I | T | P | Y | L | G | W | T | S | Y | A | D | S | V | K | G |
| 63-31 | 641 | H | I | S | P | Y | L | G | S | T | S | Y | A | D | S | V | K | G |
| 63-32 | 642 | I | I | S | P | Y | L | G | S | T | G | Y | A | D | S | V | K | G |
| 63-33 | 643 | S | I | T | P | Y | Y | G | W | T | R | Y | A | D | S | V | K | G |
| 63-34 | 644 | W | I | S | P | Y | L | G | R | T | S | Y | A | D | S | V | K | G |
| 63-35 | 645 | Y | I | S | P | Y | Y | G | S | T | S | Y | A | D | S | V | K | G |
| 63-36 | 646 | Y | I | S | P | Y | Y | G | S | T | S | Y | A | D | S | V | K | G |
| 63-37 | 647 | Y | I | S | P | Y | Y | G | S | T | S | Y | A | D | S | V | K | G |
| 63-38 | 648 | Y | I | S | P | Y | Y | G | S | T | S | Y | A | D | S | V | K | G |
| 63-39 | 649 | Y | I | G | P | F | T | G | S | T | N | Y | A | D | S | V | K | G |
| 63-40 | 650 | Y | I | S | P | F | L | S | T | T | S | Y | A | D | S | V | K | G |
| 63-41 | 651 | Y | I | S | P | Y | Y | G | S | T | S | Y | A | D | S | V | K | G |
| 63-42 | 652 | Y | I | S | P | Y | S | G | S | T | K | Y | A | D | S | V | K | G |
| 63-43 | 653 | Y | I | S | P | Y | Y | S | S | T | S | Y | A | D | S | V | K | G |
| 63-44 | 654 | Y | I | S | P | Y | L | G | S | T | S | Y | A | D | S | V | K | G |
| 63-45 | 655 | Y | I | S | P | Y | L | S | S | T | S | Y | A | D | S | V | K | G |
| 63-46 | 656 | Y | I | S | P | Y | Y | G | S | T | S | Y | A | D | S | V | K | G |
| 63-47 | 657 | Y | I | S | P | Y | Y | G | S | T | S | Y | A | D | S | V | K | G |
| 63-48 | 658 | Y | I | S | P | Y | Y | G | S | T | S | Y | A | D | S | V | K | G |
| 63-49 | 659 | Y | I | S | P | Y | Y | G | S | T | S | Y | A | D | S | V | K | G |
| 63-50 | 660 | Y | I | S | P | Y | Y | G | S | T | S | Y | A | D | S | V | K | G |
| 63-51 | 661 | Y | I | S | P | Y | Y | G | S | T | S | Y | A | D | S | V | K | G |
| Consensus | 662 | A/D/F/G/H/I/S/W/Y | I | A/P/Q/S/T/G | P/S | Y/F | L/Y/F/T | G/S | S/W/T/G/R | T | S/I/K/D/N/G/R | Y | A | D | S | V | K | G |

FIG. 15B

HVR-H3

| Clone # | SEQ ID NO: | 95 | 96 | 97 | 98 | 99 | 100 | 100a | 100b | 100c | 101 | 102 |
|---|---|---|---|---|---|---|---|---|---|---|---|---|
| 63-21 | 663 | E | Y | Y | R | W | Y | T | A | I | D | Y |
| 63-22 | 664 | E | Y | Y | R | W | Y | T | A | I | D | Y |
| 63-23 | 665 | E | Y | Y | R | W | Y | T | A | I | D | Y |
| 63-24 | 666 | E | Y | Y | R | W | Y | T | A | I | D | Y |
| 63-25 | 667 | E | Y | Y | R | W | Y | T | A | I | D | Y |
| 63-26 | 668 | E | Y | Y | R | W | Y | T | A | I | D | Y |
| 63-27 | 669 | E | Y | Y | R | W | Y | T | A | I | D | Y |
| 63-28 | 670 | E | Y | Y | R | W | Y | T | A | I | D | Y |
| 63-29 | 671 | E | Y | Y | R | W | Y | T | A | I | D | Y |
| 63-30 | 672 | E | Y | Y | R | W | Y | T | A | I | D | Y |
| 63-31 | 673 | E | Y | Y | R | W | Y | T | A | I | D | Y |
| 63-32 | 674 | E | Y | Y | R | W | Y | T | A | I | D | Y |
| 63-33 | 675 | E | Y | Y | R | W | Y | T | A | I | D | Y |
| 63-34 | 676 | E | Y | Y | R | W | Y | T | A | I | D | Y |
| 63-35 | 677 | E | Y | Y | R | W | Y | T | A | I | D | Y |
| 63-36 | 678 | E | Y | Y | R | W | Y | T | A | I | D | Y |
| 63-37 | 679 | E | Y | Y | R | W | Y | T | A | I | D | Y |
| 63-38 | 680 | E | Y | Y | R | W | Y | T | A | I | D | Y |
| 63-39 | 681 | E | Y | Y | R | W | Y | T | A | I | D | Y |
| 63-40 | 682 | E | Y | Y | R | W | Y | T | A | I | D | Y |
| 63-41 | 683 | E | Y | Y | R | W | Y | T | A | I | D | Y |
| 63-42 | 684 | E | Y | Y | R | W | Y | T | A | I | D | Y |
| 63-43 | 685 | E | Y | Y | R | W | Y | T | A | I | D | Y |
| 63-44 | 686 | E | Y | Y | R | W | Y | T | A | I | D | Y |
| 63-45 | 687 | E | Y | Y | R | W | Y | T | A | I | D | Y |
| 63-46 | 688 | E | Y | Y | R | W | Y | T | A | I | D | Y |
| 63-47 | 689 | E | Y | Y | R | W | Y | T | A | I | D | Y |
| 63-48 | 690 | E | Y | Y | R | W | Y | T | A | I | D | Y |
| 63-49 | 691 | E | Y | Y | R | W | Y | T | A | I | D | Y |
| 63-50 | 692 | E | Y | Y | R | W | Y | T | A | I | D | Y |
| 63-51 | 693 | E | Y | Y | R | W | Y | T | A | I | D | Y |
| Consensus | 694 | E | Y | Y | R | W | Y | T | A | I | D | Y |

*FIG. 15C*

HVR-H1

| Clone # | SEQ ID NO: | 26 | 27 | 28 | 29 | 30 | 31 | 32 | 33 | 34 | 35 |
|---|---|---|---|---|---|---|---|---|---|---|---|
| apu2.01 | 695 | G | F | N | I | S | Y | S | S | M | H |
| apu2.02 | 696 | G | F | N | I | F | Y | G | G | I | H |
| apu2.03 | 697 | G | F | N | I | S | Y | S | S | M | H |
| apu2.04 | 698 | G | F | N | I | S | Y | S | S | M | H |
| apu2.05 | 699 | G | F | N | I | S | Y | S | S | M | H |
| apu2.06 | 700 | G | F | N | I | S | Y | S | S | M | H |
| apu2.07 | 701 | G | F | N | I | S | Y | S | S | M | H |
| apu2.08 | 702 | G | F | N | I | S | Y | S | S | M | H |
| apu2.09 | 703 | G | F | N | I | S | Y | S | S | M | H |
| apu2.10 | 704 | G | F | N | I | S | Y | S | S | M | H |
| Consensus | 705 | G | F | N | I | S/F | Y | S/G | S/G | M/I | H |

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| apu2.01 | 706 | S | I | Y | S | Y | Y | S | Y | T | S | Y | A | D | S | V | K | G |
| apu2.02 | 707 | S | I | Y | S | Y | Y | S | Y | T | S | Y | A | D | S | V | K | G |
| apu2.03 | 708 | S | I | Y | S | Y | Y | S | Y | T | S | Y | A | D | S | V | K | G |
| apu2.04 | 709 | S | I | Y | S | Y | Y | S | Y | T | S | Y | A | D | S | V | K | G |
| apu2.05 | 710 | S | I | Y | S | Y | Y | S | Y | T | S | Y | A | D | S | V | K | G |
| apu2.06 | 711 | S | I | Y | S | Y | Y | S | Y | T | S | Y | A | D | S | V | K | G |
| apu2.07 | 712 | S | I | Y | S | Y | Y | S | Y | T | S | Y | A | D | S | V | K | G |
| apu2.08 | 713 | S | I | Y | S | Y | Y | S | Y | T | S | Y | A | D | S | V | K | G |
| apu2.09 | 714 | S | I | Y | S | Y | Y | S | Y | T | S | Y | A | D | S | V | K | G |
| apu2.10 | 715 | S | I | Y | S | Y | Y | S | Y | T | S | Y | A | D | S | V | K | G |
| Consensus | 716 | S | I | Y | S | Y | Y | S | Y | T | S | Y | A | D | S | V | K | G |

HVR-H3

| Clone # | SEQ ID NO: | 95 | 96 | 97 | 98 | 99 | 100 | 100a | 100b | 101 | 102 |
|---|---|---|---|---|---|---|---|---|---|---|---|
| apu2.01 | 717 | S | Y | S | Y | S | E | A | L | D | Y |
| apu2.02 | 718 | S | Y | S | Y | Y | S | A | M | D | Y |
| apu2.03 | 719 | S | Y | S | Y | S | L | A | F | D | Y |
| apu2.04 | 720 | S | Y | S | Y | S | F | G | M | D | Y |
| apu2.05 | 721 | S | Y | S | Y | R | M | A | F | D | Y |
| apu2.06 | 722 | G | Y | S | W | F | N | A | I | D | Y |
| apu2.07 | 723 | S | Y | S | Y | H | L | G | M | D | Y |
| apu2.08 | 724 | S | Y | S | Y | S | V | G | M | D | Y |
| apu2.09 | 725 | S | Y | S | Y | H | V | A | F | D | Y |
| apu2.10 | 726 | S | Y | S | Y | F | L | A | M | D | Y |
| Consensus | 727 | S/G | Y | S | Y/W | S/Y/R/F/H | E/S/L/F/M/N/V | A/G | L/M/F/I | D | Y |

*FIG. 16A*

HVR-L3

| Clone # | SEQ ID NO: | 89 | 90 | 91 | 92 | 93 | 94 | 95 | 95a | 96 | 97 |
|---|---|---|---|---|---|---|---|---|---|---|---|
| apu2.01 | 728 | Q | Q | S | S | Y | S | S | L | I | T |
| apu2.02 | 729 | Q | Q | S | S | Y | S | S | L | I | T |
| apu2.03 | 730 | Q | Q | S | S | Y | S | S | L | I | T |
| apu2.04 | 731 | Q | Q | S | S | Y | S | S | L | I | T |
| apu2.05 | 732 | Q | Q | S | S | Y | S | S | L | I | T |
| apu2.06 | 733 | Q | Q | S | S | Y | S | S | L | I | T |
| apu2.07 | 734 | Q | Q | S | S | Y | S | S | L | I | T |
| apu2.08 | 735 | Q | Q | S | S | Y | S | S | L | I | T |
| apu2.09 | 736 | Q | Q | S | S | Y | S | S | L | I | T |
| apu2.10 | 737 | Q | Q | S | S | Y | S | S | L | I | T |
| Consensus | 738 | Q | Q | S | S | Y | S | S | L | I | T |

*FIG. 16B*

HVR-H1

| Clone # | SEQ ID NO: | 26 | 27 | 28 | 29 | 30 | 31 | 32 | 33 | 34 | 35 |
|---|---|---|---|---|---|---|---|---|---|---|---|
| apu2.11 | 739 | G | F | N | I | S | S | S | Y | I | H |
| apu2.12 | 740 | G | F | N | I | S | S | S | Y | I | H |
| apu2.13 | 741 | G | F | N | V | K | W | N | Y | I | H |
| apu2.14 | 742 | G | F | N | I | S | S | S | Y | I | H |
| apu2.15 | 743 | G | F | N | I | K | G | S | I | M | H |
| apu2.16 | 744 | G | F | N | V | K | T | G | L | I | H |
| apu2.17 | 745 | G | F | N | I | S | S | S | Y | I | H |
| apu2.18 | 746 | G | F | N | L | V | S | S | L | M | H |
| apu2.19 | 747 | G | F | N | V | V | S | S | F | I | H |
| apu2.20 | 748 | G | F | N | I | S | S | S | Y | I | H |
| Consensus | 749 | G | F | N | I/V/L | S/K/V | S/W/G/T | S/N/G | Y/I/L/F | I/M | H |

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| apu2.11 | 750 | Y | I | S | P | Y | L | S | S | T | S | Y | A | D | S | V | K | G |
| apu2.12 | 751 | F | I | S | P | Y | L | G | S | T | N | Y | A | D | S | V | K | G |
| apu2.13 | 752 | Y | I | S | P | Y | Y | G | S | T | S | Y | A | D | S | V | K | G |
| apu2.14 | 753 | D | I | A | P | Y | L | G | T | T | K | Y | A | D | S | V | K | G |
| apu2.15 | 754 | Y | I | S | P | Y | Y | G | S | T | S | Y | A | D | S | V | K | G |
| apu2.16 | 755 | Y | I | S | P | Y | Y | G | S | T | S | Y | A | D | S | V | K | G |
| apu2.17 | 756 | H | I | S | P | Y | L | G | S | T | S | Y | A | D | S | V | K | G |
| apu2.18 | 757 | Y | I | S | P | Y | Y | G | S | T | S | Y | A | D | S | V | K | G |
| apu2.19 | 758 | Y | I | S | P | Y | Y | G | S | T | S | Y | A | D | S | V | K | G |
| apu2.20 | 759 | A | I | Q | P | Y | F | G | W | T | I | Y | A | D | S | V | K | G |
| Consensus | 760 | Y/F/D/H/A | I | S/A/Q | P | Y | L/Y/F | S/G | S/T/W | T | S/N/K/I | Y | A | D | S | V | K | G |

HVR-H3

| Clone # | SEQ ID NO: | 95 | 96 | 97 | 98 | 99 | 100 | 100a | 100b | 100c | 101 | 102 |
|---|---|---|---|---|---|---|---|---|---|---|---|---|
| apu2.11 | 761 | E | Y | Y | R | W | Y | T | A | I | D | Y |
| apu2.12 | 762 | E | Y | Y | R | W | Y | T | A | I | D | Y |
| apu2.13 | 763 | E | Y | Y | R | W | Y | T | A | I | D | Y |
| apu2.14 | 764 | E | Y | Y | R | W | Y | T | A | I | D | Y |
| apu2.15 | 765 | E | Y | Y | R | W | Y | T | A | I | D | Y |
| apu2.16 | 766 | E | Y | Y | R | W | Y | T | A | I | D | Y |
| apu2.17 | 767 | E | Y | Y | R | W | Y | T | A | I | D | Y |
| apu2.18 | 768 | E | Y | Y | R | W | Y | T | A | I | D | Y |
| apu2.19 | 769 | E | Y | Y | R | W | Y | T | A | I | D | Y |
| apu2.20 | 770 | E | Y | Y | R | W | Y | T | A | I | D | Y |
| Consensus | 771 | E | Y | Y | R | W | Y | T | A | I | D | Y |

FIG. 17A

HVR-L3

| Clone # | SEQ ID NO: | 89 | 90 | 91 | 92 | 93 | 94 | 95 | 95a | 95b | 96 | 97 |
|---|---|---|---|---|---|---|---|---|---|---|---|---|
| apu2.11 | 772 | Q | Q | Y | S | S | Y | S | S | L | F | T |
| apu2.12 | 773 | Q | Q | Y | S | S | Y | S | S | L | F | T |
| apu2.13 | 774 | Q | Q | Y | S | S | Y | S | S | L | F | T |
| apu2.14 | 775 | Q | Q | Y | S | S | Y | S | S | L | F | T |
| apu2.15 | 776 | Q | Q | Y | S | S | Y | S | S | L | F | T |
| apu2.16 | 777 | Q | Q | Y | S | S | Y | S | S | L | F | T |
| apu2.17 | 778 | Q | Q | Y | S | S | Y | S | S | L | F | T |
| apu2.18 | 779 | Q | Q | Y | S | S | Y | S | S | L | F | T |
| apu2.19 | 780 | Q | Q | Y | S | S | Y | S | S | L | F | T |
| apu2.20 | 781 | Q | Q | Y | S | S | Y | S | S | L | F | T |
| Consensus | 782 | Q | Q | Y | S | S | Y | S | S | L | F | T |

FIG. 17B

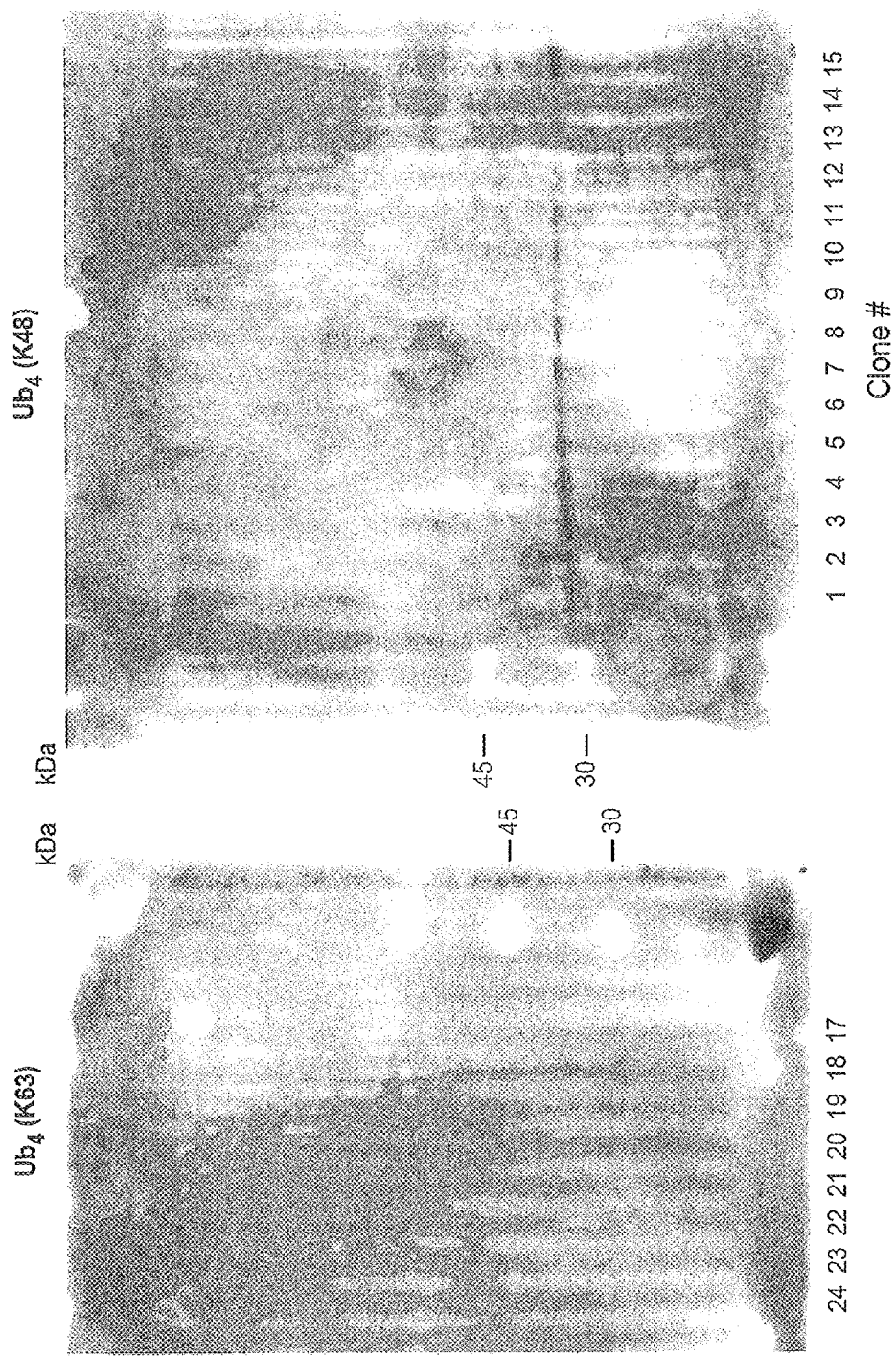

HVR-H1

| Clone # | SEQ ID NO: | 26 | 27 | 28 | 29 | 30 | 31 | 32 | 33 | 34 | 35 |
|---|---|---|---|---|---|---|---|---|---|---|---|
| apu3.01 | 789 | G | F | N | V | K | T | G | F | M | H |
| apu3.02 | 790 | G | F | N | V | K | T | G | F | I | H |
| apu3.03 | 791 | G | F | N | I | K | M | V | F | M | H |
| apu3.04 | 792 | G | F | N | V | K | N | F | I | I | H |
| apu3.05 | 793 | G | F | N | V | K | T | G | F | M | H |
| apu3.06 | 794 | G | F | N | V | K | R | G | F | M | H |
| apu3.07 | 795 | G | F | N | L | K | T | G | F | I | H |
| apu3.08 | 796 | G | F | N | V | K | T | G | Y | M | H |
| apu3.09 | 797 | G | F | N | V | K | T | G | L | I | H |
| apu3.10 | 798 | G | F | N | V | M | I | G | I | I | H |
| apu3.11 | 799 | G | F | N | I | K | T | G | F | M | H |
| apu3.12 | | ND | | | | | | | | | |
| Consensus | 800 | G | F | N | V/I/L | K/M | T/M/N/R/I | G/V/F | F/I/Y/L | M/I | H |

HVR-H2

| Clone # | SEQ ID NO: | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|
| apu3.01 | 801 | Y | I | S | P | Y | Y | G | W | T | R | Y | A | D | S | V | K | G |
| apu3.02 | 802 | Y | I | S | P | Y | L | G | V | T | R | Y | A | D | S | V | K | G |
| apu3.03 | 803 | Y | I | S | P | Y | D | G | S | T | N | Y | A | D | S | V | K | G |
| apu3.04 | 804 | Y | I | I | P | Y | S | G | N | T | V | Y | A | D | S | V | K | G |
| apu3.05 | 805 | Y | I | S | P | Y | S | G | R | T | R | Y | A | D | S | V | K | G |
| apu3.06 | 806 | Y | I | S | P | Y | L | G | S | T | R | Y | A | D | S | V | K | G |
| apu3.07 | 807 | Y | I | S | P | Y | W | G | S | T | T | Y | A | D | S | V | K | G |
| apu3.08 | 808 | Y | I | S | P | Y | Y | G | S | T | R | Y | A | D | S | V | K | G |
| apu3.09 | 809 | Y | I | S | P | Y | F | G | Y | T | S | Y | A | D | S | V | K | G |
| apu3.10 | 810 | Y | I | I | P | Y | S | G | S | T | K | Y | A | D | S | V | K | G |
| apu3.11 | 811 | Y | I | T | P | Y | W | G | S | T | K | Y | A | D | S | V | K | G |
| apu3.12 | | ND | | | | | | | | | | | | | | | | |
| Consensus | 812 | Y | I | S/I/T | P | Y | Y/L/D/S/W | G | W/V/S/N/R/Y | T | R/N/V/T/S/K | Y | A | D | S | V | K | G |

FIG. 23A

HVR-H3

| Clone # | SEQ ID NO: | 95 | 96 | 97 | 98 | 99 | 100 | 100a | 100b | 100c | 101 | 102 |
|---|---|---|---|---|---|---|---|---|---|---|---|---|
| apu3.01 | 813 | E | Y | Y | R | W | Y | T | A | I | D | Y |
| apu3.02 | 814 | E | Y | Y | R | W | Y | T | A | I | D | Y |
| apu3.03 | 815 | E | Y | Y | R | W | Y | T | A | I | D | Y |
| apu3.04 | 816 | E | Y | Y | R | W | Y | T | A | I | D | Y |
| apu3.05 | 817 | E | Y | Y | R | W | Y | T | A | I | D | Y |
| apu3.06 | 818 | E | Y | Y | R | W | Y | T | A | I | D | Y |
| apu3.07 | 819 | E | Y | Y | R | W | Y | T | A | I | D | Y |
| apu3.08 | 820 | E | Y | Y | R | W | Y | T | A | I | D | Y |
| apu3.09 | 821 | E | Y | Y | R | W | Y | T | A | I | D | Y |
| apu3.10 | 822 | E | Y | Y | R | W | Y | T | A | I | D | Y |
| apu3.11 | 823 | E | Y | Y | R | W | Y | T | A | I | D | Y |
| apu3.12 | | ND | | | | | | | | | | |
| Consensus | 824 | E | Y | Y | R | W | Y | T | A | I | D | Y |

FIG. 23B

SEQUENCE LISTING

```
<160> NUMBER OF SEQ ID NOS: 906

<210> SEQ ID NO 1
<211> LENGTH: 10
<212> TYPE: PRT
<213> ORGANISM: Artificial Sequence
<220> FEATURE:
<223> OTHER INFORMATION: Synthetic

<400> SEQUENCE: 1

Gly Phe Asn Leu Ser Tyr Ser Ser Met His
1               5                   10

<210> SEQ ID NO 2
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 2

Gly Phe Asn Val Ser Tyr Ser Ser Ile His
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Gly Phe Asn Ile Tyr Tyr Ser Ser Ile His
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Gly Phe Asn Ile Ser Tyr Tyr Tyr Ile His
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic

<400> SEQUENCE: 5

Gly Phe Asn Val Ser Tyr Tyr Tyr Met His
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Synthetic

<400> SEQUENCE: 6

Gly Phe Asn Phe Tyr Ser Ser Tyr Met His
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Gly Phe Asn Leu Tyr Tyr Ser Tyr Met His
1               5                   10

<210> SEQ ID NO 8
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 8

Gly Phe Asn Val Tyr Tyr Ser Ser Ile His
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Synthetic

<400> SEQUENCE: 9

Gly Phe Asn Ile Ser Tyr Ser Tyr Met His
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

Gly Phe Asn Val Tyr Tyr Ser Ser Ile His
1               5                   10

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Gly Phe Asn Val Ser Tyr Ser Tyr Met His
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Synthetic

<400> SEQUENCE: 12

Gly Phe Asn Leu Tyr Tyr Ser Tyr Met His
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic

<400> SEQUENCE: 13

Gly Phe Asn Val Tyr Tyr Ser Ser Ile His
1               5                   10

<210> SEQ ID NO 14
<211> LENGTH: 10
<212> TYPE: PRT
```

<213> ORGANISM: Artificial Sequence
<220> FEATURE:
<223> OTHER INFORMATION: Synthetic

<400> SEQUENCE: 14

Gly Phe Asn Ile Ser Tyr Ser Ser Met His
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Synthetic

<400> SEQUENCE: 15

Gly Phe Asn Val Ser Tyr Ser Ser Ile His
1               5                   10

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gly Phe Asn Phe Tyr Tyr Tyr Tyr Ile His
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Synthetic

<400> SEQUENCE: 17

Gly Phe Asn Val Ser Ser Tyr Ser Ile His
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Gly Phe Asn Val Ser Ser Tyr Ser Met His
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic

<400> SEQUENCE: 19

Gly Phe Asn Leu Ser Tyr Tyr Ser Ile His
1               5                   10

<210> SEQ ID NO 20
<211> LENGTH: 10
<212> TYPE: PRT
<213> ORGANISM: Artificial Sequence
<220> FEATURE:
<223> OTHER INFORMATION: Synthetic

<400> SEQUENCE: 20

Gly Phe Asn Leu Ser Tyr Tyr Ser Ile His
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic

<400> SEQUENCE: 21

Gly Phe Asn Val Ser Tyr Ser Tyr Met His
1               5                   10

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Gly Phe Asn Val Ser Tyr Tyr Ser Ile His
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Gly Phe Asn Leu Ser Tyr Ser Ser Ile His
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24

Gly Phe Asn Val Ser Tyr Ser Ser Ile His
1               5                   10

<210> SEQ ID NO 25
<211> LENGTH: 10
<212> TYPE: PRT
<213> ORGANISM: Artificial Sequence
<220> FEATURE:
<223> OTHER INFORMATION: Synthetic

<400> SEQUENCE: 25

Gly Phe Asn Leu Ser Tyr Ser Ser Met His
1               5                   10

<210> SEQ ID NO 26
<211> LENGTH: 10
<212> TYPE: PRT
<213> ORGANISM: Artificial Sequence
<220> FEATURE:

```
<223> OTHER INFORMATION: Synthetic
<220> FEATURE:
<221> NAME/KEY: MOD_RES
<222> LOCATION: (4)..(4)
<223> OTHER INFORMATION: Leu, Val, Ile or Phe
<220> FEATURE:
<221> NAME/KEY: MOD_RES
<222> LOCATION: (5)..(8)
<223> OTHER INFORMATION: Ser or Tyr
<220> FEATURE:
<221> NAME/KEY: MOD_RES
<222> LOCATION: (9)..(9)
<223> OTHER INFORMATION: Met or Ile

<400> SEQUENCE: 26

Gly Phe Asn Xaa Xaa Xaa Xaa Xaa Xaa His
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Synthetic

<400> SEQUENCE: 27

Ser Ile Tyr Pro Tyr Tyr Ser Tyr Thr Ser Tyr Ala Asp Ser Val Lys
1               5                   10                  15

Gly

<210> SEQ ID NO 28
<211> LENGTH: 17
<212> TYPE: PRT
<213> ORGANISM: Artificial Sequence
<220> FEATURE:
<223> OTHER INFORMATION: Synthetic

<400> SEQUENCE: 28

Ser Ile Ser Pro Tyr Tyr Gly Tyr Thr Ser Tyr Ala Asp Ser Val Lys
1               5                   10                  15

Gly

<210> SEQ ID NO 29
<211> LENGTH: 17
<212> TYPE: PRT
<213> ORGANISM: Artificial Sequence
<220> FEATURE:
<223> OTHER INFORMATION: Synthetic

<400> SEQUENCE: 29

Ser Ile Tyr Ser Tyr Tyr Ser Tyr Thr Ser Tyr Ala Asp Ser Val Lys
1               5                   10                  15

Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic

<400> SEQUENCE: 30

Ser Ile Ser Ser Tyr Tyr Gly Tyr Thr Ser Tyr Ala Asp Ser Val Lys
1               5                   10                  15

Gly
```

```
<210> SEQ ID NO 31
<211> LENGTH: 17
<212> TYPE: PRT
<213> ORGANISM: Artificial Sequence
<220> FEATURE:
<223> OTHER INFORMATION: Synthetic

<400> SEQUENCE: 31

Ser Ile Ser Ser Tyr Tyr Gly Tyr Thr Ser Tyr Ala Asp Ser Val Lys
1               5                   10                  15

Gly

<210> SEQ ID NO 32
<211> LENGTH: 17
<212> TYPE: PRT
<213> ORGANISM: Artificial Sequence
<220> FEATURE:
<223> OTHER INFORMATION: Synthetic

<400> SEQUENCE: 32

Ser Ile Ser Pro Tyr Tyr Gly Tyr Thr Ser Tyr Ala Asp Ser Val Lys
1               5                   10                  15

Gly

<210> SEQ ID NO 33
<211> LENGTH: 17
<212> TYPE: PRT
<213> ORGANISM: Artificial Sequence
<220> FEATURE:
<223> OTHER INFORMATION: Synthetic

<400> SEQUENCE: 33

Ser Ile Ser Ser Tyr Tyr Ser Tyr Thr Ser Tyr Ala Asp Ser Val Lys
1               5                   10                  15

Gly

<210> SEQ ID NO 34
<211> LENGTH: 17
<212> TYPE: PRT
<213> ORGANISM: Artificial Sequence
<220> FEATURE:
<223> OTHER INFORMATION: Synthetic

<400> SEQUENCE: 34

Ser Ile Tyr Pro Tyr Tyr Gly Tyr Thr Ser Tyr Ala Asp Ser Val Lys
1               5                   10                  15

Gly

<210> SEQ ID NO 35
<211> LENGTH: 17
<212> TYPE: PRT
<213> ORGANISM: Artificial Sequence
<220> FEATURE:
<223> OTHER INFORMATION: Synthetic

<400> SEQUENCE: 35

Ser Ile Ser Ser Tyr Tyr Ser Tyr Thr Ser Tyr Ala Asp Ser Val Lys
1               5                   10                  15

Gly

<210> SEQ ID NO 36
<211> LENGTH: 17
<212> TYPE: PRT
```

<213> ORGANISM: Artificial Sequence
<220> FEATURE:
<223> OTHER INFORMATION: Synthetic

<400> SEQUENCE: 36

Ser Ile Ser Pro Tyr Tyr Ser Tyr Thr Ser Tyr Ala Asp Ser Val Lys
1               5                   10                  15

Gly

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

Ser Ile Ser Pro Tyr Tyr Ser Tyr Thr Ser Tyr Ala Asp Ser Val Lys
1               5                   10                  15

Gly

<210> SEQ ID NO 38
<211> LENGTH: 17
<212> TYPE: PRT
<213> ORGANISM: Artificial Sequence
<220> FEATURE:
<223> OTHER INFORMATION: Synthetic

<400> SEQUENCE: 38

Ser Ile Ser Pro Tyr Tyr Ser Tyr Thr Ser Tyr Ala Asp Ser Val Lys
1               5                   10                  15

Gly

<210> SEQ ID NO 39
<211> LENGTH: 17
<212> TYPE: PRT
<213> ORGANISM: Artificial Sequence
<220> FEATURE:
<223> OTHER INFORMATION: Synthetic

<400> SEQUENCE: 39

Ser Ile Ser Pro Tyr Tyr Ser Tyr Thr Ser Tyr Ala Asp Ser Val Lys
1               5                   10                  15

Gly

<210> SEQ ID NO 40
<211> LENGTH: 17
<212> TYPE: PRT
<213> ORGANISM: Artificial Sequence
<220> FEATURE:
<223> OTHER INFORMATION: Synthetic

<400> SEQUENCE: 40

Ser Ile Tyr Ser Tyr Tyr Ser Tyr Thr Ser Tyr Ala Asp Ser Val Lys
1               5                   10                  15

Gly

<210> SEQ ID NO 41
<211> LENGTH: 17
<212> TYPE: PRT
<213> ORGANISM: Artificial Sequence
<220> FEATURE:
<223> OTHER INFORMATION: Synthetic

```
<400> SEQUENCE: 41

Ser Ile Tyr Ser Tyr Tyr Ser Tyr Thr Ser Tyr Ala Asp Ser Val Lys
1               5                   10                  15

Gly

<210> SEQ ID NO 42
<211> LENGTH: 17
<212> TYPE: PRT
<213> ORGANISM: Artificial Sequence
<220> FEATURE:
<223> OTHER INFORMATION: Synthetic

<400> SEQUENCE: 42

Ser Ile Ser Pro Tyr Tyr Ser Tyr Thr Ser Tyr Ala Asp Ser Val Lys
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: Synthetic

<400> SEQUENCE: 43

Ser Ile Ser Ser Ser Tyr Ser Thr Ser Tyr Ala Asp Ser Val Lys
1               5                   10                  15

Gly

<210> SEQ ID NO 44
<211> LENGTH: 17
<212> TYPE: PRT
<213> ORGANISM: Artificial Sequence
<220> FEATURE:
<223> OTHER INFORMATION: Synthetic

<400> SEQUENCE: 44

Ser Ile Tyr Ser Ser Ser Gly Ser Thr Ser Tyr Ala Asp Ser Val Lys
1               5                   10                  15

Gly

<210> SEQ ID NO 45
<211> LENGTH: 17
<212> TYPE: PRT
<213> ORGANISM: Artificial Sequence
<220> FEATURE:
<223> OTHER INFORMATION: Synthetic

<400> SEQUENCE: 45

Ser Ile Tyr Ser Ser Tyr Ser Ser Thr Tyr Tyr Ala Asp Ser Val Lys
1               5                   10                  15

Gly

<210> SEQ ID NO 46
<211> LENGTH: 17
<212> TYPE: PRT
<213> ORGANISM: Artificial Sequence
<220> FEATURE:
<223> OTHER INFORMATION: Synthetic

<400> SEQUENCE: 46

Ser Ile Tyr Pro Tyr Tyr Gly Tyr Thr Ser Tyr Ala Asp Ser Val Lys
1               5                   10                  15
```

Gly

<210> SEQ ID NO 47
<211> LENGTH: 17
<212> TYPE: PRT
<213> ORGANISM: Artificial Sequence
<220> FEATURE:
<223> OTHER INFORMATION: Synthetic

<400> SEQUENCE: 47

Ser Ile Ser Ser Tyr Tyr Ser Tyr Thr Ser Tyr Ala Asp Ser Val Lys
1               5                   10                  15
Gly

<210> SEQ ID NO 48
<211> LENGTH: 17
<212> TYPE: PRT
<213> ORGANISM: Artificial Sequence
<220> FEATURE:
<223> OTHER INFORMATION: Synthetic

<400> SEQUENCE: 48

Ser Ile Tyr Pro Tyr Tyr Ser Tyr Thr Ser Tyr Ala Asp Ser Val Lys
1               5                   10                  15
Gly

<210> SEQ ID NO 49
<211> LENGTH: 17
<212> TYPE: PRT
<213> ORGANISM: Artificial Sequence
<220> FEATURE:
<223> OTHER INFORMATION: Synthetic

<400> SEQUENCE: 49

Ser Ile Tyr Pro Tyr Tyr Gly Tyr Thr Ser Tyr Ala Asp Ser Val Lys
1               5                   10                  15
Gly

<210> SEQ ID NO 50
<211> LENGTH: 17
<212> TYPE: PRT
<213> ORGANISM: Artificial Sequence
<220> FEATURE:
<223> OTHER INFORMATION: Synthetic

<400> SEQUENCE: 50

Ser Ile Tyr Pro Tyr Tyr Ser Tyr Thr Ser Tyr Ala Asp Ser Val Lys
1               5                   10                  15
Gly

<210> SEQ ID NO 51
<211> LENGTH: 17
<212> TYPE: PRT
<213> ORGANISM: Artificial Sequence
<220> FEATURE:
<223> OTHER INFORMATION: Synthetic

<400> SEQUENCE: 51

Ser Ile Tyr Pro Tyr Tyr Ser Tyr Thr Ser Tyr Ala Asp Ser Val Lys
1               5                   10                  15
Gly

```
<210> SEQ ID NO 52
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Tyr or Ser
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (5)..(6)
<223> OTHER INFORMATION: Tyr or Ser
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (8)..(8)
<223> OTHER INFORMATION: Tyr or Ser
<220> FEATURE:
<221> NAME/KEY: MOD_RES
<222> LOCATION: (10)..(10)
<223> OTHER INFORMATION: Ser or Tyr

<400> SEQUENCE: 52

Ser Ile Xaa Xaa Xaa Xaa Xaa Xaa Thr Xaa Tyr Ala Asp Ser Val Lys
1               5                   10                  15

Gly

<210> SEQ ID NO 53
<211> LENGTH: 10
<212> TYPE: PRT
<213> ORGANISM: Artificial Sequence
<220> FEATURE:
<223> OTHER INFORMATION: Synthetic

<400> SEQUENCE: 53

Gly Tyr Glu Gly Gly Met Ala Met Asp Tyr
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic

<400> SEQUENCE: 54

Asp Gly Tyr Ala Met Asp Ala Leu Asp Tyr
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic

<400> SEQUENCE: 55

Leu Tyr His Asn Thr Leu Gly Met Asp Tyr
1               5                   10

<210> SEQ ID NO 56
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 56

Pro Tyr Ser Tyr Ser Glu Ala Met Asp Tyr
1               5                   10

<210> SEQ ID NO 57
<211> LENGTH: 10
<212> TYPE: PRT
<213> ORGANISM: Artificial Sequence
<220> FEATURE:
<223> OTHER INFORMATION: Synthetic

<400> SEQUENCE: 57

Glu Tyr Tyr Met Tyr Asp Ala Leu Asp Tyr
1               5                   10

<210> SEQ ID NO 58
<211> LENGTH: 10
<212> TYPE: PRT
<213> ORGANISM: Artificial Sequence
<220> FEATURE:
<223> OTHER INFORMATION: Synthetic

<400> SEQUENCE: 58

Asp Tyr Tyr Tyr Ile Ser Ala Ile Asp Tyr
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Synthetic

<400> SEQUENCE: 59

Ser Tyr Ser Tyr Ser Ser Ala Leu Asp Tyr
1               5                   10

<210> SEQ ID NO 60
<211> LENGTH: 10
<212> TYPE: PRT
<213> ORGANISM: Artificial Sequence
<220> FEATURE:
<223> OTHER INFORMATION: Synthetic

<400> SEQUENCE: 60

Gly Tyr Lys Tyr Trp Ser Ala Phe Asp Tyr
1               5                   10

<210> SEQ ID NO 61
<211> LENGTH: 10
<212> TYPE: PRT
<213> ORGANISM: Artificial Sequence
<220> FEATURE:
<223> OTHER INFORMATION: Synthetic

<400> SEQUENCE: 61

Ser Tyr Ser Ser Tyr Ser Ala Ile Asp Tyr
1               5                   10

<210> SEQ ID NO 62
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 62

Glu Gly Tyr Ser Gln Gly Gly Phe Asp Tyr
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Synthetic

<400> SEQUENCE: 63

Ser Tyr Gly Tyr Tyr Val Ala Phe Asp Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

Asp Tyr Lys Phe Gly Tyr Ala Ile Asp Tyr
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthetic

<400> SEQUENCE: 65

Glu Gly Tyr Ser Gln Gly Gly Phe Asp Tyr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthetic

<400> SEQUENCE: 66

Ser Tyr Ser Tyr Tyr Ser Ala Met Asp Tyr
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Synthetic

<400> SEQUENCE: 67

Gly Tyr Met Trp Tyr Gly Gly Ile Asp Tyr
1               5                   10

<210> SEQ ID NO 68
<211> LENGTH: 11
<212> TYPE: PRT
```

```
<213> ORGANISM: Artificial Sequence
<220> FEATURE:
<223> OTHER INFORMATION: Synthetic

<400> SEQUENCE: 68

Glu Tyr Tyr Ser Tyr Leu Gly Ala Ile Asp Tyr
1               5                   10

<210> SEQ ID NO 69
<211> LENGTH: 21
<212> TYPE: PRT
<213> ORGANISM: Artificial Sequence
<220> FEATURE:
<223> OTHER INFORMATION: Synthetic

<400> SEQUENCE: 69

His Thr Lys Tyr Val Tyr Leu Tyr Thr Tyr Trp Glu Asp Ser Met Asp
1               5                   10                  15

Tyr Gly Leu Asp Tyr
            20

<210> SEQ ID NO 70
<211> LENGTH: 21
<212> TYPE: PRT
<213> ORGANISM: Artificial Sequence
<220> FEATURE:
<223> OTHER INFORMATION: Synthetic

<400> SEQUENCE: 70

Ser Ser Ile Ser Glu Trp Tyr Gly Ser Trp Tyr Tyr Phe Trp Glu Ser
1               5                   10                  15

Ser Gly Ile Asp Tyr
            20

<210> SEQ ID NO 71
<211> LENGTH: 10
<212> TYPE: PRT
<213> ORGANISM: Artificial Sequence
<220> FEATURE:
<223> OTHER INFORMATION: Synthetic

<400> SEQUENCE: 71

Glu Ser Tyr Trp Ser Tyr Ala Met Asp Tyr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Synthetic

<400> SEQUENCE: 72

Ser Tyr Ser Tyr Ser Tyr Gly Ile Asp Tyr
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Synthetic

<400> SEQUENCE: 73

Ser Tyr Ser Tyr Tyr Ser Ala Ile Asp Tyr
1               5                   10
```

```
<210> SEQ ID NO 74
<211> LENGTH: 10
<212> TYPE: PRT
<213> ORGANISM: Artificial Sequence
<220> FEATURE:
<223> OTHER INFORMATION: Synthetic

<400> SEQUENCE: 74

Ser Tyr Ser Tyr Ser Tyr Gly Leu Asp Tyr
1               5                   10

<210> SEQ ID NO 75
<211> LENGTH: 10
<212> TYPE: PRT
<213> ORGANISM: Artificial Sequence
<220> FEATURE:
<223> OTHER INFORMATION: Synthetic

<400> SEQUENCE: 75

Gly Tyr Ile His Trp Glu Ala Leu Asp Tyr
1               5                   10

<210> SEQ ID NO 76
<211> LENGTH: 10
<212> TYPE: PRT
<213> ORGANISM: Artificial Sequence
<220> FEATURE:
<223> OTHER INFORMATION: Synthetic

<400> SEQUENCE: 76

Ser Tyr Ser Tyr Ser Ser Gly Leu Asp Tyr
1               5                   10

<210> SEQ ID NO 77
<211> LENGTH: 10
<212> TYPE: PRT
<213> ORGANISM: Artificial Sequence
<220> FEATURE:
<223> OTHER INFORMATION: Synthetic

<400> SEQUENCE: 77

Ser Tyr Ser Tyr Ser Tyr Gly Met Asp Tyr
1               5                   10

<210> SEQ ID NO 78
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Gly, Asp, Leu, Pro, Glu, Ser or His
<220> FEATURE:
<221> NAME/KEY: MOD_RES
<222> LOCATION: (2)..(2)
<223> OTHER INFORMATION: Tyr, Gly, Thr or Ser
<220> FEATURE:
<221> NAME/KEY: MOD_RES
<222> LOCATION: (3)..(3)
<223> OTHER INFORMATION: Glu, Tyr, His, Ser, Lys, Gly, Met or Ile
<220> FEATURE:
<221> NAME/KEY: MOD_RES
<222> LOCATION: (4)..(4)
<223> OTHER INFORMATION: Gly, Ala, Asn, Tyr, Met, Ser, Phe, Trp or His
<220> FEATURE:
<221> NAME/KEY: MOD_RES
<222> LOCATION: (5)..(5)
```

```
<223> OTHER INFORMATION: Gly, Met, Thr, Ser, Tyr, Ile, Trp, Gln, Val or
      Glu
<220> FEATURE:
<221> NAME/KEY: MOD_RES
<222> LOCATION: (6)..(6)
<223> OTHER INFORMATION: Met, Asp, Leu, Glu, Ser, Gly, Val, Tyr or Trp
<220> FEATURE:
<221> NAME/KEY: MOD_RES
<222> LOCATION: (7)..(7)
<223> OTHER INFORMATION: Ala, Gly, Leu or Tyr
<220> FEATURE:
<221> NAME/KEY: MOD_RES
<222> LOCATION: (8)..(8)
<223> OTHER INFORMATION: Met, Leu, Ile, Phe, Ala, Tyr or Gly
<220> FEATURE:
<221> NAME/KEY: MOD_RES
<222> LOCATION: (9)..(9)
<223> OTHER INFORMATION: Ile, Thr, Ser or not present
<220> FEATURE:
<221> NAME/KEY: MOD_RES
<222> LOCATION: (10)..(11)
<223> OTHER INFORMATION: Tyr, Trp or not present
<220> FEATURE:
<221> NAME/KEY: MOD_RES
<222> LOCATION: (12)..(12)
<223> OTHER INFORMATION: Glu, Tyr or not present
<220> FEATURE:
<221> NAME/KEY: MOD_RES
<222> LOCATION: (13)..(13)
<223> OTHER INFORMATION: Asp, Phe or not present
<220> FEATURE:
<221> NAME/KEY: MOD_RES
<222> LOCATION: (14)..(14)
<223> OTHER INFORMATION: Ser, Trp or not present
<220> FEATURE:
<221> NAME/KEY: MOD_RES
<222> LOCATION: (15)..(15)
<223> OTHER INFORMATION: Met, Glu or not present
<220> FEATURE:
<221> NAME/KEY: MOD_RES
<222> LOCATION: (16)..(16)
<223> OTHER INFORMATION: Asp, Ser or not present
<220> FEATURE:
<221> NAME/KEY: MOD_RES
<222> LOCATION: (17)..(17)
<223> OTHER INFORMATION: Tyr, Ser or not present
<220> FEATURE:
<221> NAME/KEY: MOD_RES
<222> LOCATION: (18)..(18)
<223> OTHER INFORMATION: Gly or not present
<220> FEATURE:
<221> NAME/KEY: MOD_RES
<222> LOCATION: (19)..(19)
<223> OTHER INFORMATION: Leu, Ile or not present

<400> SEQUENCE: 78

Xaa Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 79
<211> LENGTH: 11
<212> TYPE: PRT
<213> ORGANISM: Artificial Sequence
<220> FEATURE:
<223> OTHER INFORMATION: Synthetic

<400> SEQUENCE: 79

Arg Ala Ser Gln Ser Val Ser Ser Ala Val Ala
1               5                   10

<210> SEQ ID NO 80
<211> LENGTH: 7
```

<212> TYPE: PRT
<213> ORGANISM: Artificial Sequence
<220> FEATURE:
<223> OTHER INFORMATION: Synthetic

<400> SEQUENCE: 80

Ser Ala Ser Ser Leu Tyr Ser
1               5

<210> SEQ ID NO 81
<211> LENGTH: 10
<212> TYPE: PRT
<213> ORGANISM: Artificial Sequence
<220> FEATURE:
<223> OTHER INFORMATION: Synthetic

<400> SEQUENCE: 81

Gly Phe Asn Ile Ser Ser Ser Tyr Ile His
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Synthetic

<400> SEQUENCE: 82

Gly Phe Asn Phe Ser Tyr Ser Tyr Ile His
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Synthetic

<400> SEQUENCE: 83

Gly Phe Asn Leu Ser Tyr Tyr Tyr Ile His
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Synthetic

<400> SEQUENCE: 84

Gly Phe Asn Phe Tyr Ser Ser Tyr Ile His
1               5                   10

<210> SEQ ID NO 85
<211> LENGTH: 10
<212> TYPE: PRT
<213> ORGANISM: Artificial Sequence
<220> FEATURE:
<223> OTHER INFORMATION: Synthetic

<400> SEQUENCE: 85

Gly Phe Asn Phe Tyr Ser Ser Ser Ile His
1               5                   10

<210> SEQ ID NO 86
<211> LENGTH: 10
<212> TYPE: PRT

<213> ORGANISM: Artificial Sequence
<220> FEATURE:
<223> OTHER INFORMATION: Synthetic

<400> SEQUENCE: 86

Gly Phe Asn Ile Ser Ser Ser Ser Ile His
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Synthetic

<400> SEQUENCE: 87

Gly Phe Asn Phe Tyr Tyr Ser Ser Ile His
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic

<400> SEQUENCE: 88

Gly Phe Asn Phe Ser Tyr Ser Ser Ile His
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic

<400> SEQUENCE: 89

Gly Phe Asn Val Ser Ser Tyr Ser Ile His
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Ile, Phe, Leu or Val
<220> FEATURE:
<221> NAME/KEY: MOD_RES
<222> LOCATION: (5)..(8)
<223> OTHER INFORMATION: Ser or Tyr

<400> SEQUENCE: 90

Gly Phe Asn Xaa Xaa Xaa Xaa Xaa Ile His
1               5                   10

<210> SEQ ID NO 91
<211> LENGTH: 17
<212> TYPE: PRT
<213> ORGANISM: Artificial Sequence
<220> FEATURE:
<223> OTHER INFORMATION: Synthetic

<400> SEQUENCE: 91

Tyr Ile Ser Pro Tyr Tyr Gly Ser Thr Ser Tyr Ala Asp Ser Val Lys
1               5                   10                  15

Gly

<210> SEQ ID NO 92
<211> LENGTH: 17
<212> TYPE: PRT
<213> ORGANISM: Artificial Sequence
<220> FEATURE:
<223> OTHER INFORMATION: Synthetic

<400> SEQUENCE: 92

Ser Ile Ser Ser Ser Tyr Gly Tyr Thr Ser Tyr Ala Asp Ser Val Lys
1               5                   10                  15

Gly

<210> SEQ ID NO 93
<211> LENGTH: 17
<212> TYPE: PRT
<213> ORGANISM: Artificial Sequence
<220> FEATURE:
<223> OTHER INFORMATION: Synthetic

<400> SEQUENCE: 93

Ser Ile Ser Ser Tyr Tyr Gly Tyr Thr Ser Tyr Ala Asp Ser Val Lys
1               5                   10                  15

Gly

<210> SEQ ID NO 94
<211> LENGTH: 17
<212> TYPE: PRT
<213> ORGANISM: Artificial Sequence
<220> FEATURE:
<223> OTHER INFORMATION: Synthetic

<400> SEQUENCE: 94

Ser Ile Ser Ser Ser Tyr Gly Ser Thr Ser Tyr Ala Asp Ser Val Lys
1               5                   10                  15

Gly

<210> SEQ ID NO 95
<211> LENGTH: 17
<212> TYPE: PRT
<213> ORGANISM: Artificial Sequence
<220> FEATURE:
<223> OTHER INFORMATION: Synthetic

<400> SEQUENCE: 95

Ser Ile Ser Ser Tyr Tyr Gly Ser Thr Ser Tyr Ala Asp Ser Val Lys
1               5                   10                  15

Gly

<210> SEQ ID NO 96
<211> LENGTH: 17
<212> TYPE: PRT
<213> ORGANISM: Artificial Sequence
<220> FEATURE:
<223> OTHER INFORMATION: Synthetic

<400> SEQUENCE: 96

Ser Ile Ser Pro Ser Tyr Ser Ser Thr Ser Tyr Ala Asp Ser Val Lys
1               5                   10                  15

Gly

<210> SEQ ID NO 97
<211> LENGTH: 17
<212> TYPE: PRT
<213> ORGANISM: Artificial Sequence
<220> FEATURE:
<223> OTHER INFORMATION: Synthetic

<400> SEQUENCE: 97

Ser Ile Tyr Ser Ser Tyr Gly Tyr Thr Ser Tyr Ala Asp Ser Val Lys
1               5                   10                  15

Gly

<210> SEQ ID NO 98
<211> LENGTH: 17
<212> TYPE: PRT
<213> ORGANISM: Artificial Sequence
<220> FEATURE:
<223> OTHER INFORMATION: Synthetic

<400> SEQUENCE: 98

Ser Ile Tyr Ser Ser Tyr Ser Ser Thr Ser Tyr Ala Asp Ser Val Lys
1               5                   10                  15

Gly

<210> SEQ ID NO 99
<211> LENGTH: 17
<212> TYPE: PRT
<213> ORGANISM: Artificial Sequence
<220> FEATURE:
<223> OTHER INFORMATION: Synthetic

<400> SEQUENCE: 99

Ser Ile Tyr Pro Ser Ser Gly Ser Thr Tyr Tyr Ala Asp Ser Val Lys
1               5                   10                  15

Gly

<210> SEQ ID NO 100
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Tyr or Ser
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (5)..(6)
<223> OTHER INFORMATION: Tyr or Ser
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Ser or Tyr
<220> FEATURE:
<221> NAME/KEY: MOD_RES
<222> LOCATION: (10)..(10)
<223> OTHER INFORMATION: Ser or Tyr

<400> SEQUENCE: 100

Xaa Ile Xaa Xaa Xaa Xaa Xaa Xaa Thr Xaa Tyr Ala Asp Ser Val Lys
1               5                   10                  15
Gly

<210> SEQ ID NO 101
<211> LENGTH: 11
<212> TYPE: PRT
<213> ORGANISM: Artificial Sequence
<220> FEATURE:
<223> OTHER INFORMATION: Synthetic

<400> SEQUENCE: 101

Glu Tyr Tyr Arg Trp Tyr Thr Ala Ile Asp Tyr
1               5                   10

<210> SEQ ID NO 102
<211> LENGTH: 11
<212> TYPE: PRT
<213> ORGANISM: Artificial Sequence
<220> FEATURE:
<223> OTHER INFORMATION: Synthetic

<400> SEQUENCE: 102

Glu Lys Met Tyr Tyr Ser Tyr Gly Phe Asp Tyr
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Synthetic

<400> SEQUENCE: 103

Glu Ser Tyr Ser Ile His Phe Gly Phe Asp Tyr
1               5                   10

<210> SEQ ID NO 104
<211> LENGTH: 16
<212> TYPE: PRT
<213> ORGANISM: Artificial Sequence
<220> FEATURE:
<223> OTHER INFORMATION: Synthetic

<400> SEQUENCE: 104

Met Tyr Tyr Ser Tyr Tyr Trp Arg Pro Tyr Gly Asn Ala Ile Asp Tyr
1               5                   10                  15

<210> SEQ ID NO 105
<211> LENGTH: 19
<212> TYPE: PRT
<213> ORGANISM: Artificial Sequence
<220> FEATURE:
<223> OTHER INFORMATION: Synthetic

<400> SEQUENCE: 105

Gly Ser Ile Pro Ser Tyr Trp Ser Ala Asp Trp Tyr Tyr Tyr Gly
1               5                   10                  15
Leu Asp Tyr

<210> SEQ ID NO 106

```
<211> LENGTH: 14
<212> TYPE: PRT
<213> ORGANISM: Artificial Sequence
<220> FEATURE:
<223> OTHER INFORMATION: Synthetic

<400> SEQUENCE: 106

Tyr Lys Tyr Asn Tyr Tyr Phe Glu Ser Gly Met Asp Tyr
1               5                   10

<210> SEQ ID NO 107
<211> LENGTH: 17
<212> TYPE: PRT
<213> ORGANISM: Artificial Sequence
<220> FEATURE:
<223> OTHER INFORMATION: Synthetic

<400> SEQUENCE: 107

Glu Tyr Tyr Trp Trp Tyr Lys Glu Ala Trp Tyr Ser Ala Gly Met Asp
1               5                   10                  15

Tyr

<210> SEQ ID NO 108
<211> LENGTH: 19
<212> TYPE: PRT
<213> ORGANISM: Artificial Sequence
<220> FEATURE:
<223> OTHER INFORMATION: Synthetic

<400> SEQUENCE: 108

Gly Ile Met Phe Ser Ser Trp Trp Trp Tyr Tyr Asp Tyr Ser Asp Ala
1               5                   10                  15

Leu Asp Tyr

<210> SEQ ID NO 109
<211> LENGTH: 21
<212> TYPE: PRT
<213> ORGANISM: Artificial Sequence
<220> FEATURE:
<223> OTHER INFORMATION: Synthetic

<400> SEQUENCE: 109

Ser Gly Tyr Tyr Tyr Gln Gly Tyr Trp Trp Tyr Tyr Tyr Thr Gly Tyr
1               5                   10                  15

Tyr Gly Met Asp Tyr
            20

<210> SEQ ID NO 110
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Glu, Met, Gly, Tyr or Ser
<220> FEATURE:
<221> NAME/KEY: MOD_RES
<222> LOCATION: (2)..(2)
<223> OTHER INFORMATION: Tyr, Lys, Ser, Ile or Gly
<220> FEATURE:
<221> NAME/KEY: MOD_RES
<222> LOCATION: (3)..(3)
<223> OTHER INFORMATION: Tyr, Met or Ile
<220> FEATURE:
<221> NAME/KEY: MOD_RES
<222> LOCATION: (4)..(4)
```

```
<223> OTHER INFORMATION: Arg, Tyr, Ser, Pro, Asn, Trp or Phe
<220> FEATURE:
<221> NAME/KEY: MOD_RES
<222> LOCATION: (5)..(5)
<223> OTHER INFORMATION: Trp, Tyr, Ile or Ser
<220> FEATURE:
<221> NAME/KEY: MOD_RES
<222> LOCATION: (6)..(6)
<223> OTHER INFORMATION: Tyr, Ser, His or Gln
<220> FEATURE:
<221> NAME/KEY: MOD_RES
<222> LOCATION: (7)..(7)
<223> OTHER INFORMATION: Thr, Tyr, Phe, Trp, Lys or Gly
<220> FEATURE:
<221> NAME/KEY: MOD_RES
<222> LOCATION: (8)..(8)
<223> OTHER INFORMATION: Ala, Gly, Arg, Ser, Phe, Glu, Trp or Tyr
<220> FEATURE:
<221> NAME/KEY: MOD_RES
<222> LOCATION: (9)..(9)
<223> OTHER INFORMATION: Ile, Phe, Pro, Ala, Glu or Trp
<220> FEATURE:
<221> NAME/KEY: MOD_RES
<222> LOCATION: (10)..(10)
<223> OTHER INFORMATION: Tyr, Asp, Ser, Trp or not present
<220> FEATURE:
<221> NAME/KEY: MOD_RES
<222> LOCATION: (11)..(11)
<223> OTHER INFORMATION: Gly, Trp, Tyr or not present
<220> FEATURE:
<221> NAME/KEY: MOD_RES
<222> LOCATION: (12)..(12)
<223> OTHER INFORMATION: Asn, Tyr, Met, Ser, Asp or not present
<220> FEATURE:
<221> NAME/KEY: MOD_RES
<222> LOCATION: (13)..(13)
<223> OTHER INFORMATION: Ala, Tyr or not present
<220> FEATURE:
<221> NAME/KEY: MOD_RES
<222> LOCATION: (14)..(14)
<223> OTHER INFORMATION: Ile, Tyr, Gly, Ser, Thr or not present
<220> FEATURE:
<221> NAME/KEY: MOD_RES
<222> LOCATION: (15)..(15)
<223> OTHER INFORMATION: Tyr, Met, Asp, Gly or not present
<220> FEATURE:
<221> NAME/KEY: MOD_RES
<222> LOCATION: (16)..(16)
<223> OTHER INFORMATION: Gly, Ala, Tyr or not present
<220> FEATURE:
<221> NAME/KEY: MOD_RES
<222> LOCATION: (17)..(17)
<223> OTHER INFORMATION: Leu, Tyr or not present
<220> FEATURE:
<221> NAME/KEY: MOD_RES
<222> LOCATION: (18)..(18)
<223> OTHER INFORMATION: Gly or not present
<220> FEATURE:
<221> NAME/KEY: MOD_RES
<222> LOCATION: (19)..(19)
<223> OTHER INFORMATION: Met or not present

<400> SEQUENCE: 110

Xaa Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 111
<211> LENGTH: 30
<212> TYPE: PRT
<213> ORGANISM: Homo sapiens

<400> SEQUENCE: 111

Gln Val Gln Leu Val Gln Ser Gly Ala Glu Val Lys Lys Pro Gly Ala
```

```
1               5                   10                  15
Ser Val Lys Val Ser Cys Lys Ala Ser Gly Tyr Thr Phe Thr
            20                  25                  30
```

<210> SEQ ID NO 112
<211> LENGTH: 25
<212> TYPE: PRT
<213> ORGANISM: Homo sapiens

<400> SEQUENCE: 112

```
Gln Val Gln Leu Val Gln Ser Gly Ala Glu Val Lys Lys Pro Gly Ala
1               5                   10                  15
Ser Val Lys Val Ser Cys Lys Ala Ser
            20                  25
```

<210> SEQ ID NO 113
<211> LENGTH: 25
<212> TYPE: PRT
<213> ORGANISM: Homo sapiens

<400> SEQUENCE: 113

```
Gln Val Gln Leu Val Gln Ser Gly Ala Glu Val Lys Lys Pro Gly Ala
1               5                   10                  15
Ser Val Lys Val Ser Cys Lys Ala Ser
            20                  25
```

<210> SEQ ID NO 114
<211> LENGTH: 25
<212> TYPE: PRT
<213> ORGANISM: Homo sapiens

<400> SEQUENCE: 114

```
Gln Val Gln Leu Val Gln Ser Gly Ala Glu Val Lys Lys Pro Gly Ala
1               5                   10                  15
Ser Val Lys Val Ser Cys Lys Ala Ser
            20                  25
```

<210> SEQ ID NO 115
<211> LENGTH: 30
<212> TYPE: PRT
<213> ORGANISM: Homo sapiens

<400> SEQUENCE: 115

```
Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Val Ser
            20                  25                  30
```

<210> SEQ ID NO 116
<211> LENGTH: 25
<212> TYPE: PRT
<213> ORGANISM: Homo sapiens

<400> SEQUENCE: 116

```
Gln Val Gln Leu Gln Glu Ser Gly Pro Gly Leu Val Lys Pro Ser Gln
1               5                   10                  15
Thr Leu Ser Leu Thr Cys Thr Val Ser
            20                  25
```

<210> SEQ ID NO 117
<211> LENGTH: 25
<212> TYPE: PRT

```
<213> ORGANISM: Homo sapiens

<400> SEQUENCE: 117

Gln Val Gln Leu Gln Glu Ser Gly Pro Gly Leu Val Lys Pro Ser Gln
1               5                   10                  15
Thr Leu Ser Leu Thr Cys Thr Val Ser
            20                  25

<210> SEQ ID NO 118
<211> LENGTH: 25
<212> TYPE: PRT
<213> ORGANISM: Homo sapiens

<400> SEQUENCE: 118

Gln Val Gln Leu Gln Glu Ser Gly Pro Gly Leu Val Lys Pro Ser Gln
1               5                   10                  15
Thr Leu Ser Leu Thr Cys Thr Val Ser
            20                  25

<210> SEQ ID NO 119
<211> LENGTH: 30
<212> TYPE: PRT
<213> ORGANISM: Homo sapiens

<400> SEQUENCE: 119

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser
            20                  25                  30

<210> SEQ ID NO 120
<211> LENGTH: 25
<212> TYPE: PRT
<213> ORGANISM: Homo sapiens

<400> SEQUENCE: 120

Glu Val Gln Leu Val Glu Ser Gly Gly Gly Leu Val Gln Pro Gly Gly
1               5                   10                  15
Ser Leu Arg Leu Ser Cys Ala Ala Ser
            20                  25

<210> SEQ ID NO 121
<211> LENGTH: 25
<212> TYPE: PRT
<213> ORGANISM: Homo sapiens

<400> SEQUENCE: 121

Glu Val Gln Leu Val Glu Ser Gly Gly Gly Leu Val Gln Pro Gly Gly
1               5                   10                  15
Ser Leu Arg Leu Ser Cys Ala Ala Ser
            20                  25

<210> SEQ ID NO 122
<211> LENGTH: 25
<212> TYPE: PRT
<213> ORGANISM: Homo sapiens

<400> SEQUENCE: 122

Glu Val Gln Leu Val Glu Ser Gly Gly Gly Leu Val Gln Pro Gly Gly
1               5                   10                  15
Ser Leu Arg Leu Ser Cys Ala Ala Ser
            20                  25
```

<210> SEQ ID NO 123
<211> LENGTH: 30
<212> TYPE: PRT
<213> ORGANISM: Homo sapiens

<400> SEQUENCE: 123

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30

<210> SEQ ID NO 124
<211> LENGTH: 25
<212> TYPE: PRT
<213> ORGANISM: Homo sapiens

<400> SEQUENCE: 124

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 125
<211> LENGTH: 25
<212> TYPE: PRT
<213> ORGANISM: Homo sapiens

<400> SEQUENCE: 125

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 126
<211> LENGTH: 30
<212> TYPE: PRT
<213> ORGANISM: Homo sapiens

<400> SEQUENCE: 126

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys
            20                  25                  30

<210> SEQ ID NO 127
<211> LENGTH: 25
<212> TYPE: PRT
<213> ORGANISM: Homo sapiens

<400> SEQUENCE: 127

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 128
<211> LENGTH: 25
<212> TYPE: PRT
<213> ORGANISM: Homo sapiens

<400> SEQUENCE: 128

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 129
<211> LENGTH: 25
<212> TYPE: PRT
<213> ORGANISM: Homo sapiens

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 130
<211> LENGTH: 23
<212> TYPE: PRT
<213> ORGANISM: Homo sapiens

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 131
<211> LENGTH: 23
<212> TYPE: PRT
<213> ORGANISM: Homo sapiens

<400> SEQUENCE: 131

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 132
<211> LENGTH: 23
<212> TYPE: PRT
<213> ORGANISM: Homo sapiens

<400> SEQUENCE: 132

Glu Ile Val Leu Thr Gln Ser Pro Gly Thr Leu Ser Leu Ser Pro Gly
1               5                   10                  15

Glu Arg Ala Thr Leu Ser Cys
            20

<210> SEQ ID NO 133
<211> LENGTH: 23
<212> TYPE: PRT
<213> ORGANISM: Homo sapiens

<400> SEQUENCE: 133

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 134
<211> LENGTH: 23

<212> TYPE: PRT
<213> ORGANISM: Homo sapiens

<400> SEQUENCE: 134

Asp Ile Gln Met Thr Gln Ser Pro Ser Ser Leu Ser Ala Ser Val Gly
1               5                   10                  15
Asp Arg Val Thr Ile Thr Cys
            20

<210> SEQ ID NO 135
<211> LENGTH: 15
<212> TYPE: PRT
<213> ORGANISM: Homo sapiens

<400> SEQUENCE: 135

Trp Tyr Gln Gln Lys Pro Gly Lys Ala Pro Lys Leu Leu Ile Tyr
1               5                   10                  15

<210> SEQ ID NO 136
<211> LENGTH: 32
<212> TYPE: PRT
<213> ORGANISM: Homo sapiens

<400> SEQUENCE: 136

Gly Val Pro Ser Arg Phe Ser Gly Ser Arg Ser Gly Thr Asp Phe Thr
1               5                   10                  15
Leu Thr Ile Ser Ser Leu Gln Pro Glu Asp Phe Ala Thr Tyr Tyr Cys
            20                  25                  30

<210> SEQ ID NO 137
<211> LENGTH: 10
<212> TYPE: PRT
<213> ORGANISM: Homo sapiens

<400> SEQUENCE: 137

Phe Gly Gln Gly Thr Lys Val Glu Ile Lys
1               5                   10

<210> SEQ ID NO 138
<211> LENGTH: 25
<212> TYPE: PRT
<213> ORGANISM: Homo sapiens

<400> SEQUENCE: 138

Glu Val Gln Leu Val Glu Ser Gly Gly Leu Val Gln Pro Gly Gly
1               5                   10                  15
Ser Leu Arg Leu Ser Cys Ala Ala Ser
            20                  25

<210> SEQ ID NO 139
<211> LENGTH: 13
<212> TYPE: PRT
<213> ORGANISM: Homo sapiens

<400> SEQUENCE: 139

Trp Val Arg Gln Ala Pro Gly Lys Gly Leu Glu Trp Val
1               5                   10

<210> SEQ ID NO 140
<211> LENGTH: 30
<212> TYPE: PRT
<213> ORGANISM: Homo sapiens

<400> SEQUENCE: 140

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 141
<211> LENGTH: 11
<212> TYPE: PRT
<213> ORGANISM: Homo sapiens

<400> SEQUENCE: 141

Trp Gly Gln Gly Thr Leu Val Thr Val Ser Ser
1               5                   10

<210> SEQ ID NO 142
<211> LENGTH: 23
<212> TYPE: PRT
<213> ORGANISM: Homo sapiens

<400> SEQUENCE: 142

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 143
<211> LENGTH: 15
<212> TYPE: PRT
<213> ORGANISM: Homo sapiens

<400> SEQUENCE: 143

Trp Tyr Gln Gln Lys Pro Gly Lys Ala Pro Lys Leu Leu Ile Tyr
1               5                   10                  15

<210> SEQ ID NO 144
<211> LENGTH: 32
<212> TYPE: PRT
<213> ORGANISM: Homo sapiens

<400> SEQUENCE: 144

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 145
<211> LENGTH: 10
<212> TYPE: PRT
<213> ORGANISM: Homo sapiens

<400> SEQUENCE: 145

Phe Arg Gln Gly Thr Lys Val Glu Ile Lys
1               5                   10

<210> SEQ ID NO 146
<211> LENGTH: 25
<212> TYPE: PRT
<213> ORGANISM: Homo sapiens

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 147
<211> LENGTH: 13
<212> TYPE: PRT
<213> ORGANISM: Homo sapiens

<400> SEQUENCE: 147

Trp Val Arg Gln Ala Pro Gly Lys Gly Leu Glu Trp Val
1               5                  10

<210> SEQ ID NO 148
<211> LENGTH: 30
<212> TYPE: PRT
<213> ORGANISM: Homo sapiens

<400> SEQUENCE: 148

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 149
<211> LENGTH: 11
<212> TYPE: PRT
<213> ORGANISM: Homo sapiens

<400> SEQUENCE: 149

Trp Gly Gln Gly Thr Leu Val Thr Val Ser Ser
1               5                   10

<210> SEQ ID NO 150
<211> LENGTH: 66
<212> TYPE: DNA
<213> ORGANISM: Artificial Sequence
<220> FEATURE:
<223> OTHER INFORMATION: Synthetic

<400> SEQUENCE: 150
tcttgtgaca aaactcacca tcaccatcac catcactagg gcggtggctc tggttccggt      60
gatttt                                                                66

<210> SEQ ID NO 151
<211> LENGTH: 10
<212> TYPE: PRT
<213> ORGANISM: Artificial Sequence
<220> FEATURE:
<223> OTHER INFORMATION: Synthetic

<400> SEQUENCE: 151

Gly Phe Asn Val Tyr Tyr Ser Ser Ile His
1               5                   10

<210> SEQ ID NO 152
<211> LENGTH: 10
<212> TYPE: PRT
<213> ORGANISM: Artificial Sequence
<220> FEATURE:
<223> OTHER INFORMATION: Synthetic

<400> SEQUENCE: 152

Gly Phe Asn Val Ser Tyr Ser Tyr Met His
1               5                   10

<210> SEQ ID NO 153
<211> LENGTH: 10
<212> TYPE: PRT
<213> ORGANISM: Artificial Sequence
<220> FEATURE:
<223> OTHER INFORMATION: Synthetic

<400> SEQUENCE: 153

Gly Phe Asn Phe Ser Tyr Tyr Ser Met His
1               5                   10

<210> SEQ ID NO 154
<211> LENGTH: 10
<212> TYPE: PRT
<213> ORGANISM: Artificial Sequence
<220> FEATURE:
<223> OTHER INFORMATION: Synthetic

<400> SEQUENCE: 154

Gly Phe Asn Leu Ser Tyr Tyr Ser Ile His
1               5                   10

<210> SEQ ID NO 155
<211> LENGTH: 10
<212> TYPE: PRT
<213> ORGANISM: Artificial Sequence
<220> FEATURE:
<223> OTHER INFORMATION: Synthetic

<400> SEQUENCE: 155

Gly Phe Asn Ile Ser Tyr Ser Ser Met His
1               5                   10

<210> SEQ ID NO 156
<211> LENGTH: 10
<212> TYPE: PRT
<213> ORGANISM: Artificial Sequence
<220> FEATURE:
<223> OTHER INFORMATION: Synthetic

<400> SEQUENCE: 156

Gly Phe Asn Val Tyr Tyr Ser Ser Ile His
1               5                   10

<210> SEQ ID NO 157
<211> LENGTH: 10
<212> TYPE: PRT
<213> ORGANISM: Artificial Sequence
<220> FEATURE:
<223> OTHER INFORMATION: Synthetic

<400> SEQUENCE: 157

Gly Phe Asn Leu Ser Tyr Ser Tyr Ile His
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Synthetic

<400> SEQUENCE: 158

Gly Phe Asn Phe Tyr Tyr Tyr Tyr Ile His
1               5                   10

```
<210> SEQ ID NO 159
<211> LENGTH: 10
<212> TYPE: PRT
<213> ORGANISM: Artificial Sequence
<220> FEATURE:
<223> OTHER INFORMATION: Synthetic

<400> SEQUENCE: 159

Gly Phe Asn Leu Ser Tyr Ser Ser Ile His
1               5                   10

<210> SEQ ID NO 160
<211> LENGTH: 10
<212> TYPE: PRT
<213> ORGANISM: Artificial Sequence
<220> FEATURE:
<223> OTHER INFORMATION: Synthetic

<400> SEQUENCE: 160

Gly Phe Asn Val Ser Tyr Ser Ser Ile His
1               5                   10

<210> SEQ ID NO 161
<211> LENGTH: 10
<212> TYPE: PRT
<213> ORGANISM: Artificial Sequence
<220> FEATURE:
<223> OTHER INFORMATION: Synthetic

<400> SEQUENCE: 161

Gly Phe Asn Val Ser Tyr Ser Ser Ile His
1               5                   10

<210> SEQ ID NO 162
<211> LENGTH: 10
<212> TYPE: PRT
<213> ORGANISM: Artificial Sequence
<220> FEATURE:
<223> OTHER INFORMATION: Synthetic

<400> SEQUENCE: 162

Gly Phe Asn Val Tyr Tyr Ser Ser Ile His
1               5                   10

<210> SEQ ID NO 163
<211> LENGTH: 10
<212> TYPE: PRT
<213> ORGANISM: Artificial Sequence
<220> FEATURE:
<223> OTHER INFORMATION: Synthetic

<400> SEQUENCE: 163

Gly Phe Asn Val Ser Tyr Tyr Tyr Ile His
1               5                   10

<210> SEQ ID NO 164
<211> LENGTH: 10
<212> TYPE: PRT
<213> ORGANISM: Artificial Sequence
<220> FEATURE:
<223> OTHER INFORMATION: Synthetic

<400> SEQUENCE: 164

Gly Phe Asn Leu Ser Tyr Ser Ser Ile His
1               5                   10

<210> SEQ ID NO 165
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 165

Gly Phe Asn Ile Ser Tyr Ser Tyr Met His
1               5                   10

<210> SEQ ID NO 166
<211> LENGTH: 10
<212> TYPE: PRT
<213> ORGANISM: Artificial Sequence
<220> FEATURE:
<223> OTHER INFORMATION: Synthetic

<400> SEQUENCE: 166

Gly Phe Asn Leu Tyr Tyr Ser Tyr Met His
1               5                   10

<210> SEQ ID NO 167
<211> LENGTH: 10
<212> TYPE: PRT
<213> ORGANISM: Artificial Sequence
<220> FEATURE:
<223> OTHER INFORMATION: Synthetic

<400> SEQUENCE: 167

Gly Phe Asn Val Ser Tyr Tyr Tyr Met His
1               5                   10

<210> SEQ ID NO 168
<211> LENGTH: 10
<212> TYPE: PRT
<213> ORGANISM: Artificial Sequence
<220> FEATURE:
<223> OTHER INFORMATION: Synthetic

<400> SEQUENCE: 168

Gly Phe Asn Ile Ser Tyr Ser Tyr Met His
1               5                   10

<210> SEQ ID NO 169
<211> LENGTH: 10
<212> TYPE: PRT
<213> ORGANISM: Artificial Sequence
<220> FEATURE:
<223> OTHER INFORMATION: Synthetic

<400> SEQUENCE: 169

Gly Phe Asn Ile Ser Tyr Ser Ser Ile His
1               5                   10

<210> SEQ ID NO 170
<211> LENGTH: 10
<212> TYPE: PRT
<213> ORGANISM: Artificial Sequence
<220> FEATURE:
<223> OTHER INFORMATION: Synthetic

<400> SEQUENCE: 170

Gly Phe Asn Val Ser Tyr Ser Ser Met His
1               5                   10

<210> SEQ ID NO 171
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 171

Gly Phe Asn Leu Ser Tyr Tyr Ser Ile His
1               5                   10

<210> SEQ ID NO 172
<211> LENGTH: 10
<212> TYPE: PRT
<213> ORGANISM: Artificial Sequence
<220> FEATURE:
<223> OTHER INFORMATION: Synthetic

<400> SEQUENCE: 172

Gly Phe Asn Val Ser Tyr Tyr Ser Ile His
1               5                   10

<210> SEQ ID NO 173
<211> LENGTH: 10
<212> TYPE: PRT
<213> ORGANISM: Artificial Sequence
<220> FEATURE:
<223> OTHER INFORMATION: Synthetic

<400> SEQUENCE: 173

Gly Phe Asn Ile Ser Tyr Ser Ser Ile His
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Synthetic

<400> SEQUENCE: 174

Gly Phe Asn Phe Ser Tyr Tyr Ser Ile His
1               5                   10

<210> SEQ ID NO 175
<211> LENGTH: 10
<212> TYPE: PRT
<213> ORGANISM: Artificial Sequence
<220> FEATURE:
<223> OTHER INFORMATION: Synthetic

<400> SEQUENCE: 175

Gly Phe Asn Leu Ser Tyr Ser Ser Met His
1               5                   10

<210> SEQ ID NO 176
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Val, Phe, Leu or Ile
<220> FEATURE:
<221> NAME/KEY: MOD_RES
<222> LOCATION: (5)..(5)
<223> OTHER INFORMATION: Tyr or Ser
<220> FEATURE:
<221> NAME/KEY: MOD_RES
```

```
<222> LOCATION: (7)..(8)
<223> OTHER INFORMATION: Ser or Tyr
<220> FEATURE:
<221> NAME/KEY: MOD_RES
<222> LOCATION: (9)..(9)
<223> OTHER INFORMATION: Ile or Met

<400> SEQUENCE: 176

Gly Phe Asn Xaa Xaa Tyr Xaa Xaa Xaa His
1               5                   10

<210> SEQ ID NO 177
<211> LENGTH: 17
<212> TYPE: PRT
<213> ORGANISM: Artificial Sequence
<220> FEATURE:
<223> OTHER INFORMATION: Synthetic

<400> SEQUENCE: 177

Ser Ile Ser Pro Tyr Tyr Ser Tyr Thr Ser Tyr Ala Asp Ser Val Lys
1               5                   10                  15
Gly

<210> SEQ ID NO 178
<211> LENGTH: 17
<212> TYPE: PRT
<213> ORGANISM: Artificial Sequence
<220> FEATURE:
<223> OTHER INFORMATION: Synthetic

<400> SEQUENCE: 178

Ser Ile Ser Ser Tyr Tyr Ser Tyr Thr Ser Tyr Ala Asp Ser Val Lys
1               5                   10                  15
Gly

<210> SEQ ID NO 179
<211> LENGTH: 17
<212> TYPE: PRT
<213> ORGANISM: Artificial Sequence
<220> FEATURE:
<223> OTHER INFORMATION: Synthetic

<400> SEQUENCE: 179

Ser Ile Tyr Pro Tyr Tyr Gly Tyr Thr Tyr Tyr Ala Asp Ser Val Lys
1               5                   10                  15
Gly

<210> SEQ ID NO 180
<211> LENGTH: 17
<212> TYPE: PRT
<213> ORGANISM: Artificial Sequence
<220> FEATURE:
<223> OTHER INFORMATION: Synthetic

<400> SEQUENCE: 180

Ser Ile Tyr Pro Tyr Tyr Gly Tyr Thr Ser Tyr Ala Asp Ser Val Lys
1               5                   10                  15
Gly

<210> SEQ ID NO 181
<211> LENGTH: 17
<212> TYPE: PRT
<213> ORGANISM: Artificial Sequence
<220> FEATURE:
<223> OTHER INFORMATION: Synthetic
```

```
<400> SEQUENCE: 181

Ser Ile Tyr Ser Tyr Tyr Ser Tyr Thr Ser Tyr Ala Asp Ser Val Lys
1               5                   10                  15

Gly

<210> SEQ ID NO 182
<211> LENGTH: 17
<212> TYPE: PRT
<213> ORGANISM: Artificial Sequence
<220> FEATURE:
<223> OTHER INFORMATION: Synthetic

<400> SEQUENCE: 182

Ser Ile Tyr Pro Tyr Tyr Gly Tyr Thr Ser Tyr Ala Asp Ser Val Lys
1               5                   10                  15

Gly

<210> SEQ ID NO 183
<211> LENGTH: 17
<212> TYPE: PRT
<213> ORGANISM: Artificial Sequence
<220> FEATURE:
<223> OTHER INFORMATION: Synthetic

<400> SEQUENCE: 183

Ser Ile Ser Ser Tyr Tyr Gly Ser Thr Ser Tyr Ala Asp Ser Val Lys
1               5                   10                  15

Gly

<210> SEQ ID NO 184
<211> LENGTH: 17
<212> TYPE: PRT
<213> ORGANISM: Artificial Sequence
<220> FEATURE:
<223> OTHER INFORMATION: Synthetic

<400> SEQUENCE: 184

Ser Ile Ser Pro Tyr Tyr Ser Tyr Thr Ser Tyr Ala Asp Ser Val Lys
1               5                   10                  15

Gly

<210> SEQ ID NO 185
<211> LENGTH: 17
<212> TYPE: PRT
<213> ORGANISM: Artificial Sequence
<220> FEATURE:
<223> OTHER INFORMATION: Synthetic

<400> SEQUENCE: 185

Ser Ile Tyr Pro Tyr Tyr Ser Tyr Thr Ser Tyr Ala Asp Ser Val Lys
1               5                   10                  15

Gly

<210> SEQ ID NO 186
<211> LENGTH: 17
<212> TYPE: PRT
<213> ORGANISM: Artificial Sequence
<220> FEATURE:
<223> OTHER INFORMATION: Synthetic

<400> SEQUENCE: 186

Ser Ile Tyr Pro Tyr Tyr Ser Tyr Thr Ser Tyr Ala Asp Ser Val Lys
```

```
1               5                   10                  15

Gly

<210> SEQ ID NO 187
<211> LENGTH: 17
<212> TYPE: PRT
<213> ORGANISM: Artificial Sequence
<220> FEATURE:
<223> OTHER INFORMATION: Synthetic

<400> SEQUENCE: 187

Ser Ile Tyr Ser Tyr Tyr Ser Tyr Thr Ser Tyr Ala Asp Ser Val Lys
1               5                   10                  15

Gly

<210> SEQ ID NO 188
<211> LENGTH: 17
<212> TYPE: PRT
<213> ORGANISM: Artificial Sequence
<220> FEATURE:
<223> OTHER INFORMATION: Synthetic

<400> SEQUENCE: 188

Ser Ile Tyr Pro Tyr Tyr Gly Tyr Thr Ser Tyr Ala Asp Ser Val Lys
1               5                   10                  15

Gly

<210> SEQ ID NO 189
<211> LENGTH: 17
<212> TYPE: PRT
<213> ORGANISM: Artificial Sequence
<220> FEATURE:
<223> OTHER INFORMATION: Synthetic

<400> SEQUENCE: 189

Ser Ile Ser Ser Tyr Tyr Gly Tyr Thr Ser Tyr Ala Asp Ser Val Lys
1               5                   10                  15

Gly

<210> SEQ ID NO 190
<211> LENGTH: 17
<212> TYPE: PRT
<213> ORGANISM: Artificial Sequence
<220> FEATURE:
<223> OTHER INFORMATION: Synthetic

<400> SEQUENCE: 190

Ser Ile Tyr Ser Tyr Tyr Gly Tyr Thr Ser Tyr Ala Asp Ser Val Lys
1               5                   10                  15

Gly

<210> SEQ ID NO 191
<211> LENGTH: 17
<212> TYPE: PRT
<213> ORGANISM: Artificial Sequence
<220> FEATURE:
<223> OTHER INFORMATION: Synthetic

<400> SEQUENCE: 191

Ser Ile Ser Pro Tyr Tyr Gly Tyr Thr Ser Tyr Ala Asp Ser Val Lys
1               5                   10                  15

Gly
```

<210> SEQ ID NO 192
<211> LENGTH: 17
<212> TYPE: PRT
<213> ORGANISM: Artificial Sequence
<220> FEATURE:
<223> OTHER INFORMATION: Synthetic

<400> SEQUENCE: 192

Ser Ile Ser Ser Tyr Tyr Ser Tyr Thr Ser Tyr Ala Asp Ser Val Lys
1               5                   10                  15

Gly

<210> SEQ ID NO 193
<211> LENGTH: 17
<212> TYPE: PRT
<213> ORGANISM: Artificial Sequence
<220> FEATURE:
<223> OTHER INFORMATION: Synthetic

<400> SEQUENCE: 193

Ser Ile Ser Ser Tyr Tyr Ser Tyr Thr Ser Tyr Ala Asp Ser Val Lys
1               5                   10                  15

Gly

<210> SEQ ID NO 194
<211> LENGTH: 17
<212> TYPE: PRT
<213> ORGANISM: Artificial Sequence
<220> FEATURE:
<223> OTHER INFORMATION: Synthetic

<400> SEQUENCE: 194

Ser Ile Ser Ser Tyr Tyr Ser Tyr Thr Ser Tyr Ala Asp Ser Val Lys
1               5                   10                  15

Gly

<210> SEQ ID NO 195
<211> LENGTH: 17
<212> TYPE: PRT
<213> ORGANISM: Artificial Sequence
<220> FEATURE:
<223> OTHER INFORMATION: Synthetic

<400> SEQUENCE: 195

Ser Ile Ser Ser Ser Tyr Ser Ser Thr Tyr Tyr Ala Asp Ser Val Lys
1               5                   10                  15

Gly

<210> SEQ ID NO 196
<211> LENGTH: 17
<212> TYPE: PRT
<213> ORGANISM: Artificial Sequence
<220> FEATURE:
<223> OTHER INFORMATION: Synthetic

<400> SEQUENCE: 196

Ser Ile Ser Pro Tyr Tyr Gly Tyr Thr Ser Tyr Ala Asp Ser Val Lys
1               5                   10                  15

Gly

<210> SEQ ID NO 197
<211> LENGTH: 17
<212> TYPE: PRT

```
<213> ORGANISM: Artificial Sequence
<220> FEATURE:
<223> OTHER INFORMATION: Synthetic

<400> SEQUENCE: 197

Ser Ile Tyr Ser Ser Tyr Ser Ser Thr Tyr Tyr Ala Asp Ser Val Lys
1               5                   10                  15

Gly

<210> SEQ ID NO 198
<211> LENGTH: 17
<212> TYPE: PRT
<213> ORGANISM: Artificial Sequence
<220> FEATURE:
<223> OTHER INFORMATION: Synthetic

<400> SEQUENCE: 198

Ser Ile Tyr Pro Tyr Tyr Ser Tyr Thr Ser Tyr Ala Asp Ser Val Lys
1               5                   10                  15

Gly

<210> SEQ ID NO 199
<211> LENGTH: 17
<212> TYPE: PRT
<213> ORGANISM: Artificial Sequence
<220> FEATURE:
<223> OTHER INFORMATION: Synthetic

<400> SEQUENCE: 199

Ser Ile Tyr Pro Tyr Tyr Ser Tyr Thr Ser Tyr Ala Asp Ser Val Lys
1               5                   10                  15

Gly

<210> SEQ ID NO 200
<211> LENGTH: 17
<212> TYPE: PRT
<213> ORGANISM: Artificial Sequence
<220> FEATURE:
<223> OTHER INFORMATION: Synthetic

<400> SEQUENCE: 200

Ser Ile Tyr Pro Tyr Tyr Ser Tyr Thr Tyr Tyr Ala Asp Ser Val Lys
1               5                   10                  15

Gly

<210> SEQ ID NO 201
<211> LENGTH: 17
<212> TYPE: PRT
<213> ORGANISM: Artificial Sequence
<220> FEATURE:
<223> OTHER INFORMATION: Synthetic

<400> SEQUENCE: 201

Ser Ile Tyr Pro Tyr Tyr Ser Tyr Thr Ser Tyr Ala Asp Ser Val Lys
1               5                   10                  15

Gly

<210> SEQ ID NO 202
<211> LENGTH: 17
<212> TYPE: PRT
<213> ORGANISM: Artificial Sequence
<220> FEATURE:
<223> OTHER INFORMATION: Synthetic
<220> FEATURE:
```

```
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (5)..(5)
<223> OTHER INFORMATION: Tyr or Ser
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (8)..(8)
<223> OTHER INFORMATION: Tyr or Ser
<220> FEATURE:
<221> NAME/KEY: MOD_RES
<222> LOCATION: (10)..(10)
<223> OTHER INFORMATION: Ser or Tyr

<400> SEQUENCE: 202

Ser Ile Xaa Xaa Xaa Tyr Xaa Xaa Thr Xaa Tyr Ala Asp Ser Val Lys
1               5                   10                  15
Gly

<210> SEQ ID NO 203
<211> LENGTH: 10
<212> TYPE: PRT
<213> ORGANISM: Artificial Sequence
<220> FEATURE:
<223> OTHER INFORMATION: Synthetic

<400> SEQUENCE: 203

Glu Gly Tyr Ser Gln Gly Gly Phe Asp Tyr
1               5                   10

<210> SEQ ID NO 204
<211> LENGTH: 10
<212> TYPE: PRT
<213> ORGANISM: Artificial Sequence
<220> FEATURE:
<223> OTHER INFORMATION: Synthetic

<400> SEQUENCE: 204

Ser Tyr Ser Tyr Tyr Ser Ala Ile Asp Tyr
1               5                   10

<210> SEQ ID NO 205
<211> LENGTH: 10
<212> TYPE: PRT
<213> ORGANISM: Artificial Sequence
<220> FEATURE:
<223> OTHER INFORMATION: Synthetic

<400> SEQUENCE: 205

Ser Tyr Ser Tyr Ser Tyr Gly Met Asp Tyr
1               5                   10

<210> SEQ ID NO 206
<211> LENGTH: 10
<212> TYPE: PRT
<213> ORGANISM: Artificial Sequence
<220> FEATURE:
<223> OTHER INFORMATION: Synthetic

<400> SEQUENCE: 206
```

```
Ser Tyr Ser Tyr Ser Tyr Gly Ile Asp Tyr
1               5                   10
```

<210> SEQ ID NO 207
<211> LENGTH: 10
<212> TYPE: PRT
<213> ORGANISM: Artificial Sequence
<220> FEATURE:
<223> OTHER INFORMATION: Synthetic

<400> SEQUENCE: 207

```
Ser Tyr Ser Tyr Tyr Ser Ala Met Asp Tyr
1               5                   10
```

<210> SEQ ID NO 208
<211> LENGTH: 10
<212> TYPE: PRT
<213> ORGANISM: Artificial Sequence
<220> FEATURE:
<223> OTHER INFORMATION: Synthetic

<400> SEQUENCE: 208

```
Gly Tyr Lys Tyr Trp Ser Ala Phe Asp Tyr
1               5                   10
```

<210> SEQ ID NO 209
<211> LENGTH: 11
<212> TYPE: PRT
<213> ORGANISM: Artificial Sequence
<220> FEATURE:
<223> OTHER INFORMATION: Synthetic

<400> SEQUENCE: 209

```
Glu Ser Phe Tyr Tyr Ser Pro Ala Phe Asp Tyr
1               5                   10
```

<210> SEQ ID NO 210
<211> LENGTH: 11
<212> TYPE: PRT
<213> ORGANISM: Artificial Sequence
<220> FEATURE:
<223> OTHER INFORMATION: Synthetic

<400> SEQUENCE: 210

```
Glu Tyr Tyr Ser Tyr Leu Gly Ala Ile Asp Tyr
1               5                   10
```

<210> SEQ ID NO 211
<211> LENGTH: 10
<212> TYPE: PRT
<213> ORGANISM: Artificial Sequence
<220> FEATURE:
<223> OTHER INFORMATION: Synthetic

<400> SEQUENCE: 211

```
Gly Tyr Glu Gly Gly Met Ala Met Asp Tyr
1               5                   10
```

<210> SEQ ID NO 212
<211> LENGTH: 10
<212> TYPE: PRT
<213> ORGANISM: Artificial Sequence
<220> FEATURE:
<223> OTHER INFORMATION: Synthetic

<400> SEQUENCE: 212

Ser Tyr Ser Tyr Ser Ser Gly Leu Asp Tyr
1               5                   10

<210> SEQ ID NO 213
<211> LENGTH: 10
<212> TYPE: PRT
<213> ORGANISM: Artificial Sequence
<220> FEATURE:
<223> OTHER INFORMATION: Synthetic

<400> SEQUENCE: 213

Gly Tyr Met Trp Tyr Gly Gly Ile Asp Tyr
1               5                   10

<210> SEQ ID NO 214
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: Variable amino acid

<400> SEQUENCE: 214

Asp Cys Tyr Tyr Xaa Ala Ala Phe Asp Tyr
1               5                   10

<210> SEQ ID NO 215
<211> LENGTH: 9
<212> TYPE: PRT
<213> ORGANISM: Artificial Sequence
<220> FEATURE:
<223> OTHER INFORMATION: Synthetic

<400> SEQUENCE: 215

Glu Asn Tyr Trp Trp Ala Ile Asp Tyr
1               5

<210> SEQ ID NO 216
<211> LENGTH: 10
<212> TYPE: PRT
<213> ORGANISM: Artificial Sequence
<220> FEATURE:
<223> OTHER INFORMATION: Synthetic

<400> SEQUENCE: 216

Ser Tyr Ser Tyr Tyr Ser Ala Phe Asp Tyr
1               5                   10

<210> SEQ ID NO 217
<211> LENGTH: 10
<212> TYPE: PRT
<213> ORGANISM: Artificial Sequence
<220> FEATURE:
<223> OTHER INFORMATION: Synthetic

<400> SEQUENCE: 217

Asp Tyr Tyr Phe Phe Ser Ala Ile Asp Tyr
1               5                   10

<210> SEQ ID NO 218
<211> LENGTH: 10
<212> TYPE: PRT
<213> ORGANISM: Artificial Sequence
<220> FEATURE:
<223> OTHER INFORMATION: Synthetic

<400> SEQUENCE: 218

Ser Tyr Ser Tyr Ser Ser Ala Leu Asp Tyr
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Synthetic

<400> SEQUENCE: 219

Glu Gly Tyr Ile Ser Gly Asp Ala Ile Asp Tyr
1               5                   10

<210> SEQ ID NO 220
<211> LENGTH: 10
<212> TYPE: PRT
<213> ORGANISM: Artificial Sequence
<220> FEATURE:
<223> OTHER INFORMATION: Synthetic

<400> SEQUENCE: 220

Ser Tyr Ser Ser Tyr Ser Ala Ile Asp Tyr
1               5                   10

<210> SEQ ID NO 221
<211> LENGTH: 11
<212> TYPE: PRT
<213> ORGANISM: Artificial Sequence
<220> FEATURE:
<223> OTHER INFORMATION: Synthetic

<400> SEQUENCE: 221

Gly Tyr Phe Glu Gly Trp Tyr Gly Leu Asp Tyr
1               5                   10

<210> SEQ ID NO 222
<211> LENGTH: 10
<212> TYPE: PRT
<213> ORGANISM: Artificial Sequence
<220> FEATURE:
<223> OTHER INFORMATION: Synthetic

<400> SEQUENCE: 222

Glu Tyr Ser Tyr Tyr Gly Gly Phe Asp Tyr
1               5                   10

<210> SEQ ID NO 223
<211> LENGTH: 10
<212> TYPE: PRT
<213> ORGANISM: Artificial Sequence
<220> FEATURE:
<223> OTHER INFORMATION: Synthetic

<400> SEQUENCE: 223

Glu Ser Tyr Trp Ser Tyr Ala Met Asp Tyr
1               5                   10

<210> SEQ ID NO 224
<211> LENGTH: 10
<212> TYPE: PRT
<213> ORGANISM: Artificial Sequence
<220> FEATURE:
<223> OTHER INFORMATION: Synthetic

```
<400> SEQUENCE: 224

Ser Tyr Ser Tyr Ser Tyr Gly Leu Asp Tyr
1               5                   10

<210> SEQ ID NO 225
<211> LENGTH: 10
<212> TYPE: PRT
<213> ORGANISM: Artificial Sequence
<220> FEATURE:
<223> OTHER INFORMATION: Synthetic

<400> SEQUENCE: 225

Tyr Tyr Ser Tyr Ser Ser Gly Leu Asp Tyr
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Synthetic

<400> SEQUENCE: 226

Ser Tyr Ser Tyr Ser Tyr Gly Leu Asp Tyr
1               5                   10

<210> SEQ ID NO 227
<211> LENGTH: 10
<212> TYPE: PRT
<213> ORGANISM: Artificial Sequence
<220> FEATURE:
<223> OTHER INFORMATION: Synthetic

<400> SEQUENCE: 227

Ser Tyr Ser Tyr Ser Tyr Gly Met Asp Tyr
1               5                   10

<210> SEQ ID NO 228
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Glu, Ser, Gly, Asp or Tyr
<220> FEATURE:
<221> NAME/KEY: MOD_RES
<222> LOCATION: (2)..(2)
<223> OTHER INFORMATION: Gly, Tyr, Ser, Cys or Asn
<220> FEATURE:
<221> NAME/KEY: MOD_RES
<222> LOCATION: (3)..(3)
<223> OTHER INFORMATION: Tyr, Ser, Lys, Phe, Glu or Met
<220> FEATURE:
<221> NAME/KEY: MOD_RES
<222> LOCATION: (4)..(4)
<223> OTHER INFORMATION: Ser, Tyr, Gly, Trp, Phe, Ile or Glu
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (6)..(6)
<223> OTHER INFORMATION: Gly, Ser, Tyr, Leu, Met, Gly, Ala or Trp
<220> FEATURE:
<221> NAME/KEY: MOD_RES
<222> LOCATION: (7)..(7)
<223> OTHER INFORMATION: Gly, Ala, Pro, Ile, Asp or Tyr
```

```
<220> FEATURE:
<221> NAME/KEY: MOD_RES
<222> LOCATION: (8)..(8)
<223> OTHER INFORMATION: Phe, Ile, Met, Ala, Leu, Gly or not present
<220> FEATURE:
<221> NAME/KEY: MOD_RES
<222> LOCATION: (9)..(9)
<223> OTHER INFORMATION: Phe, Ile, Leu or not present

<400> SEQUENCE: 228

Xaa Xaa Xaa Xaa Xaa Xaa Xaa Xaa Xaa Asp Tyr
1               5                   10

<210> SEQ ID NO 229
<211> LENGTH: 10
<212> TYPE: PRT
<213> ORGANISM: Artificial Sequence
<220> FEATURE:
<223> OTHER INFORMATION: Synthetic

<400> SEQUENCE: 229

Gly Phe Asn Ile Ser Ser Ser Tyr Ile His
1               5                   10

<210> SEQ ID NO 230
<211> LENGTH: 10
<212> TYPE: PRT
<213> ORGANISM: Artificial Sequence
<220> FEATURE:
<223> OTHER INFORMATION: Synthetic

<400> SEQUENCE: 230

Gly Phe Asn Val Ser Ser Tyr Ser Ile His
1               5                   10

<210> SEQ ID NO 231
<211> LENGTH: 10
<212> TYPE: PRT
<213> ORGANISM: Artificial Sequence
<220> FEATURE:
<223> OTHER INFORMATION: Synthetic

<400> SEQUENCE: 231

Gly Phe Asn Phe Ser Tyr Ser Ser Ile His
1               5                   10

<210> SEQ ID NO 232
<211> LENGTH: 10
<212> TYPE: PRT
<213> ORGANISM: Artificial Sequence
<220> FEATURE:
<223> OTHER INFORMATION: Synthetic

<400> SEQUENCE: 232

Gly Phe Asn Phe Tyr Ser Ser Ser Ile His
1               5                   10

<210> SEQ ID NO 233
<211> LENGTH: 10
<212> TYPE: PRT
<213> ORGANISM: Artificial Sequence
<220> FEATURE:
<223> OTHER INFORMATION: Synthetic

<400> SEQUENCE: 233

Gly Phe Asn Phe Tyr Tyr Ser Ser Ile His
1               5                   10
```

<210> SEQ ID NO 234
<211> LENGTH: 10
<212> TYPE: PRT
<213> ORGANISM: Artificial Sequence
<220> FEATURE:
<223> OTHER INFORMATION: Synthetic

<400> SEQUENCE: 234

Gly Phe Asn Val Tyr Tyr Ser Ser Ile His
1               5                   10

<210> SEQ ID NO 235
<211> LENGTH: 10
<212> TYPE: PRT
<213> ORGANISM: Artificial Sequence
<220> FEATURE:
<223> OTHER INFORMATION: Synthetic

<400> SEQUENCE: 235

Gly Phe Asn Phe Tyr Tyr Ser Tyr Ile His
1               5                   10

<210> SEQ ID NO 236
<211> LENGTH: 10
<212> TYPE: PRT
<213> ORGANISM: Artificial Sequence
<220> FEATURE:
<223> OTHER INFORMATION: Synthetic

<400> SEQUENCE: 236

Gly Phe Asn Val Ser Ser Ser Tyr Ile His
1               5                   10

<210> SEQ ID NO 237
<211> LENGTH: 10
<212> TYPE: PRT
<213> ORGANISM: Artificial Sequence
<220> FEATURE:
<223> OTHER INFORMATION: Synthetic

<400> SEQUENCE: 237

Gly Phe Asn Phe Tyr Tyr Ser Ser Ile His
1               5                   10

<210> SEQ ID NO 238
<211> LENGTH: 10
<212> TYPE: PRT
<213> ORGANISM: Artificial Sequence
<220> FEATURE:
<223> OTHER INFORMATION: Synthetic

<400> SEQUENCE: 238

Gly Phe Asn Phe Tyr Ser Ser Tyr Met His
1               5                   10

<210> SEQ ID NO 239
<211> LENGTH: 10
<212> TYPE: PRT
<213> ORGANISM: Artificial Sequence
<220> FEATURE:
<223> OTHER INFORMATION: Synthetic

<400> SEQUENCE: 239

Gly Phe Asn Val Ser Ser Tyr Ser Ile His
1               5                   10

```
<210> SEQ ID NO 240
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Ile, Val or Phe
<220> FEATURE:
<221> NAME/KEY: MOD_RES
<222> LOCATION: (5)..(8)
<223> OTHER INFORMATION: Ser or Tyr
<220> FEATURE:
<221> NAME/KEY: MOD_RES
<222> LOCATION: (9)..(9)
<223> OTHER INFORMATION: Ile or Met

<400> SEQUENCE: 240

Gly Phe Asn Xaa Xaa Xaa Xaa Xaa Xaa His
1               5                   10

<210> SEQ ID NO 241
<211> LENGTH: 17
<212> TYPE: PRT
<213> ORGANISM: Artificial Sequence
<220> FEATURE:
<223> OTHER INFORMATION: Synthetic

<400> SEQUENCE: 241

Tyr Ile Ser Pro Tyr Tyr Gly Ser Thr Ser Tyr Ala Asp Ser Val Lys
1               5                   10                  15

Gly

<210> SEQ ID NO 242
<211> LENGTH: 17
<212> TYPE: PRT
<213> ORGANISM: Artificial Sequence
<220> FEATURE:
<223> OTHER INFORMATION: Synthetic

<400> SEQUENCE: 242

Ser Ile Tyr Pro Ser Ser Gly Ser Thr Tyr Tyr Ala Asp Ser Val Lys
1               5                   10                  15

Gly

<210> SEQ ID NO 243
<211> LENGTH: 17
<212> TYPE: PRT
<213> ORGANISM: Artificial Sequence
<220> FEATURE:
<223> OTHER INFORMATION: Synthetic

<400> SEQUENCE: 243

Ser Ile Tyr Ser Ser Tyr Ser Ser Thr Ser Tyr Ala Asp Ser Val Lys
1               5                   10                  15

Gly

<210> SEQ ID NO 244
<211> LENGTH: 17
<212> TYPE: PRT
<213> ORGANISM: Artificial Sequence
<220> FEATURE:
<223> OTHER INFORMATION: Synthetic

<400> SEQUENCE: 244
```

```
Ser Ile Ser Ser Tyr Tyr Gly Ser Thr Ser Tyr Ala Asp Ser Val Lys
1               5                   10                  15

Gly

<210> SEQ ID NO 245
<211> LENGTH: 17
<212> TYPE: PRT
<213> ORGANISM: Artificial Sequence
<220> FEATURE:
<223> OTHER INFORMATION: Synthetic

<400> SEQUENCE: 245

Ser Ile Tyr Ser Ser Tyr Gly Tyr Thr Ser Tyr Ala Asp Ser Val Lys
1               5                   10                  15

Gly

<210> SEQ ID NO 246
<211> LENGTH: 17
<212> TYPE: PRT
<213> ORGANISM: Artificial Sequence
<220> FEATURE:
<223> OTHER INFORMATION: Synthetic

<400> SEQUENCE: 246

Ser Ile Ser Pro Ser Tyr Gly Tyr Thr Tyr Tyr Ala Asp Ser Val Lys
1               5                   10                  15

Gly

<210> SEQ ID NO 247
<211> LENGTH: 17
<212> TYPE: PRT
<213> ORGANISM: Artificial Sequence
<220> FEATURE:
<223> OTHER INFORMATION: Synthetic

<400> SEQUENCE: 247

Tyr Ile Ser Pro Ser Tyr Ser Ser Thr Tyr Tyr Ala Asp Ser Val Lys
1               5                   10                  15

Gly

<210> SEQ ID NO 248
<211> LENGTH: 17
<212> TYPE: PRT
<213> ORGANISM: Artificial Sequence
<220> FEATURE:
<223> OTHER INFORMATION: Synthetic

<400> SEQUENCE: 248

Ser Ile Ser Ser Ser Tyr Ser Tyr Thr Ser Tyr Ala Asp Ser Val Lys
1               5                   10                  15

Gly

<210> SEQ ID NO 249
<211> LENGTH: 17
<212> TYPE: PRT
<213> ORGANISM: Artificial Sequence
<220> FEATURE:
<223> OTHER INFORMATION: Synthetic

<400> SEQUENCE: 249

Ser Ile Tyr Ser Ser Tyr Ser Ser Thr Ser Tyr Ala Asp Ser Val Lys
1               5                   10                  15

Gly
```

<210> SEQ ID NO 250
<211> LENGTH: 17
<212> TYPE: PRT
<213> ORGANISM: Artificial Sequence
<220> FEATURE:
<223> OTHER INFORMATION: Synthetic

<400> SEQUENCE: 250

Tyr Ile Ser Ser Tyr Ser Gly Tyr Thr Tyr Tyr Ala Asp Ser Val Lys
1               5                   10                  15

Gly

<210> SEQ ID NO 251
<211> LENGTH: 17
<212> TYPE: PRT
<213> ORGANISM: Artificial Sequence
<220> FEATURE:
<223> OTHER INFORMATION: Synthetic

<400> SEQUENCE: 251

Ser Ile Tyr Pro Ser Ser Gly Ser Thr Tyr Tyr Ala Asp Ser Val Lys
1               5                   10                  15

Gly

<210> SEQ ID NO 252
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Tyr or Ser
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (5)..(6)
<223> OTHER INFORMATION: Tyr or Ser
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Ser or Tyr
<220> FEATURE:
<221> NAME/KEY: MOD_RES
<222> LOCATION: (10)..(10)
<223> OTHER INFORMATION: Ser or Tyr

<400> SEQUENCE: 252

Xaa Ile Xaa Xaa Xaa Xaa Xaa Thr Xaa Tyr Ala Asp Ser Val Lys
1               5                   10                  15

Gly

<210> SEQ ID NO 253
<211> LENGTH: 11
<212> TYPE: PRT
<213> ORGANISM: Artificial Sequence

```
<220> FEATURE:
<223> OTHER INFORMATION: Synthetic

<400> SEQUENCE: 253

Glu Tyr Tyr Arg Trp Tyr Thr Ala Ile Asp Tyr
1               5                   10

<210> SEQ ID NO 254
<211> LENGTH: 21
<212> TYPE: PRT
<213> ORGANISM: Artificial Sequence
<220> FEATURE:
<223> OTHER INFORMATION: Synthetic

<400> SEQUENCE: 254

Ser Gly Tyr Tyr Tyr Gln Gly Tyr Trp Trp Tyr Tyr Tyr Thr Gly Tyr
1               5                   10                  15

Tyr Gly Met Asp Tyr
            20

<210> SEQ ID NO 255
<211> LENGTH: 19
<212> TYPE: PRT
<213> ORGANISM: Artificial Sequence
<220> FEATURE:
<223> OTHER INFORMATION: Synthetic

<400> SEQUENCE: 255

Gly Ile Met Phe Ser Ser Trp Trp Trp Tyr Tyr Asp Tyr Ser Asp Ala
1               5                   10                  15

Leu Asp Tyr

<210> SEQ ID NO 256
<211> LENGTH: 19
<212> TYPE: PRT
<213> ORGANISM: Artificial Sequence
<220> FEATURE:
<223> OTHER INFORMATION: Synthetic

<400> SEQUENCE: 256

Gly Ser Ile Pro Ser Tyr Trp Ser Ala Asp Trp Tyr Tyr Tyr Tyr Gly
1               5                   10                  15

Leu Asp Tyr

<210> SEQ ID NO 257
<211> LENGTH: 17
<212> TYPE: PRT
<213> ORGANISM: Artificial Sequence
<220> FEATURE:
<223> OTHER INFORMATION: Synthetic

<400> SEQUENCE: 257

Glu Tyr Tyr Trp Trp Tyr Lys Glu Ala Trp Tyr Ser Ala Gly Met Asp
1               5                   10                  15

Tyr

<210> SEQ ID NO 258
<211> LENGTH: 21
<212> TYPE: PRT
<213> ORGANISM: Artificial Sequence
<220> FEATURE:
<223> OTHER INFORMATION: Synthetic

<400> SEQUENCE: 258
```

```
Trp Gln Gly Tyr Gly Phe Lys Tyr Tyr Trp Ser Tyr Tyr Val Ser Tyr
1               5                   10                  15

Gly Gly Leu Asp Tyr
            20

<210> SEQ ID NO 259
<211> LENGTH: 14
<212> TYPE: PRT
<213> ORGANISM: Artificial Sequence
<220> FEATURE:
<223> OTHER INFORMATION: Synthetic

<400> SEQUENCE: 259

Ser Tyr Ser Tyr Tyr Tyr Ser Ser Tyr Gly Phe Asp Tyr
1               5                   10

<210> SEQ ID NO 260
<211> LENGTH: 13
<212> TYPE: PRT
<213> ORGANISM: Artificial Sequence
<220> FEATURE:
<223> OTHER INFORMATION: Synthetic

<400> SEQUENCE: 260

Glu Ser Tyr Ala Gly Val Pro Pro Tyr Gly Phe Asp Tyr
1               5                   10

<210> SEQ ID NO 261
<211> LENGTH: 19
<212> TYPE: PRT
<213> ORGANISM: Artificial Sequence
<220> FEATURE:
<223> OTHER INFORMATION: Synthetic

<400> SEQUENCE: 261

Gly Ile Met Phe Ser Ser Trp Trp Trp Tyr Tyr Asp Tyr Ser Asp Ala
1               5                   10                  15

Leu Asp Tyr

<210> SEQ ID NO 262
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Glu, Ser, Gly or Trp
<220> FEATURE:
<221> NAME/KEY: MOD_RES
<222> LOCATION: (2)..(2)
<223> OTHER INFORMATION: Tyr, Gly, Ile, Ser or Gln
<220> FEATURE:
<221> NAME/KEY: MOD_RES
<222> LOCATION: (3)..(3)
<223> OTHER INFORMATION: Tyr, Met, Ile, Gly or Ser
<220> FEATURE:
<221> NAME/KEY: MOD_RES
<222> LOCATION: (4)..(4)
<223> OTHER INFORMATION: Arg, Tyr, Phe, Pro or Trp
<220> FEATURE:
<221> NAME/KEY: MOD_RES
<222> LOCATION: (5)..(5)
<223> OTHER INFORMATION: Trp, Tyr, Ser or Gly
<220> FEATURE:
<221> NAME/KEY: MOD_RES
<222> LOCATION: (6)..(6)
<223> OTHER INFORMATION: Tyr, Gln, Ser, Phe or Val
<220> FEATURE:
```

```
<221> NAME/KEY: MOD_RES
<222> LOCATION: (7)..(7)
<223> OTHER INFORMATION: Thr, Gly, Trp, Lys, Tyr or Pro
<220> FEATURE:
<221> NAME/KEY: MOD_RES
<222> LOCATION: (8)..(8)
<223> OTHER INFORMATION: Ala, Tyr, Trp, Ser, Glu or Pro
<220> FEATURE:
<221> NAME/KEY: MOD_RES
<222> LOCATION: (9)..(9)
<223> OTHER INFORMATION: Ile, Trp, Ala, Tyr or Ser
<220> FEATURE:
<221> NAME/KEY: MOD_RES
<222> LOCATION: (10)..(10)
<223> OTHER INFORMATION: Trp, Tyr, Asp or Gly
<220> FEATURE:
<221> NAME/KEY: MOD_RES
<222> LOCATION: (11)..(11)
<223> OTHER INFORMATION: Tyr, Trp, Ser, Gly or Phe
<220> FEATURE:
<221> NAME/KEY: MOD_RES
<222> LOCATION: (12)..(12)
<223> OTHER INFORMATION: Tyr, Asp, Ser, Phe or not present
<220> FEATURE:
<221> NAME/KEY: MOD_RES
<222> LOCATION: (13)..(13)
<223> OTHER INFORMATION: Tyr, Ala or not present
<220> FEATURE:
<221> NAME/KEY: MOD_RES
<222> LOCATION: (14)..(14)
<223> OTHER INFORMATION: Thr, Ser, Tyr, Gly, Val or not present
<220> FEATURE:
<221> NAME/KEY: MOD_RES
<222> LOCATION: (15)..(15)
<223> OTHER INFORMATION: Gly, Asp, Tyr, Met, Ser or not present
<220> FEATURE:
<221> NAME/KEY: MOD_RES
<222> LOCATION: (16)..(16)
<223> OTHER INFORMATION: Tyr, Ala, Gly or not present
<220> FEATURE:
<221> NAME/KEY: MOD_RES
<222> LOCATION: (17)..(17)
<223> OTHER INFORMATION: Tyr, Leu, Gly or not present
<220> FEATURE:
<221> NAME/KEY: MOD_RES
<222> LOCATION: (18)..(18)
<223> OTHER INFORMATION: Gly or not present
<220> FEATURE:
<221> NAME/KEY: MOD_RES
<222> LOCATION: (19)..(19)
<223> OTHER INFORMATION: Met, Leu or not present

<400> SEQUENCE: 262

Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 263
<211> LENGTH: 10
<212> TYPE: PRT
<213> ORGANISM: Artificial Sequence
<220> FEATURE:
<223> OTHER INFORMATION: Synthetic

<400> SEQUENCE: 263

Gly Phe Asn Val Tyr Tyr Ser Ser Ile His
1               5                   10

<210> SEQ ID NO 264
<211> LENGTH: 10
<212> TYPE: PRT
<213> ORGANISM: Artificial Sequence
<220> FEATURE:
```

<223> OTHER INFORMATION: Synthetic

<400> SEQUENCE: 264

Gly Phe Asn Val Ser Tyr Ser Tyr Met His
1               5                   10

<210> SEQ ID NO 265
<211> LENGTH: 10
<212> TYPE: PRT
<213> ORGANISM: Artificial Sequence
<220> FEATURE:
<223> OTHER INFORMATION: Synthetic

<400> SEQUENCE: 265

Gly Phe Asn Phe Ser Tyr Tyr Ser Met His
1               5                   10

<210> SEQ ID NO 266
<211> LENGTH: 10
<212> TYPE: PRT
<213> ORGANISM: Artificial Sequence
<220> FEATURE:
<223> OTHER INFORMATION: Synthetic

<400> SEQUENCE: 266

Gly Phe Asn Leu Ser Tyr Tyr Ser Ile His
1               5                   10

<210> SEQ ID NO 267
<211> LENGTH: 10
<212> TYPE: PRT
<213> ORGANISM: Artificial Sequence
<220> FEATURE:
<223> OTHER INFORMATION: Synthetic

<400> SEQUENCE: 267

Gly Phe Asn Ile Ser Tyr Ser Ser Met His
1               5                   10

<210> SEQ ID NO 268
<211> LENGTH: 10
<212> TYPE: PRT
<213> ORGANISM: Artificial Sequence
<220> FEATURE:
<223> OTHER INFORMATION: Synthetic

<400> SEQUENCE: 268

Gly Phe Asn Val Tyr Tyr Ser Ser Ile His
1               5                   10

<210> SEQ ID NO 269
<211> LENGTH: 10
<212> TYPE: PRT
<213> ORGANISM: Artificial Sequence
<220> FEATURE:
<223> OTHER INFORMATION: Synthetic

<400> SEQUENCE: 269

Gly Phe Asn Leu Ser Tyr Ser Tyr Ile His
1               5                   10

<210> SEQ ID NO 270
<211> LENGTH: 10
<212> TYPE: PRT
<213> ORGANISM: Artificial Sequence
<220> FEATURE:
<223> OTHER INFORMATION: Synthetic

<400> SEQUENCE: 270

Gly Phe Asn Leu Ser Tyr Ser Ser Met His
1               5                   10

<210> SEQ ID NO 271
<211> LENGTH: 10
<212> TYPE: PRT
<213> ORGANISM: Artificial Sequence
<220> FEATURE:
<223> OTHER INFORMATION: Synthetic

<400> SEQUENCE: 271

Gly Phe Asn Val Ser Tyr Ser Ser Ile His
1               5                   10

<210> SEQ ID NO 272
<211> LENGTH: 10
<212> TYPE: PRT
<213> ORGANISM: Artificial Sequence
<220> FEATURE:
<223> OTHER INFORMATION: Synthetic

<400> SEQUENCE: 272

Gly Phe Asn Val Ser Tyr Ser Ser Ile His
1               5                   10

<210> SEQ ID NO 273
<211> LENGTH: 10
<212> TYPE: PRT
<213> ORGANISM: Artificial Sequence
<220> FEATURE:
<223> OTHER INFORMATION: Synthetic

<400> SEQUENCE: 273

Gly Phe Asn Val Ser Tyr Tyr Tyr Ile His
1               5                   10

<210> SEQ ID NO 274
<211> LENGTH: 10
<212> TYPE: PRT
<213> ORGANISM: Artificial Sequence
<220> FEATURE:
<223> OTHER INFORMATION: Synthetic

<400> SEQUENCE: 274

Gly Phe Asn Leu Tyr Tyr Ser Tyr Met His
1               5                   10

<210> SEQ ID NO 275
<211> LENGTH: 10
<212> TYPE: PRT
<213> ORGANISM: Artificial Sequence
<220> FEATURE:
<223> OTHER INFORMATION: Synthetic

<400> SEQUENCE: 275

Gly Phe Asn Val Ser Tyr Tyr Ser Ile His
1               5                   10

<210> SEQ ID NO 276
<211> LENGTH: 10
<212> TYPE: PRT
<213> ORGANISM: Artificial Sequence
<220> FEATURE:
<223> OTHER INFORMATION: Synthetic

```
<400> SEQUENCE: 276

Gly Phe Asn Ile Ser Tyr Ser Ser Ile His
1               5                   10

<210> SEQ ID NO 277
<211> LENGTH: 10
<212> TYPE: PRT
<213> ORGANISM: Artificial Sequence
<220> FEATURE:
<223> OTHER INFORMATION: Synthetic

<400> SEQUENCE: 277

Gly Phe Asn Phe Ser Tyr Tyr Ser Ile His
1               5                   10

<210> SEQ ID NO 278
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Val, Phe, Leu or Ile
<220> FEATURE:
<221> NAME/KEY: MOD_RES
<222> LOCATION: (5)..(5)
<223> OTHER INFORMATION: Tyr or Ser
<220> FEATURE:
<221> NAME/KEY: MOD_RES
<222> LOCATION: (7)..(8)
<223> OTHER INFORMATION: Ser or Tyr
<220> FEATURE:
<221> NAME/KEY: MOD_RES
<222> LOCATION: (9)..(9)
<223> OTHER INFORMATION: Ile or Met

<400> SEQUENCE: 278

Gly Phe Asn Xaa Xaa Tyr Xaa Xaa Xaa His
1               5                   10

<210> SEQ ID NO 279
<211> LENGTH: 17
<212> TYPE: PRT
<213> ORGANISM: Artificial Sequence
<220> FEATURE:
<223> OTHER INFORMATION: Synthetic

<400> SEQUENCE: 279

Ser Ile Ser Pro Tyr Tyr Ser Tyr Thr Ser Tyr Ala Asp Ser Val Lys
1               5                   10                  15

Gly

<210> SEQ ID NO 280
<211> LENGTH: 17
<212> TYPE: PRT
<213> ORGANISM: Artificial Sequence
<220> FEATURE:
<223> OTHER INFORMATION: Synthetic

<400> SEQUENCE: 280

Ser Ile Ser Ser Tyr Tyr Ser Tyr Thr Ser Tyr Ala Asp Ser Val Lys
1               5                   10                  15

Gly

<210> SEQ ID NO 281
```

```
<211> LENGTH: 17
<212> TYPE: PRT
<213> ORGANISM: Artificial Sequence
<220> FEATURE:
<223> OTHER INFORMATION: Synthetic

<400> SEQUENCE: 281

Ser Ile Tyr Pro Tyr Tyr Gly Tyr Thr Tyr Tyr Ala Asp Ser Val Lys
1               5                   10                  15
Gly

<210> SEQ ID NO 282
<211> LENGTH: 17
<212> TYPE: PRT
<213> ORGANISM: Artificial Sequence
<220> FEATURE:
<223> OTHER INFORMATION: Synthetic

<400> SEQUENCE: 282

Ser Ile Tyr Pro Tyr Tyr Gly Tyr Thr Ser Tyr Ala Asp Ser Val Lys
1               5                   10                  15
Gly

<210> SEQ ID NO 283
<211> LENGTH: 17
<212> TYPE: PRT
<213> ORGANISM: Artificial Sequence
<220> FEATURE:
<223> OTHER INFORMATION: Synthetic

<400> SEQUENCE: 283

Ser Ile Tyr Ser Tyr Tyr Ser Tyr Thr Ser Tyr Ala Asp Ser Val Lys
1               5                   10                  15
Gly

<210> SEQ ID NO 284
<211> LENGTH: 17
<212> TYPE: PRT
<213> ORGANISM: Artificial Sequence
<220> FEATURE:
<223> OTHER INFORMATION: Synthetic

<400> SEQUENCE: 284

Ser Ile Tyr Pro Tyr Tyr Gly Tyr Thr Ser Tyr Ala Asp Ser Val Lys
1               5                   10                  15
Gly

<210> SEQ ID NO 285
<211> LENGTH: 17
<212> TYPE: PRT
<213> ORGANISM: Artificial Sequence
<220> FEATURE:
<223> OTHER INFORMATION: Synthetic

<400> SEQUENCE: 285

Ser Ile Ser Ser Tyr Tyr Gly Ser Thr Ser Tyr Ala Asp Ser Val Lys
1               5                   10                  15
Gly

<210> SEQ ID NO 286
<211> LENGTH: 17
<212> TYPE: PRT
<213> ORGANISM: Artificial Sequence
<220> FEATURE:
```

<223> OTHER INFORMATION: Synthetic

<400> SEQUENCE: 286

Ser Ile Tyr Pro Tyr Tyr Ser Tyr Thr Ser Tyr Ala Asp Ser Val Lys
1               5                   10                  15

Gly

<210> SEQ ID NO 287
<211> LENGTH: 17
<212> TYPE: PRT
<213> ORGANISM: Artificial Sequence
<220> FEATURE:
<223> OTHER INFORMATION: Synthetic

<400> SEQUENCE: 287

Ser Ile Tyr Pro Tyr Tyr Ser Tyr Thr Ser Tyr Ala Asp Ser Val Lys
1               5                   10                  15

Gly

<210> SEQ ID NO 288
<211> LENGTH: 17
<212> TYPE: PRT
<213> ORGANISM: Artificial Sequence
<220> FEATURE:
<223> OTHER INFORMATION: Synthetic

<400> SEQUENCE: 288

Ser Ile Tyr Ser Tyr Tyr Ser Tyr Thr Ser Tyr Ala Asp Ser Val Lys
1               5                   10                  15

Gly

<210> SEQ ID NO 289
<211> LENGTH: 17
<212> TYPE: PRT
<213> ORGANISM: Artificial Sequence
<220> FEATURE:
<223> OTHER INFORMATION: Synthetic

<400> SEQUENCE: 289

Ser Ile Ser Ser Tyr Tyr Gly Tyr Thr Ser Tyr Ala Asp Ser Val Lys
1               5                   10                  15

Gly

<210> SEQ ID NO 290
<211> LENGTH: 17
<212> TYPE: PRT
<213> ORGANISM: Artificial Sequence
<220> FEATURE:
<223> OTHER INFORMATION: Synthetic

<400> SEQUENCE: 290

Ser Ile Ser Ser Tyr Tyr Ser Tyr Thr Ser Tyr Ala Asp Ser Val Lys
1               5                   10                  15

Gly

<210> SEQ ID NO 291
<211> LENGTH: 17
<212> TYPE: PRT
<213> ORGANISM: Artificial Sequence
<220> FEATURE:
<223> OTHER INFORMATION: Synthetic

<400> SEQUENCE: 291

Ser Ile Tyr Pro Tyr Tyr Ser Tyr Thr Ser Tyr Ala Asp Ser Val Lys
1               5                   10                  15

Gly

<210> SEQ ID NO 292
<211> LENGTH: 17
<212> TYPE: PRT
<213> ORGANISM: Artificial Sequence
<220> FEATURE:
<223> OTHER INFORMATION: Synthetic

<400> SEQUENCE: 292

Ser Ile Tyr Pro Tyr Tyr Ser Tyr Thr Ser Tyr Ala Asp Ser Val Lys
1               5                   10                  15

Gly

<210> SEQ ID NO 293
<211> LENGTH: 17
<212> TYPE: PRT
<213> ORGANISM: Artificial Sequence
<220> FEATURE:
<223> OTHER INFORMATION: Synthetic

<400> SEQUENCE: 293

Ser Ile Tyr Pro Tyr Tyr Ser Tyr Thr Tyr Tyr Ala Asp Ser Val Lys
1               5                   10                  15

Gly

<210> SEQ ID NO 294
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (8)..(8)
<223> OTHER INFORMATION: Tyr or Ser
<220> FEATURE:
<221> NAME/KEY: MOD_RES
<222> LOCATION: (10)..(10)
<223> OTHER INFORMATION: Ser or Tyr

<400> SEQUENCE: 294

Ser Ile Xaa Xaa Tyr Tyr Xaa Xaa Thr Xaa Tyr Ala Asp Ser Val Lys
1               5                   10                  15

Gly

<210> SEQ ID NO 295
<211> LENGTH: 10
<212> TYPE: PRT
<213> ORGANISM: Artificial Sequence
<220> FEATURE:
<223> OTHER INFORMATION: Synthetic

<400> SEQUENCE: 295

```
Glu Gly Tyr Ser Gln Gly Gly Phe Asp Tyr
1               5                   10

<210> SEQ ID NO 296
<211> LENGTH: 10
<212> TYPE: PRT
<213> ORGANISM: Artificial Sequence
<220> FEATURE:
<223> OTHER INFORMATION: Synthetic

<400> SEQUENCE: 296

Ser Tyr Ser Tyr Tyr Ser Ala Ile Asp Tyr
1               5                   10

<210> SEQ ID NO 297
<211> LENGTH: 10
<212> TYPE: PRT
<213> ORGANISM: Artificial Sequence
<220> FEATURE:
<223> OTHER INFORMATION: Synthetic

<400> SEQUENCE: 297

Ser Tyr Ser Tyr Ser Tyr Gly Met Asp Tyr
1               5                   10

<210> SEQ ID NO 298
<211> LENGTH: 10
<212> TYPE: PRT
<213> ORGANISM: Artificial Sequence
<220> FEATURE:
<223> OTHER INFORMATION: Synthetic

<400> SEQUENCE: 298

Ser Tyr Ser Tyr Ser Tyr Gly Ile Asp Tyr
1               5                   10

<210> SEQ ID NO 299
<211> LENGTH: 10
<212> TYPE: PRT
<213> ORGANISM: Artificial Sequence
<220> FEATURE:
<223> OTHER INFORMATION: Synthetic

<400> SEQUENCE: 299

Ser Tyr Ser Tyr Tyr Ser Ala Met Asp Tyr
1               5                   10

<210> SEQ ID NO 300
<211> LENGTH: 10
<212> TYPE: PRT
<213> ORGANISM: Artificial Sequence
<220> FEATURE:
<223> OTHER INFORMATION: Synthetic

<400> SEQUENCE: 300

Gly Tyr Lys Tyr Trp Ser Ala Phe Asp Tyr
1               5                   10

<210> SEQ ID NO 301
<211> LENGTH: 11
<212> TYPE: PRT
<213> ORGANISM: Artificial Sequence
<220> FEATURE:
<223> OTHER INFORMATION: Synthetic

<400> SEQUENCE: 301
```

Glu Ser Phe Tyr Tyr Ser Pro Ala Phe Asp Tyr
1               5                   10

<210> SEQ ID NO 302
<211> LENGTH: 10
<212> TYPE: PRT
<213> ORGANISM: Artificial Sequence
<220> FEATURE:
<223> OTHER INFORMATION: Synthetic

<400> SEQUENCE: 302

Gly Tyr Glu Gly Gly Met Ala Met Asp Tyr
1               5                   10

<210> SEQ ID NO 303
<211> LENGTH: 10
<212> TYPE: PRT
<213> ORGANISM: Artificial Sequence
<220> FEATURE:
<223> OTHER INFORMATION: Synthetic

<400> SEQUENCE: 303

Ser Tyr Ser Tyr Ser Ser Gly Leu Asp Tyr
1               5                   10

<210> SEQ ID NO 304
<211> LENGTH: 10
<212> TYPE: PRT
<213> ORGANISM: Artificial Sequence
<220> FEATURE:
<223> OTHER INFORMATION: Synthetic

<400> SEQUENCE: 304

Gly Tyr Met Trp Tyr Gly Gly Ile Asp Tyr
1               5                   10

<210> SEQ ID NO 305
<211> LENGTH: 9
<212> TYPE: PRT
<213> ORGANISM: Artificial Sequence
<220> FEATURE:
<223> OTHER INFORMATION: Synthetic

<400> SEQUENCE: 305

Glu Asn Tyr Trp Trp Ala Ile Asp Tyr
1               5

<210> SEQ ID NO 306
<211> LENGTH: 10
<212> TYPE: PRT
<213> ORGANISM: Artificial Sequence
<220> FEATURE:
<223> OTHER INFORMATION: Synthetic

<400> SEQUENCE: 306

Ser Tyr Ser Tyr Ser Ser Ala Leu Asp Tyr
1               5                   10

<210> SEQ ID NO 307
<211> LENGTH: 10
<212> TYPE: PRT
<213> ORGANISM: Artificial Sequence
<220> FEATURE:
<223> OTHER INFORMATION: Synthetic

<400> SEQUENCE: 307

Ser Tyr Ser Tyr Ser Tyr Gly Leu Asp Tyr

<210> SEQ ID NO 308
<211> LENGTH: 10
<212> TYPE: PRT
<213> ORGANISM: Artificial Sequence
<220> FEATURE:
<223> OTHER INFORMATION: Synthetic

<400> SEQUENCE: 308

Tyr Tyr Ser Tyr Ser Ser Gly Leu Asp Tyr
1               5                   10

<210> SEQ ID NO 309
<211> LENGTH: 10
<212> TYPE: PRT
<213> ORGANISM: Artificial Sequence
<220> FEATURE:
<223> OTHER INFORMATION: Synthetic

<400> SEQUENCE: 309

Ser Tyr Ser Tyr Ser Tyr Gly Leu Asp Tyr
1               5                   10

<210> SEQ ID NO 310
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Glu, Ser, Gly or Tyr
<220> FEATURE:
<221> NAME/KEY: MOD_RES
<222> LOCATION: (2)..(2)
<223> OTHER INFORMATION: Gly, Tyr, Ser or Asn
<220> FEATURE:
<221> NAME/KEY: MOD_RES
<222> LOCATION: (3)..(3)
<223> OTHER INFORMATION: Tyr, Ser, Lys, Phe or Glu
<220> FEATURE:
<221> NAME/KEY: MOD_RES
<222> LOCATION: (4)..(4)
<223> OTHER INFORMATION: Ser, Tyr, Gly or Trp
<220> FEATURE:
<221> NAME/KEY: MOD_RES
<222> LOCATION: (5)..(5)
<223> OTHER INFORMATION: Gln, Tyr, Ser or Gly
<220> FEATURE:
<221> NAME/KEY: MOD_RES
<222> LOCATION: (6)..(6)
<223> OTHER INFORMATION: Gly, Ser, Tyr, Met or Ala
<220> FEATURE:
<221> NAME/KEY: MOD_RES
<222> LOCATION: (7)..(7)
<223> OTHER INFORMATION: Gly, Ala, Pro or Ile
<220> FEATURE:
<221> NAME/KEY: MOD_RES
<222> LOCATION: (8)..(8)
<223> OTHER INFORMATION: Phe, Ile, Met, Ala, Leu or not present
<220> FEATURE:
<221> NAME/KEY: MOD_RES
<222> LOCATION: (9)..(9)
<223> OTHER INFORMATION: Phe or not present

<400> SEQUENCE: 310

Xaa Xaa Xaa Xaa Xaa Xaa Xaa Xaa Xaa Asp Tyr
1               5                   10

<210> SEQ ID NO 311

```
<211> LENGTH: 10
<212> TYPE: PRT
<213> ORGANISM: Artificial Sequence
<220> FEATURE:
<223> OTHER INFORMATION: Synthetic

<400> SEQUENCE: 311

Gln Gln Ser Ser Tyr Ser Ser Leu Phe Thr
1               5                   10

<210> SEQ ID NO 312
<211> LENGTH: 10
<212> TYPE: PRT
<213> ORGANISM: Artificial Sequence
<220> FEATURE:
<223> OTHER INFORMATION: Synthetic

<400> SEQUENCE: 312

Gln Gln Ser Ser Tyr Ser Ser Leu Phe Thr
1               5                   10

<210> SEQ ID NO 313
<211> LENGTH: 11
<212> TYPE: PRT
<213> ORGANISM: Artificial Sequence
<220> FEATURE:
<223> OTHER INFORMATION: Synthetic

<400> SEQUENCE: 313

Gln Gln Tyr Ser Ser Tyr Ser Ser Pro Ile Thr
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Synthetic

<400> SEQUENCE: 314

Gln Gln Tyr Ser Ser Tyr Tyr Ser Pro Val Thr
1               5                   10

<210> SEQ ID NO 315
<211> LENGTH: 10
<212> TYPE: PRT
<213> ORGANISM: Artificial Sequence
<220> FEATURE:
<223> OTHER INFORMATION: Synthetic

<400> SEQUENCE: 315

Gln Gln Ser Ser Tyr Ser Ser Leu Ile Thr
1               5                   10

<210> SEQ ID NO 316
<211> LENGTH: 10
<212> TYPE: PRT
<213> ORGANISM: Artificial Sequence
<220> FEATURE:
<223> OTHER INFORMATION: Synthetic

<400> SEQUENCE: 316

Gln Gln Ser Ser Tyr Ser Ser Leu Val Thr
1               5                   10

<210> SEQ ID NO 317
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 317

Gln Gln Ser Tyr Tyr Tyr Ser Leu Phe Thr
1               5                   10

<210> SEQ ID NO 318
<211> LENGTH: 10
<212> TYPE: PRT
<213> ORGANISM: Artificial Sequence
<220> FEATURE:
<223> OTHER INFORMATION: Synthetic

<400> SEQUENCE: 318

Gln Gln Ser Ser Tyr Ser Ser Leu Val Thr
1               5                   10

<210> SEQ ID NO 319
<211> LENGTH: 10
<212> TYPE: PRT
<213> ORGANISM: Artificial Sequence
<220> FEATURE:
<223> OTHER INFORMATION: Synthetic

<400> SEQUENCE: 319

Gln Gln Ser Ser Tyr Ser Ser Leu Phe Thr
1               5                   10

<210> SEQ ID NO 320
<211> LENGTH: 10
<212> TYPE: PRT
<213> ORGANISM: Artificial Sequence
<220> FEATURE:
<223> OTHER INFORMATION: Synthetic

<400> SEQUENCE: 320

Gln Gln Tyr Ser Tyr Ser Ser Leu Phe Thr
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Synthetic

<400> SEQUENCE: 321

Gln Gln Ser Tyr Tyr Tyr Tyr Pro Ile Thr
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Synthetic

<400> SEQUENCE: 322

Gln Gln Ser Ser Tyr Ser Ser Leu Val Thr
1               5                   10

<210> SEQ ID NO 323
<211> LENGTH: 11
<212> TYPE: PRT
```

```
<213> ORGANISM: Artificial Sequence
<220> FEATURE:
<223> OTHER INFORMATION: Synthetic

<400> SEQUENCE: 323

Gln Gln Tyr Ser Ser Ser Tyr Tyr Pro Phe Thr
1               5                   10

<210> SEQ ID NO 324
<211> LENGTH: 10
<212> TYPE: PRT
<213> ORGANISM: Artificial Sequence
<220> FEATURE:
<223> OTHER INFORMATION: Synthetic

<400> SEQUENCE: 324

Gln Gln Ser Ser Tyr Ser Ser Leu Leu Thr
1               5                   10

<210> SEQ ID NO 325
<211> LENGTH: 11
<212> TYPE: PRT
<213> ORGANISM: Artificial Sequence
<220> FEATURE:
<223> OTHER INFORMATION: Synthetic

<400> SEQUENCE: 325

Gln Gln Tyr Tyr Tyr Tyr Tyr Tyr Pro Ile Thr
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(7)
<223> OTHER INFORMATION: Ser or Tyr
<220> FEATURE:
<221> NAME/KEY: MOD_RES
<222> LOCATION: (8)..(8)
<223> OTHER INFORMATION: Leu, Ser, Pro or Tyr
<220> FEATURE:
<221> NAME/KEY: MOD_RES
<222> LOCATION: (9)..(9)
<223> OTHER INFORMATION: Pro or not present
<220> FEATURE:
<221> NAME/KEY: MOD_RES
<222> LOCATION: (10)..(10)
<223> OTHER INFORMATION: Phe, Ile, Val or Leu

<400> SEQUENCE: 326

Gln Gln Xaa Xaa Xaa Xaa Xaa Xaa Xaa Xaa Thr
1               5                   10

<210> SEQ ID NO 327
<211> LENGTH: 10
<212> TYPE: PRT
<213> ORGANISM: Artificial Sequence
<220> FEATURE:
<223> OTHER INFORMATION: Synthetic

<400> SEQUENCE: 327

Gly Phe Asn Val Ser Ser Tyr Ser Ile His
1               5                   10

<210> SEQ ID NO 328
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 328

Gly Phe Asn Ile Ser Ser Ser Tyr Ile His
1               5                   10

<210> SEQ ID NO 329
<211> LENGTH: 10
<212> TYPE: PRT
<213> ORGANISM: Artificial Sequence
<220> FEATURE:
<223> OTHER INFORMATION: Synthetic

<400> SEQUENCE: 329

Gly Phe Asn Phe Ser Tyr Ser Ser Ile His
1               5                   10

<210> SEQ ID NO 330
<211> LENGTH: 10
<212> TYPE: PRT
<213> ORGANISM: Artificial Sequence
<220> FEATURE:
<223> OTHER INFORMATION: Synthetic

<400> SEQUENCE: 330

Gly Phe Asn Val Tyr Tyr Ser Ser Ile His
1               5                   10

<210> SEQ ID NO 331
<211> LENGTH: 10
<212> TYPE: PRT
<213> ORGANISM: Artificial Sequence
<220> FEATURE:
<223> OTHER INFORMATION: Synthetic

<400> SEQUENCE: 331

Gly Phe Asn Phe Tyr Tyr Ser Ser Ile His
1               5                   10

<210> SEQ ID NO 332
<211> LENGTH: 10
<212> TYPE: PRT
<213> ORGANISM: Artificial Sequence
<220> FEATURE:
<223> OTHER INFORMATION: Synthetic

<400> SEQUENCE: 332

Gly Phe Asn Val Ser Ser Ser Tyr Ile His
1               5                   10

<210> SEQ ID NO 333
<211> LENGTH: 10
<212> TYPE: PRT
<213> ORGANISM: Artificial Sequence
<220> FEATURE:
<223> OTHER INFORMATION: Synthetic

<400> SEQUENCE: 333

Gly Phe Asn Phe Tyr Ser Ser Tyr Met His
1               5                   10

<210> SEQ ID NO 334
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 334

Gly Phe Asn Phe Tyr Ser Ser Ser Ile His
1               5                   10

<210> SEQ ID NO 335
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Val, Ile or Phe
<220> FEATURE:
<221> NAME/KEY: MOD_RES
<222> LOCATION: (5)..(8)
<223> OTHER INFORMATION: Ser or Tyr
<220> FEATURE:
<221> NAME/KEY: MOD_RES
<222> LOCATION: (9)..(9)
<223> OTHER INFORMATION: Ile or Met

<400> SEQUENCE: 335

Gly Phe Asn Xaa Xaa Xaa Xaa Xaa Xaa His
1               5                   10

<210> SEQ ID NO 336
<211> LENGTH: 17
<212> TYPE: PRT
<213> ORGANISM: Artificial Sequence
<220> FEATURE:
<223> OTHER INFORMATION: Synthetic

<400> SEQUENCE: 336

Ser Ile Tyr Pro Ser Ser Gly Ser Thr Tyr Tyr Ala Asp Ser Val Lys
1               5                   10                  15

Gly

<210> SEQ ID NO 337
<211> LENGTH: 17
<212> TYPE: PRT
<213> ORGANISM: Artificial Sequence
<220> FEATURE:
<223> OTHER INFORMATION: Synthetic

<400> SEQUENCE: 337

Tyr Ile Ser Pro Tyr Tyr Gly Ser Thr Ser Tyr Ala Asp Ser Val Lys
1               5                   10                  15

Gly

<210> SEQ ID NO 338
<211> LENGTH: 17
<212> TYPE: PRT
<213> ORGANISM: Artificial Sequence
<220> FEATURE:
<223> OTHER INFORMATION: Synthetic

<400> SEQUENCE: 338

Ser Ile Tyr Ser Ser Tyr Ser Ser Thr Ser Tyr Ala Asp Ser Val Lys
1               5                   10                  15

Gly
```

<210> SEQ ID NO 339
<211> LENGTH: 17
<212> TYPE: PRT
<213> ORGANISM: Artificial Sequence
<220> FEATURE:
<223> OTHER INFORMATION: Synthetic

<400> SEQUENCE: 339

Ser Ile Ser Pro Ser Tyr Gly Tyr Thr Tyr Tyr Ala Asp Ser Val Lys
1               5                   10                  15

Gly

<210> SEQ ID NO 340
<211> LENGTH: 17
<212> TYPE: PRT
<213> ORGANISM: Artificial Sequence
<220> FEATURE:
<223> OTHER INFORMATION: Synthetic

<400> SEQUENCE: 340

Ser Ile Tyr Ser Ser Tyr Gly Tyr Thr Ser Tyr Ala Asp Ser Val Lys
1               5                   10                  15

Gly

<210> SEQ ID NO 341
<211> LENGTH: 17
<212> TYPE: PRT
<213> ORGANISM: Artificial Sequence
<220> FEATURE:
<223> OTHER INFORMATION: Synthetic

<400> SEQUENCE: 341

Ser Ile Ser Ser Ser Tyr Ser Tyr Thr Ser Tyr Ala Asp Ser Val Lys
1               5                   10                  15

Gly

<210> SEQ ID NO 342
<211> LENGTH: 17
<212> TYPE: PRT
<213> ORGANISM: Artificial Sequence
<220> FEATURE:
<223> OTHER INFORMATION: Synthetic

<400> SEQUENCE: 342

Tyr Ile Ser Ser Tyr Ser Gly Tyr Thr Tyr Tyr Ala Asp Ser Val Lys
1               5                   10                  15

Gly

<210> SEQ ID NO 343
<211> LENGTH: 17
<212> TYPE: PRT
<213> ORGANISM: Artificial Sequence
<220> FEATURE:
<223> OTHER INFORMATION: Synthetic

<400> SEQUENCE: 343

Ser Ile Ser Ser Tyr Tyr Gly Ser Thr Ser Tyr Ala Asp Ser Val Lys
1               5                   10                  15

Gly

<210> SEQ ID NO 344
<211> LENGTH: 17

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ser or Tyr
<220> FEATURE:
<221> NAME/KEY: MOD_RES
<222> LOCATION: (3)..(3)
<223> OTHER INFORMATION: Tyr or Ser
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (5)..(6)
<223> OTHER INFORMATION: Ser or Tyr
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Ser or Tyr
<220> FEATURE:
<221> NAME/KEY: MOD_RES
<222> LOCATION: (10)..(10)
<223> OTHER INFORMATION: Tyr or Ser

<400> SEQUENCE: 344

Xaa Ile Xaa Xaa Xaa Xaa Xaa Xaa Thr Xaa Tyr Ala Asp Ser Val Lys
1               5                   10                  15

Gly

<210> SEQ ID NO 345
<211> LENGTH: 21
<212> TYPE: PRT
<213> ORGANISM: Artificial Sequence
<220> FEATURE:
<223> OTHER INFORMATION: Synthetic

<400> SEQUENCE: 345

Ser Gly Tyr Tyr Tyr Gln Gly Tyr Trp Trp Tyr Tyr Tyr Thr Gly Tyr
1               5                   10                  15

Tyr Gly Met Asp Tyr
            20

<210> SEQ ID NO 346
<211> LENGTH: 11
<212> TYPE: PRT
<213> ORGANISM: Artificial Sequence
<220> FEATURE:
<223> OTHER INFORMATION: Synthetic

<400> SEQUENCE: 346

Glu Tyr Tyr Arg Trp Tyr Thr Ala Ile Asp Tyr
1               5                   10

<210> SEQ ID NO 347
<211> LENGTH: 19
<212> TYPE: PRT
<213> ORGANISM: Artificial Sequence
<220> FEATURE:
<223> OTHER INFORMATION: Synthetic

<400> SEQUENCE: 347
```

```
Gly Ile Met Phe Ser Ser Trp Trp Tyr Tyr Asp Tyr Ser Asp Ala
1               5                   10                  15

Leu Asp Tyr
```

<210> SEQ ID NO 348
<211> LENGTH: 21
<212> TYPE: PRT
<213> ORGANISM: Artificial Sequence
<220> FEATURE:
<223> OTHER INFORMATION: Synthetic

<400> SEQUENCE: 348

```
Trp Gln Gly Tyr Gly Phe Lys Tyr Tyr Trp Ser Tyr Tyr Val Ser Tyr
1               5                   10                  15

Gly Gly Leu Asp Tyr
            20
```

<210> SEQ ID NO 349
<211> LENGTH: 17
<212> TYPE: PRT
<213> ORGANISM: Artificial Sequence
<220> FEATURE:
<223> OTHER INFORMATION: Synthetic

<400> SEQUENCE: 349

```
Glu Tyr Tyr Trp Trp Tyr Lys Glu Ala Trp Tyr Ser Ala Gly Met Asp
1               5                   10                  15

Tyr
```

<210> SEQ ID NO 350
<211> LENGTH: 13
<212> TYPE: PRT
<213> ORGANISM: Artificial Sequence
<220> FEATURE:
<223> OTHER INFORMATION: Synthetic

<400> SEQUENCE: 350

```
Glu Ser Tyr Ala Gly Val Pro Pro Tyr Gly Phe Asp Tyr
1               5                   10
```

<210> SEQ ID NO 351
<211> LENGTH: 19
<212> TYPE: PRT
<213> ORGANISM: Artificial Sequence
<220> FEATURE:
<223> OTHER INFORMATION: Synthetic

<400> SEQUENCE: 351

```
Gly Ile Met Phe Ser Ser Trp Trp Tyr Tyr Asp Tyr Ser Asp Ala
1               5                   10                  15

Leu Asp Tyr
```

<210> SEQ ID NO 352
<211> LENGTH: 19
<212> TYPE: PRT
<213> ORGANISM: Artificial Sequence
<220> FEATURE:
<223> OTHER INFORMATION: Synthetic

<400> SEQUENCE: 352

```
Gly Ser Ile Pro Ser Tyr Trp Ser Ala Asp Trp Tyr Tyr Tyr Gly
1               5                   10                  15

Leu Asp Tyr
```

```
<210> SEQ ID NO 353
<211> LENGTH: 21
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ser, Glu, Gly or Trp
<220> FEATURE:
<221> NAME/KEY: MOD_RES
<222> LOCATION: (2)..(2)
<223> OTHER INFORMATION: Gly, Tyr, Ile, Gln or Ser
<220> FEATURE:
<221> NAME/KEY: MOD_RES
<222> LOCATION: (3)..(3)
<223> OTHER INFORMATION: Tyr, Met, Gly or Ile
<220> FEATURE:
<221> NAME/KEY: MOD_RES
<222> LOCATION: (4)..(4)
<223> OTHER INFORMATION: Tyr, Arg, Phe, Trp, Ala or Pro
<220> FEATURE:
<221> NAME/KEY: MOD_RES
<222> LOCATION: (5)..(5)
<223> OTHER INFORMATION: Tyr, Trp, Ser or Gly
<220> FEATURE:
<221> NAME/KEY: MOD_RES
<222> LOCATION: (6)..(6)
<223> OTHER INFORMATION: Gln, Tyr, Ser, Phe or Val
<220> FEATURE:
<221> NAME/KEY: MOD_RES
<222> LOCATION: (7)..(7)
<223> OTHER INFORMATION: Gly, Thr, Trp, Lys or Pro
<220> FEATURE:
<221> NAME/KEY: MOD_RES
<222> LOCATION: (8)..(8)
<223> OTHER INFORMATION: Tyr, Ala, Trp, Glu, Pro or Ser
<220> FEATURE:
<221> NAME/KEY: MOD_RES
<222> LOCATION: (9)..(9)
<223> OTHER INFORMATION: Trp, Ile, Tyr or Ala
<220> FEATURE:
<221> NAME/KEY: MOD_RES
<222> LOCATION: (10)..(10)
<223> OTHER INFORMATION: Trp, Tyr, Gly, Asp or not present
<220> FEATURE:
<221> NAME/KEY: MOD_RES
<222> LOCATION: (11)..(11)
<223> OTHER INFORMATION: Tyr, Ser, Phe, Trp or not present
<220> FEATURE:
<221> NAME/KEY: MOD_RES
<222> LOCATION: (12)..(12)
<223> OTHER INFORMATION: Tyr, Asp, Ser or not present
<220> FEATURE:
<221> NAME/KEY: MOD_RES
<222> LOCATION: (13)..(13)
<223> OTHER INFORMATION: Tyr, Ala or not present
<220> FEATURE:
<221> NAME/KEY: MOD_RES
<222> LOCATION: (14)..(14)
<223> OTHER INFORMATION: Thr, Ser, Val, Gly, Tyr or not present
<220> FEATURE:
<221> NAME/KEY: MOD_RES
<222> LOCATION: (15)..(15)
<223> OTHER INFORMATION: Gly, Asp, Ser, Met, Tyr or not present
<220> FEATURE:
<221> NAME/KEY: MOD_RES
<222> LOCATION: (16)..(16)
<223> OTHER INFORMATION: Tyr, Ala, Gly or not present
<220> FEATURE:
<221> NAME/KEY: MOD_RES
<222> LOCATION: (17)..(17)
<223> OTHER INFORMATION: Tyr, Leu, Gly or not present
<220> FEATURE:
<221> NAME/KEY: MOD_RES
<222> LOCATION: (18)..(18)
<223> OTHER INFORMATION: Gly or not present
```

```
<220> FEATURE:
<221> NAME/KEY: MOD_RES
<222> LOCATION: (19)..(19)
<223> OTHER INFORMATION: Met, Leu or not present

<400> SEQUENCE: 353

Xaa Xaa Xaa Xaa Xaa Xaa Xaa Xaa Xaa Xaa Xaa Xaa Xaa Xaa Xaa
1               5                   10                  15

Xaa Xaa Xaa Asp Tyr
            20

<210> SEQ ID NO 354
<211> LENGTH: 9
<212> TYPE: PRT
<213> ORGANISM: Artificial Sequence
<220> FEATURE:
<223> OTHER INFORMATION: Synthetic

<400> SEQUENCE: 354

Gln Gln Tyr Ser Tyr Tyr Pro Phe Arg
1               5

<210> SEQ ID NO 355
<211> LENGTH: 11
<212> TYPE: PRT
<213> ORGANISM: Artificial Sequence
<220> FEATURE:
<223> OTHER INFORMATION: Synthetic

<400> SEQUENCE: 355

Gln Gln Tyr Ser Ser Tyr Ser Ser Leu Phe Thr
1               5                   10

<210> SEQ ID NO 356
<211> LENGTH: 9
<212> TYPE: PRT
<213> ORGANISM: Artificial Sequence
<220> FEATURE:
<223> OTHER INFORMATION: Synthetic

<400> SEQUENCE: 356

Gln Gln Tyr Ser Ser Ser Leu Val Thr
1               5

<210> SEQ ID NO 357
<211> LENGTH: 11
<212> TYPE: PRT
<213> ORGANISM: Artificial Sequence
<220> FEATURE:
<223> OTHER INFORMATION: Synthetic

<400> SEQUENCE: 357

Gln Gln Tyr Ser Ser Ser Ser Pro Phe Thr Phe
1               5                   10

<210> SEQ ID NO 358
<211> LENGTH: 9
<212> TYPE: PRT
<213> ORGANISM: Artificial Sequence
<220> FEATURE:
<223> OTHER INFORMATION: Synthetic

<400> SEQUENCE: 358

Gln Gln Ser Ser Tyr Ser Pro Ile Thr
1               5
```

```
<210> SEQ ID NO 359
<211> LENGTH: 11
<212> TYPE: PRT
<213> ORGANISM: Artificial Sequence
<220> FEATURE:
<223> OTHER INFORMATION: Synthetic

<400> SEQUENCE: 359

Gln Gln Tyr Ser Tyr Ser Ser Tyr Leu Ile Thr
1               5                   10

<210> SEQ ID NO 360
<211> LENGTH: 9
<212> TYPE: PRT
<213> ORGANISM: Artificial Sequence
<220> FEATURE:
<223> OTHER INFORMATION: Synthetic

<400> SEQUENCE: 360

Gln Gln Ser Tyr Tyr Ser Pro Phe Thr
1               5

<210> SEQ ID NO 361
<211> LENGTH: 9
<212> TYPE: PRT
<213> ORGANISM: Artificial Sequence
<220> FEATURE:
<223> OTHER INFORMATION: Synthetic

<400> SEQUENCE: 361

Gln Gln Tyr Tyr Ser Ser Leu Val Thr
1               5

<210> SEQ ID NO 362
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(6)
<223> OTHER INFORMATION: Tyr or Ser
<220> FEATURE:
<221> NAME/KEY: MOD_RES
<222> LOCATION: (7)..(7)
<223> OTHER INFORMATION: Pro, Ser or Leu
<220> FEATURE:
<221> NAME/KEY: MOD_RES
<222> LOCATION: (8)..(8)
<223> OTHER INFORMATION: Ser, Pro, Tyr or not present
<220> FEATURE:
<221> NAME/KEY: MOD_RES
<222> LOCATION: (9)..(9)
<223> OTHER INFORMATION: Leu, Phe or not present
<220> FEATURE:
<221> NAME/KEY: MOD_RES
<222> LOCATION: (10)..(10)
<223> OTHER INFORMATION: Phe, Val, Thr or Ile
<220> FEATURE:
<221> NAME/KEY: MOD_RES
<222> LOCATION: (11)..(11)
<223> OTHER INFORMATION: Arg, Thr or Phe

<400> SEQUENCE: 362

Gln Gln Xaa Xaa Xaa Xaa Xaa Xaa Xaa Xaa Xaa
1               5                   10

<210> SEQ ID NO 363
<211> LENGTH: 42
<212> TYPE: DNA
```

```
<213> ORGANISM: Artificial Sequence
<220> FEATURE:
<223> OTHER INFORMATION: Synthetic

<400> SEQUENCE: 363
cgtctattat tgtgctcgct aataagacta ctggggtcaa gg                          42

<210> SEQ ID NO 364
<211> LENGTH: 42
<212> TYPE: DNA
<213> ORGANISM: Artificial Sequence
<220> FEATURE:
<223> OTHER INFORMATION: Synthetic

<400> SEQUENCE: 364
cgtctattat tgtgctcgct aataagacta ctggggtcaa gg                          42

<210> SEQ ID NO 365
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(22)
<223> OTHER INFORMATION: a, c, g or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: modified_base
<222> LOCATION: (26)..(30)
<223> OTHER INFORMATION: a, c, g or t
<220> FEATURE:
<221> NAME/KEY: misc_feature
<222> LOCATION: (26)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, g or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (35)..(37)
<223> OTHER INFORMATION: a, c, g or t
<220> FEATURE:
<221> NAME/KEY: misc_feature
<222> LOCATION: (35)..(37)
<223> OTHER INFORMATION: n is a, c, g, or t

<400> SEQUENCE: 365
cgtctattat tgtgctcgcn nntacnnnnn snnsnnngst wtsgactact ggggtcaagg        60

<210> SEQ ID NO 366
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(24)
<223> OTHER INFORMATION: a, c, g or t
<220> FEATURE:
<221> NAME/KEY: misc_feature
<222> LOCATION: (20)..(24)
<223> OTHER INFORMATION: n is a, c, g, or t
```

```
<220> FEATURE:
<221> NAME/KEY: modified_base
<222> LOCATION: (26)..(28)
<223> OTHER INFORMATION: a, c, g or t
<220> FEATURE:
<221> NAME/KEY: misc_feature
<222> LOCATION: (26)..(28)
<223> OTHER INFORMATION: n is a, c, g, or t
<220> FEATURE:
<221> NAME/KEY: modified_base
<222> LOCATION: (32)..(33)
<223> OTHER INFORMATION: a, c, g or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (35)..(37)
<223> OTHER INFORMATION: a, c, g or t
<220> FEATURE:
<221> NAME/KEY: misc_feature
<222> LOCATION: (35)..(37)
<223> OTHER INFORMATION: n is a, c, g, or t

<400> SEQUENCE: 366
cgtctattat tgtgctcgcn nnnnsnnnta cnnsnnngst wtsgactact ggggtcaagg    60

<210> SEQ ID NO 367
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(24)
<223> OTHER INFORMATION: a, c, g or t
<220> FEATURE:
<221> NAME/KEY: misc_feature
<222> LOCATION: (20)..(24)
<223> OTHER INFORMATION: n is a, c, g, or t
<220> FEATURE:
<221> NAME/KEY: modified_base
<222> LOCATION: (26)..(30)
<223> OTHER INFORMATION: a, c, g or t
<220> FEATURE:
<221> NAME/KEY: misc_feature
<222> LOCATION: (26)..(30)
<223> OTHER INFORMATION: n is a, c, g, or t
<220> FEATURE:
<221> NAME/KEY: modified_base
<222> LOCATION: (35)..(37)
<223> OTHER INFORMATION: a, c, g or t
<220> FEATURE:
<221> NAME/KEY: misc_feature
<222> LOCATION: (35)..(37)
<223> OTHER INFORMATION: n is a, c, g, or t

<400> SEQUENCE: 367
cgtctattat tgtgctcgcn nnnnsnnnnn stacnnngst wtsgactact ggggtcaagg    60

<210> SEQ ID NO 368
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(24)
<223> OTHER INFORMATION: a, c, g or t
<220> FEATURE:
<221> NAME/KEY: misc_feature
<222> LOCATION: (20)..(24)
```

```
<223> OTHER INFORMATION: n is a, c, g, or t
<220> FEATURE:
<221> NAME/KEY: modified_base
<222> LOCATION: (26)..(30)
<223> OTHER INFORMATION: a, c, g or t
<220> FEATURE:
<221> NAME/KEY: misc_feature
<222> LOCATION: (26)..(30)
<223> OTHER INFORMATION: n is a, c, g, or t
<220> FEATURE:
<221> NAME/KEY: modified_base
<222> LOCATION: (32)..(33)
<223> OTHER INFORMATION: a, c, g or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (35)..(37)
<223> OTHER INFORMATION: a, c, g or t
<220> FEATURE:
<221> NAME/KEY: misc_feature
<222> LOCATION: (35)..(37)
<223> OTHER INFORMATION: n is a, c, g, or t

<400> SEQUENCE: 368
cgtctattat tgtgctcgcn nnnnsnnnnn snnsnnngst wtsgactact ggggtcaagg      60

<210> SEQ ID NO 369
<211> LENGTH: 40
<212> TYPE: DNA
<213> ORGANISM: Artificial Sequence
<220> FEATURE:
<223> OTHER INFORMATION: Synthetic

<400> SEQUENCE: 369
gcagcttctg gcttcaacta ataacactgg gtgcgtcagg                           40

<210> SEQ ID NO 370
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (19)..(19)
<223> OTHER INFORMATION: a, c, g or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: modified_base
<222> LOCATION: (22)..(23)
<223> OTHER INFORMATION: a, c, g or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: modified_base
<222> LOCATION: (31)..(32)
<223> OTHER INFORMATION: a, c, g or t
<220> FEATURE:
<221> NAME/KEY: misc_feature
<222> LOCATION: (31)..(32)
<223> OTHER INFORMATION: n is a, c, g, or t

<400> SEQUENCE: 370
gcagcttctg gcttcaacnt cnnstactct nnsatscact gggtgcgtca gg             52
```

```
<210> SEQ ID NO 371
<211> LENGTH: 43
<212> TYPE: DNA
<213> ORGANISM: Artificial Sequence
<220> FEATURE:
<223> OTHER INFORMATION: Synthetic

<400> SEQUENCE: 371
ggcctggaat gggttgcata ataatatgcc gatagcgtca agg          43

<210> SEQ ID NO 372
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(26)
<223> OTHER INFORMATION: a, c, g or t
<220> FEATURE:
<221> NAME/KEY: misc_feature
<222> LOCATION: (25)..(26)
<223> OTHER INFORMATION: n is a, c, g, or t

<400> SEQUENCE: 372
ggcctggaat gggttgcatc tatcnnsyct tactactctt acacctctta tgccgatagc    60
gtcaagg                                                              67

<210> SEQ ID NO 373
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (32)..(33)
<223> OTHER INFORMATION: a, c, g or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: modified_base
<222> LOCATION: (35)..(36)
<223> OTHER INFORMATION: a, c, g or t
<220> FEATURE:
<221> NAME/KEY: misc_feature
<222> LOCATION: (35)..(36)
<223> OTHER INFORMATION: n is a, c, g, or t

<400> SEQUENCE: 373
cgtctattat tgtgctcgct cttactctta cnnsnnsgst wtsgactact ggggtcaagg    60

<210> SEQ ID NO 374
<211> LENGTH: 46
<212> TYPE: DNA
<213> ORGANISM: Artificial Sequence
<220> FEATURE:
<223> OTHER INFORMATION: Synthetic

<400> SEQUENCE: 374
cgcaacttat tactgtcagc aataataaac gttcggacag ggtacc                   46

<210> SEQ ID NO 375
<211> LENGTH: 76
<212> TYPE: PRT
<213> ORGANISM: Homo sapiens
```

<400> SEQUENCE: 375

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 376
<211> LENGTH: 61
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(24)
<223> OTHER INFORMATION: a, c, g or t
<220> FEATURE:
<221> NAME/KEY: misc_feature
<222> LOCATION: (23)..(24)
<223> OTHER INFORMATION: n is a, c, g, or t

<400> SEQUENCE: 376
cgcaacttat tactgtcagc aannstctta ctcttctctg dttacgttcg gacagggtac    60
c                                                                   61

<210> SEQ ID NO 377
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(22)
<223> OTHER INFORMATION: a, c, g or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: modified_base
<222> LOCATION: (29)..(33)
<223> OTHER INFORMATION: a, c, g or t
<220> FEATURE:
<221> NAME/KEY: misc_feature
<222> LOCATION: (29)..(33)
<223> OTHER INFORMATION: n is a, c, g, or t
<220> FEATURE:
<221> NAME/KEY: modified_base
<222> LOCATION: (35)..(36)
<223> OTHER INFORMATION: a, c, g or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (38)..(40)
<223> OTHER INFORMATION: a, c, g or t
<220> FEATURE:
<221> NAME/KEY: misc_feature
<222> LOCATION: (38)..(40)
<223> OTHER INFORMATION: n is a, c, g, or t -continued

<400> SEQUENCE: 377
cgtctattat tgtgctcgcn nntactacnn nnnsnnsnnn gstwtsgact actggggtca    60
agg                                                                  63

<210> SEQ ID NO 378
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(24)
<223> OTHER INFORMATION: a, c, g or t
<220> FEATURE:
<221> NAME/KEY: misc_feature
<222> LOCATION: (20)..(24)
<223> OTHER INFORMATION: n is a, c, g, or t
<220> FEATURE:
<221> NAME/KEY: modified_base
<222> LOCATION: (26)..(27)
<223> OTHER INFORMATION: a, c, g or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(31)
<223> OTHER INFORMATION: a, c, g or t
<220> FEATURE:
<221> NAME/KEY: misc_feature
<222> LOCATION: (29)..(31)
<223> OTHER INFORMATION: n is a, c, g, or t
<220> FEATURE:
<221> NAME/KEY: modified_base
<222> LOCATION: (38)..(40)
<223> OTHER INFORMATION: a, c, g or t
<220> FEATURE:
<221> NAME/KEY: misc_feature
<222> LOCATION: (38)..(40)
<223> OTHER INFORMATION: n is a, c, g, or t

<400> SEQUENCE: 378
cgtctattat tgtgctcgcn nnnsnnsnn ntggtacnnn gstwtsgact actggggtca    60
agg                                                                  63

<210> SEQ ID NO 379
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(22)
<223> OTHER INFORMATION: a, c, g or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: modified_base
<222> LOCATION: (29)..(33)
<223> OTHER INFORMATION: a, c, g or t
<220> FEATURE:
<221> NAME/KEY: misc_feature
<222> LOCATION: (29)..(33)
<223> OTHER INFORMATION: n is a, c, g, or t
<220> FEATURE:
<221> NAME/KEY: modified_base
<222> LOCATION: (38)..(40)
<223> OTHER INFORMATION: a, c, g or t
<220> FEATURE:
<221> NAME/KEY: misc_feature
<222> LOCATION: (38)..(40)
<223> OTHER INFORMATION: n is a, c, g, or t

<400> SEQUENCE: 379
cgtctattat tgtgctcgcn nntacbbsnn nnnstacnnn gstwtsgact actggggtca    60
agg                                                                 63

<210> SEQ ID NO 380
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(24)
<223> OTHER INFORMATION: a, c, g or t
<220> FEATURE:
<221> NAME/KEY: misc_feature
<222> LOCATION: (20)..(24)
<223> OTHER INFORMATION: n is a, c, g, or t
<220> FEATURE:
<221> NAME/KEY: modified_base
<222> LOCATION: (29)..(31)
<223> OTHER INFORMATION: a, c, g or t
<220> FEATURE:
<221> NAME/KEY: misc_feature
<222> LOCATION: (29)..(31)
<223> OTHER INFORMATION: n is a, c, g, or t
<220> FEATURE:
<221> NAME/KEY: modified_base
<222> LOCATION: (35)..(36)
<223> OTHER INFORMATION: a, c, g or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (38)..(40)
<223> OTHER INFORMATION: a, c, g or t
<220> FEATURE:
<221> NAME/KEY: misc_feature
<222> LOCATION: (38)..(40)
<223> OTHER INFORMATION: n is a, c, g, or t

<400> SEQUENCE: 380
cgtctattat tgtgctcgcn nnnnstacnn ntggnnsnnn gstwtsgact actggggtca    60
agg                                                                 63

<210> SEQ ID NO 381
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(22)
<223> OTHER INFORMATION: a, c, g or t
<220> FEATURE:
<221> NAME/KEY: misc_feature
<222> LOCATION: (20)..(22)
<223> OTHER INFORMATION: n is a, c, g, or t
<220> FEATURE:
<221> NAME/KEY: modified_base
<222> LOCATION: (26)..(27)
<223> OTHER INFORMATION: a, c, g or t
<220> FEATURE:
<221> NAME/KEY: misc_feature
<222> LOCATION: (26)..(27)

```
<223> OTHER INFORMATION: n is a, c, g, or t
<220> FEATURE:
<221> NAME/KEY: modified_base
<222> LOCATION: (29)..(31)
<223> OTHER INFORMATION: a, c, g or t
<220> FEATURE:
<221> NAME/KEY: misc_feature
<222> LOCATION: (29)..(31)
<223> OTHER INFORMATION: n is a, c, g, or t
<220> FEATURE:
<221> NAME/KEY: modified_base
<222> LOCATION: (35)..(36)
<223> OTHER INFORMATION: a, c, g or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (38)..(40)
<223> OTHER INFORMATION: a, c, g or t
<220> FEATURE:
<221> NAME/KEY: misc_feature
<222> LOCATION: (38)..(40)
<223> OTHER INFORMATION: n is a, c, g, or t

<400> SEQUENCE: 381
cgtctattat tgtgctcgcn nntacnnsnn ntggnnsnnn gstwtsgact actggggtca    60
agg                                                                 63

<210> SEQ ID NO 382
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (20)..(24)
<223> OTHER INFORMATION: a, c, g or t
<220> FEATURE:
<221> NAME/KEY: misc_feature
<222> LOCATION: (20)..(24)
<223> OTHER INFORMATION: n is a, c, g, or t
<220> FEATURE:
<221> NAME/KEY: modified_base
<222> LOCATION: (29)..(33)
<223> OTHER INFORMATION: a, c, g or t
<220> FEATURE:
<221> NAME/KEY: misc_feature
<222> LOCATION: (29)..(33)
<223> OTHER INFORMATION: n is a, c, g, or t
<220> FEATURE:
<221> NAME/KEY: modified_base
<222> LOCATION: (38)..(40)
<223> OTHER INFORMATION: a, c, g or t
<220> FEATURE:
<221> NAME/KEY: misc_feature
<222> LOCATION: (38)..(40)
<223> OTHER INFORMATION: n is a, c, g, or t

<400> SEQUENCE: 382
cgtctattat tgtgctcgcn nnnstacnn nnnstacnnn gstwtsgact actggggtca    60
agg                                                                 63

<210> SEQ ID NO 383
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: modified_base
```

```
<222> LOCATION: (20)..(24)
<223> OTHER INFORMATION: a, c, g or t
<220> FEATURE:
<221> NAME/KEY: misc_feature
<222> LOCATION: (20)..(24)
<223> OTHER INFORMATION: n is a, c, g, or t
<220> FEATURE:
<221> NAME/KEY: modified_base
<222> LOCATION: (26)..(27)
<223> OTHER INFORMATION: a, c, g or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (29)..(33)
<223> OTHER INFORMATION: a, c, g or t
<220> FEATURE:
<221> NAME/KEY: misc_feature
<222> LOCATION: (29)..(33)
<223> OTHER INFORMATION: n is a, c, g, or t
<220> FEATURE:
<221> NAME/KEY: modified_base
<222> LOCATION: (35)..(36)
<223> OTHER INFORMATION: a, c, g or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: modified_base
<222> LOCATION: (38)..(40)
<223> OTHER INFORMATION: a, c, g or t
<220> FEATURE:
<221> NAME/KEY: misc_feature
<222> LOCATION: (38)..(40)
<223> OTHER INFORMATION: n is a, c, g, or t

<400> SEQUENCE: 383
cgtctattat tgtgctcgcn nnnsnnsnn nnnsnnsnnn gstwtsgact actggggtca    60
agg                                                                63

<210> SEQ ID NO 384
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(26)
<223> OTHER INFORMATION: a, c, g or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: modified_base
<222> LOCATION: (31)..(32)
<223> OTHER INFORMATION: a, c, g or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: modified_base
<222> LOCATION: (34)..(35)
<223> OTHER INFORMATION: a, c, g or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (40)..(42)
```

```
<223> OTHER INFORMATION: a, c, g or t
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: modified_base
<222> LOCATION: (46)..(48)
<223> OTHER INFORMATION: a, c, g or t
<220> FEATURE:
<221> NAME/KEY: misc_feature
<222> LOCATION: (46)..(48)
<223> OTHER INFORMATION: n is a, c, g, or t

<400> SEQUENCE: 384
ggcctggaat gggttgcata catcnnsyct nnsnnsrgcn nnaccnnnta tgccgatagc    60
gtcaagg                                                              67

<210> SEQ ID NO 385
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (19)..(20)
<223> OTHER INFORMATION: a, c, g or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: modified_base
<222> LOCATION: (25)..(26)
<223> OTHER INFORMATION: a, c, g or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: modified_base
<222> LOCATION: (34)..(35)
<223> OTHER INFORMATION: a, c, g or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (40)..(42)
<223> OTHER INFORMATION: a, c, g or t
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: modified_base
<222> LOCATION: (46)..(48)
<223> OTHER INFORMATION: a, c, g or t
<220> FEATURE:
<221> NAME/KEY: misc_feature
<222> LOCATION: (46)..(48)
<223> OTHER INFORMATION: n is a, c, g, or t

<400> SEQUENCE: 385
ggcctggaat gggttgcann satcnnsyct tacnnsrgcn nnaccnnnta tgccgatagc    60
gtcaagg                                                              67

<210> SEQ ID NO 386
<211> LENGTH: 67
<212> TYPE: DNA
<213> ORGANISM: Artificial Sequence
```

```
<220> FEATURE:
<223> OTHER INFORMATION: Synthetic
<220> FEATURE:
<221> NAME/KEY: modified_base
<222> LOCATION: (19)..(20)
<223> OTHER INFORMATION: a, c, g or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: modified_base
<222> LOCATION: (25)..(26)
<223> OTHER INFORMATION: a, c, g or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: modified_base
<222> LOCATION: (31)..(32)
<223> OTHER INFORMATION: a, c, g or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: modified_base
<222> LOCATION: (40)..(42)
<223> OTHER INFORMATION: a, c, g or t
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: modified_base
<222> LOCATION: (46)..(48)
<223> OTHER INFORMATION: a, c, g or t
<220> FEATURE:
<221> NAME/KEY: misc_feature
<222> LOCATION: (46)..(48)
<223> OTHER INFORMATION: n is a, c, g, or t

<400> SEQUENCE: 386
ggcctggaat gggttgcann satcnnsyct nnstacrgcn nnaccnnnta tgccgatagc    60
gtcaagg                                                             67

<210> SEQ ID NO 387
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (19)..(20)
<223> OTHER INFORMATION: a, c, g or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: modified_base
<222> LOCATION: (25)..(26)
<223> OTHER INFORMATION: a, c, g or t
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: modified_base
<222> LOCATION: (31)..(32)
<223> OTHER INFORMATION: a, c, g or t
<220> FEATURE:
<221> NAME/KEY: misc_feature
<222> LOCATION: (31)..(32)
```

```
<223> OTHER INFORMATION: n is a, c, g, or t
<220> FEATURE:
<221> NAME/KEY: modified_base
<222> LOCATION: (34)..(35)
<223> OTHER INFORMATION: a, c, g or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (40)..(42)
<223> OTHER INFORMATION: a, c, g or t
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: modified_base
<222> LOCATION: (46)..(48)
<223> OTHER INFORMATION: a, c, g or t
<220> FEATURE:
<221> NAME/KEY: misc_feature
<222> LOCATION: (46)..(48)
<223> OTHER INFORMATION: n is a, c, g, or t

<400> SEQUENCE: 387
ggcctggaat gggttgcann satcnnsyct nnsnnsrgcn nnaccnnnta tgccgatagc    60
gtcaagg                                                             67

<210> SEQ ID NO 388
<211> LENGTH: 64
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(24)
<223> OTHER INFORMATION: a, c, g or t
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: modified_base
<222> LOCATION: (26)..(33)
<223> OTHER INFORMATION: a, c, g or t
<220> FEATURE:
<221> NAME/KEY: misc_feature
<222> LOCATION: (26)..(33)
<223> OTHER INFORMATION: n is a, c, g, or t
<220> FEATURE:
<221> NAME/KEY: modified_base
<222> LOCATION: (35)..(39)
<223> OTHER INFORMATION: a, c, g or t
<220> FEATURE:
<221> NAME/KEY: misc_feature
<222> LOCATION: (35)..(39)
<223> OTHER INFORMATION: n is a, c, g, or t

<400> SEQUENCE: 388
cgcaacttat tactgtcagc aannsnnnnn nnnsnnnnns ctgdttacgt tcggacaggg    60
tacc                                                                64

<210> SEQ ID NO 389
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: modified_base
```

```
<222> LOCATION: (19)..(19)
<223> OTHER INFORMATION: a, c, g or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: modified_base
<222> LOCATION: (22)..(23)
<223> OTHER INFORMATION: a, c, g or t
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: modified_base
<222> LOCATION: (25)..(32)
<223> OTHER INFORMATION: a, c, g or t
<220> FEATURE:
<221> NAME/KEY: misc_feature
<222> LOCATION: (25)..(32)
<223> OTHER INFORMATION: n is a, c, g, or t

<400> SEQUENCE: 389
gcagcttctg gcttcaacnt cnnsnnnnnn nnsatscact gggtgcgtca gg            52

<210> SEQ ID NO 390
<211> LENGTH: 10
<212> TYPE: PRT
<213> ORGANISM: Artificial Sequence
<220> FEATURE:
<223> OTHER INFORMATION: Synthetic

<400> SEQUENCE: 390

Gly Phe Asn Ile Ser Tyr Ser Ser Met His
1               5                   10

<210> SEQ ID NO 391
<211> LENGTH: 10
<212> TYPE: PRT
<213> ORGANISM: Artificial Sequence
<220> FEATURE:
<223> OTHER INFORMATION: Synthetic

<400> SEQUENCE: 391

Gly Phe Asn Ile Ser Tyr Ser Ser Met His
1               5                   10

<210> SEQ ID NO 392
<211> LENGTH: 10
<212> TYPE: PRT
<213> ORGANISM: Artificial Sequence
<220> FEATURE:
<223> OTHER INFORMATION: Synthetic

<400> SEQUENCE: 392

Gly Phe Asn Ile Ser Tyr Ser Ser Met His
1               5                   10

<210> SEQ ID NO 393
<211> LENGTH: 10
<212> TYPE: PRT
<213> ORGANISM: Artificial Sequence
<220> FEATURE:
<223> OTHER INFORMATION: Synthetic

<400> SEQUENCE: 393

Gly Phe Asn Ile Ser Tyr Ser Ser Met His
1               5                   10
```

<210> SEQ ID NO 394
<211> LENGTH: 10
<212> TYPE: PRT
<213> ORGANISM: Artificial Sequence
<220> FEATURE:
<223> OTHER INFORMATION: Synthetic

<400> SEQUENCE: 394

Gly Phe Asn Ile Gly Tyr Ser Phe Met His
1               5                   10

<210> SEQ ID NO 395
<211> LENGTH: 10
<212> TYPE: PRT
<213> ORGANISM: Artificial Sequence
<220> FEATURE:
<223> OTHER INFORMATION: Synthetic

<400> SEQUENCE: 395

Gly Phe Asn Val Asp Tyr Ser Tyr Met His
1               5                   10

<210> SEQ ID NO 396
<211> LENGTH: 10
<212> TYPE: PRT
<213> ORGANISM: Artificial Sequence
<220> FEATURE:
<223> OTHER INFORMATION: Synthetic

<400> SEQUENCE: 396

Gly Phe Asn Val Asp Tyr Ser Tyr Met His
1               5                   10

<210> SEQ ID NO 397
<211> LENGTH: 10
<212> TYPE: PRT
<213> ORGANISM: Artificial Sequence
<220> FEATURE:
<223> OTHER INFORMATION: Synthetic

<400> SEQUENCE: 397

Gly Phe Asn Phe Ser Tyr Ser Phe Met His
1               5                   10

<210> SEQ ID NO 398
<211> LENGTH: 10
<212> TYPE: PRT
<213> ORGANISM: Artificial Sequence
<220> FEATURE:
<223> OTHER INFORMATION: Synthetic

<400> SEQUENCE: 398

Gly Phe Asn Ile Val Tyr Ser Phe Met His
1               5                   10

<210> SEQ ID NO 399
<211> LENGTH: 10
<212> TYPE: PRT
<213> ORGANISM: Artificial Sequence
<220> FEATURE:
<223> OTHER INFORMATION: Synthetic

<400> SEQUENCE: 399

Gly Phe Asn Ile Ile Tyr Ser Phe Met His
1               5                   10

```
<210> SEQ ID NO 400
<211> LENGTH: 10
<212> TYPE: PRT
<213> ORGANISM: Artificial Sequence
<220> FEATURE:
<223> OTHER INFORMATION: Synthetic

<400> SEQUENCE: 400

Gly Phe Asn Ile Val Tyr Ser Phe Ile His
1               5                   10

<210> SEQ ID NO 401
<211> LENGTH: 10
<212> TYPE: PRT
<213> ORGANISM: Artificial Sequence
<220> FEATURE:
<223> OTHER INFORMATION: Synthetic

<400> SEQUENCE: 401

Gly Phe Asn Leu Ser Tyr Ser Phe Met His
1               5                   10

<210> SEQ ID NO 402
<211> LENGTH: 10
<212> TYPE: PRT
<213> ORGANISM: Artificial Sequence
<220> FEATURE:
<223> OTHER INFORMATION: Synthetic

<400> SEQUENCE: 402

Gly Phe Asn Val Asp Tyr Ser Phe Met His
1               5                   10

<210> SEQ ID NO 403
<211> LENGTH: 10
<212> TYPE: PRT
<213> ORGANISM: Artificial Sequence
<220> FEATURE:
<223> OTHER INFORMATION: Synthetic

<400> SEQUENCE: 403

Gly Phe Asn Val Ile Tyr Ser Phe Met His
1               5                   10

<210> SEQ ID NO 404
<211> LENGTH: 10
<212> TYPE: PRT
<213> ORGANISM: Artificial Sequence
<220> FEATURE:
<223> OTHER INFORMATION: Synthetic

<400> SEQUENCE: 404

Gly Phe Asn Val Ala Tyr Ser Leu Met His
1               5                   10

<210> SEQ ID NO 405
<211> LENGTH: 10
<212> TYPE: PRT
<213> ORGANISM: Artificial Sequence
<220> FEATURE:
<223> OTHER INFORMATION: Synthetic

<400> SEQUENCE: 405

Gly Phe Asn Ile Ser Tyr Ser Trp Met His
1               5                   10

<210> SEQ ID NO 406
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 406

Gly Phe Asn Leu Asp Tyr Ser Phe Met His
1               5                   10

<210> SEQ ID NO 407
<211> LENGTH: 10
<212> TYPE: PRT
<213> ORGANISM: Artificial Sequence
<220> FEATURE:
<223> OTHER INFORMATION: Synthetic

<400> SEQUENCE: 407

Gly Phe Asn Phe Leu Tyr Ser Gly Ile His
1               5                   10

<210> SEQ ID NO 408
<211> LENGTH: 10
<212> TYPE: PRT
<213> ORGANISM: Artificial Sequence
<220> FEATURE:
<223> OTHER INFORMATION: Synthetic

<400> SEQUENCE: 408

Gly Phe Asn Ile Ser Tyr Ser Ser Met His
1               5                   10

<210> SEQ ID NO 409
<211> LENGTH: 10
<212> TYPE: PRT
<213> ORGANISM: Artificial Sequence
<220> FEATURE:
<223> OTHER INFORMATION: Synthetic

<400> SEQUENCE: 409

Gly Phe Asn Ile Ser Tyr Ser Ser Met His
1               5                   10

<210> SEQ ID NO 410
<211> LENGTH: 10
<212> TYPE: PRT
<213> ORGANISM: Artificial Sequence
<220> FEATURE:
<223> OTHER INFORMATION: Synthetic

<400> SEQUENCE: 410

Gly Phe Asn Ile Ser Tyr Ser Ser Met His
1               5                   10

<210> SEQ ID NO 411
<211> LENGTH: 10
<212> TYPE: PRT
<213> ORGANISM: Artificial Sequence
<220> FEATURE:
<223> OTHER INFORMATION: Synthetic

<400> SEQUENCE: 411

Gly Phe Asn Ile Ser Tyr Ser Ser Met His
1               5                   10

<210> SEQ ID NO 412
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 412

Gly Phe Asn Ile Ser Tyr Ser Ser Met His
1               5                   10

<210> SEQ ID NO 413
<211> LENGTH: 10
<212> TYPE: PRT
<213> ORGANISM: Artificial Sequence
<220> FEATURE:
<223> OTHER INFORMATION: Synthetic

<400> SEQUENCE: 413

Gly Phe Asn Ile Leu Tyr Ser Gly Ile His
1               5                   10

<210> SEQ ID NO 414
<211> LENGTH: 10
<212> TYPE: PRT
<213> ORGANISM: Artificial Sequence
<220> FEATURE:
<223> OTHER INFORMATION: Synthetic

<400> SEQUENCE: 414

Gly Phe Asn Ile Ser Tyr Ser Ser Met His
1               5                   10

<210> SEQ ID NO 415
<211> LENGTH: 10
<212> TYPE: PRT
<213> ORGANISM: Artificial Sequence
<220> FEATURE:
<223> OTHER INFORMATION: Synthetic

<400> SEQUENCE: 415

Gly Phe Asn Ile Ser Tyr Ser Ser Met His
1               5                   10

<210> SEQ ID NO 416
<211> LENGTH: 10
<212> TYPE: PRT
<213> ORGANISM: Artificial Sequence
<220> FEATURE:
<223> OTHER INFORMATION: Synthetic

<400> SEQUENCE: 416

Gly Phe Asn Ile Ser Tyr Ser Ser Met His
1               5                   10

<210> SEQ ID NO 417
<211> LENGTH: 10
<212> TYPE: PRT
<213> ORGANISM: Artificial Sequence
<220> FEATURE:
<223> OTHER INFORMATION: Synthetic

<400> SEQUENCE: 417

Gly Phe Asn Ile Ser Tyr Ser Ser Met His
1               5                   10

<210> SEQ ID NO 418
<211> LENGTH: 10
<212> TYPE: PRT
```

```
<213> ORGANISM: Artificial Sequence
<220> FEATURE:
<223> OTHER INFORMATION: Synthetic

<400> SEQUENCE: 418

Gly Phe Asn Ile Ser Tyr Ser Ser Met His
1               5                   10

<210> SEQ ID NO 419
<211> LENGTH: 10
<212> TYPE: PRT
<213> ORGANISM: Artificial Sequence
<220> FEATURE:
<223> OTHER INFORMATION: Synthetic

<400> SEQUENCE: 419

Gly Phe Asn Ile Ser Tyr Ser Ser Met His
1               5                   10

<210> SEQ ID NO 420
<211> LENGTH: 10
<212> TYPE: PRT
<213> ORGANISM: Artificial Sequence
<220> FEATURE:
<223> OTHER INFORMATION: Synthetic

<400> SEQUENCE: 420

Gly Phe Asn Ile Ser Tyr Ser Ser Met His
1               5                   10

<210> SEQ ID NO 421
<211> LENGTH: 10
<212> TYPE: PRT
<213> ORGANISM: Artificial Sequence
<220> FEATURE:
<223> OTHER INFORMATION: Synthetic

<400> SEQUENCE: 421

Gly Phe Asn Ile Ser Tyr Ser Ser Met His
1               5                   10

<210> SEQ ID NO 422
<211> LENGTH: 10
<212> TYPE: PRT
<213> ORGANISM: Artificial Sequence
<220> FEATURE:
<223> OTHER INFORMATION: Synthetic

<400> SEQUENCE: 422

Gly Phe Asn Ile Ser Tyr Ser Ser Met His
1               5                   10

<210> SEQ ID NO 423
<211> LENGTH: 10
<212> TYPE: PRT
<213> ORGANISM: Artificial Sequence
<220> FEATURE:
<223> OTHER INFORMATION: Synthetic

<400> SEQUENCE: 423

Gly Phe Asn Ile Ser Tyr Ser Ser Met His
1               5                   10

<210> SEQ ID NO 424
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 424

Gly Phe Asn Ile Ser Tyr Ser Ser Met His
1               5                   10

<210> SEQ ID NO 425
<211> LENGTH: 10
<212> TYPE: PRT
<213> ORGANISM: Artificial Sequence
<220> FEATURE:
<223> OTHER INFORMATION: Synthetic

<400> SEQUENCE: 425

Gly Phe Asn Ile Phe Tyr Ser Gly Ile His
1               5                   10

<210> SEQ ID NO 426
<211> LENGTH: 10
<212> TYPE: PRT
<213> ORGANISM: Artificial Sequence
<220> FEATURE:
<223> OTHER INFORMATION: Synthetic

<400> SEQUENCE: 426

Gly Phe Asn Ile Ser Tyr Ser Ser Met His
1               5                   10

<210> SEQ ID NO 427
<211> LENGTH: 10
<212> TYPE: PRT
<213> ORGANISM: Artificial Sequence
<220> FEATURE:
<223> OTHER INFORMATION: Synthetic

<400> SEQUENCE: 427

Gly Phe Asn Ile Ser Tyr Ser Ser Met His
1               5                   10

<210> SEQ ID NO 428
<211> LENGTH: 10
<212> TYPE: PRT
<213> ORGANISM: Artificial Sequence
<220> FEATURE:
<223> OTHER INFORMATION: Synthetic

<400> SEQUENCE: 428

Gly Phe Asn Ile Ser Tyr Ser Ser Met His
1               5                   10

<210> SEQ ID NO 429
<211> LENGTH: 10
<212> TYPE: PRT
<213> ORGANISM: Artificial Sequence
<220> FEATURE:
<223> OTHER INFORMATION: Synthetic

<400> SEQUENCE: 429

Gly Phe Asn Ile Ser Tyr Ser Ser Met His
1               5                   10

<210> SEQ ID NO 430
<211> LENGTH: 10
<212> TYPE: PRT
<213> ORGANISM: Artificial Sequence
<220> FEATURE:
```

<223> OTHER INFORMATION: Synthetic

<400> SEQUENCE: 430

Gly Phe Asn Ile Ser Tyr Ser Ser Met His
1               5                   10

<210> SEQ ID NO 431
<211> LENGTH: 10
<212> TYPE: PRT
<213> ORGANISM: Artificial Sequence
<220> FEATURE:
<223> OTHER INFORMATION: Synthetic

<400> SEQUENCE: 431

Gly Phe Asn Ile Ser Tyr Ser Ser Met His
1               5                   10

<210> SEQ ID NO 432
<211> LENGTH: 10
<212> TYPE: PRT
<213> ORGANISM: Artificial Sequence
<220> FEATURE:
<223> OTHER INFORMATION: Synthetic

<400> SEQUENCE: 432

Gly Phe Asn Ile Ser Tyr Ser Ser Met His
1               5                   10

<210> SEQ ID NO 433
<211> LENGTH: 10
<212> TYPE: PRT
<213> ORGANISM: Artificial Sequence
<220> FEATURE:
<223> OTHER INFORMATION: Synthetic

<400> SEQUENCE: 433

Gly Phe Asn Ile Ser Tyr Ser Ser Met His
1               5                   10

<210> SEQ ID NO 434
<211> LENGTH: 10
<212> TYPE: PRT
<213> ORGANISM: Artificial Sequence
<220> FEATURE:
<223> OTHER INFORMATION: Synthetic

<400> SEQUENCE: 434

Gly Phe Asn Ile Ser Tyr Ser Ser Met His
1               5                   10

<210> SEQ ID NO 435
<211> LENGTH: 10
<212> TYPE: PRT
<213> ORGANISM: Artificial Sequence
<220> FEATURE:
<223> OTHER INFORMATION: Synthetic

<400> SEQUENCE: 435

Gly Phe Asn Ile Ser Tyr Ser Ser Met His
1               5                   10

<210> SEQ ID NO 436
<211> LENGTH: 10
<212> TYPE: PRT
<213> ORGANISM: Artificial Sequence
<220> FEATURE:
<223> OTHER INFORMATION: Synthetic

<400> SEQUENCE: 436

Gly Phe Asn Ile Ser Tyr Ser Ser Met His
1               5                   10

<210> SEQ ID NO 437
<211> LENGTH: 10
<212> TYPE: PRT
<213> ORGANISM: Artificial Sequence
<220> FEATURE:
<223> OTHER INFORMATION: Synthetic

<400> SEQUENCE: 437

Gly Phe Asn Ile Ser Tyr Ser Ser Met His
1               5                   10

<210> SEQ ID NO 438
<211> LENGTH: 10
<212> TYPE: PRT
<213> ORGANISM: Artificial Sequence
<220> FEATURE:
<223> OTHER INFORMATION: Synthetic

<400> SEQUENCE: 438

Gly Phe Asn Ile Ser Tyr Ser Ser Met His
1               5                   10

<210> SEQ ID NO 439
<211> LENGTH: 10
<212> TYPE: PRT
<213> ORGANISM: Artificial Sequence
<220> FEATURE:
<223> OTHER INFORMATION: Synthetic

<400> SEQUENCE: 439

Gly Phe Asn Ile Ser Tyr Ser Ser Met His
1               5                   10

<210> SEQ ID NO 440
<211> LENGTH: 10
<212> TYPE: PRT
<213> ORGANISM: Artificial Sequence
<220> FEATURE:
<223> OTHER INFORMATION: Synthetic

<400> SEQUENCE: 440

Gly Phe Asn Ile Ser Tyr Ser Ser Met His
1               5                   10

<210> SEQ ID NO 441
<211> LENGTH: 10
<212> TYPE: PRT
<213> ORGANISM: Artificial Sequence
<220> FEATURE:
<223> OTHER INFORMATION: Synthetic

<400> SEQUENCE: 441

Gly Phe Asn Ile Ser Tyr Ser Ser Met His
1               5                   10

<210> SEQ ID NO 442
<211> LENGTH: 10
<212> TYPE: PRT
<213> ORGANISM: Artificial Sequence
<220> FEATURE:
<223> OTHER INFORMATION: Synthetic

<400> SEQUENCE: 442

Gly Phe Asn Ile Ser Tyr Ser Ser Met His
1               5                   10

<210> SEQ ID NO 443
<211> LENGTH: 10
<212> TYPE: PRT
<213> ORGANISM: Artificial Sequence
<220> FEATURE:
<223> OTHER INFORMATION: Synthetic

<400> SEQUENCE: 443

Gly Phe Asn Ile Ser Tyr Ser Ser Met His
1               5                   10

<210> SEQ ID NO 444
<211> LENGTH: 10
<212> TYPE: PRT
<213> ORGANISM: Artificial Sequence
<220> FEATURE:
<223> OTHER INFORMATION: Synthetic

<400> SEQUENCE: 444

Gly Phe Asn Ile Ser Tyr Ser Ser Met His
1               5                   10

<210> SEQ ID NO 445
<211> LENGTH: 10
<212> TYPE: PRT
<213> ORGANISM: Artificial Sequence
<220> FEATURE:
<223> OTHER INFORMATION: Synthetic

<400> SEQUENCE: 445

Gly Phe Asn Ile Ser Tyr Ser Ser Met His
1               5                   10

<210> SEQ ID NO 446
<211> LENGTH: 10
<212> TYPE: PRT
<213> ORGANISM: Artificial Sequence
<220> FEATURE:
<223> OTHER INFORMATION: Synthetic

<400> SEQUENCE: 446

Gly Phe Asn Ile Ser Tyr Ser Ser Met His
1               5                   10

<210> SEQ ID NO 447
<211> LENGTH: 10
<212> TYPE: PRT
<213> ORGANISM: Artificial Sequence
<220> FEATURE:
<223> OTHER INFORMATION: Synthetic

<400> SEQUENCE: 447

Gly Phe Asn Ile Ser Tyr Ser Ser Met His
1               5                   10

<210> SEQ ID NO 448
<211> LENGTH: 10
<212> TYPE: PRT
<213> ORGANISM: Artificial Sequence
<220> FEATURE:
<223> OTHER INFORMATION: Synthetic

<400> SEQUENCE: 448

Gly Phe Asn Ile Ser Tyr Ser Ser Met His
1               5                   10

<210> SEQ ID NO 449
<211> LENGTH: 10
<212> TYPE: PRT
<213> ORGANISM: Artificial Sequence
<220> FEATURE:
<223> OTHER INFORMATION: Synthetic

<400> SEQUENCE: 449

Gly Phe Asn Ile Ser Tyr Ser Ser Met His
1               5                   10

<210> SEQ ID NO 450
<211> LENGTH: 10
<212> TYPE: PRT
<213> ORGANISM: Artificial Sequence
<220> FEATURE:
<223> OTHER INFORMATION: Synthetic

<400> SEQUENCE: 450

Gly Phe Asn Ile Ser Tyr Ser Ser Met His
1               5                   10

<210> SEQ ID NO 451
<211> LENGTH: 10
<212> TYPE: PRT
<213> ORGANISM: Artificial Sequence
<220> FEATURE:
<223> OTHER INFORMATION: Synthetic

<400> SEQUENCE: 451

Gly Phe Asn Leu Ser Tyr Ser Gly Met His
1               5                   10

<210> SEQ ID NO 452
<211> LENGTH: 10
<212> TYPE: PRT
<213> ORGANISM: Artificial Sequence
<220> FEATURE:
<223> OTHER INFORMATION: Synthetic

<400> SEQUENCE: 452

Gly Phe Asn Leu Leu Tyr Ser Gly Met His
1               5                   10

<210> SEQ ID NO 453
<211> LENGTH: 10
<212> TYPE: PRT
<213> ORGANISM: Artificial Sequence
<220> FEATURE:
<223> OTHER INFORMATION: Synthetic

<400> SEQUENCE: 453

Gly Phe Asn Val Ala Tyr Ser Gly Ile His
1               5                   10

<210> SEQ ID NO 454
<211> LENGTH: 10
<212> TYPE: PRT
<213> ORGANISM: Artificial Sequence
<220> FEATURE:
<223> OTHER INFORMATION: Synthetic

<400> SEQUENCE: 454

```
Gly Phe Asn Val Asp Tyr Ser Gly Met His
1               5                   10

<210> SEQ ID NO 455
<211> LENGTH: 10
<212> TYPE: PRT
<213> ORGANISM: Artificial Sequence
<220> FEATURE:
<223> OTHER INFORMATION: Synthetic

<400> SEQUENCE: 455

Gly Phe Asn Val Asp Tyr Ser Gly Met His
1               5                   10

<210> SEQ ID NO 456
<211> LENGTH: 10
<212> TYPE: PRT
<213> ORGANISM: Artificial Sequence
<220> FEATURE:
<223> OTHER INFORMATION: Synthetic

<400> SEQUENCE: 456

Gly Phe Asn Val Ser Tyr Ser Ser Ile His
1               5                   10

<210> SEQ ID NO 457
<211> LENGTH: 10
<212> TYPE: PRT
<213> ORGANISM: Artificial Sequence
<220> FEATURE:
<223> OTHER INFORMATION: Synthetic

<400> SEQUENCE: 457

Gly Phe Asn Val Val Tyr Ser Gly Ile His
1               5                   10

<210> SEQ ID NO 458
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Ile, Val, Phe or Leu
<220> FEATURE:
<221> NAME/KEY: MOD_RES
<222> LOCATION: (5)..(5)
<223> OTHER INFORMATION: Ser, Gly, Asp, Val, Ile, Leu, Phe or Ala
<220> FEATURE:
<221> NAME/KEY: MOD_RES
<222> LOCATION: (8)..(8)
<223> OTHER INFORMATION: Ser, Phe, Tyr, Leu, Trp or Gly
<220> FEATURE:
<221> NAME/KEY: MOD_RES
<222> LOCATION: (9)..(9)
<223> OTHER INFORMATION: Met or Ile

<400> SEQUENCE: 458

Gly Phe Asn Xaa Xaa Tyr Ser Xaa Xaa His
1               5                   10

<210> SEQ ID NO 459
<211> LENGTH: 17
<212> TYPE: PRT
<213> ORGANISM: Artificial Sequence
<220> FEATURE:
<223> OTHER INFORMATION: Synthetic
```

<400> SEQUENCE: 459

Ser Ile Tyr Ser Tyr Tyr Ser Tyr Thr Ser Tyr Ala Asp Ser Val Lys
1               5                   10                  15

Gly

<210> SEQ ID NO 460
<211> LENGTH: 17
<212> TYPE: PRT
<213> ORGANISM: Artificial Sequence
<220> FEATURE:
<223> OTHER INFORMATION: Synthetic

<400> SEQUENCE: 460

Ser Ile Tyr Ser Tyr Tyr Ser Tyr Thr Ser Tyr Ala Asp Ser Val Lys
1               5                   10                  15

Gly

<210> SEQ ID NO 461
<211> LENGTH: 17
<212> TYPE: PRT
<213> ORGANISM: Artificial Sequence
<220> FEATURE:
<223> OTHER INFORMATION: Synthetic

<400> SEQUENCE: 461

Ser Ile Tyr Ser Tyr Tyr Ser Tyr Thr Ser Tyr Ala Asp Ser Val Lys
1               5                   10                  15

Gly

<210> SEQ ID NO 462
<211> LENGTH: 17
<212> TYPE: PRT
<213> ORGANISM: Artificial Sequence
<220> FEATURE:
<223> OTHER INFORMATION: Synthetic

<400> SEQUENCE: 462

Ser Ile Tyr Ser Tyr Tyr Ser Tyr Thr Ser Tyr Ala Asp Ser Val Lys
1               5                   10                  15

Gly

<210> SEQ ID NO 463
<211> LENGTH: 17
<212> TYPE: PRT
<213> ORGANISM: Artificial Sequence
<220> FEATURE:
<223> OTHER INFORMATION: Synthetic

<400> SEQUENCE: 463

Ser Ile Ala Ser Tyr Tyr Ser Tyr Thr Ser Tyr Ala Asp Ser Val Lys
1               5                   10                  15

Gly

<210> SEQ ID NO 464
<211> LENGTH: 17
<212> TYPE: PRT
<213> ORGANISM: Artificial Sequence
<220> FEATURE:
<223> OTHER INFORMATION: Synthetic

<400> SEQUENCE: 464

Ser Ile Ala Pro Tyr Tyr Ser Tyr Thr Ser Tyr Ala Asp Ser Val Lys
1               5                   10                  15

<210> SEQ ID NO 465
<211> LENGTH: 17
<212> TYPE: PRT
<213> ORGANISM: Artificial Sequence
<220> FEATURE:
<223> OTHER INFORMATION: Synthetic

<400> SEQUENCE: 465

Ser Ile Ala Pro Tyr Tyr Ser Tyr Thr Ser Tyr Ala Asp Ser Val Lys
1               5                   10                  15
Gly

<210> SEQ ID NO 466
<211> LENGTH: 17
<212> TYPE: PRT
<213> ORGANISM: Artificial Sequence
<220> FEATURE:
<223> OTHER INFORMATION: Synthetic

<400> SEQUENCE: 466

Ser Ile Ser Ser Tyr Tyr Ser Tyr Thr Ser Tyr Ala Asp Ser Val Lys
1               5                   10                  15
Gly

<210> SEQ ID NO 467
<211> LENGTH: 17
<212> TYPE: PRT
<213> ORGANISM: Artificial Sequence
<220> FEATURE:
<223> OTHER INFORMATION: Synthetic

<400> SEQUENCE: 467

Ser Ile Ser Pro Tyr Tyr Ser Tyr Thr Ser Tyr Ala Asp Ser Val Lys
1               5                   10                  15
Gly

<210> SEQ ID NO 468
<211> LENGTH: 17
<212> TYPE: PRT
<213> ORGANISM: Artificial Sequence
<220> FEATURE:
<223> OTHER INFORMATION: Synthetic

<400> SEQUENCE: 468

Ser Ile Ser Ser Tyr Tyr Ser Tyr Thr Ser Tyr Ala Asp Ser Val Lys
1               5                   10                  15
Gly

<210> SEQ ID NO 469
<211> LENGTH: 17
<212> TYPE: PRT
<213> ORGANISM: Artificial Sequence
<220> FEATURE:
<223> OTHER INFORMATION: Synthetic

<400> SEQUENCE: 469

Ser Ile Ser Ser Tyr Tyr Ser Tyr Thr Ser Tyr Ala Asp Ser Val Lys
1               5                   10                  15
Gly

<210> SEQ ID NO 470
<211> LENGTH: 17
<212> TYPE: PRT
<213> ORGANISM: Artificial Sequence
<220> FEATURE:
<223> OTHER INFORMATION: Synthetic

<400> SEQUENCE: 470

Ser Ile Ser Ser Tyr Tyr Ser Tyr Thr Ser Tyr Ala Asp Ser Val Lys
1               5                   10                  15
Gly

<210> SEQ ID NO 471
<211> LENGTH: 17
<212> TYPE: PRT
<213> ORGANISM: Artificial Sequence
<220> FEATURE:
<223> OTHER INFORMATION: Synthetic

<400> SEQUENCE: 471

Ser Ile Ser Ser Tyr Tyr Ser Tyr Thr Ser Tyr Ala Asp Ser Val Lys
1               5                   10                  15
Gly

<210> SEQ ID NO 472
<211> LENGTH: 17
<212> TYPE: PRT
<213> ORGANISM: Artificial Sequence
<220> FEATURE:
<223> OTHER INFORMATION: Synthetic

<400> SEQUENCE: 472

Ser Ile Ser Ser Tyr Tyr Ser Tyr Thr Ser Tyr Ala Asp Ser Val Lys
1               5                   10                  15
Gly

<210> SEQ ID NO 473
<211> LENGTH: 17
<212> TYPE: PRT
<213> ORGANISM: Artificial Sequence
<220> FEATURE:
<223> OTHER INFORMATION: Synthetic

<400> SEQUENCE: 473

Ser Ile Ser Ser Tyr Tyr Ser Tyr Thr Ser Tyr Ala Asp Ser Val Lys
1               5                   10                  15
Gly

<210> SEQ ID NO 474
<211> LENGTH: 17
<212> TYPE: PRT
<213> ORGANISM: Artificial Sequence
<220> FEATURE:
<223> OTHER INFORMATION: Synthetic

<400> SEQUENCE: 474

Ser Ile Thr Ser Tyr Tyr Ser Tyr Thr Ser Tyr Ala Asp Ser Val Lys
1               5                   10                  15
Gly

<210> SEQ ID NO 475
<211> LENGTH: 17
<212> TYPE: PRT
<213> ORGANISM: Artificial Sequence
<220> FEATURE:
<223> OTHER INFORMATION: Synthetic

<400> SEQUENCE: 475

Ser Ile Thr Pro Tyr Tyr Ser Tyr Thr Ser Tyr Ala Asp Ser Val Lys
1               5                   10                  15
Gly

<210> SEQ ID NO 476
<211> LENGTH: 17
<212> TYPE: PRT
<213> ORGANISM: Artificial Sequence
<220> FEATURE:
<223> OTHER INFORMATION: Synthetic

<400> SEQUENCE: 476

Ser Ile Tyr Ser Tyr Tyr Ser Tyr Thr Ser Tyr Ala Asp Ser Val Lys
1               5                   10                  15
Gly

<210> SEQ ID NO 477
<211> LENGTH: 17
<212> TYPE: PRT
<213> ORGANISM: Artificial Sequence
<220> FEATURE:
<223> OTHER INFORMATION: Synthetic

<400> SEQUENCE: 477

Ser Ile Tyr Ser Tyr Tyr Ser Tyr Thr Ser Tyr Ala Asp Ser Val Lys
1               5                   10                  15
Gly

<210> SEQ ID NO 478
<211> LENGTH: 17
<212> TYPE: PRT
<213> ORGANISM: Artificial Sequence
<220> FEATURE:
<223> OTHER INFORMATION: Synthetic

<400> SEQUENCE: 478

Ser Ile Tyr Ser Tyr Tyr Ser Tyr Thr Ser Tyr Ala Asp Ser Val Lys
1               5                   10                  15
Gly

<210> SEQ ID NO 479
<211> LENGTH: 17
<212> TYPE: PRT
<213> ORGANISM: Artificial Sequence
<220> FEATURE:
<223> OTHER INFORMATION: Synthetic

<400> SEQUENCE: 479

Ser Ile Tyr Ser Tyr Tyr Ser Tyr Thr Ser Tyr Ala Asp Ser Val Lys
1               5                   10                  15
Gly

<210> SEQ ID NO 480
<211> LENGTH: 17
<212> TYPE: PRT
<213> ORGANISM: Artificial Sequence
<220> FEATURE:
<223> OTHER INFORMATION: Synthetic

<400> SEQUENCE: 480

Ser Ile Tyr Ser Tyr Tyr Ser Tyr Thr Ser Tyr Ala Asp Ser Val Lys
1               5                   10                  15

Gly

<210> SEQ ID NO 481
<211> LENGTH: 17
<212> TYPE: PRT
<213> ORGANISM: Artificial Sequence
<220> FEATURE:
<223> OTHER INFORMATION: Synthetic

<400> SEQUENCE: 481

Ser Ile Tyr Pro Tyr Tyr Ser Tyr Thr Ser Tyr Ala Asp Ser Val Lys
1               5                   10                  15

Gly

<210> SEQ ID NO 482
<211> LENGTH: 17
<212> TYPE: PRT
<213> ORGANISM: Artificial Sequence
<220> FEATURE:
<223> OTHER INFORMATION: Synthetic

<400> SEQUENCE: 482

Ser Ile Tyr Ser Tyr Tyr Ser Tyr Thr Ser Tyr Ala Asp Ser Val Lys
1               5                   10                  15

Gly

<210> SEQ ID NO 483
<211> LENGTH: 17
<212> TYPE: PRT
<213> ORGANISM: Artificial Sequence
<220> FEATURE:
<223> OTHER INFORMATION: Synthetic

<400> SEQUENCE: 483

Ser Ile Tyr Ser Tyr Tyr Ser Tyr Thr Ser Tyr Ala Asp Ser Val Lys
1               5                   10                  15

Gly

<210> SEQ ID NO 484
<211> LENGTH: 17
<212> TYPE: PRT
<213> ORGANISM: Artificial Sequence
<220> FEATURE:
<223> OTHER INFORMATION: Synthetic

<400> SEQUENCE: 484

Ser Ile Tyr Ser Tyr Tyr Ser Tyr Thr Ser Tyr Ala Asp Ser Val Lys
1               5                   10                  15

Gly

<210> SEQ ID NO 485
<211> LENGTH: 17
<212> TYPE: PRT
<213> ORGANISM: Artificial Sequence
<220> FEATURE:
<223> OTHER INFORMATION: Synthetic

<400> SEQUENCE: 485

Ser Ile Tyr Ser Tyr Tyr Ser Tyr Thr Ser Tyr Ala Asp Ser Val Lys
1               5                   10                  15

Gly

<210> SEQ ID NO 486
<211> LENGTH: 17
<212> TYPE: PRT
<213> ORGANISM: Artificial Sequence
<220> FEATURE:
<223> OTHER INFORMATION: Synthetic

<400> SEQUENCE: 486

Ser Ile Tyr Ser Tyr Tyr Ser Tyr Thr Ser Tyr Ala Asp Ser Val Lys
1               5                   10                  15

Gly

<210> SEQ ID NO 487
<211> LENGTH: 17
<212> TYPE: PRT
<213> ORGANISM: Artificial Sequence
<220> FEATURE:
<223> OTHER INFORMATION: Synthetic

<400> SEQUENCE: 487

Ser Ile Tyr Ser Tyr Tyr Ser Tyr Thr Ser Tyr Ala Asp Ser Val Lys
1               5                   10                  15

Gly

<210> SEQ ID NO 488
<211> LENGTH: 17
<212> TYPE: PRT
<213> ORGANISM: Artificial Sequence
<220> FEATURE:
<223> OTHER INFORMATION: Synthetic

<400> SEQUENCE: 488

Ser Ile Tyr Ser Tyr Tyr Ser Tyr Thr Ser Tyr Ala Asp Ser Val Lys
1               5                   10                  15

Gly

<210> SEQ ID NO 489
<211> LENGTH: 17
<212> TYPE: PRT
<213> ORGANISM: Artificial Sequence
<220> FEATURE:
<223> OTHER INFORMATION: Synthetic

<400> SEQUENCE: 489

Ser Ile Tyr Ser Tyr Tyr Ser Tyr Thr Ser Tyr Ala Asp Ser Val Lys
1               5                   10                  15

Gly

<210> SEQ ID NO 490
<211> LENGTH: 17
<212> TYPE: PRT
<213> ORGANISM: Artificial Sequence
<220> FEATURE:
<223> OTHER INFORMATION: Synthetic

<400> SEQUENCE: 490

Ser Ile Tyr Ser Tyr Tyr Ser Tyr Thr Ser Tyr Ala Asp Ser Val Lys
1               5                   10                  15

Gly

<210> SEQ ID NO 491

```
<211> LENGTH: 17
<212> TYPE: PRT
<213> ORGANISM: Artificial Sequence
<220> FEATURE:
<223> OTHER INFORMATION: Synthetic

<400> SEQUENCE: 491

Ser Ile Tyr Ser Tyr Tyr Ser Tyr Thr Ser Tyr Ala Asp Ser Val Lys
1               5                   10                  15

Gly

<210> SEQ ID NO 492
<211> LENGTH: 17
<212> TYPE: PRT
<213> ORGANISM: Artificial Sequence
<220> FEATURE:
<223> OTHER INFORMATION: Synthetic

<400> SEQUENCE: 492

Ser Ile Tyr Ser Tyr Tyr Ser Tyr Thr Ser Tyr Ala Asp Ser Val Lys
1               5                   10                  15

Gly

<210> SEQ ID NO 493
<211> LENGTH: 17
<212> TYPE: PRT
<213> ORGANISM: Artificial Sequence
<220> FEATURE:
<223> OTHER INFORMATION: Synthetic

<400> SEQUENCE: 493

Ser Ile Tyr Ser Tyr Tyr Ser Tyr Thr Ser Tyr Ala Asp Ser Val Lys
1               5                   10                  15

Gly

<210> SEQ ID NO 494
<211> LENGTH: 17
<212> TYPE: PRT
<213> ORGANISM: Artificial Sequence
<220> FEATURE:
<223> OTHER INFORMATION: Synthetic

<400> SEQUENCE: 494

Ser Ile Tyr Ser Tyr Tyr Ser Tyr Thr Ser Tyr Ala Asp Ser Val Lys
1               5                   10                  15

Gly

<210> SEQ ID NO 495
<211> LENGTH: 17
<212> TYPE: PRT
<213> ORGANISM: Artificial Sequence
<220> FEATURE:
<223> OTHER INFORMATION: Synthetic

<400> SEQUENCE: 495

Ser Ile Tyr Ser Tyr Tyr Ser Tyr Thr Ser Tyr Ala Asp Ser Val Lys
1               5                   10                  15

Gly

<210> SEQ ID NO 496
<211> LENGTH: 17
<212> TYPE: PRT
<213> ORGANISM: Artificial Sequence
<220> FEATURE:
```

<223> OTHER INFORMATION: Synthetic

<400> SEQUENCE: 496

Ser Ile Tyr Ser Tyr Tyr Ser Tyr Thr Ser Tyr Ala Asp Ser Val Lys
1               5                   10                  15

Gly

<210> SEQ ID NO 497
<211> LENGTH: 17
<212> TYPE: PRT
<213> ORGANISM: Artificial Sequence
<220> FEATURE:
<223> OTHER INFORMATION: Synthetic

<400> SEQUENCE: 497

Ser Ile Tyr Ser Tyr Tyr Ser Tyr Thr Ser Tyr Ala Asp Ser Val Lys
1               5                   10                  15

Gly

<210> SEQ ID NO 498
<211> LENGTH: 17
<212> TYPE: PRT
<213> ORGANISM: Artificial Sequence
<220> FEATURE:
<223> OTHER INFORMATION: Synthetic

<400> SEQUENCE: 498

Ser Ile Tyr Ser Tyr Tyr Ser Tyr Thr Ser Tyr Ala Asp Ser Val Lys
1               5                   10                  15

Gly

<210> SEQ ID NO 499
<211> LENGTH: 17
<212> TYPE: PRT
<213> ORGANISM: Artificial Sequence
<220> FEATURE:
<223> OTHER INFORMATION: Synthetic

<400> SEQUENCE: 499

Ser Ile Tyr Ser Tyr Tyr Ser Tyr Thr Ser Tyr Ala Asp Ser Val Lys
1               5                   10                  15

Gly

<210> SEQ ID NO 500
<211> LENGTH: 17
<212> TYPE: PRT
<213> ORGANISM: Artificial Sequence
<220> FEATURE:
<223> OTHER INFORMATION: Synthetic

<400> SEQUENCE: 500

Ser Ile Tyr Ser Tyr Tyr Ser Tyr Thr Ser Tyr Ala Asp Ser Val Lys
1               5                   10                  15

Gly

<210> SEQ ID NO 501
<211> LENGTH: 17
<212> TYPE: PRT
<213> ORGANISM: Artificial Sequence
<220> FEATURE:
<223> OTHER INFORMATION: Synthetic

<400> SEQUENCE: 501

Ser Ile Tyr Ser Tyr Tyr Ser Tyr Thr Ser Tyr Ala Asp Ser Val Lys
1               5                   10                  15

Gly

<210> SEQ ID NO 502
<211> LENGTH: 17
<212> TYPE: PRT
<213> ORGANISM: Artificial Sequence
<220> FEATURE:
<223> OTHER INFORMATION: Synthetic

<400> SEQUENCE: 502

Ser Ile Tyr Ser Tyr Tyr Ser Tyr Thr Ser Tyr Ala Asp Ser Val Lys
1               5                   10                  15

Gly

<210> SEQ ID NO 503
<211> LENGTH: 17
<212> TYPE: PRT
<213> ORGANISM: Artificial Sequence
<220> FEATURE:
<223> OTHER INFORMATION: Synthetic

<400> SEQUENCE: 503

Ser Ile Tyr Ser Tyr Tyr Ser Tyr Thr Ser Tyr Ala Asp Ser Val Lys
1               5                   10                  15

Gly

<210> SEQ ID NO 504
<211> LENGTH: 17
<212> TYPE: PRT
<213> ORGANISM: Artificial Sequence
<220> FEATURE:
<223> OTHER INFORMATION: Synthetic

<400> SEQUENCE: 504

Ser Ile Tyr Ser Tyr Tyr Ser Tyr Thr Ser Tyr Ala Asp Ser Val Lys
1               5                   10                  15

Gly

<210> SEQ ID NO 505
<211> LENGTH: 17
<212> TYPE: PRT
<213> ORGANISM: Artificial Sequence
<220> FEATURE:
<223> OTHER INFORMATION: Synthetic

<400> SEQUENCE: 505

Ser Ile Tyr Ser Tyr Tyr Ser Tyr Thr Ser Tyr Ala Asp Ser Val Lys
1               5                   10                  15

Gly

<210> SEQ ID NO 506
<211> LENGTH: 17
<212> TYPE: PRT
<213> ORGANISM: Artificial Sequence
<220> FEATURE:
<223> OTHER INFORMATION: Synthetic

<400> SEQUENCE: 506

Ser Ile Tyr Ser Tyr Tyr Ser Tyr Thr Ser Tyr Ala Asp Ser Val Lys
1               5                   10                  15

Gly

-continued

```
<210> SEQ ID NO 507
<211> LENGTH: 17
<212> TYPE: PRT
<213> ORGANISM: Artificial Sequence
<220> FEATURE:
<223> OTHER INFORMATION: Synthetic

<400> SEQUENCE: 507

Ser Ile Tyr Pro Tyr Tyr Ser Tyr Thr Ser Tyr Ala Asp Ser Val Lys
1               5                   10                  15

Gly

<210> SEQ ID NO 508
<211> LENGTH: 17
<212> TYPE: PRT
<213> ORGANISM: Artificial Sequence
<220> FEATURE:
<223> OTHER INFORMATION: Synthetic

<400> SEQUENCE: 508

Ser Ile Tyr Ser Tyr Tyr Ser Tyr Thr Ser Tyr Ala Asp Ser Val Lys
1               5                   10                  15

Gly

<210> SEQ ID NO 509
<211> LENGTH: 17
<212> TYPE: PRT
<213> ORGANISM: Artificial Sequence
<220> FEATURE:
<223> OTHER INFORMATION: Synthetic

<400> SEQUENCE: 509

Ser Ile Tyr Ser Tyr Tyr Ser Tyr Thr Ser Tyr Ala Asp Ser Val Lys
1               5                   10                  15

Gly

<210> SEQ ID NO 510
<211> LENGTH: 17
<212> TYPE: PRT
<213> ORGANISM: Artificial Sequence
<220> FEATURE:
<223> OTHER INFORMATION: Synthetic

<400> SEQUENCE: 510

Ser Ile Tyr Ser Tyr Tyr Ser Tyr Thr Ser Tyr Ala Asp Ser Val Lys
1               5                   10                  15

Gly

<210> SEQ ID NO 511
<211> LENGTH: 17
<212> TYPE: PRT
<213> ORGANISM: Artificial Sequence
<220> FEATURE:
<223> OTHER INFORMATION: Synthetic

<400> SEQUENCE: 511

Ser Ile Tyr Ser Tyr Tyr Ser Tyr Thr Ser Tyr Ala Asp Ser Val Lys
1               5                   10                  15

Gly

<210> SEQ ID NO 512
<211> LENGTH: 17
```

<212> TYPE: PRT
<213> ORGANISM: Artificial Sequence
<220> FEATURE:
<223> OTHER INFORMATION: Synthetic

<400> SEQUENCE: 512

Ser Ile Tyr Ser Tyr Tyr Ser Tyr Thr Ser Tyr Ala Asp Ser Val Lys
1               5                   10                  15
Gly

<210> SEQ ID NO 513
<211> LENGTH: 17
<212> TYPE: PRT
<213> ORGANISM: Artificial Sequence
<220> FEATURE:
<223> OTHER INFORMATION: Synthetic

<400> SEQUENCE: 513

Ser Ile Tyr Ser Tyr Tyr Ser Tyr Thr Ser Tyr Ala Asp Ser Val Lys
1               5                   10                  15
Gly

<210> SEQ ID NO 514
<211> LENGTH: 17
<212> TYPE: PRT
<213> ORGANISM: Artificial Sequence
<220> FEATURE:
<223> OTHER INFORMATION: Synthetic

<400> SEQUENCE: 514

Ser Ile Tyr Ser Tyr Tyr Ser Tyr Thr Ser Tyr Ala Asp Ser Val Lys
1               5                   10                  15
Gly

<210> SEQ ID NO 515
<211> LENGTH: 17
<212> TYPE: PRT
<213> ORGANISM: Artificial Sequence
<220> FEATURE:
<223> OTHER INFORMATION: Synthetic

<400> SEQUENCE: 515

Ser Ile Tyr Ser Tyr Tyr Ser Tyr Thr Ser Tyr Ala Asp Ser Val Lys
1               5                   10                  15
Gly

<210> SEQ ID NO 516
<211> LENGTH: 17
<212> TYPE: PRT
<213> ORGANISM: Artificial Sequence
<220> FEATURE:
<223> OTHER INFORMATION: Synthetic

<400> SEQUENCE: 516

Ser Ile Tyr Ser Tyr Tyr Ser Tyr Thr Ser Tyr Ala Asp Ser Val Lys
1               5                   10                  15
Gly

<210> SEQ ID NO 517
<211> LENGTH: 17
<212> TYPE: PRT
<213> ORGANISM: Artificial Sequence
<220> FEATURE:
<223> OTHER INFORMATION: Synthetic

<400> SEQUENCE: 517

Ser Ile Tyr Ser Tyr Tyr Ser Tyr Thr Ser Tyr Ala Asp Ser Val Lys
1               5                   10                  15

Gly

<210> SEQ ID NO 518
<211> LENGTH: 17
<212> TYPE: PRT
<213> ORGANISM: Artificial Sequence
<220> FEATURE:
<223> OTHER INFORMATION: Synthetic

<400> SEQUENCE: 518

Ser Ile Tyr Ser Tyr Tyr Ser Tyr Thr Ser Tyr Ala Asp Ser Val Lys
1               5                   10                  15

Gly

<210> SEQ ID NO 519
<211> LENGTH: 17
<212> TYPE: PRT
<213> ORGANISM: Artificial Sequence
<220> FEATURE:
<223> OTHER INFORMATION: Synthetic

<400> SEQUENCE: 519

Ser Ile Tyr Ser Tyr Tyr Ser Tyr Thr Ser Tyr Ala Asp Ser Val Lys
1               5                   10                  15

Gly

<210> SEQ ID NO 520
<211> LENGTH: 17
<212> TYPE: PRT
<213> ORGANISM: Artificial Sequence
<220> FEATURE:
<223> OTHER INFORMATION: Synthetic

<400> SEQUENCE: 520

Ser Ile Tyr Ser Tyr Tyr Ser Tyr Thr Ser Tyr Ala Asp Ser Val Lys
1               5                   10                  15

Gly

<210> SEQ ID NO 521
<211> LENGTH: 17
<212> TYPE: PRT
<213> ORGANISM: Artificial Sequence
<220> FEATURE:
<223> OTHER INFORMATION: Synthetic

<400> SEQUENCE: 521

Ser Ile Tyr Ser Tyr Tyr Ser Tyr Thr Ser Tyr Ala Asp Ser Val Lys
1               5                   10                  15

Gly

<210> SEQ ID NO 522
<211> LENGTH: 17
<212> TYPE: PRT
<213> ORGANISM: Artificial Sequence
<220> FEATURE:
<223> OTHER INFORMATION: Synthetic

<400> SEQUENCE: 522

Ser Ile Tyr Ser Tyr Tyr Ser Tyr Thr Ser Tyr Ala Asp Ser Val Lys

```
                             1               5                  10                 15
Gly

<210> SEQ ID NO 523
<211> LENGTH: 17
<212> TYPE: PRT
<213> ORGANISM: Artificial Sequence
<220> FEATURE:
<223> OTHER INFORMATION: Synthetic

<400> SEQUENCE: 523

Ser Ile Tyr Ser Tyr Tyr Ser Tyr Thr Ser Tyr Ala Asp Ser Val Lys
1               5                  10                 15

Gly

<210> SEQ ID NO 524
<211> LENGTH: 17
<212> TYPE: PRT
<213> ORGANISM: Artificial Sequence
<220> FEATURE:
<223> OTHER INFORMATION: Synthetic

<400> SEQUENCE: 524

Ser Ile Tyr Ser Tyr Tyr Thr Tyr Thr Ser Tyr Ala Asp Ser Val Lys
1               5                  10                 15

Gly

<210> SEQ ID NO 525
<211> LENGTH: 17
<212> TYPE: PRT
<213> ORGANISM: Artificial Sequence
<220> FEATURE:
<223> OTHER INFORMATION: Synthetic

<400> SEQUENCE: 525

Ser Ile Tyr Ser Tyr Tyr Ser Tyr Thr Ser Tyr Ala Asp Ser Val Lys
1               5                  10                 15

Gly

<210> SEQ ID NO 526
<211> LENGTH: 17
<212> TYPE: PRT
<213> ORGANISM: Artificial Sequence
<220> FEATURE:
<223> OTHER INFORMATION: Synthetic

<400> SEQUENCE: 526

Ser Ile Tyr Ser Tyr Tyr Ser Tyr Thr Ser Tyr Ala Asp Ser Val Lys
1               5                  10                 15

Gly

<210> SEQ ID NO 527
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Tyr, Ala, Ser or Thr
<220> FEATURE:
<221> NAME/KEY: MOD_RES
<222> LOCATION: (4)..(4)
<223> OTHER INFORMATION: Ser or Pro
```

```
<220> FEATURE:
<221> NAME/KEY: MOD_RES
<222> LOCATION: (7)..(7)
<223> OTHER INFORMATION: Ser or Thr

<400> SEQUENCE: 527

Ser Ile Xaa Xaa Tyr Tyr Xaa Tyr Thr Ser Tyr Ala Asp Ser Val Lys
1               5                   10                  15
Gly

<210> SEQ ID NO 528
<211> LENGTH: 10
<212> TYPE: PRT
<213> ORGANISM: Artificial Sequence
<220> FEATURE:
<223> OTHER INFORMATION: Synthetic

<400> SEQUENCE: 528

Ser Tyr Asn Asn Thr Thr Ser Ile Asp Tyr
1               5                   10

<210> SEQ ID NO 529
<211> LENGTH: 10
<212> TYPE: PRT
<213> ORGANISM: Artificial Sequence
<220> FEATURE:
<223> OTHER INFORMATION: Synthetic

<400> SEQUENCE: 529

Gly Tyr Ser Trp Tyr Asn Ala Met Asp Tyr
1               5                   10

<210> SEQ ID NO 530
<211> LENGTH: 10
<212> TYPE: PRT
<213> ORGANISM: Artificial Sequence
<220> FEATURE:
<223> OTHER INFORMATION: Synthetic

<400> SEQUENCE: 530

Gly Tyr Ser Trp Phe Asn Ala Ile Asp Tyr
1               5                   10

<210> SEQ ID NO 531
<211> LENGTH: 10
<212> TYPE: PRT
<213> ORGANISM: Artificial Sequence
<220> FEATURE:
<223> OTHER INFORMATION: Synthetic

<400> SEQUENCE: 531

Gly Tyr Tyr Trp Phe Asp Ala Met Asp Tyr
1               5                   10

<210> SEQ ID NO 532
<211> LENGTH: 10
<212> TYPE: PRT
<213> ORGANISM: Artificial Sequence
<220> FEATURE:
<223> OTHER INFORMATION: Synthetic

<400> SEQUENCE: 532

Ser Tyr Ser Tyr Tyr Ser Ala Met Asp Tyr
1               5                   10

<210> SEQ ID NO 533
```

```
<211> LENGTH: 10
<212> TYPE: PRT
<213> ORGANISM: Artificial Sequence
<220> FEATURE:
<223> OTHER INFORMATION: Synthetic

<400> SEQUENCE: 533

Ser Tyr Ser Tyr Arg Glu Thr Met Asp Tyr
1               5                   10

<210> SEQ ID NO 534
<211> LENGTH: 10
<212> TYPE: PRT
<213> ORGANISM: Artificial Sequence
<220> FEATURE:
<223> OTHER INFORMATION: Synthetic

<400> SEQUENCE: 534

Ser Tyr Ser Tyr Arg Glu Thr Met Asp Tyr
1               5                   10

<210> SEQ ID NO 535
<211> LENGTH: 10
<212> TYPE: PRT
<213> ORGANISM: Artificial Sequence
<220> FEATURE:
<223> OTHER INFORMATION: Synthetic

<400> SEQUENCE: 535

Ser Tyr Ser Tyr Tyr Ser Ala Met Asp Tyr
1               5                   10

<210> SEQ ID NO 536
<211> LENGTH: 10
<212> TYPE: PRT
<213> ORGANISM: Artificial Sequence
<220> FEATURE:
<223> OTHER INFORMATION: Synthetic

<400> SEQUENCE: 536

Ser Tyr Ser Tyr Tyr Ser Ala Met Asp Tyr
1               5                   10

<210> SEQ ID NO 537
<211> LENGTH: 10
<212> TYPE: PRT
<213> ORGANISM: Artificial Sequence
<220> FEATURE:
<223> OTHER INFORMATION: Synthetic

<400> SEQUENCE: 537

Ser Tyr Ser Tyr Tyr Ser Ala Met Asp Tyr
1               5                   10

<210> SEQ ID NO 538
<211> LENGTH: 10
<212> TYPE: PRT
<213> ORGANISM: Artificial Sequence
<220> FEATURE:
<223> OTHER INFORMATION: Synthetic

<400> SEQUENCE: 538

Ser Tyr Ser Tyr Tyr Ser Ala Met Asp Tyr
1               5                   10

<210> SEQ ID NO 539
<211> LENGTH: 10
```

```
<212> TYPE: PRT
<213> ORGANISM: Artificial Sequence
<220> FEATURE:
<223> OTHER INFORMATION: Synthetic

<400> SEQUENCE: 539

Ser Tyr Ser Tyr Tyr Ser Ala Met Asp Tyr
1               5                   10

<210> SEQ ID NO 540
<211> LENGTH: 10
<212> TYPE: PRT
<213> ORGANISM: Artificial Sequence
<220> FEATURE:
<223> OTHER INFORMATION: Synthetic

<400> SEQUENCE: 540

Ser Tyr Ser Tyr Tyr Ser Ala Met Asp Tyr
1               5                   10

<210> SEQ ID NO 541
<211> LENGTH: 10
<212> TYPE: PRT
<213> ORGANISM: Artificial Sequence
<220> FEATURE:
<223> OTHER INFORMATION: Synthetic

<400> SEQUENCE: 541

Ser Tyr Ser Tyr Tyr Ser Ala Met Asp Tyr
1               5                   10

<210> SEQ ID NO 542
<211> LENGTH: 10
<212> TYPE: PRT
<213> ORGANISM: Artificial Sequence
<220> FEATURE:
<223> OTHER INFORMATION: Synthetic

<400> SEQUENCE: 542

Ser Tyr Ser Tyr Tyr Ser Ala Met Asp Tyr
1               5                   10

<210> SEQ ID NO 543
<211> LENGTH: 10
<212> TYPE: PRT
<213> ORGANISM: Artificial Sequence
<220> FEATURE:
<223> OTHER INFORMATION: Synthetic

<400> SEQUENCE: 543

Ser Tyr Ser Tyr Tyr Ser Ala Met Asp Tyr
1               5                   10

<210> SEQ ID NO 544
<211> LENGTH: 10
<212> TYPE: PRT
<213> ORGANISM: Artificial Sequence
<220> FEATURE:
<223> OTHER INFORMATION: Synthetic

<400> SEQUENCE: 544

Ser Tyr Ser Tyr Tyr Ser Ala Met Asp Tyr
1               5                   10

<210> SEQ ID NO 545
<211> LENGTH: 10
<212> TYPE: PRT
```

```
<213> ORGANISM: Artificial Sequence
<220> FEATURE:
<223> OTHER INFORMATION: Synthetic

<400> SEQUENCE: 545

Ser Tyr Ser Tyr Tyr Ser Ala Met Asp Tyr
1               5                   10

<210> SEQ ID NO 546
<211> LENGTH: 10
<212> TYPE: PRT
<213> ORGANISM: Artificial Sequence
<220> FEATURE:
<223> OTHER INFORMATION: Synthetic

<400> SEQUENCE: 546

Ser Tyr Ser Tyr Tyr Ser Ala Met Asp Tyr
1               5                   10

<210> SEQ ID NO 547
<211> LENGTH: 10
<212> TYPE: PRT
<213> ORGANISM: Artificial Sequence
<220> FEATURE:
<223> OTHER INFORMATION: Synthetic

<400> SEQUENCE: 547

Ser Tyr Ser Tyr Ser Phe Gly Met Asp Tyr
1               5                   10

<210> SEQ ID NO 548
<211> LENGTH: 10
<212> TYPE: PRT
<213> ORGANISM: Artificial Sequence
<220> FEATURE:
<223> OTHER INFORMATION: Synthetic

<400> SEQUENCE: 548

Ser Tyr Ser Tyr Phe Met Gly Met Asp Tyr
1               5                   10

<210> SEQ ID NO 549
<211> LENGTH: 10
<212> TYPE: PRT
<213> ORGANISM: Artificial Sequence
<220> FEATURE:
<223> OTHER INFORMATION: Synthetic

<400> SEQUENCE: 549

Ser Tyr Ser Tyr His Val Ala Phe Asp Tyr
1               5                   10

<210> SEQ ID NO 550
<211> LENGTH: 10
<212> TYPE: PRT
<213> ORGANISM: Artificial Sequence
<220> FEATURE:
<223> OTHER INFORMATION: Synthetic

<400> SEQUENCE: 550

Ser Tyr Ser Tyr Tyr Ser Ala Met Asp Tyr
1               5                   10

<210> SEQ ID NO 551
<211> LENGTH: 10
<212> TYPE: PRT
<213> ORGANISM: Artificial Sequence
```

```
<220> FEATURE:
<223> OTHER INFORMATION: Synthetic

<400> SEQUENCE: 551

Ser Tyr Ser Tyr Tyr Ser Ala Met Asp Tyr
1               5                   10

<210> SEQ ID NO 552
<211> LENGTH: 10
<212> TYPE: PRT
<213> ORGANISM: Artificial Sequence
<220> FEATURE:
<223> OTHER INFORMATION: Synthetic

<400> SEQUENCE: 552

Ser Tyr Ser Tyr His Leu Ala Phe Asp Tyr
1               5                   10

<210> SEQ ID NO 553
<211> LENGTH: 10
<212> TYPE: PRT
<213> ORGANISM: Artificial Sequence
<220> FEATURE:
<223> OTHER INFORMATION: Synthetic

<400> SEQUENCE: 553

Ser Tyr Ser Tyr Ser Leu Ala Phe Asp Tyr
1               5                   10

<210> SEQ ID NO 554
<211> LENGTH: 10
<212> TYPE: PRT
<213> ORGANISM: Artificial Sequence
<220> FEATURE:
<223> OTHER INFORMATION: Synthetic

<400> SEQUENCE: 554

Ser Tyr Ser Tyr Tyr Ile Ala Met Asp Tyr
1               5                   10

<210> SEQ ID NO 555
<211> LENGTH: 10
<212> TYPE: PRT
<213> ORGANISM: Artificial Sequence
<220> FEATURE:
<223> OTHER INFORMATION: Synthetic

<400> SEQUENCE: 555

Ser Tyr Ser Tyr Tyr Met Gly Met Asp Tyr
1               5                   10

<210> SEQ ID NO 556
<211> LENGTH: 10
<212> TYPE: PRT
<213> ORGANISM: Artificial Sequence
<220> FEATURE:
<223> OTHER INFORMATION: Synthetic

<400> SEQUENCE: 556

Ser Tyr Ser Tyr Ser Met Gly Met Asp Tyr
1               5                   10

<210> SEQ ID NO 557
<211> LENGTH: 10
<212> TYPE: PRT
<213> ORGANISM: Artificial Sequence
<220> FEATURE:
```

<223> OTHER INFORMATION: Synthetic

<400> SEQUENCE: 557

Ser Tyr Ser Tyr His Val Ala Met Asp Tyr
1               5                   10

<210> SEQ ID NO 558
<211> LENGTH: 10
<212> TYPE: PRT
<213> ORGANISM: Artificial Sequence
<220> FEATURE:
<223> OTHER INFORMATION: Synthetic

<400> SEQUENCE: 558

Ser Tyr Ser Tyr His Met Gly Met Asp Tyr
1               5                   10

<210> SEQ ID NO 559
<211> LENGTH: 10
<212> TYPE: PRT
<213> ORGANISM: Artificial Sequence
<220> FEATURE:
<223> OTHER INFORMATION: Synthetic

<400> SEQUENCE: 559

Ser Tyr Ser Tyr His Leu Gly Met Asp Tyr
1               5                   10

<210> SEQ ID NO 560
<211> LENGTH: 10
<212> TYPE: PRT
<213> ORGANISM: Artificial Sequence
<220> FEATURE:
<223> OTHER INFORMATION: Synthetic

<400> SEQUENCE: 560

Ser Tyr Ser Tyr Tyr Gln Gly Phe Asp Tyr
1               5                   10

<210> SEQ ID NO 561
<211> LENGTH: 10
<212> TYPE: PRT
<213> ORGANISM: Artificial Sequence
<220> FEATURE:
<223> OTHER INFORMATION: Synthetic

<400> SEQUENCE: 561

Ser Tyr Ser Tyr Ser Met Gly Met Asp Tyr
1               5                   10

<210> SEQ ID NO 562
<211> LENGTH: 10
<212> TYPE: PRT
<213> ORGANISM: Artificial Sequence
<220> FEATURE:
<223> OTHER INFORMATION: Synthetic

<400> SEQUENCE: 562

Ser Tyr Ser Tyr Phe Leu Ala Met Asp Tyr
1               5                   10

<210> SEQ ID NO 563
<211> LENGTH: 10
<212> TYPE: PRT
<213> ORGANISM: Artificial Sequence
<220> FEATURE:
<223> OTHER INFORMATION: Synthetic

```
<400> SEQUENCE: 563

Ser Tyr Ser Tyr Tyr Ser Ala Met Asp Tyr
1               5                   10

<210> SEQ ID NO 564
<211> LENGTH: 10
<212> TYPE: PRT
<213> ORGANISM: Artificial Sequence
<220> FEATURE:
<223> OTHER INFORMATION: Synthetic

<400> SEQUENCE: 564

Ser Tyr Ser Tyr Ser Glu Ala Leu Asp Tyr
1               5                   10

<210> SEQ ID NO 565
<211> LENGTH: 10
<212> TYPE: PRT
<213> ORGANISM: Artificial Sequence
<220> FEATURE:
<223> OTHER INFORMATION: Synthetic

<400> SEQUENCE: 565

Ser Tyr Ser Tyr Ser Leu Gly Met Asp Tyr
1               5                   10

<210> SEQ ID NO 566
<211> LENGTH: 10
<212> TYPE: PRT
<213> ORGANISM: Artificial Sequence
<220> FEATURE:
<223> OTHER INFORMATION: Synthetic

<400> SEQUENCE: 566

Ser Tyr Ser Tyr Tyr Ser Ala Met Asp Tyr
1               5                   10

<210> SEQ ID NO 567
<211> LENGTH: 10
<212> TYPE: PRT
<213> ORGANISM: Artificial Sequence
<220> FEATURE:
<223> OTHER INFORMATION: Synthetic

<400> SEQUENCE: 567

Ser Tyr Ser Tyr Phe Met Gly Met Asp Tyr
1               5                   10

<210> SEQ ID NO 568
<211> LENGTH: 10
<212> TYPE: PRT
<213> ORGANISM: Artificial Sequence
<220> FEATURE:
<223> OTHER INFORMATION: Synthetic

<400> SEQUENCE: 568

Ser Tyr Ser Tyr Phe Leu Ala Met Asp Tyr
1               5                   10

<210> SEQ ID NO 569
<211> LENGTH: 10
<212> TYPE: PRT
<213> ORGANISM: Artificial Sequence
<220> FEATURE:
<223> OTHER INFORMATION: Synthetic
```

```
<400> SEQUENCE: 569

Ser Tyr Ser Tyr Phe Leu Ala Met Asp Tyr
1               5                   10

<210> SEQ ID NO 570
<211> LENGTH: 10
<212> TYPE: PRT
<213> ORGANISM: Artificial Sequence
<220> FEATURE:
<223> OTHER INFORMATION: Synthetic

<400> SEQUENCE: 570

Ser Tyr Ser Tyr Tyr Leu Ala Met Asp Tyr
1               5                   10

<210> SEQ ID NO 571
<211> LENGTH: 10
<212> TYPE: PRT
<213> ORGANISM: Artificial Sequence
<220> FEATURE:
<223> OTHER INFORMATION: Synthetic

<400> SEQUENCE: 571

Ser Tyr Ser Tyr Phe Ile Gly Met Asp Tyr
1               5                   10

<210> SEQ ID NO 572
<211> LENGTH: 10
<212> TYPE: PRT
<213> ORGANISM: Artificial Sequence
<220> FEATURE:
<223> OTHER INFORMATION: Synthetic

<400> SEQUENCE: 572

Ser Tyr Ser Tyr His Leu Gly Met Asp Tyr
1               5                   10

<210> SEQ ID NO 573
<211> LENGTH: 10
<212> TYPE: PRT
<213> ORGANISM: Artificial Sequence
<220> FEATURE:
<223> OTHER INFORMATION: Synthetic

<400> SEQUENCE: 573

Ser Tyr Ser Tyr Thr Glu Ala Phe Asp Tyr
1               5                   10

<210> SEQ ID NO 574
<211> LENGTH: 10
<212> TYPE: PRT
<213> ORGANISM: Artificial Sequence
<220> FEATURE:
<223> OTHER INFORMATION: Synthetic

<400> SEQUENCE: 574

Ser Tyr Ser Tyr Tyr Ser Ala Met Asp Tyr
1               5                   10

<210> SEQ ID NO 575
<211> LENGTH: 10
<212> TYPE: PRT
<213> ORGANISM: Artificial Sequence
<220> FEATURE:
<223> OTHER INFORMATION: Synthetic

<400> SEQUENCE: 575
```

```
Ser Tyr Ser Tyr Thr Tyr Gly Leu Asp Tyr
1               5                   10

<210> SEQ ID NO 576
<211> LENGTH: 10
<212> TYPE: PRT
<213> ORGANISM: Artificial Sequence
<220> FEATURE:
<223> OTHER INFORMATION: Synthetic

<400> SEQUENCE: 576

Ser Tyr Ser Tyr Tyr Ser Ala Met Asp Tyr
1               5                   10

<210> SEQ ID NO 577
<211> LENGTH: 10
<212> TYPE: PRT
<213> ORGANISM: Artificial Sequence
<220> FEATURE:
<223> OTHER INFORMATION: Synthetic

<400> SEQUENCE: 577

Ser Tyr Ser Tyr Ser Leu Gly Met Asp Tyr
1               5                   10

<210> SEQ ID NO 578
<211> LENGTH: 10
<212> TYPE: PRT
<213> ORGANISM: Artificial Sequence
<220> FEATURE:
<223> OTHER INFORMATION: Synthetic

<400> SEQUENCE: 578

Ser Tyr Ser Tyr Trp Val Gly Met Asp Tyr
1               5                   10

<210> SEQ ID NO 579
<211> LENGTH: 10
<212> TYPE: PRT
<213> ORGANISM: Artificial Sequence
<220> FEATURE:
<223> OTHER INFORMATION: Synthetic

<400> SEQUENCE: 579

Ser Tyr Ser Tyr Thr Leu Ala Met Asp Tyr
1               5                   10

<210> SEQ ID NO 580
<211> LENGTH: 10
<212> TYPE: PRT
<213> ORGANISM: Artificial Sequence
<220> FEATURE:
<223> OTHER INFORMATION: Synthetic

<400> SEQUENCE: 580

Ser Tyr Ser Tyr Thr Met Gly Leu Asp Tyr
1               5                   10

<210> SEQ ID NO 581
<211> LENGTH: 10
<212> TYPE: PRT
<213> ORGANISM: Artificial Sequence
<220> FEATURE:
<223> OTHER INFORMATION: Synthetic

<400> SEQUENCE: 581
```

Ser Tyr Ser Tyr Phe Leu Gly Met Asp Tyr
1               5                   10

<210> SEQ ID NO 582
<211> LENGTH: 10
<212> TYPE: PRT
<213> ORGANISM: Artificial Sequence
<220> FEATURE:
<223> OTHER INFORMATION: Synthetic

<400> SEQUENCE: 582

Ser Tyr Ser Tyr His Met Gly Phe Asp Tyr
1               5                   10

<210> SEQ ID NO 583
<211> LENGTH: 10
<212> TYPE: PRT
<213> ORGANISM: Artificial Sequence
<220> FEATURE:
<223> OTHER INFORMATION: Synthetic

<400> SEQUENCE: 583

Ser Tyr Ser Tyr Ser Leu Gly Met Asp Tyr
1               5                   10

<210> SEQ ID NO 584
<211> LENGTH: 10
<212> TYPE: PRT
<213> ORGANISM: Artificial Sequence
<220> FEATURE:
<223> OTHER INFORMATION: Synthetic

<400> SEQUENCE: 584

Ser Tyr Ser Tyr Glu Ala Phe Asp Tyr
1               5                   10

<210> SEQ ID NO 585
<211> LENGTH: 10
<212> TYPE: PRT
<213> ORGANISM: Artificial Sequence
<220> FEATURE:
<223> OTHER INFORMATION: Synthetic

<400> SEQUENCE: 585

Ser Tyr Ser Tyr Arg Met Ala Phe Asp Tyr
1               5                   10

<210> SEQ ID NO 586
<211> LENGTH: 10
<212> TYPE: PRT
<213> ORGANISM: Artificial Sequence
<220> FEATURE:
<223> OTHER INFORMATION: Synthetic

<400> SEQUENCE: 586

Ser Tyr Ser Tyr His Ile Ala Phe Asp Tyr
1               5                   10

<210> SEQ ID NO 587
<211> LENGTH: 10
<212> TYPE: PRT
<213> ORGANISM: Artificial Sequence
<220> FEATURE:
<223> OTHER INFORMATION: Synthetic

<400> SEQUENCE: 587

Ser Tyr Ser Tyr Ser Val Gly Met Asp Tyr

```
1               5                  10
```

<210> SEQ ID NO 588
<211> LENGTH: 10
<212> TYPE: PRT
<213> ORGANISM: Artificial Sequence
<220> FEATURE:
<223> OTHER INFORMATION: Synthetic

<400> SEQUENCE: 588

```
Ser Tyr Ser Tyr Thr Leu Gly Met Asp Tyr
1               5                  10
```

<210> SEQ ID NO 589
<211> LENGTH: 10
<212> TYPE: PRT
<213> ORGANISM: Artificial Sequence
<220> FEATURE:
<223> OTHER INFORMATION: Synthetic

<400> SEQUENCE: 589

```
Ser Tyr Ser Tyr Tyr Ser Ala Met Asp Tyr
1               5                  10
```

<210> SEQ ID NO 590
<211> LENGTH: 10
<212> TYPE: PRT
<213> ORGANISM: Artificial Sequence
<220> FEATURE:
<223> OTHER INFORMATION: Synthetic

<400> SEQUENCE: 590

```
Ser Tyr Ser Tyr Tyr Ser Ala Met Asp Tyr
1               5                  10
```

<210> SEQ ID NO 591
<211> LENGTH: 10
<212> TYPE: PRT
<213> ORGANISM: Artificial Sequence
<220> FEATURE:
<223> OTHER INFORMATION: Synthetic

<400> SEQUENCE: 591

```
Ser Tyr Ser Tyr Tyr Ser Ala Met Asp Tyr
1               5                  10
```

<210> SEQ ID NO 592
<211> LENGTH: 10
<212> TYPE: PRT
<213> ORGANISM: Artificial Sequence
<220> FEATURE:
<223> OTHER INFORMATION: Synthetic

<400> SEQUENCE: 592

```
Ser Tyr Ser Tyr Tyr Ser Ala Met Asp Tyr
1               5                  10
```

<210> SEQ ID NO 593
<211> LENGTH: 10
<212> TYPE: PRT
<213> ORGANISM: Artificial Sequence
<220> FEATURE:
<223> OTHER INFORMATION: Synthetic

<400> SEQUENCE: 593

```
Ser Tyr Ser Tyr Tyr Ser Ala Met Asp Tyr
1               5                  10
```

<210> SEQ ID NO 594
<211> LENGTH: 10
<212> TYPE: PRT
<213> ORGANISM: Artificial Sequence
<220> FEATURE:
<223> OTHER INFORMATION: Synthetic

<400> SEQUENCE: 594

Ser Tyr Ser Tyr Tyr Ser Ala Met Asp Tyr
1               5                   10

<210> SEQ ID NO 595
<211> LENGTH: 10
<212> TYPE: PRT
<213> ORGANISM: Artificial Sequence
<220> FEATURE:
<223> OTHER INFORMATION: Synthetic

<400> SEQUENCE: 595

Ser Tyr Ser Tyr Tyr Ser Ala Met Asp Tyr
1               5                   10

<210> SEQ ID NO 596
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ser or Gly
<220> FEATURE:
<221> NAME/KEY: MOD_RES
<222> LOCATION: (3)..(3)
<223> OTHER INFORMATION: Ser, Asn or Tyr
<220> FEATURE:
<221> NAME/KEY: MOD_RES
<222> LOCATION: (4)..(4)
<223> OTHER INFORMATION: Tyr, Asn or Trp
<220> FEATURE:
<221> NAME/KEY: MOD_RES
<222> LOCATION: (5)..(5)
<223> OTHER INFORMATION: Thr, Tyr, Phe, Arg, Ser, His or Trp
<220> FEATURE:
<221> NAME/KEY: MOD_RES
<222> LOCATION: (6)..(6)
<223> OTHER INFORMATION: Thr, Asn, Asp, Ser, Glu, Phe, Met, Val, Leu,
      Ile or Tyr
<220> FEATURE:
<221> NAME/KEY: MOD_RES
<222> LOCATION: (7)..(7)
<223> OTHER INFORMATION: Ser, Ala, Thr or Gly
<220> FEATURE:
<221> NAME/KEY: MOD_RES
<222> LOCATION: (8)..(8)
<223> OTHER INFORMATION: Ile, Met, Phe or Leu

<400> SEQUENCE: 596

Xaa Tyr Xaa Xaa Xaa Xaa Xaa Xaa Asp Tyr
1               5                   10

<210> SEQ ID NO 597
<211> LENGTH: 10
<212> TYPE: PRT
<213> ORGANISM: Artificial Sequence
<220> FEATURE:
<223> OTHER INFORMATION: Synthetic

<400> SEQUENCE: 597

Gly Phe Asn Ile Ser Ser Ser Tyr Ile His
1               5                   10

<210> SEQ ID NO 598
<211> LENGTH: 10
<212> TYPE: PRT
<213> ORGANISM: Artificial Sequence
<220> FEATURE:
<223> OTHER INFORMATION: Synthetic

<400> SEQUENCE: 598

Gly Phe Asn Ile Ser Ser Ser Tyr Ile His
1               5                   10

<210> SEQ ID NO 599
<211> LENGTH: 10
<212> TYPE: PRT
<213> ORGANISM: Artificial Sequence
<220> FEATURE:
<223> OTHER INFORMATION: Synthetic

<400> SEQUENCE: 599

Gly Phe Asn Ile Ser Ser Ser Tyr Ile His
1               5                   10

<210> SEQ ID NO 600
<211> LENGTH: 10
<212> TYPE: PRT
<213> ORGANISM: Artificial Sequence
<220> FEATURE:
<223> OTHER INFORMATION: Synthetic

<400> SEQUENCE: 600

Gly Phe Asn Ile Ser Ser Ser Tyr Ile His
1               5                   10

<210> SEQ ID NO 601
<211> LENGTH: 10
<212> TYPE: PRT
<213> ORGANISM: Artificial Sequence
<220> FEATURE:
<223> OTHER INFORMATION: Synthetic

<400> SEQUENCE: 601

Gly Phe Asn Ile Ser Ser Ser Tyr Ile His
1               5                   10

<210> SEQ ID NO 602
<211> LENGTH: 10
<212> TYPE: PRT
<213> ORGANISM: Artificial Sequence
<220> FEATURE:
<223> OTHER INFORMATION: Synthetic

<400> SEQUENCE: 602

Gly Phe Asn Ile Ser Ser Ser Tyr Ile His
1               5                   10

<210> SEQ ID NO 603
<211> LENGTH: 10
<212> TYPE: PRT
<213> ORGANISM: Artificial Sequence
<220> FEATURE:
<223> OTHER INFORMATION: Synthetic

<400> SEQUENCE: 603

Gly Phe Asn Ile Ser Ser Ser Tyr Ile His

```
1               5                   10
```

<210> SEQ ID NO 604
<211> LENGTH: 10
<212> TYPE: PRT
<213> ORGANISM: Artificial Sequence
<220> FEATURE:
<223> OTHER INFORMATION: Synthetic

<400> SEQUENCE: 604

Gly Phe Asn Ile Ser Ser Ser Tyr Ile His
1               5                   10

<210> SEQ ID NO 605
<211> LENGTH: 10
<212> TYPE: PRT
<213> ORGANISM: Artificial Sequence
<220> FEATURE:
<223> OTHER INFORMATION: Synthetic

<400> SEQUENCE: 605

Gly Phe Asn Ile Ser Ser Ser Tyr Ile His
1               5                   10

<210> SEQ ID NO 606
<211> LENGTH: 10
<212> TYPE: PRT
<213> ORGANISM: Artificial Sequence
<220> FEATURE:
<223> OTHER INFORMATION: Synthetic

<400> SEQUENCE: 606

Gly Phe Asn Ile Ser Ser Ser Tyr Ile His
1               5                   10

<210> SEQ ID NO 607
<211> LENGTH: 10
<212> TYPE: PRT
<213> ORGANISM: Artificial Sequence
<220> FEATURE:
<223> OTHER INFORMATION: Synthetic

<400> SEQUENCE: 607

Gly Phe Asn Ile Ser Ser Ser Tyr Ile His
1               5                   10

<210> SEQ ID NO 608
<211> LENGTH: 10
<212> TYPE: PRT
<213> ORGANISM: Artificial Sequence
<220> FEATURE:
<223> OTHER INFORMATION: Synthetic

<400> SEQUENCE: 608

Gly Phe Asn Ile Ser Ser Ser Tyr Ile His
1               5                   10

<210> SEQ ID NO 609
<211> LENGTH: 10
<212> TYPE: PRT
<213> ORGANISM: Artificial Sequence
<220> FEATURE:
<223> OTHER INFORMATION: Synthetic

<400> SEQUENCE: 609

Gly Phe Asn Ile Ser Ser Ser Tyr Ile His
1               5                   10

```
<210> SEQ ID NO 610
<211> LENGTH: 10
<212> TYPE: PRT
<213> ORGANISM: Artificial Sequence
<220> FEATURE:
<223> OTHER INFORMATION: Synthetic

<400> SEQUENCE: 610

Gly Phe Asn Ile Ser Ser Ser Tyr Ile His
1               5                   10

<210> SEQ ID NO 611
<211> LENGTH: 10
<212> TYPE: PRT
<213> ORGANISM: Artificial Sequence
<220> FEATURE:
<223> OTHER INFORMATION: Synthetic

<400> SEQUENCE: 611

Gly Phe Asn Phe Ser Ser Ser Tyr Ile His
1               5                   10

<210> SEQ ID NO 612
<211> LENGTH: 10
<212> TYPE: PRT
<213> ORGANISM: Artificial Sequence
<220> FEATURE:
<223> OTHER INFORMATION: Synthetic

<400> SEQUENCE: 612

Gly Phe Asn Ile Lys Gly Ser Leu Ile His
1               5                   10

<210> SEQ ID NO 613
<211> LENGTH: 10
<212> TYPE: PRT
<213> ORGANISM: Artificial Sequence
<220> FEATURE:
<223> OTHER INFORMATION: Synthetic

<400> SEQUENCE: 613

Gly Phe Asn Ile Lys Gly Ser Ile Met His
1               5                   10

<210> SEQ ID NO 614
<211> LENGTH: 10
<212> TYPE: PRT
<213> ORGANISM: Artificial Sequence
<220> FEATURE:
<223> OTHER INFORMATION: Synthetic

<400> SEQUENCE: 614

Gly Phe Asn Ile Lys Ser Ser Ile Met His
1               5                   10

<210> SEQ ID NO 615
<211> LENGTH: 10
<212> TYPE: PRT
<213> ORGANISM: Artificial Sequence
<220> FEATURE:
<223> OTHER INFORMATION: Synthetic

<400> SEQUENCE: 615

Gly Phe Asn Ile Ser Ser Ser Tyr Ile His
1               5                   10
```

<210> SEQ ID NO 616
<211> LENGTH: 10
<212> TYPE: PRT
<213> ORGANISM: Artificial Sequence
<220> FEATURE:
<223> OTHER INFORMATION: Synthetic

<400> SEQUENCE: 616

Gly Phe Asn Ile Ser Ser Ser Tyr Ile His
1               5                   10

<210> SEQ ID NO 617
<211> LENGTH: 10
<212> TYPE: PRT
<213> ORGANISM: Artificial Sequence
<220> FEATURE:
<223> OTHER INFORMATION: Synthetic

<400> SEQUENCE: 617

Gly Phe Asn Ile Ser Ser Ser Tyr Ile His
1               5                   10

<210> SEQ ID NO 618
<211> LENGTH: 10
<212> TYPE: PRT
<213> ORGANISM: Artificial Sequence
<220> FEATURE:
<223> OTHER INFORMATION: Synthetic

<400> SEQUENCE: 618

Gly Phe Asn Ile Ser Ser Ser Tyr Ile His
1               5                   10

<210> SEQ ID NO 619
<211> LENGTH: 10
<212> TYPE: PRT
<213> ORGANISM: Artificial Sequence
<220> FEATURE:
<223> OTHER INFORMATION: Synthetic

<400> SEQUENCE: 619

Gly Phe Asn Ile Ser Ser Ser Tyr Ile His
1               5                   10

<210> SEQ ID NO 620
<211> LENGTH: 10
<212> TYPE: PRT
<213> ORGANISM: Artificial Sequence
<220> FEATURE:
<223> OTHER INFORMATION: Synthetic

<400> SEQUENCE: 620

Gly Phe Asn Ile Ser Ser Ser Tyr Ile His
1               5                   10

<210> SEQ ID NO 621
<211> LENGTH: 10
<212> TYPE: PRT
<213> ORGANISM: Artificial Sequence
<220> FEATURE:
<223> OTHER INFORMATION: Synthetic

<400> SEQUENCE: 621

Gly Phe Asn Ile Ser Ser Ser Tyr Ile His
1               5                   10

```
<210> SEQ ID NO 622
<211> LENGTH: 10
<212> TYPE: PRT
<213> ORGANISM: Artificial Sequence
<220> FEATURE:
<223> OTHER INFORMATION: Synthetic

<400> SEQUENCE: 622

Gly Phe Asn Ile Ser Ser Ser Tyr Ile His
1               5                   10

<210> SEQ ID NO 623
<211> LENGTH: 10
<212> TYPE: PRT
<213> ORGANISM: Artificial Sequence
<220> FEATURE:
<223> OTHER INFORMATION: Synthetic

<400> SEQUENCE: 623

Gly Phe Asn Leu Ala Ser Ser Phe Met His
1               5                   10

<210> SEQ ID NO 624
<211> LENGTH: 10
<212> TYPE: PRT
<213> ORGANISM: Artificial Sequence
<220> FEATURE:
<223> OTHER INFORMATION: Synthetic

<400> SEQUENCE: 624

Gly Phe Asn Leu Val Ser Ser Leu Met His
1               5                   10

<210> SEQ ID NO 625
<211> LENGTH: 10
<212> TYPE: PRT
<213> ORGANISM: Artificial Sequence
<220> FEATURE:
<223> OTHER INFORMATION: Synthetic

<400> SEQUENCE: 625

Gly Phe Asn Val Lys Thr Gly Leu Ile His
1               5                   10

<210> SEQ ID NO 626
<211> LENGTH: 10
<212> TYPE: PRT
<213> ORGANISM: Artificial Sequence
<220> FEATURE:
<223> OTHER INFORMATION: Synthetic

<400> SEQUENCE: 626

Gly Phe Asn Val Lys Trp Asn Tyr Ile His
1               5                   10

<210> SEQ ID NO 627
<211> LENGTH: 10
<212> TYPE: PRT
<213> ORGANISM: Artificial Sequence
<220> FEATURE:
<223> OTHER INFORMATION: Synthetic

<400> SEQUENCE: 627

Gly Phe Asn Val Val Ser Ser Phe Ile His
1               5                   10

<210> SEQ ID NO 628
```

```
<211> LENGTH: 10
<212> TYPE: PRT
<213> ORGANISM: Artificial Sequence
<220> FEATURE:
<223> OTHER INFORMATION: Synthetic 220>
<220> FEATURE:
<221> NAME/KEY: MOD_RES
<222> LOCATION: (4)..(4)
<223> OTHER INFORMATION: Ile, Phe, Leu or Val
<220> FEATURE:
<221> NAME/KEY: MOD_RES
<222> LOCATION: (5)..(5)
<223> OTHER INFORMATION: Ser, Lys, Ala or Val
<220> FEATURE:
<221> NAME/KEY: MOD_RES
<222> LOCATION: (6)..(6)
<223> OTHER INFORMATION: Ser, Gly, Thr or Trp
<220> FEATURE:
<221> NAME/KEY: MOD_RES
<222> LOCATION: (7)..(7)
<223> OTHER INFORMATION: Ser, Gly or Asn
<220> FEATURE:
<221> NAME/KEY: MOD_RES
<222> LOCATION: (8)..(8)
<223> OTHER INFORMATION: Tyr, Leu, Ile or Phe
<220> FEATURE:
<221> NAME/KEY: MOD_RES
<222> LOCATION: (9)..(9)
<223> OTHER INFORMATION: Ile or Met

<400> SEQUENCE: 628

Gly Phe Asn Xaa Xaa Xaa Xaa Xaa Xaa His
1               5                   10

<210> SEQ ID NO 629
<211> LENGTH: 17
<212> TYPE: PRT
<213> ORGANISM: Artificial Sequence
<220> FEATURE:
<223> OTHER INFORMATION: Synthetic

<400> SEQUENCE: 629

Ala Ile Ala Pro Tyr Leu Gly Ser Thr Ser Tyr Ala Asp Ser Val Lys
1               5                   10                  15

Gly

<210> SEQ ID NO 630
<211> LENGTH: 17
<212> TYPE: PRT
<213> ORGANISM: Artificial Sequence
<220> FEATURE:
<223> OTHER INFORMATION: Synthetic

<400> SEQUENCE: 630

Ala Ile Pro Pro Phe Tyr Gly Trp Thr Ser Tyr Ala Asp Ser Val Lys
1               5                   10                  15

Gly

<210> SEQ ID NO 631
<211> LENGTH: 17
<212> TYPE: PRT
<213> ORGANISM: Artificial Sequence
<220> FEATURE:
<223> OTHER INFORMATION: Synthetic

<400> SEQUENCE: 631

Ala Ile Gln Pro Tyr Phe Gly Trp Thr Ile Tyr Ala Asp Ser Val Lys
1               5                   10                  15

Gly
```

```
<210> SEQ ID NO 632
<211> LENGTH: 17
<212> TYPE: PRT
<213> ORGANISM: Artificial Sequence
<220> FEATURE:
<223> OTHER INFORMATION: Synthetic

<400> SEQUENCE: 632

Ala Ile Ser Pro Tyr Leu Gly Ser Thr Ser Tyr Ala Asp Ser Val Lys
1               5                   10                  15

Gly

<210> SEQ ID NO 633
<211> LENGTH: 17
<212> TYPE: PRT
<213> ORGANISM: Artificial Sequence
<220> FEATURE:
<223> OTHER INFORMATION: Synthetic

<400> SEQUENCE: 633

Asp Ile Ala Pro Tyr Leu Gly Thr Thr Lys Tyr Ala Asp Ser Val Lys
1               5                   10                  15

Gly

<210> SEQ ID NO 634
<211> LENGTH: 17
<212> TYPE: PRT
<213> ORGANISM: Artificial Sequence
<220> FEATURE:
<223> OTHER INFORMATION: Synthetic

<400> SEQUENCE: 634

Asp Ile Ser Pro Trp Tyr Gly Gly Thr Ser Tyr Ala Asp Ser Val Lys
1               5                   10                  15

Gly

<210> SEQ ID NO 635
<211> LENGTH: 17
<212> TYPE: PRT
<213> ORGANISM: Artificial Sequence
<220> FEATURE:
<223> OTHER INFORMATION: Synthetic

<400> SEQUENCE: 635

Asp Ile Ser Ser Tyr Thr Gly Ser Thr Asp Tyr Ala Asp Ser Val Lys
1               5                   10                  15

Gly

<210> SEQ ID NO 636
<211> LENGTH: 17
<212> TYPE: PRT
<213> ORGANISM: Artificial Sequence
<220> FEATURE:
<223> OTHER INFORMATION: Synthetic

<400> SEQUENCE: 636

Phe Ile Gln Pro Tyr Tyr Gly Ser Thr Ile Tyr Ala Asp Ser Val Lys
1               5                   10                  15

Gly

<210> SEQ ID NO 637
<211> LENGTH: 17
```

```
<212> TYPE: PRT
<213> ORGANISM: Artificial Sequence
<220> FEATURE:
<223> OTHER INFORMATION: Synthetic

<400> SEQUENCE: 637

Phe Ile Ser Pro Tyr Leu Gly Ser Thr Asn Tyr Ala Asp Ser Val Lys
1               5                   10                  15
Gly

<210> SEQ ID NO 638
<211> LENGTH: 17
<212> TYPE: PRT
<213> ORGANISM: Artificial Sequence
<220> FEATURE:
<223> OTHER INFORMATION: Synthetic

<400> SEQUENCE: 638

Gly Ile Thr Pro Tyr Leu Gly Trp Thr Ser Tyr Ala Asp Ser Val Lys
1               5                   10                  15
Gly

<210> SEQ ID NO 639
<211> LENGTH: 17
<212> TYPE: PRT
<213> ORGANISM: Artificial Sequence
<220> FEATURE:
<223> OTHER INFORMATION: Synthetic

<400> SEQUENCE: 639

His Ile Ser Pro Tyr Leu Gly Ser Thr Ser Tyr Ala Asp Ser Val Lys
1               5                   10                  15
Gly

<210> SEQ ID NO 640
<211> LENGTH: 17
<212> TYPE: PRT
<213> ORGANISM: Artificial Sequence
<220> FEATURE:
<223> OTHER INFORMATION: Synthetic

<400> SEQUENCE: 640

Ile Ile Ser Pro Tyr Leu Gly Ser Thr Gly Tyr Ala Asp Ser Val Lys
1               5                   10                  15
Gly

<210> SEQ ID NO 641
<211> LENGTH: 17
<212> TYPE: PRT
<213> ORGANISM: Artificial Sequence
<220> FEATURE:
<223> OTHER INFORMATION: Synthetic

<400> SEQUENCE: 641

Ser Ile Thr Pro Tyr Tyr Gly Trp Thr Arg Tyr Ala Asp Ser Val Lys
1               5                   10                  15
Gly

<210> SEQ ID NO 642
<211> LENGTH: 17
<212> TYPE: PRT
<213> ORGANISM: Artificial Sequence
<220> FEATURE:
<223> OTHER INFORMATION: Synthetic
```

-continued

<400> SEQUENCE: 642

Trp Ile Ser Pro Tyr Leu Gly Arg Thr Ser Tyr Ala Asp Ser Val Lys
1               5                   10                  15
Gly

<210> SEQ ID NO 643
<211> LENGTH: 17
<212> TYPE: PRT
<213> ORGANISM: Artificial Sequence
<220> FEATURE:
<223> OTHER INFORMATION: Synthetic

<400> SEQUENCE: 643

Tyr Ile Ser Pro Tyr Tyr Gly Ser Thr Ser Tyr Ala Asp Ser Val Lys
1               5                   10                  15
Gly

<210> SEQ ID NO 644
<211> LENGTH: 17
<212> TYPE: PRT
<213> ORGANISM: Artificial Sequence
<220> FEATURE:
<223> OTHER INFORMATION: Synthetic

<400> SEQUENCE: 644

Tyr Ile Ser Pro Tyr Tyr Gly Ser Thr Ser Tyr Ala Asp Ser Val Lys
1               5                   10                  15
Gly

<210> SEQ ID NO 645
<211> LENGTH: 17
<212> TYPE: PRT
<213> ORGANISM: Artificial Sequence
<220> FEATURE:
<223> OTHER INFORMATION: Synthetic

<400> SEQUENCE: 645

Tyr Ile Ser Pro Tyr Tyr Gly Ser Thr Ser Tyr Ala Asp Ser Val Lys
1               5                   10                  15
Gly

<210> SEQ ID NO 646
<211> LENGTH: 17
<212> TYPE: PRT
<213> ORGANISM: Artificial Sequence
<220> FEATURE:
<223> OTHER INFORMATION: Synthetic

<400> SEQUENCE: 646

Tyr Ile Ser Pro Tyr Tyr Gly Ser Thr Ser Tyr Ala Asp Ser Val Lys
1               5                   10                  15
Gly

<210> SEQ ID NO 647
<211> LENGTH: 17
<212> TYPE: PRT
<213> ORGANISM: Artificial Sequence
<220> FEATURE:
<223> OTHER INFORMATION: Synthetic

<400> SEQUENCE: 647

Tyr Ile Gly Pro Phe Thr Gly Ser Thr Asn Tyr Ala Asp Ser Val Lys

<210> SEQ ID NO 648
<211> LENGTH: 17
<212> TYPE: PRT
<213> ORGANISM: Artificial Sequence
<220> FEATURE:
<223> OTHER INFORMATION: Synthetic

<400> SEQUENCE: 648

Tyr Ile Ser Pro Phe Leu Ser Thr Thr Ser Tyr Ala Asp Ser Val Lys
1               5                   10                  15
Gly

<210> SEQ ID NO 649
<211> LENGTH: 17
<212> TYPE: PRT
<213> ORGANISM: Artificial Sequence
<220> FEATURE:
<223> OTHER INFORMATION: Synthetic

<400> SEQUENCE: 649

Tyr Ile Ser Pro Tyr Tyr Gly Ser Thr Ser Tyr Ala Asp Ser Val Lys
1               5                   10                  15
Gly

<210> SEQ ID NO 650
<211> LENGTH: 17
<212> TYPE: PRT
<213> ORGANISM: Artificial Sequence
<220> FEATURE:
<223> OTHER INFORMATION: Synthetic

<400> SEQUENCE: 650

Tyr Ile Ser Pro Tyr Ser Gly Ser Thr Lys Tyr Ala Asp Ser Val Lys
1               5                   10                  15
Gly

<210> SEQ ID NO 651
<211> LENGTH: 17
<212> TYPE: PRT
<213> ORGANISM: Artificial Sequence
<220> FEATURE:
<223> OTHER INFORMATION: Synthetic

<400> SEQUENCE: 651

Tyr Ile Ser Pro Tyr Tyr Ser Ser Thr Ser Tyr Ala Asp Ser Val Lys
1               5                   10                  15
Gly

<210> SEQ ID NO 652
<211> LENGTH: 17
<212> TYPE: PRT
<213> ORGANISM: Artificial Sequence
<220> FEATURE:
<223> OTHER INFORMATION: Synthetic

<400> SEQUENCE: 652

Tyr Ile Ser Pro Tyr Leu Gly Ser Thr Ser Tyr Ala Asp Ser Val Lys
1               5                   10                  15
Gly

```
<210> SEQ ID NO 653
<211> LENGTH: 17
<212> TYPE: PRT
<213> ORGANISM: Artificial Sequence
<220> FEATURE:
<223> OTHER INFORMATION: Synthetic

<400> SEQUENCE: 653

Tyr Ile Ser Pro Tyr Leu Ser Ser Thr Ser Tyr Ala Asp Ser Val Lys
1               5                   10                  15

Gly

<210> SEQ ID NO 654
<211> LENGTH: 17
<212> TYPE: PRT
<213> ORGANISM: Artificial Sequence
<220> FEATURE:
<223> OTHER INFORMATION: Synthetic

<400> SEQUENCE: 654

Tyr Ile Ser Pro Tyr Tyr Gly Ser Thr Ser Tyr Ala Asp Ser Val Lys
1               5                   10                  15

Gly

<210> SEQ ID NO 655
<211> LENGTH: 17
<212> TYPE: PRT
<213> ORGANISM: Artificial Sequence
<220> FEATURE:
<223> OTHER INFORMATION: Synthetic

<400> SEQUENCE: 655

Tyr Ile Ser Pro Tyr Tyr Gly Ser Thr Ser Tyr Ala Asp Ser Val Lys
1               5                   10                  15

Gly

<210> SEQ ID NO 656
<211> LENGTH: 17
<212> TYPE: PRT
<213> ORGANISM: Artificial Sequence
<220> FEATURE:
<223> OTHER INFORMATION: Synthetic

<400> SEQUENCE: 656

Tyr Ile Ser Pro Tyr Tyr Gly Ser Thr Ser Tyr Ala Asp Ser Val Lys
1               5                   10                  15

Gly

<210> SEQ ID NO 657
<211> LENGTH: 17
<212> TYPE: PRT
<213> ORGANISM: Artificial Sequence
<220> FEATURE:
<223> OTHER INFORMATION: Synthetic

<400> SEQUENCE: 657

Tyr Ile Ser Pro Tyr Tyr Gly Ser Thr Ser Tyr Ala Asp Ser Val Lys
1               5                   10                  15

Gly

<210> SEQ ID NO 658
<211> LENGTH: 17
<212> TYPE: PRT
```

```
<213> ORGANISM: Artificial Sequence
<220> FEATURE:
<223> OTHER INFORMATION: Synthetic

<400> SEQUENCE: 658

Tyr Ile Ser Pro Tyr Tyr Gly Ser Thr Ser Tyr Ala Asp Ser Val Lys
1               5                   10                  15

Gly

<210> SEQ ID NO 659
<211> LENGTH: 17
<212> TYPE: PRT
<213> ORGANISM: Artificial Sequence
<220> FEATURE:
<223> OTHER INFORMATION: Synthetic

<400> SEQUENCE: 659

Tyr Ile Ser Pro Tyr Tyr Gly Ser Thr Ser Tyr Ala Asp Ser Val Lys
1               5                   10                  15

Gly

<210> SEQ ID NO 660
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ala, Asp, Phe, Gly, His, Ile, Ser, Trp or Tyr
<220> FEATURE:
<221> NAME/KEY: MOD_RES
<222> LOCATION: (3)..(3)
<223> OTHER INFORMATION: Ala, Pro, Gln, Ser, Thr or Gly
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (5)..(5)
<223> OTHER INFORMATION: Tyr or Phe
<220> FEATURE:
<221> NAME/KEY: MOD_RES
<222> LOCATION: (6)..(6)
<223> OTHER INFORMATION: Leu, Tyr, Phe or Thr
<220> FEATURE:
<221> NAME/KEY: MOD_RES
<222> LOCATION: (7)..(7)
<223> OTHER INFORMATION: Gly or Ser
<220> FEATURE:
<221> NAME/KEY: MOD_RES
<222> LOCATION: (8)..(8)
<223> OTHER INFORMATION: Ser, Trp, Thr, Gly or Arg
<220> FEATURE:
<221> NAME/KEY: MOD_RES
<222> LOCATION: (10)..(10)
<223> OTHER INFORMATION: Ser, Ile, Lys, Asp, Asn, Gly or Arg

<400> SEQUENCE: 660

Xaa Ile Xaa Xaa Xaa Xaa Xaa Xaa Thr Xaa Tyr Ala Asp Ser Val Lys
1               5                   10                  15

Gly

<210> SEQ ID NO 661
<211> LENGTH: 11
<212> TYPE: PRT
<213> ORGANISM: Artificial Sequence
<220> FEATURE:
```

<223> OTHER INFORMATION: Synthetic

<400> SEQUENCE: 661

Glu Tyr Tyr Arg Trp Tyr Thr Ala Ile Asp Tyr
1               5                   10

<210> SEQ ID NO 662
<211> LENGTH: 11
<212> TYPE: PRT
<213> ORGANISM: Artificial Sequence
<220> FEATURE:
<223> OTHER INFORMATION: Synthetic

<400> SEQUENCE: 662

Glu Tyr Tyr Arg Trp Tyr Thr Ala Ile Asp Tyr
1               5                   10

<210> SEQ ID NO 663
<211> LENGTH: 11
<212> TYPE: PRT
<213> ORGANISM: Artificial Sequence
<220> FEATURE:
<223> OTHER INFORMATION: Synthetic

<400> SEQUENCE: 663

Glu Tyr Tyr Arg Trp Tyr Thr Ala Ile Asp Tyr
1               5                   10

<210> SEQ ID NO 664
<211> LENGTH: 11
<212> TYPE: PRT
<213> ORGANISM: Artificial Sequence
<220> FEATURE:
<223> OTHER INFORMATION: Synthetic

<400> SEQUENCE: 664

Glu Tyr Tyr Arg Trp Tyr Thr Ala Ile Asp Tyr
1               5                   10

<210> SEQ ID NO 665
<211> LENGTH: 11
<212> TYPE: PRT
<213> ORGANISM: Artificial Sequence
<220> FEATURE:
<223> OTHER INFORMATION: Synthetic

<400> SEQUENCE: 665

Glu Tyr Tyr Arg Trp Tyr Thr Ala Ile Asp Tyr
1               5                   10

<210> SEQ ID NO 666
<211> LENGTH: 11
<212> TYPE: PRT
<213> ORGANISM: Artificial Sequence
<220> FEATURE:
<223> OTHER INFORMATION: Synthetic

<400> SEQUENCE: 666

Glu Tyr Tyr Arg Trp Tyr Thr Ala Ile Asp Tyr
1               5                   10

<210> SEQ ID NO 667
<211> LENGTH: 11
<212> TYPE: PRT
<213> ORGANISM: Artificial Sequence
<220> FEATURE:
<223> OTHER INFORMATION: Synthetic

<400> SEQUENCE: 667

Glu Tyr Tyr Arg Trp Tyr Thr Ala Ile Asp Tyr
1               5                   10

<210> SEQ ID NO 668
<211> LENGTH: 11
<212> TYPE: PRT
<213> ORGANISM: Artificial Sequence
<220> FEATURE:
<223> OTHER INFORMATION: Synthetic

<400> SEQUENCE: 668

Glu Tyr Tyr Arg Trp Tyr Thr Ala Ile Asp Tyr
1               5                   10

<210> SEQ ID NO 669
<211> LENGTH: 11
<212> TYPE: PRT
<213> ORGANISM: Artificial Sequence
<220> FEATURE:
<223> OTHER INFORMATION: Synthetic

<400> SEQUENCE: 669

Glu Tyr Tyr Arg Trp Tyr Thr Ala Ile Asp Tyr
1               5                   10

<210> SEQ ID NO 670
<211> LENGTH: 11
<212> TYPE: PRT
<213> ORGANISM: Artificial Sequence
<220> FEATURE:
<223> OTHER INFORMATION: Synthetic

<400> SEQUENCE: 670

Glu Tyr Tyr Arg Trp Tyr Thr Ala Ile Asp Tyr
1               5                   10

<210> SEQ ID NO 671
<211> LENGTH: 11
<212> TYPE: PRT
<213> ORGANISM: Artificial Sequence
<220> FEATURE:
<223> OTHER INFORMATION: Synthetic

<400> SEQUENCE: 671

Glu Tyr Tyr Arg Trp Tyr Thr Ala Ile Asp Tyr
1               5                   10

<210> SEQ ID NO 672
<211> LENGTH: 11
<212> TYPE: PRT
<213> ORGANISM: Artificial Sequence
<220> FEATURE:
<223> OTHER INFORMATION: Synthetic

<400> SEQUENCE: 672

Glu Tyr Tyr Arg Trp Tyr Thr Ala Ile Asp Tyr
1               5                   10

<210> SEQ ID NO 673
<211> LENGTH: 11
<212> TYPE: PRT
<213> ORGANISM: Artificial Sequence
<220> FEATURE:
<223> OTHER INFORMATION: Synthetic

<400> SEQUENCE: 673

Glu Tyr Tyr Arg Trp Tyr Thr Ala Ile Asp Tyr
1               5                   10

<210> SEQ ID NO 674
<211> LENGTH: 11
<212> TYPE: PRT
<213> ORGANISM: Artificial Sequence
<220> FEATURE:
<223> OTHER INFORMATION: Synthetic

<400> SEQUENCE: 674

Glu Tyr Tyr Arg Trp Tyr Thr Ala Ile Asp Tyr
1               5                   10

<210> SEQ ID NO 675
<211> LENGTH: 11
<212> TYPE: PRT
<213> ORGANISM: Artificial Sequence
<220> FEATURE:
<223> OTHER INFORMATION: Synthetic

<400> SEQUENCE: 675

Glu Tyr Tyr Arg Trp Tyr Thr Ala Ile Asp Tyr
1               5                   10

<210> SEQ ID NO 676
<211> LENGTH: 11
<212> TYPE: PRT
<213> ORGANISM: Artificial Sequence
<220> FEATURE:
<223> OTHER INFORMATION: Synthetic

<400> SEQUENCE: 676

Glu Tyr Tyr Arg Trp Tyr Thr Ala Ile Asp Tyr
1               5                   10

<210> SEQ ID NO 677
<211> LENGTH: 11
<212> TYPE: PRT
<213> ORGANISM: Artificial Sequence
<220> FEATURE:
<223> OTHER INFORMATION: Synthetic

<400> SEQUENCE: 677

Glu Tyr Tyr Arg Trp Tyr Thr Ala Ile Asp Tyr
1               5                   10

<210> SEQ ID NO 678
<211> LENGTH: 11
<212> TYPE: PRT
<213> ORGANISM: Artificial Sequence
<220> FEATURE:
<223> OTHER INFORMATION: Synthetic

<400> SEQUENCE: 678

Glu Tyr Tyr Arg Trp Tyr Thr Ala Ile Asp Tyr
1               5                   10

<210> SEQ ID NO 679
<211> LENGTH: 11
<212> TYPE: PRT
<213> ORGANISM: Artificial Sequence
<220> FEATURE:
<223> OTHER INFORMATION: Synthetic

<400> SEQUENCE: 679

Glu Tyr Tyr Arg Trp Tyr Thr Ala Ile Asp Tyr
1               5                   10

<210> SEQ ID NO 680
<211> LENGTH: 11
<212> TYPE: PRT
<213> ORGANISM: Artificial Sequence
<220> FEATURE:
<223> OTHER INFORMATION: Synthetic

<400> SEQUENCE: 680

Glu Tyr Tyr Arg Trp Tyr Thr Ala Ile Asp Tyr
1               5                   10

<210> SEQ ID NO 681
<211> LENGTH: 11
<212> TYPE: PRT
<213> ORGANISM: Artificial Sequence
<220> FEATURE:
<223> OTHER INFORMATION: Synthetic

<400> SEQUENCE: 681

Glu Tyr Tyr Arg Trp Tyr Thr Ala Ile Asp Tyr
1               5                   10

<210> SEQ ID NO 682
<211> LENGTH: 11
<212> TYPE: PRT
<213> ORGANISM: Artificial Sequence
<220> FEATURE:
<223> OTHER INFORMATION: Synthetic

<400> SEQUENCE: 682

Glu Tyr Tyr Arg Trp Tyr Thr Ala Ile Asp Tyr
1               5                   10

<210> SEQ ID NO 683
<211> LENGTH: 11
<212> TYPE: PRT
<213> ORGANISM: Artificial Sequence
<220> FEATURE:
<223> OTHER INFORMATION: Synthetic

<400> SEQUENCE: 683

Glu Tyr Tyr Arg Trp Tyr Thr Ala Ile Asp Tyr
1               5                   10

<210> SEQ ID NO 684
<211> LENGTH: 11
<212> TYPE: PRT
<213> ORGANISM: Artificial Sequence
<220> FEATURE:
<223> OTHER INFORMATION: Synthetic

<400> SEQUENCE: 684

Glu Tyr Tyr Arg Trp Tyr Thr Ala Ile Asp Tyr
1               5                   10

<210> SEQ ID NO 685
<211> LENGTH: 11
<212> TYPE: PRT
<213> ORGANISM: Artificial Sequence
<220> FEATURE:
<223> OTHER INFORMATION: Synthetic

<400> SEQUENCE: 685

Glu Tyr Tyr Arg Trp Tyr Thr Ala Ile Asp Tyr
1               5                   10

<210> SEQ ID NO 686
<211> LENGTH: 11
<212> TYPE: PRT
<213> ORGANISM: Artificial Sequence
<220> FEATURE:
<223> OTHER INFORMATION: Synthetic

<400> SEQUENCE: 686

Glu Tyr Tyr Arg Trp Tyr Thr Ala Ile Asp Tyr
1               5                   10

<210> SEQ ID NO 687
<211> LENGTH: 11
<212> TYPE: PRT
<213> ORGANISM: Artificial Sequence
<220> FEATURE:
<223> OTHER INFORMATION: Synthetic

<400> SEQUENCE: 687

Glu Tyr Tyr Arg Trp Tyr Thr Ala Ile Asp Tyr
1               5                   10

<210> SEQ ID NO 688
<211> LENGTH: 11
<212> TYPE: PRT
<213> ORGANISM: Artificial Sequence
<220> FEATURE:
<223> OTHER INFORMATION: Synthetic

<400> SEQUENCE: 688

Glu Tyr Tyr Arg Trp Tyr Thr Ala Ile Asp Tyr
1               5                   10

<210> SEQ ID NO 689
<211> LENGTH: 11
<212> TYPE: PRT
<213> ORGANISM: Artificial Sequence
<220> FEATURE:
<223> OTHER INFORMATION: Synthetic

<400> SEQUENCE: 689

Glu Tyr Tyr Arg Trp Tyr Thr Ala Ile Asp Tyr
1               5                   10

<210> SEQ ID NO 690
<211> LENGTH: 11
<212> TYPE: PRT
<213> ORGANISM: Artificial Sequence
<220> FEATURE:
<223> OTHER INFORMATION: Synthetic

<400> SEQUENCE: 690

Glu Tyr Tyr Arg Trp Tyr Thr Ala Ile Asp Tyr
1               5                   10

<210> SEQ ID NO 691
<211> LENGTH: 11
<212> TYPE: PRT
<213> ORGANISM: Artificial Sequence
<220> FEATURE:
<223> OTHER INFORMATION: Synthetic

<400> SEQUENCE: 691

Glu Tyr Tyr Arg Trp Tyr Thr Ala Ile Asp Tyr

<210> SEQ ID NO 692
<211> LENGTH: 11
<212> TYPE: PRT
<213> ORGANISM: Artificial Sequence
<220> FEATURE:
<223> OTHER INFORMATION: Synthetic

<400> SEQUENCE: 692

Glu Tyr Tyr Arg Trp Tyr Thr Ala Ile Asp Tyr
1               5                   10

<210> SEQ ID NO 693
<211> LENGTH: 10
<212> TYPE: PRT
<213> ORGANISM: Artificial Sequence
<220> FEATURE:
<223> OTHER INFORMATION: Synthetic

<400> SEQUENCE: 693

Gly Phe Asn Ile Ser Tyr Ser Ser Met His
1               5                   10

<210> SEQ ID NO 694
<211> LENGTH: 10
<212> TYPE: PRT
<213> ORGANISM: Artificial Sequence
<220> FEATURE:
<223> OTHER INFORMATION: Synthetic

<400> SEQUENCE: 694

Gly Phe Asn Ile Phe Tyr Gly Gly Ile His
1               5                   10

<210> SEQ ID NO 695
<211> LENGTH: 10
<212> TYPE: PRT
<213> ORGANISM: Artificial Sequence
<220> FEATURE:
<223> OTHER INFORMATION: Synthetic

<400> SEQUENCE: 695

Gly Phe Asn Ile Ser Tyr Ser Ser Met His
1               5                   10

<210> SEQ ID NO 696
<211> LENGTH: 10
<212> TYPE: PRT
<213> ORGANISM: Artificial Sequence
<220> FEATURE:
<223> OTHER INFORMATION: Synthetic

<400> SEQUENCE: 696

Gly Phe Asn Ile Ser Tyr Ser Ser Met His
1               5                   10

<210> SEQ ID NO 697
<211> LENGTH: 10
<212> TYPE: PRT
<213> ORGANISM: Artificial Sequence
<220> FEATURE:
<223> OTHER INFORMATION: Synthetic

<400> SEQUENCE: 697

Gly Phe Asn Ile Ser Tyr Ser Ser Met His
1               5                   10

```
<210> SEQ ID NO 698
<211> LENGTH: 10
<212> TYPE: PRT
<213> ORGANISM: Artificial Sequence
<220> FEATURE:
<223> OTHER INFORMATION: Synthetic

<400> SEQUENCE: 698

Gly Phe Asn Ile Ser Tyr Ser Ser Met His
1               5                   10

<210> SEQ ID NO 699
<211> LENGTH: 10
<212> TYPE: PRT
<213> ORGANISM: Artificial Sequence
<220> FEATURE:
<223> OTHER INFORMATION: Synthetic

<400> SEQUENCE: 699

Gly Phe Asn Ile Ser Tyr Ser Ser Met His
1               5                   10

<210> SEQ ID NO 700
<211> LENGTH: 10
<212> TYPE: PRT
<213> ORGANISM: Artificial Sequence
<220> FEATURE:
<223> OTHER INFORMATION: Synthetic

<400> SEQUENCE: 700

Gly Phe Asn Ile Ser Tyr Ser Ser Met His
1               5                   10

<210> SEQ ID NO 701
<211> LENGTH: 10
<212> TYPE: PRT
<213> ORGANISM: Artificial Sequence
<220> FEATURE:
<223> OTHER INFORMATION: Synthetic

<400> SEQUENCE: 701

Gly Phe Asn Ile Ser Tyr Ser Ser Met His
1               5                   10

<210> SEQ ID NO 702
<211> LENGTH: 10
<212> TYPE: PRT
<213> ORGANISM: Artificial Sequence
<220> FEATURE:
<223> OTHER INFORMATION: Synthetic

<400> SEQUENCE: 702

Gly Phe Asn Ile Ser Tyr Ser Ser Met His
1               5                   10

<210> SEQ ID NO 703
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: Ser or Phe
<220> FEATURE:
<221> NAME/KEY: MOD_RES
```

```
<222> LOCATION: (7)..(8)
<223> OTHER INFORMATION: Ser or Gly
<220> FEATURE:
<221> NAME/KEY: MOD_RES
<222> LOCATION: (9)..(9)
<223> OTHER INFORMATION: Met or Ile

<400> SEQUENCE: 703

Gly Phe Asn Ile Xaa Tyr Xaa Xaa Xaa His
1               5                   10

<210> SEQ ID NO 704
<211> LENGTH: 17
<212> TYPE: PRT
<213> ORGANISM: Artificial Sequence
<220> FEATURE:
<223> OTHER INFORMATION: Synthetic

<400> SEQUENCE: 704

Ser Ile Tyr Ser Tyr Tyr Ser Tyr Thr Ser Tyr Ala Asp Ser Val Lys
1               5                   10                  15
Gly

<210> SEQ ID NO 705
<211> LENGTH: 17
<212> TYPE: PRT
<213> ORGANISM: Artificial Sequence
<220> FEATURE:
<223> OTHER INFORMATION: Synthetic

<400> SEQUENCE: 705

Ser Ile Tyr Ser Tyr Tyr Ser Tyr Thr Ser Tyr Ala Asp Ser Val Lys
1               5                   10                  15
Gly

<210> SEQ ID NO 706
<211> LENGTH: 17
<212> TYPE: PRT
<213> ORGANISM: Artificial Sequence
<220> FEATURE:
<223> OTHER INFORMATION: Synthetic

<400> SEQUENCE: 706

Ser Ile Tyr Ser Tyr Tyr Ser Tyr Thr Ser Tyr Ala Asp Ser Val Lys
1               5                   10                  15
Gly

<210> SEQ ID NO 707
<211> LENGTH: 17
<212> TYPE: PRT
<213> ORGANISM: Artificial Sequence
<220> FEATURE:
<223> OTHER INFORMATION: Synthetic

<400> SEQUENCE: 707

Ser Ile Tyr Ser Tyr Tyr Ser Tyr Thr Ser Tyr Ala Asp Ser Val Lys
1               5                   10                  15
Gly

<210> SEQ ID NO 708
<211> LENGTH: 17
<212> TYPE: PRT
<213> ORGANISM: Artificial Sequence
<220> FEATURE:
<223> OTHER INFORMATION: Synthetic
```

-continued

<400> SEQUENCE: 708

Ser Ile Tyr Ser Tyr Tyr Ser Tyr Thr Ser Tyr Ala Asp Ser Val Lys
1               5                   10                  15
Gly

<210> SEQ ID NO 709
<211> LENGTH: 17
<212> TYPE: PRT
<213> ORGANISM: Artificial Sequence
<220> FEATURE:
<223> OTHER INFORMATION: Synthetic

<400> SEQUENCE: 709

Ser Ile Tyr Ser Tyr Tyr Ser Tyr Thr Ser Tyr Ala Asp Ser Val Lys
1               5                   10                  15
Gly

<210> SEQ ID NO 710
<211> LENGTH: 17
<212> TYPE: PRT
<213> ORGANISM: Artificial Sequence
<220> FEATURE:
<223> OTHER INFORMATION: Synthetic

<400> SEQUENCE: 710

Ser Ile Tyr Ser Tyr Tyr Ser Tyr Thr Ser Tyr Ala Asp Ser Val Lys
1               5                   10                  15
Gly

<210> SEQ ID NO 711
<211> LENGTH: 17
<212> TYPE: PRT
<213> ORGANISM: Artificial Sequence
<220> FEATURE:
<223> OTHER INFORMATION: Synthetic

<400> SEQUENCE: 711

Ser Ile Tyr Ser Tyr Tyr Ser Tyr Thr Ser Tyr Ala Asp Ser Val Lys
1               5                   10                  15
Gly

<210> SEQ ID NO 712
<211> LENGTH: 17
<212> TYPE: PRT
<213> ORGANISM: Artificial Sequence
<220> FEATURE:
<223> OTHER INFORMATION: Synthetic

<400> SEQUENCE: 712

Ser Ile Tyr Ser Tyr Tyr Ser Tyr Thr Ser Tyr Ala Asp Ser Val Lys
1               5                   10                  15
Gly

<210> SEQ ID NO 713
<211> LENGTH: 17
<212> TYPE: PRT
<213> ORGANISM: Artificial Sequence
<220> FEATURE:
<223> OTHER INFORMATION: Synthetic

<400> SEQUENCE: 713

Ser Ile Tyr Ser Tyr Tyr Ser Tyr Thr Ser Tyr Ala Asp Ser Val Lys

```
1               5                   10                  15

Gly

<210> SEQ ID NO 714
<211> LENGTH: 17
<212> TYPE: PRT
<213> ORGANISM: Artificial Sequence
<220> FEATURE:
<223> OTHER INFORMATION: Synthetic

<400> SEQUENCE: 714

Ser Ile Tyr Ser Tyr Tyr Ser Tyr Thr Ser Tyr Ala Asp Ser Val Lys
1               5                   10                  15

Gly

<210> SEQ ID NO 715
<211> LENGTH: 10
<212> TYPE: PRT
<213> ORGANISM: Artificial Sequence
<220> FEATURE:
<223> OTHER INFORMATION: Synthetic

<400> SEQUENCE: 715

Ser Tyr Ser Tyr Ser Glu Ala Leu Asp Tyr
1               5                   10

<210> SEQ ID NO 716
<211> LENGTH: 10
<212> TYPE: PRT
<213> ORGANISM: Artificial Sequence
<220> FEATURE:
<223> OTHER INFORMATION: Synthetic

<400> SEQUENCE: 716

Ser Tyr Ser Tyr Tyr Ser Ala Met Asp Tyr
1               5                   10

<210> SEQ ID NO 717
<211> LENGTH: 10
<212> TYPE: PRT
<213> ORGANISM: Artificial Sequence
<220> FEATURE:
<223> OTHER INFORMATION: Synthetic

<400> SEQUENCE: 717

Ser Tyr Ser Tyr Ser Leu Ala Phe Asp Tyr
1               5                   10

<210> SEQ ID NO 718
<211> LENGTH: 10
<212> TYPE: PRT
<213> ORGANISM: Artificial Sequence
<220> FEATURE:
<223> OTHER INFORMATION: Synthetic

<400> SEQUENCE: 718

Ser Tyr Ser Tyr Ser Phe Gly Met Asp Tyr
1               5                   10

<210> SEQ ID NO 719
<211> LENGTH: 10
<212> TYPE: PRT
<213> ORGANISM: Artificial Sequence
<220> FEATURE:
<223> OTHER INFORMATION: Synthetic
```

<400> SEQUENCE: 719

Ser Tyr Ser Tyr Arg Met Ala Phe Asp Tyr
1               5                   10

<210> SEQ ID NO 720
<211> LENGTH: 10
<212> TYPE: PRT
<213> ORGANISM: Artificial Sequence
<220> FEATURE:
<223> OTHER INFORMATION: Synthetic

<400> SEQUENCE: 720

Gly Tyr Ser Trp Phe Asn Ala Ile Asp Tyr
1               5                   10

<210> SEQ ID NO 721
<211> LENGTH: 10
<212> TYPE: PRT
<213> ORGANISM: Artificial Sequence
<220> FEATURE:
<223> OTHER INFORMATION: Synthetic

<400> SEQUENCE: 721

Ser Tyr Ser Tyr His Leu Gly Met Asp Tyr
1               5                   10

<210> SEQ ID NO 722
<211> LENGTH: 10
<212> TYPE: PRT
<213> ORGANISM: Artificial Sequence
<220> FEATURE:
<223> OTHER INFORMATION: Synthetic

<400> SEQUENCE: 722

Ser Tyr Ser Tyr Ser Val Gly Met Asp Tyr
1               5                   10

<210> SEQ ID NO 723
<211> LENGTH: 10
<212> TYPE: PRT
<213> ORGANISM: Artificial Sequence
<220> FEATURE:
<223> OTHER INFORMATION: Synthetic

<400> SEQUENCE: 723

Ser Tyr Ser Tyr His Val Ala Phe Asp Tyr
1               5                   10

<210> SEQ ID NO 724
<211> LENGTH: 10
<212> TYPE: PRT
<213> ORGANISM: Artificial Sequence
<220> FEATURE:
<223> OTHER INFORMATION: Synthetic

<400> SEQUENCE: 724

Ser Tyr Ser Tyr Phe Leu Ala Met Asp Tyr
1               5                   10

<210> SEQ ID NO 725
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES

```
<222> LOCATION: (1)..(1)
<223> OTHER INFORMATION: Ser or Gly
<220> FEATURE:
<221> NAME/KEY: MOD_RES
<222> LOCATION: (4)..(4)
<223> OTHER INFORMATION: Tyr or Trp
<220> FEATURE:
<221> NAME/KEY: MOD_RES
<222> LOCATION: (5)..(5)
<223> OTHER INFORMATION: Ser, Tyr, Arg, Phe or His
<220> FEATURE:
<221> NAME/KEY: MOD_RES
<222> LOCATION: (6)..(6)
<223> OTHER INFORMATION: Glu, Ser, Leu, Phe, Met, Asn or Val
<220> FEATURE:
<221> NAME/KEY: MOD_RES
<222> LOCATION: (7)..(7)
<223> OTHER INFORMATION: Ala or Gly
<220> FEATURE:
<221> NAME/KEY: MOD_RES
<222> LOCATION: (8)..(8)
<223> OTHER INFORMATION: Leu, Met, Phe or Ile

<400> SEQUENCE: 725

Xaa Tyr Ser Xaa Xaa Xaa Xaa Xaa Asp Tyr
1               5                   10

<210> SEQ ID NO 726
<211> LENGTH: 10
<212> TYPE: PRT
<213> ORGANISM: Artificial Sequence
<220> FEATURE:
<223> OTHER INFORMATION: Synthetic

<400> SEQUENCE: 726

Gln Gln Ser Ser Tyr Ser Ser Leu Ile Thr
1               5                   10

<210> SEQ ID NO 727
<211> LENGTH: 10
<212> TYPE: PRT
<213> ORGANISM: Artificial Sequence
<220> FEATURE:
<223> OTHER INFORMATION: Synthetic

<400> SEQUENCE: 727

Gln Gln Ser Ser Tyr Ser Ser Leu Ile Thr
1               5                   10

<210> SEQ ID NO 728
<211> LENGTH: 10
<212> TYPE: PRT
<213> ORGANISM: Artificial Sequence
<220> FEATURE:
<223> OTHER INFORMATION: Synthetic

<400> SEQUENCE: 728

Gln Gln Ser Ser Tyr Ser Ser Leu Ile Thr
1               5                   10

<210> SEQ ID NO 729
<211> LENGTH: 10
<212> TYPE: PRT
<213> ORGANISM: Artificial Sequence
<220> FEATURE:
<223> OTHER INFORMATION: Synthetic

<400> SEQUENCE: 729

Gln Gln Ser Ser Tyr Ser Ser Leu Ile Thr
1               5                   10
```

```
<210> SEQ ID NO 730
<211> LENGTH: 10
<212> TYPE: PRT
<213> ORGANISM: Artificial Sequence
<220> FEATURE:
<223> OTHER INFORMATION: Synthetic

<400> SEQUENCE: 730

Gln Gln Ser Ser Tyr Ser Ser Leu Ile Thr
1               5                   10

<210> SEQ ID NO 731
<211> LENGTH: 10
<212> TYPE: PRT
<213> ORGANISM: Artificial Sequence
<220> FEATURE:
<223> OTHER INFORMATION: Synthetic

<400> SEQUENCE: 731

Gln Gln Ser Ser Tyr Ser Ser Leu Ile Thr
1               5                   10

<210> SEQ ID NO 732
<211> LENGTH: 10
<212> TYPE: PRT
<213> ORGANISM: Artificial Sequence
<220> FEATURE:
<223> OTHER INFORMATION: Synthetic

<400> SEQUENCE: 732

Gln Gln Ser Ser Tyr Ser Ser Leu Ile Thr
1               5                   10

<210> SEQ ID NO 733
<211> LENGTH: 10
<212> TYPE: PRT
<213> ORGANISM: Artificial Sequence
<220> FEATURE:
<223> OTHER INFORMATION: Synthetic

<400> SEQUENCE: 733

Gln Gln Ser Ser Tyr Ser Ser Leu Ile Thr
1               5                   10

<210> SEQ ID NO 734
<211> LENGTH: 10
<212> TYPE: PRT
<213> ORGANISM: Artificial Sequence
<220> FEATURE:
<223> OTHER INFORMATION: Synthetic

<400> SEQUENCE: 734

Gln Gln Ser Ser Tyr Ser Ser Leu Ile Thr
1               5                   10

<210> SEQ ID NO 735
<211> LENGTH: 10
<212> TYPE: PRT
<213> ORGANISM: Artificial Sequence
<220> FEATURE:
<223> OTHER INFORMATION: Synthetic

<400> SEQUENCE: 735

Gln Gln Ser Ser Tyr Ser Ser Leu Ile Thr
1               5                   10
```

<210> SEQ ID NO 736
<211> LENGTH: 10
<212> TYPE: PRT
<213> ORGANISM: Artificial Sequence
<220> FEATURE:
<223> OTHER INFORMATION: Synthetic

<400> SEQUENCE: 736

Gln Gln Ser Ser Tyr Ser Ser Leu Ile Thr
1               5                   10

<210> SEQ ID NO 737
<211> LENGTH: 10
<212> TYPE: PRT
<213> ORGANISM: Artificial Sequence
<220> FEATURE:
<223> OTHER INFORMATION: Synthetic

<400> SEQUENCE: 737

Gly Phe Asn Ile Ser Ser Ser Tyr Ile His
1               5                   10

<210> SEQ ID NO 738
<211> LENGTH: 10
<212> TYPE: PRT
<213> ORGANISM: Artificial Sequence
<220> FEATURE:
<223> OTHER INFORMATION: Synthetic

<400> SEQUENCE: 738

Gly Phe Asn Ile Ser Ser Ser Tyr Ile His
1               5                   10

<210> SEQ ID NO 739
<211> LENGTH: 10
<212> TYPE: PRT
<213> ORGANISM: Artificial Sequence
<220> FEATURE:
<223> OTHER INFORMATION: Synthetic

<400> SEQUENCE: 739

Gly Phe Asn Val Lys Trp Asn Tyr Ile His
1               5                   10

<210> SEQ ID NO 740
<211> LENGTH: 10
<212> TYPE: PRT
<213> ORGANISM: Artificial Sequence
<220> FEATURE:
<223> OTHER INFORMATION: Synthetic

<400> SEQUENCE: 740

Gly Phe Asn Ile Ser Ser Ser Tyr Ile His
1               5                   10

<210> SEQ ID NO 741
<211> LENGTH: 10
<212> TYPE: PRT
<213> ORGANISM: Artificial Sequence
<220> FEATURE:
<223> OTHER INFORMATION: Synthetic

<400> SEQUENCE: 741

Gly Phe Asn Ile Lys Gly Ser Ile Met His
1               5                   10

```
<210> SEQ ID NO 742
<211> LENGTH: 10
<212> TYPE: PRT
<213> ORGANISM: Artificial Sequence
<220> FEATURE:
<223> OTHER INFORMATION: Synthetic

<400> SEQUENCE: 742

Gly Phe Asn Val Lys Thr Gly Leu Ile His
1               5                   10

<210> SEQ ID NO 743
<211> LENGTH: 10
<212> TYPE: PRT
<213> ORGANISM: Artificial Sequence
<220> FEATURE:
<223> OTHER INFORMATION: Synthetic

<400> SEQUENCE: 743

Gly Phe Asn Ile Ser Ser Ser Tyr Ile His
1               5                   10

<210> SEQ ID NO 744
<211> LENGTH: 10
<212> TYPE: PRT
<213> ORGANISM: Artificial Sequence
<220> FEATURE:
<223> OTHER INFORMATION: Synthetic

<400> SEQUENCE: 744

Gly Phe Asn Leu Val Ser Ser Leu Met His
1               5                   10

<210> SEQ ID NO 745
<211> LENGTH: 10
<212> TYPE: PRT
<213> ORGANISM: Artificial Sequence
<220> FEATURE:
<223> OTHER INFORMATION: Synthetic

<400> SEQUENCE: 745

Gly Phe Asn Val Val Ser Ser Phe Ile His
1               5                   10

<210> SEQ ID NO 746
<211> LENGTH: 10
<212> TYPE: PRT
<213> ORGANISM: Artificial Sequence
<220> FEATURE:
<223> OTHER INFORMATION: Synthetic

<400> SEQUENCE: 746

Gly Phe Asn Ile Ser Ser Ser Tyr Ile His
1               5                   10

<210> SEQ ID NO 747
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Ile, Val or Leu
<220> FEATURE:
<221> NAME/KEY: MOD_RES
<222> LOCATION: (5)..(5)
<223> OTHER INFORMATION: Ser, Lys or Val
```

```
<220> FEATURE:
<221> NAME/KEY: MOD_RES
<222> LOCATION: (6)..(6)
<223> OTHER INFORMATION: Ser, Trp, Gly or Thr
<220> FEATURE:
<221> NAME/KEY: MOD_RES
<222> LOCATION: (7)..(7)
<223> OTHER INFORMATION: Ser, Asn or Gly
<220> FEATURE:
<221> NAME/KEY: MOD_RES
<222> LOCATION: (8)..(8)
<223> OTHER INFORMATION: Tyr, Ile, Leu or Phe
<220> FEATURE:
<221> NAME/KEY: MOD_RES
<222> LOCATION: (9)..(9)
<223> OTHER INFORMATION: Ile or Met

<400> SEQUENCE: 747

Gly Phe Asn Xaa Xaa Xaa Xaa Xaa Xaa His
1               5                   10

<210> SEQ ID NO 748
<211> LENGTH: 17
<212> TYPE: PRT
<213> ORGANISM: Artificial Sequence
<220> FEATURE:
<223> OTHER INFORMATION: Synthetic

<400> SEQUENCE: 748

Tyr Ile Ser Pro Tyr Leu Ser Ser Thr Ser Tyr Ala Asp Ser Val Lys
1               5                   10                  15

Gly

<210> SEQ ID NO 749
<211> LENGTH: 17
<212> TYPE: PRT
<213> ORGANISM: Artificial Sequence
<220> FEATURE:
<223> OTHER INFORMATION: Synthetic

<400> SEQUENCE: 749

Phe Ile Ser Pro Tyr Leu Gly Ser Thr Asn Tyr Ala Asp Ser Val Lys
1               5                   10                  15

Gly

<210> SEQ ID NO 750
<211> LENGTH: 17
<212> TYPE: PRT
<213> ORGANISM: Artificial Sequence
<220> FEATURE:
<223> OTHER INFORMATION: Synthetic

<400> SEQUENCE: 750

Tyr Ile Ser Pro Tyr Tyr Gly Ser Thr Ser Tyr Ala Asp Ser Val Lys
1               5                   10                  15

Gly

<210> SEQ ID NO 751
<211> LENGTH: 17
<212> TYPE: PRT
<213> ORGANISM: Artificial Sequence
<220> FEATURE:
<223> OTHER INFORMATION: Synthetic

<400> SEQUENCE: 751

Asp Ile Ala Pro Tyr Leu Gly Thr Thr Lys Tyr Ala Asp Ser Val Lys
1               5                   10                  15
```

Gly

<210> SEQ ID NO 752
<211> LENGTH: 17
<212> TYPE: PRT
<213> ORGANISM: Artificial Sequence
<220> FEATURE:
<223> OTHER INFORMATION: Synthetic

<400> SEQUENCE: 752

Tyr Ile Ser Pro Tyr Tyr Gly Ser Thr Ser Tyr Ala Asp Ser Val Lys
1               5                   10                  15
Gly

<210> SEQ ID NO 753
<211> LENGTH: 17
<212> TYPE: PRT
<213> ORGANISM: Artificial Sequence
<220> FEATURE:
<223> OTHER INFORMATION: Synthetic

<400> SEQUENCE: 753

Tyr Ile Ser Pro Tyr Tyr Gly Ser Thr Ser Tyr Ala Asp Ser Val Lys
1               5                   10                  15
Gly

<210> SEQ ID NO 754
<211> LENGTH: 17
<212> TYPE: PRT
<213> ORGANISM: Artificial Sequence
<220> FEATURE:
<223> OTHER INFORMATION: Synthetic

<400> SEQUENCE: 754

His Ile Ser Pro Tyr Leu Gly Ser Thr Ser Tyr Ala Asp Ser Val Lys
1               5                   10                  15
Gly

<210> SEQ ID NO 755
<211> LENGTH: 17
<212> TYPE: PRT
<213> ORGANISM: Artificial Sequence
<220> FEATURE:
<223> OTHER INFORMATION: Synthetic

<400> SEQUENCE: 755

Tyr Ile Ser Pro Tyr Tyr Gly Ser Thr Ser Tyr Ala Asp Ser Val Lys
1               5                   10                  15
Gly

<210> SEQ ID NO 756
<211> LENGTH: 17
<212> TYPE: PRT
<213> ORGANISM: Artificial Sequence
<220> FEATURE:
<223> OTHER INFORMATION: Synthetic

<400> SEQUENCE: 756

Tyr Ile Ser Pro Tyr Tyr Gly Ser Thr Ser Tyr Ala Asp Ser Val Lys
1               5                   10                  15
Gly

```
<210> SEQ ID NO 757
<211> LENGTH: 17
<212> TYPE: PRT
<213> ORGANISM: Artificial Sequence
<220> FEATURE:
<223> OTHER INFORMATION: Synthetic

<400> SEQUENCE: 757

Ala Ile Gln Pro Tyr Phe Gly Trp Thr Ile Tyr Ala Asp Ser Val Lys
1               5                   10                  15

Gly

<210> SEQ ID NO 758
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Tyr, Phe, Asp, His or Ala
<220> FEATURE:
<221> NAME/KEY: MOD_RES
<222> LOCATION: (3)..(3)
<223> OTHER INFORMATION: Ser, Ala or Gln
<220> FEATURE:
<221> NAME/KEY: MOD_RES
<222> LOCATION: (6)..(6)
<223> OTHER INFORMATION: Leu, Tyr or Phe
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (8)..(8)
<223> OTHER INFORMATION: Ser, Thr or Trp
<220> FEATURE:
<221> NAME/KEY: MOD_RES
<222> LOCATION: (10)..(10)
<223> OTHER INFORMATION: Ser, Asn, Lys or Ile

<400> SEQUENCE: 758

Xaa Ile Xaa Pro Tyr Xaa Xaa Xaa Thr Xaa Tyr Ala Asp Ser Val Lys
1               5                   10                  15

Gly

<210> SEQ ID NO 759
<211> LENGTH: 11
<212> TYPE: PRT
<213> ORGANISM: Artificial Sequence
<220> FEATURE:
<223> OTHER INFORMATION: Synthetic

<400> SEQUENCE: 759

Glu Tyr Tyr Arg Trp Tyr Thr Ala Ile Asp Tyr
1               5                   10

<210> SEQ ID NO 760
<211> LENGTH: 11
<212> TYPE: PRT
<213> ORGANISM: Artificial Sequence
<220> FEATURE:
<223> OTHER INFORMATION: Synthetic

<400> SEQUENCE: 760

Glu Tyr Tyr Arg Trp Tyr Thr Ala Ile Asp Tyr
1               5                   10
```

<210> SEQ ID NO 761
<211> LENGTH: 11
<212> TYPE: PRT
<213> ORGANISM: Artificial Sequence
<220> FEATURE:
<223> OTHER INFORMATION: Synthetic

<400> SEQUENCE: 761

Glu Tyr Tyr Arg Trp Tyr Thr Ala Ile Asp Tyr
1               5                   10

<210> SEQ ID NO 762
<211> LENGTH: 11
<212> TYPE: PRT
<213> ORGANISM: Artificial Sequence
<220> FEATURE:
<223> OTHER INFORMATION: Synthetic

<400> SEQUENCE: 762

Glu Tyr Tyr Arg Trp Tyr Thr Ala Ile Asp Tyr
1               5                   10

<210> SEQ ID NO 763
<211> LENGTH: 11
<212> TYPE: PRT
<213> ORGANISM: Artificial Sequence
<220> FEATURE:
<223> OTHER INFORMATION: Synthetic

<400> SEQUENCE: 763

Glu Tyr Tyr Arg Trp Tyr Thr Ala Ile Asp Tyr
1               5                   10

<210> SEQ ID NO 764
<211> LENGTH: 11
<212> TYPE: PRT
<213> ORGANISM: Artificial Sequence
<220> FEATURE:
<223> OTHER INFORMATION: Synthetic

<400> SEQUENCE: 764

Glu Tyr Tyr Arg Trp Tyr Thr Ala Ile Asp Tyr
1               5                   10

<210> SEQ ID NO 765
<211> LENGTH: 11
<212> TYPE: PRT
<213> ORGANISM: Artificial Sequence
<220> FEATURE:
<223> OTHER INFORMATION: Synthetic

<400> SEQUENCE: 765

Glu Tyr Tyr Arg Trp Tyr Thr Ala Ile Asp Tyr
1               5                   10

<210> SEQ ID NO 766
<211> LENGTH: 11
<212> TYPE: PRT
<213> ORGANISM: Artificial Sequence
<220> FEATURE:
<223> OTHER INFORMATION: Synthetic

<400> SEQUENCE: 766

Glu Tyr Tyr Arg Trp Tyr Thr Ala Ile Asp Tyr
1               5                   10

<210> SEQ ID NO 767
<211> LENGTH: 11
<212> TYPE: PRT
<213> ORGANISM: Artificial Sequence
<220> FEATURE:
<223> OTHER INFORMATION: Synthetic

<400> SEQUENCE: 767

Glu Tyr Tyr Arg Trp Tyr Thr Ala Ile Asp Tyr
1               5                   10

<210> SEQ ID NO 768
<211> LENGTH: 11
<212> TYPE: PRT
<213> ORGANISM: Artificial Sequence
<220> FEATURE:
<223> OTHER INFORMATION: Synthetic

<400> SEQUENCE: 768

Glu Tyr Tyr Arg Trp Tyr Thr Ala Ile Asp Tyr
1               5                   10

<210> SEQ ID NO 769
<211> LENGTH: 11
<212> TYPE: PRT
<213> ORGANISM: Artificial Sequence
<220> FEATURE:
<223> OTHER INFORMATION: Synthetic

<400> SEQUENCE: 769

Glu Tyr Tyr Arg Trp Tyr Thr Ala Ile Asp Tyr
1               5                   10

<210> SEQ ID NO 770
<211> LENGTH: 11
<212> TYPE: PRT
<213> ORGANISM: Artificial Sequence
<220> FEATURE:
<223> OTHER INFORMATION: Synthetic

<400> SEQUENCE: 770

Gln Gln Tyr Ser Ser Tyr Ser Ser Leu Phe Thr
1               5                   10

<210> SEQ ID NO 771
<211> LENGTH: 11
<212> TYPE: PRT
<213> ORGANISM: Artificial Sequence
<220> FEATURE:
<223> OTHER INFORMATION: Synthetic

<400> SEQUENCE: 771

Gln Gln Tyr Ser Ser Tyr Ser Ser Leu Phe Thr
1               5                   10

<210> SEQ ID NO 772
<211> LENGTH: 11
<212> TYPE: PRT
<213> ORGANISM: Artificial Sequence
<220> FEATURE:
<223> OTHER INFORMATION: Synthetic

<400> SEQUENCE: 772

Gln Gln Tyr Ser Ser Tyr Ser Ser Leu Phe Thr
1               5                   10

<210> SEQ ID NO 773

```
<211> LENGTH: 11
<212> TYPE: PRT
<213> ORGANISM: Artificial Sequence
<220> FEATURE:
<223> OTHER INFORMATION: Synthetic

<400> SEQUENCE: 773

Gln Gln Tyr Ser Ser Tyr Ser Ser Leu Phe Thr
1               5                   10

<210> SEQ ID NO 774
<211> LENGTH: 11
<212> TYPE: PRT
<213> ORGANISM: Artificial Sequence
<220> FEATURE:
<223> OTHER INFORMATION: Synthetic

<400> SEQUENCE: 774

Gln Gln Tyr Ser Ser Tyr Ser Ser Leu Phe Thr
1               5                   10

<210> SEQ ID NO 775
<211> LENGTH: 11
<212> TYPE: PRT
<213> ORGANISM: Artificial Sequence
<220> FEATURE:
<223> OTHER INFORMATION: Synthetic

<400> SEQUENCE: 775

Gln Gln Tyr Ser Ser Tyr Ser Ser Leu Phe Thr
1               5                   10

<210> SEQ ID NO 776
<211> LENGTH: 11
<212> TYPE: PRT
<213> ORGANISM: Artificial Sequence
<220> FEATURE:
<223> OTHER INFORMATION: Synthetic

<400> SEQUENCE: 776

Gln Gln Tyr Ser Ser Tyr Ser Ser Leu Phe Thr
1               5                   10

<210> SEQ ID NO 777
<211> LENGTH: 11
<212> TYPE: PRT
<213> ORGANISM: Artificial Sequence
<220> FEATURE:
<223> OTHER INFORMATION: Synthetic

<400> SEQUENCE: 777

Gln Gln Tyr Ser Ser Tyr Ser Ser Leu Phe Thr
1               5                   10

<210> SEQ ID NO 778
<211> LENGTH: 11
<212> TYPE: PRT
<213> ORGANISM: Artificial Sequence
<220> FEATURE:
<223> OTHER INFORMATION: Synthetic

<400> SEQUENCE: 778

Gln Gln Tyr Ser Ser Tyr Ser Ser Leu Phe Thr
1               5                   10

<210> SEQ ID NO 779
<211> LENGTH: 11
```

<212> TYPE: PRT
<213> ORGANISM: Artificial Sequence
<220> FEATURE:
<223> OTHER INFORMATION: Synthetic

<400> SEQUENCE: 779

Gln Gln Tyr Ser Ser Tyr Ser Ser Leu Phe Thr
1               5                   10

<210> SEQ ID NO 780
<211> LENGTH: 11
<212> TYPE: PRT
<213> ORGANISM: Artificial Sequence
<220> FEATURE:
<223> OTHER INFORMATION: Synthetic

<400> SEQUENCE: 780

Gln Gln Tyr Ser Ser Tyr Ser Ser Leu Phe Thr
1               5                   10

<210> SEQ ID NO 781
<211> LENGTH: 107
<212> TYPE: PRT
<213> ORGANISM: Homo sapiens

<400> SEQUENCE: 781

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 782
<211> LENGTH: 107
<212> TYPE: PRT
<213> ORGANISM: Homo sapiens

<400> SEQUENCE: 782

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Ser Ala
            20                  25                  30

Val Ala Trp Tyr Gln Gln Lys Pro Gly Lys Ala Pro Lys Leu Leu Ile
        35                  40                  45

Tyr Ser Ala Ser Ser Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys

<210> SEQ ID NO 783
<211> LENGTH: 52
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (19)..(19)
<223> OTHER INFORMATION: a, c, g, or t
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: modified_base
<222> LOCATION: (22)..(33)
<223> OTHER INFORMATION: a, c, g, or t
<220> FEATURE:
<221> NAME/KEY: misc_feature
<222> LOCATION: (22)..(33)
<223> OTHER INFORMATION: n is a, c, g, or t

<400> SEQUENCE: 783
gcagcttctg gcttcaacnt cnnnnnnnnn nnnatscact gggtgcgtca gg             52

<210> SEQ ID NO 784
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (19)..(20)
<223> OTHER INFORMATION: a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: modified_base
<222> LOCATION: (25)..(27)
<223> OTHER INFORMATION: a, c, g, or t
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: modified_base
<222> LOCATION: (40)..(42)
<223> OTHER INFORMATION: a, c, g, or t
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: modified_base
<222> LOCATION: (46)..(48)
<223> OTHER INFORMATION: a, c, g, or t
<220> FEATURE:
<221> NAME/KEY: misc_feature
<222> LOCATION: (46)..(48)
<223> OTHER INFORMATION: n is a, c, g, or t

<400> SEQUENCE: 784
ggcctggaat gggttgcann satcnnnccg tactacggtn nnaccnnnta tgccgatagc     60
gtcaagg                                                               67

<210> SEQ ID NO 785
<211> LENGTH: 67

```
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(27)
<223> OTHER INFORMATION: a, c, g, or t
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: modified_base
<222> LOCATION: (34)..(35)
<223> OTHER INFORMATION: a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (40)..(42)
<223> OTHER INFORMATION: a, c, g, or t
<220> FEATURE:
<221> NAME/KEY: misc_feature
<222> LOCATION: (40)..(42)
<223> OTHER INFORMATION: n is a, c, g, or t
<220> FEATURE:
<221> NAME/KEY: modified_base
<222> LOCATION: (46)..(48)
<223> OTHER INFORMATION: a, c, g, or t
<220> FEATURE:
<221> NAME/KEY: misc_feature
<222> LOCATION: (46)..(48)
<223> OTHER INFORMATION: n is a, c, g, or t

<400> SEQUENCE: 785
ggcctggaat gggttgcata catcnnnccg tacnnsggtn nnaccnnnta tgccgatagc    60
gtcaagg                                                             67

<210> SEQ ID NO 786
<211> LENGTH: 67
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (19)..(20)
<223> OTHER INFORMATION: a, c, g, or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: modified_base
<222> LOCATION: (25)..(27)
<223> OTHER INFORMATION: a, c, g, or t
<220> FEATURE:
<221> NAME/KEY: misc_feature
<222> LOCATION: (25)..(27)
<223> OTHER INFORMATION: n is a, c, g, or t
<220> FEATURE:
<221> NAME/KEY: modified_base
<222> LOCATION: (34)..(35)
<223> OTHER INFORMATION: a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: modified_base
<222> LOCATION: (40)..(42)
<223> OTHER INFORMATION: a, c, g, or t
<220> FEATURE:
```

```
<221> NAME/KEY: misc_feature
<222> LOCATION: (40)..(42)
<223> OTHER INFORMATION: n is a, c, g, or t
<220> FEATURE:
<221> NAME/KEY: modified_base
<222> LOCATION: (46)..(48)
<223> OTHER INFORMATION: a, c, g, or t
<220> FEATURE:
<221> NAME/KEY: misc_feature
<222> LOCATION: (46)..(48)
<223> OTHER INFORMATION: n is a, c, g, or t

<400> SEQUENCE: 786
ggcctggaat gggttgcann satcnnnccg tacnnsggtn nnaccnnnta tgccgatagc    60
gtcaagg                                                              67

<210> SEQ ID NO 787
<211> LENGTH: 10
<212> TYPE: PRT
<213> ORGANISM: Artificial Sequence
<220> FEATURE:
<223> OTHER INFORMATION: Synthetic

<400> SEQUENCE: 787

Gly Phe Asn Val Lys Thr Gly Phe Met His
1               5                   10

<210> SEQ ID NO 788
<211> LENGTH: 10
<212> TYPE: PRT
<213> ORGANISM: Artificial Sequence
<220> FEATURE:
<223> OTHER INFORMATION: Synthetic

<400> SEQUENCE: 788

Gly Phe Asn Val Lys Thr Gly Phe Ile His
1               5                   10

<210> SEQ ID NO 789
<211> LENGTH: 10
<212> TYPE: PRT
<213> ORGANISM: Artificial Sequence
<220> FEATURE:
<223> OTHER INFORMATION: Synthetic

<400> SEQUENCE: 789

Gly Phe Asn Ile Lys Met Val Phe Met His
1               5                   10

<210> SEQ ID NO 790
<211> LENGTH: 10
<212> TYPE: PRT
<213> ORGANISM: Artificial Sequence
<220> FEATURE:
<223> OTHER INFORMATION: Synthetic

<400> SEQUENCE: 790

Gly Phe Asn Val Lys Asn Phe Ile Ile His
1               5                   10

<210> SEQ ID NO 791
<211> LENGTH: 10
<212> TYPE: PRT
<213> ORGANISM: Artificial Sequence
<220> FEATURE:
<223> OTHER INFORMATION: Synthetic

<400> SEQUENCE: 791
```

```
Gly Phe Asn Val Lys Thr Gly Phe Met His
1               5                   10

<210> SEQ ID NO 792
<211> LENGTH: 10
<212> TYPE: PRT
<213> ORGANISM: Artificial Sequence
<220> FEATURE:
<223> OTHER INFORMATION: Synthetic

<400> SEQUENCE: 792

Gly Phe Asn Val Lys Arg Gly Phe Met His
1               5                   10

<210> SEQ ID NO 793
<211> LENGTH: 10
<212> TYPE: PRT
<213> ORGANISM: Artificial Sequence
<220> FEATURE:
<223> OTHER INFORMATION: Synthetic

<400> SEQUENCE: 793

Gly Phe Asn Leu Lys Thr Gly Phe Ile His
1               5                   10

<210> SEQ ID NO 794
<211> LENGTH: 10
<212> TYPE: PRT
<213> ORGANISM: Artificial Sequence
<220> FEATURE:
<223> OTHER INFORMATION: Synthetic

<400> SEQUENCE: 794

Gly Phe Asn Val Lys Thr Gly Tyr Met His
1               5                   10

<210> SEQ ID NO 795
<211> LENGTH: 10
<212> TYPE: PRT
<213> ORGANISM: Artificial Sequence
<220> FEATURE:
<223> OTHER INFORMATION: Synthetic

<400> SEQUENCE: 795

Gly Phe Asn Val Lys Thr Gly Leu Ile His
1               5                   10

<210> SEQ ID NO 796
<211> LENGTH: 10
<212> TYPE: PRT
<213> ORGANISM: Artificial Sequence
<220> FEATURE:
<223> OTHER INFORMATION: Synthetic

<400> SEQUENCE: 796

Gly Phe Asn Val Met Ile Gly Ile Ile His
1               5                   10

<210> SEQ ID NO 797
<211> LENGTH: 10
<212> TYPE: PRT
<213> ORGANISM: Artificial Sequence
<220> FEATURE:
<223> OTHER INFORMATION: Synthetic

<400> SEQUENCE: 797
```

Gly Phe Asn Ile Lys Thr Gly Phe Met His
1               5                   10

<210> SEQ ID NO 798
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Val, Ile or Leu
<220> FEATURE:
<221> NAME/KEY: MOD_RES
<222> LOCATION: (5)..(5)
<223> OTHER INFORMATION: Lys or Met
<220> FEATURE:
<221> NAME/KEY: MOD_RES
<222> LOCATION: (6)..(6)
<223> OTHER INFORMATION: Thr, Met, Asn, Arg or Ile
<220> FEATURE:
<221> NAME/KEY: MOD_RES
<222> LOCATION: (7)..(7)
<223> OTHER INFORMATION: Gly, Val or Phe
<220> FEATURE:
<221> NAME/KEY: MOD_RES
<222> LOCATION: (8)..(8)
<223> OTHER INFORMATION: Phe, Ile, Tyr or Leu
<220> FEATURE:
<221> NAME/KEY: MOD_RES
<222> LOCATION: (9)..(9)
<223> OTHER INFORMATION: Met or Ile

<400> SEQUENCE: 798

Gly Phe Asn Xaa Xaa Xaa Xaa Xaa Xaa His
1               5                   10

<210> SEQ ID NO 799
<211> LENGTH: 17
<212> TYPE: PRT
<213> ORGANISM: Artificial Sequence
<220> FEATURE:
<223> OTHER INFORMATION: Synthetic

<400> SEQUENCE: 799

Tyr Ile Ser Pro Tyr Tyr Gly Trp Thr Arg Tyr Ala Asp Ser Val Lys
1               5                   10                  15

Gly

<210> SEQ ID NO 800
<211> LENGTH: 17
<212> TYPE: PRT
<213> ORGANISM: Artificial Sequence
<220> FEATURE:
<223> OTHER INFORMATION: Synthetic

<400> SEQUENCE: 800

Tyr Ile Ser Pro Tyr Leu Gly Val Thr Arg Tyr Ala Asp Ser Val Lys
1               5                   10                  15

Gly

<210> SEQ ID NO 801
<211> LENGTH: 17
<212> TYPE: PRT
<213> ORGANISM: Artificial Sequence
<220> FEATURE:
<223> OTHER INFORMATION: Synthetic

<400> SEQUENCE: 801

Tyr Ile Ser Pro Tyr Asp Gly Ser Thr Asn Tyr Ala Asp Ser Val Lys
1               5                   10                  15

Gly

<210> SEQ ID NO 802
<211> LENGTH: 17
<212> TYPE: PRT
<213> ORGANISM: Artificial Sequence
<220> FEATURE:
<223> OTHER INFORMATION: Synthetic

<400> SEQUENCE: 802

Tyr Ile Ile Pro Tyr Ser Gly Asn Thr Val Tyr Ala Asp Ser Val Lys
1               5                   10                  15

Gly

<210> SEQ ID NO 803
<211> LENGTH: 17
<212> TYPE: PRT
<213> ORGANISM: Artificial Sequence
<220> FEATURE:
<223> OTHER INFORMATION: Synthetic

<400> SEQUENCE: 803

Tyr Ile Ser Pro Tyr Ser Gly Arg Thr Arg Tyr Ala Asp Ser Val Lys
1               5                   10                  15

Gly

<210> SEQ ID NO 804
<211> LENGTH: 17
<212> TYPE: PRT
<213> ORGANISM: Artificial Sequence
<220> FEATURE:
<223> OTHER INFORMATION: Synthetic

<400> SEQUENCE: 804

Tyr Ile Ser Pro Tyr Leu Gly Ser Thr Arg Tyr Ala Asp Ser Val Lys
1               5                   10                  15

Gly

<210> SEQ ID NO 805
<211> LENGTH: 17
<212> TYPE: PRT
<213> ORGANISM: Artificial Sequence
<220> FEATURE:
<223> OTHER INFORMATION: Synthetic

<400> SEQUENCE: 805

Tyr Ile Ser Pro Tyr Trp Gly Ser Thr Thr Tyr Ala Asp Ser Val Lys
1               5                   10                  15

Gly

<210> SEQ ID NO 806
<211> LENGTH: 17
<212> TYPE: PRT
<213> ORGANISM: Artificial Sequence
<220> FEATURE:
<223> OTHER INFORMATION: Synthetic

<400> SEQUENCE: 806

Tyr Ile Ser Pro Tyr Tyr Gly Ser Thr Arg Tyr Ala Asp Ser Val Lys
1               5                   10                  15

Gly

<210> SEQ ID NO 807
<211> LENGTH: 17
<212> TYPE: PRT
<213> ORGANISM: Artificial Sequence
<220> FEATURE:
<223> OTHER INFORMATION: Synthetic

<400> SEQUENCE: 807

Tyr Ile Ser Pro Tyr Phe Gly Tyr Thr Ser Tyr Ala Asp Ser Val Lys
1               5                   10                  15

Gly

<210> SEQ ID NO 808
<211> LENGTH: 17
<212> TYPE: PRT
<213> ORGANISM: Artificial Sequence
<220> FEATURE:
<223> OTHER INFORMATION: Synthetic

<400> SEQUENCE: 808

Tyr Ile Ile Pro Tyr Ser Gly Ser Thr Lys Tyr Ala Asp Ser Val Lys
1               5                   10                  15

Gly

<210> SEQ ID NO 809
<211> LENGTH: 17
<212> TYPE: PRT
<213> ORGANISM: Artificial Sequence
<220> FEATURE:
<223> OTHER INFORMATION: Synthetic

<400> SEQUENCE: 809

Tyr Ile Thr Pro Tyr Trp Gly Ser Thr Lys Tyr Ala Asp Ser Val Lys
1               5                   10                  15

Gly

<210> SEQ ID NO 810
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ser, Ile or Thr
<220> FEATURE:
<221> NAME/KEY: MOD_RES
<222> LOCATION: (6)..(6)
<223> OTHER INFORMATION: Tyr, Leu, Asp, Ser or Trp
<220> FEATURE:
<221> NAME/KEY: MOD_RES
<222> LOCATION: (8)..(8)
<223> OTHER INFORMATION: Trp, Val, Ser, Asn, Arg or Tyr
<220> FEATURE:
<221> NAME/KEY: MOD_RES
<222> LOCATION: (10)..(10)
<223> OTHER INFORMATION: Arg, Asn, Val, Thr, Ser or Lys

<400> SEQUENCE: 810

Tyr Ile Xaa Pro Tyr Xaa Gly Xaa Thr Xaa Tyr Ala Asp Ser Val Lys
1               5                   10                  15

Gly

```
<210> SEQ ID NO 811
<211> LENGTH: 11
<212> TYPE: PRT
<213> ORGANISM: Artificial Sequence
<220> FEATURE:
<223> OTHER INFORMATION: Synthetic

<400> SEQUENCE: 811

Glu Tyr Tyr Arg Trp Tyr Thr Ala Ile Asp Tyr
1               5                   10

<210> SEQ ID NO 812
<211> LENGTH: 11
<212> TYPE: PRT
<213> ORGANISM: Artificial Sequence
<220> FEATURE:
<223> OTHER INFORMATION: Synthetic

<400> SEQUENCE: 812

Glu Tyr Tyr Arg Trp Tyr Thr Ala Ile Asp Tyr
1               5                   10

<210> SEQ ID NO 813
<211> LENGTH: 11
<212> TYPE: PRT
<213> ORGANISM: Artificial Sequence
<220> FEATURE:
<223> OTHER INFORMATION: Synthetic

<400> SEQUENCE: 813

Glu Tyr Tyr Arg Trp Tyr Thr Ala Ile Asp Tyr
1               5                   10

<210> SEQ ID NO 814
<211> LENGTH: 11
<212> TYPE: PRT
<213> ORGANISM: Artificial Sequence
<220> FEATURE:
<223> OTHER INFORMATION: Synthetic

<400> SEQUENCE: 814

Glu Tyr Tyr Arg Trp Tyr Thr Ala Ile Asp Tyr
1               5                   10

<210> SEQ ID NO 815
<211> LENGTH: 11
<212> TYPE: PRT
<213> ORGANISM: Artificial Sequence
<220> FEATURE:
<223> OTHER INFORMATION: Synthetic

<400> SEQUENCE: 815

Glu Tyr Tyr Arg Trp Tyr Thr Ala Ile Asp Tyr
1               5                   10

<210> SEQ ID NO 816
<211> LENGTH: 11
<212> TYPE: PRT
<213> ORGANISM: Artificial Sequence
<220> FEATURE:
<223> OTHER INFORMATION: Synthetic

<400> SEQUENCE: 816

Glu Tyr Tyr Arg Trp Tyr Thr Ala Ile Asp Tyr
1               5                   10

<210> SEQ ID NO 817
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 817

Glu Tyr Tyr Arg Trp Tyr Thr Ala Ile Asp Tyr
1               5                   10

<210> SEQ ID NO 818
<211> LENGTH: 11
<212> TYPE: PRT
<213> ORGANISM: Artificial Sequence
<220> FEATURE:
<223> OTHER INFORMATION: Synthetic

<400> SEQUENCE: 818

Glu Tyr Tyr Arg Trp Tyr Thr Ala Ile Asp Tyr
1               5                   10

<210> SEQ ID NO 819
<211> LENGTH: 11
<212> TYPE: PRT
<213> ORGANISM: Artificial Sequence
<220> FEATURE:
<223> OTHER INFORMATION: Synthetic

<400> SEQUENCE: 819

Glu Tyr Tyr Arg Trp Tyr Thr Ala Ile Asp Tyr
1               5                   10

<210> SEQ ID NO 820
<211> LENGTH: 11
<212> TYPE: PRT
<213> ORGANISM: Artificial Sequence
<220> FEATURE:
<223> OTHER INFORMATION: Synthetic

<400> SEQUENCE: 820

Glu Tyr Tyr Arg Trp Tyr Thr Ala Ile Asp Tyr
1               5                   10

<210> SEQ ID NO 821
<211> LENGTH: 11
<212> TYPE: PRT
<213> ORGANISM: Artificial Sequence
<220> FEATURE:
<223> OTHER INFORMATION: Synthetic

<400> SEQUENCE: 821

Glu Tyr Tyr Arg Trp Tyr Thr Ala Ile Asp Tyr
1               5                   10

<210> SEQ ID NO 822
<211> LENGTH: 11
<212> TYPE: PRT
<213> ORGANISM: Artificial Sequence
<220> FEATURE:
<223> OTHER INFORMATION: Synthetic

<400> SEQUENCE: 822

Glu Tyr Tyr Arg Trp Tyr Thr Ala Ile Asp Tyr
1               5                   10

<210> SEQ ID NO 823
<211> LENGTH: 10
```

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Val, Phe, Leu or Ile
<220> FEATURE:
<221> NAME/KEY: MOD_RES
<222> LOCATION: (5)..(5)
<223> OTHER INFORMATION: Ser or Tyr
<220> FEATURE:
<221> NAME/KEY: MOD_RES
<222> LOCATION: (7)..(8)
<223> OTHER INFORMATION: Ser or Tyr
<220> FEATURE:
<221> NAME/KEY: MOD_RES
<222> LOCATION: (9)..(9)
<223> OTHER INFORMATION: Ile or Met

<400> SEQUENCE: 823

Gly Phe Asn Xaa Xaa Tyr Xaa Xaa Xaa His
1               5                   10

<210> SEQ ID NO 824
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (8)..(8)
<223> OTHER INFORMATION: Ser or Tyr
<220> FEATURE:
<221> NAME/KEY: MOD_RES
<222> LOCATION: (10)..(10)
<223> OTHER INFORMATION: Ser or Tyr

<400> SEQUENCE: 824

Ser Ile Xaa Xaa Tyr Tyr Xaa Xaa Thr Xaa Tyr Ala Asp Ser Val Lys
1               5                   10                  15

Gly

<210> SEQ ID NO 825
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (5)..(5)
<223> OTHER INFORMATION: Ser or Phe
<220> FEATURE:
<221> NAME/KEY: MOD_RES
<222> LOCATION: (7)..(8)
<223> OTHER INFORMATION: Ser or Gly
<220> FEATURE:
<221> NAME/KEY: MOD_RES
<222> LOCATION: (9)..(9)
```

```
<223> OTHER INFORMATION: Ile or Met

<400> SEQUENCE: 825

Gly Phe Asn Ile Xaa Tyr Xaa Xaa Xaa His
1               5                   10

<210> SEQ ID NO 826
<211> LENGTH: 17
<212> TYPE: PRT
<213> ORGANISM: Artificial Sequence
<220> FEATURE:
<223> OTHER INFORMATION: Synthetic

<400> SEQUENCE: 826

Ser Ile Tyr Ser Tyr Tyr Ser Tyr Thr Ser Tyr Ala Asp Ser Val Lys
1               5                   10                  15

Gly

<210> SEQ ID NO 827
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ser or Gly
<220> FEATURE:
<221> NAME/KEY: MOD_RES
<222> LOCATION: (4)..(4)
<223> OTHER INFORMATION: Tyr or Trp
<220> FEATURE:
<221> NAME/KEY: MOD_RES
<222> LOCATION: (5)..(5)
<223> OTHER INFORMATION: Ser, Tyr, Arg, Phe or His
<220> FEATURE:
<221> NAME/KEY: MOD_RES
<222> LOCATION: (6)..(6)
<223> OTHER INFORMATION: Glu, Ser, Leu, Phe, Met, Asn or Val
<220> FEATURE:
<221> NAME/KEY: MOD_RES
<222> LOCATION: (7)..(7)
<223> OTHER INFORMATION: Ala or Gly
<220> FEATURE:
<221> NAME/KEY: MOD_RES
<222> LOCATION: (8)..(8)
<223> OTHER INFORMATION: Leu, Met, Phe or Ile

<400> SEQUENCE: 827

Xaa Tyr Ser Xaa Xaa Xaa Xaa Xaa Asp Tyr
1               5                   10

<210> SEQ ID NO 828
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (3)..(7)
<223> OTHER INFORMATION: Ser or Tyr
<220> FEATURE:
<221> NAME/KEY: MOD_RES
<222> LOCATION: (8)..(8)
<223> OTHER INFORMATION: Leu, Ser, Pro or Tyr
<220> FEATURE:
<221> NAME/KEY: MOD_RES
<222> LOCATION: (9)..(9)
<223> OTHER INFORMATION: Pro or not present
<220> FEATURE:
```

<221> NAME/KEY: MOD_RES
<222> LOCATION: (10)..(10)
<223> OTHER INFORMATION: Phe, Ile, Val or Leu

<400> SEQUENCE: 828

Gln Gln Xaa Xaa Xaa Xaa Xaa Xaa Xaa Thr
1               5                   10

<210> SEQ ID NO 829
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Val, Ile or Phe
<220> FEATURE:
<221> NAME/KEY: MOD_RES
<222> LOCATION: (5)..(8)
<223> OTHER INFORMATION: Ser or Tyr
<220> FEATURE:
<221> NAME/KEY: MOD_RES
<222> LOCATION: (9)..(9)
<223> OTHER INFORMATION: Ile or Met

<400> SEQUENCE: 829

Gly Phe Asn Xaa Xaa Xaa Xaa Xaa Xaa His
1               5                   10

<210> SEQ ID NO 830
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Ser or Tyr
<220> FEATURE:
<221> NAME/KEY: MOD_RES
<222> LOCATION: (3)..(3)
<223> OTHER INFORMATION: Ser or Tyr
<220> FEATURE:
<221> NAME/KEY: MOD_RES
<222> LOCATION: (4)..(4)
<223> OTHER INFORMATION: Pro or Ser
<220> FEATURE:
<221> NAME/KEY: MOD_RES
<222> LOCATION: (5)..(6)
<223> OTHER INFORMATION: Ser or Tyr
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (8)..(8)
<223> OTHER INFORMATION: Ser or Tyr
<220> FEATURE:
<221> NAME/KEY: MOD_RES
<222> LOCATION: (10)..(10)
<223> OTHER INFORMATION: Ser or Tyr

<400> SEQUENCE: 830

Xaa Ile Xaa Xaa Xaa Xaa Xaa Xaa Thr Xaa Tyr Ala Asp Ser Val Lys
1               5                   10                  15

Gly

<210> SEQ ID NO 831

```
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Ile, Val or Leu
<220> FEATURE:
<221> NAME/KEY: MOD_RES
<222> LOCATION: (5)..(5)
<223> OTHER INFORMATION: Ser, Lys or Val
<220> FEATURE:
<221> NAME/KEY: MOD_RES
<222> LOCATION: (6)..(6)
<223> OTHER INFORMATION: Ser, Trp, Gly or Thr
<220> FEATURE:
<221> NAME/KEY: MOD_RES
<222> LOCATION: (7)..(7)
<223> OTHER INFORMATION: Ser, Asn or Gly
<220> FEATURE:
<221> NAME/KEY: MOD_RES
<222> LOCATION: (8)..(8)
<223> OTHER INFORMATION: Tyr, Ile, Leu or Phe
<220> FEATURE:
<221> NAME/KEY: MOD_RES
<222> LOCATION: (9)..(9)
<223> OTHER INFORMATION: Ile or Met

<400> SEQUENCE: 831

Gly Phe Asn Xaa Xaa Xaa Xaa Xaa Xaa His
1               5                   10

<210> SEQ ID NO 832
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: Tyr, Phe, Asp, His or Ala
<220> FEATURE:
<221> NAME/KEY: MOD_RES
<222> LOCATION: (3)..(3)
<223> OTHER INFORMATION: Ser, Ala or Gln
<220> FEATURE:
<221> NAME/KEY: MOD_RES
<222> LOCATION: (6)..(6)
<223> OTHER INFORMATION: Leu, Tyr or Phe
<220> FEATURE:
<221> NAME/KEY: MOD_RES
<222> LOCATION: (7)..(7)
<223> OTHER INFORMATION: Ser or Gly
<220> FEATURE:
<221> NAME/KEY: MOD_RES
<222> LOCATION: (8)..(8)
<223> OTHER INFORMATION: Ser, Thr or Trp
<220> FEATURE:
<221> NAME/KEY: MOD_RES
<222> LOCATION: (10)..(10)
<223> OTHER INFORMATION: Ser, Asn, Lys or Ile

<400> SEQUENCE: 832

Xaa Ile Xaa Pro Tyr Xaa Xaa Xaa Thr Xaa Tyr Ala Asp Ser Val Lys
1               5                   10                  15
Gly

<210> SEQ ID NO 833
<211> LENGTH: 10
<212> TYPE: PRT
<213> ORGANISM: Artificial Sequence
```

```
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Ile, Val or Leu
<220> FEATURE:
<221> NAME/KEY: MOD_RES
<222> LOCATION: (5)..(5)
<223> OTHER INFORMATION: Lys or Met
<220> FEATURE:
<221> NAME/KEY: MOD_RES
<222> LOCATION: (6)..(6)
<223> OTHER INFORMATION: Thr, Met, Asn, Arg or Ile
<220> FEATURE:
<221> NAME/KEY: MOD_RES
<222> LOCATION: (7)..(7)
<223> OTHER INFORMATION: Gly, Val or Phe
<220> FEATURE:
<221> NAME/KEY: MOD_RES
<222> LOCATION: (8)..(8)
<223> OTHER INFORMATION: Tyr, Ile, Leu or Phe
<220> FEATURE:
<221> NAME/KEY: MOD_RES
<222> LOCATION: (9)..(9)
<223> OTHER INFORMATION: Ile or Met

<400> SEQUENCE: 833

Gly Phe Asn Xaa Xaa Xaa Xaa Xaa Xaa His
1               5                   10

<210> SEQ ID NO 834
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (4)..(4)
<223> OTHER INFORMATION: Ser, Ile or Thr
<220> FEATURE:
<221> NAME/KEY: MOD_RES
<222> LOCATION: (7)..(7)
<223> OTHER INFORMATION: Leu, Tyr, Asp, Ser or Trp
<220> FEATURE:
<221> NAME/KEY: MOD_RES
<222> LOCATION: (9)..(9)
<223> OTHER INFORMATION: Trp, Val, Ser, Asn, Arg or Tyr
<220> FEATURE:
<221> NAME/KEY: MOD_RES
<222> LOCATION: (11)..(11)
<223> OTHER INFORMATION: Arg, Asp, Val, Thr, Ser or Lys

<400> SEQUENCE: 834

Ala Tyr Ile Xaa Pro Tyr Xaa Gly Xaa Thr Xaa Tyr Ala Asp Ser Val
1               5                   10                  15

Lys Gly

<210> SEQ ID NO 835
<211> LENGTH: 13
<212> TYPE: PRT
<213> ORGANISM: Artificial Sequence
<220> FEATURE:
<223> OTHER INFORMATION: Synthetic

<400> SEQUENCE: 835

Ser Arg Glu Tyr Tyr Arg Trp Tyr Thr Ala Ile Asp Tyr
1               5                   10

<210> SEQ ID NO 836
<211> LENGTH: 18
```

```
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (2)..(2)
<223> OTHER INFORMATION: Tyr, Phe, Asp, His or Ala
<220> FEATURE:
<221> NAME/KEY: MOD_RES
<222> LOCATION: (4)..(4)
<223> OTHER INFORMATION: Ser, Ala or Gln
<220> FEATURE:
<221> NAME/KEY: MOD_RES
<222> LOCATION: (7)..(7)
<223> OTHER INFORMATION: Leu, Tyr and Phe
<220> FEATURE:
<221> NAME/KEY: MOD_RES
<222> LOCATION: (8)..(8)
<223> OTHER INFORMATION: Ser or Gly
<220> FEATURE:
<221> NAME/KEY: MOD_RES
<222> LOCATION: (9)..(9)
<223> OTHER INFORMATION: Ser, Thr or Trp
<220> FEATURE:
<221> NAME/KEY: MOD_RES
<222> LOCATION: (11)..(11)
<223> OTHER INFORMATION: Ser, Asn, Lys or Ile

<400> SEQUENCE: 836

Ala Xaa Ile Xaa Pro Tyr Xaa Xaa Xaa Thr Xaa Tyr Ala Asp Ser Val
1               5                   10                  15

Lys Gly

<210> SEQ ID NO 837
<211> LENGTH: 14
<212> TYPE: PRT
<213> ORGANISM: Homo sapiens

<400> SEQUENCE: 837

Trp Val Arg Gln Ala Pro Gly Gln Gly Leu Glu Trp Met Gly
1               5                   10

<210> SEQ ID NO 838
<211> LENGTH: 13
<212> TYPE: PRT
<213> ORGANISM: Homo sapiens

<400> SEQUENCE: 838

Trp Val Arg Gln Ala Pro Gly Gln Gly Leu Glu Trp Met
1               5                   10

<210> SEQ ID NO 839
<211> LENGTH: 13
<212> TYPE: PRT
<213> ORGANISM: Homo sapiens

<400> SEQUENCE: 839

Trp Val Arg Gln Ala Pro Gly Gln Gly Leu Glu Trp Met
1               5                   10

<210> SEQ ID NO 840
<211> LENGTH: 13
<212> TYPE: PRT
<213> ORGANISM: Homo sapiens

<400> SEQUENCE: 840

Trp Val Arg Gln Ala Pro Gly Gln Gly Leu Glu Trp Met
1               5                   10
```

```
<210> SEQ ID NO 841
<211> LENGTH: 14
<212> TYPE: PRT
<213> ORGANISM: Homo sapiens

<400> SEQUENCE: 841

Trp Ile Arg Gln Pro Pro Gly Lys Gly Leu Glu Trp Ile Gly
1               5                   10

<210> SEQ ID NO 842
<211> LENGTH: 13
<212> TYPE: PRT
<213> ORGANISM: Homo sapiens

<400> SEQUENCE: 842

Trp Ile Arg Gln Pro Pro Gly Lys Gly Leu Glu Trp Ile
1               5                   10

<210> SEQ ID NO 843
<211> LENGTH: 13
<212> TYPE: PRT
<213> ORGANISM: Homo sapiens

<400> SEQUENCE: 843

Trp Ile Arg Gln Pro Pro Gly Lys Gly Leu Glu Trp Ile
1               5                   10

<210> SEQ ID NO 844
<211> LENGTH: 13
<212> TYPE: PRT
<213> ORGANISM: Homo sapiens

<400> SEQUENCE: 844

Trp Ile Arg Gln Pro Pro Gly Lys Gly Leu Glu Trp Ile
1               5                   10

<210> SEQ ID NO 845
<211> LENGTH: 14
<212> TYPE: PRT
<213> ORGANISM: Homo sapiens

<400> SEQUENCE: 845

Trp Val Arg Gln Ala Pro Gly Lys Gly Leu Glu Trp Val Ser
1               5                   10

<210> SEQ ID NO 846
<211> LENGTH: 13
<212> TYPE: PRT
<213> ORGANISM: Homo sapiens

<400> SEQUENCE: 846

Trp Val Arg Gln Ala Pro Gly Lys Gly Leu Glu Trp Val
1               5                   10

<210> SEQ ID NO 847
<211> LENGTH: 13
<212> TYPE: PRT
<213> ORGANISM: Homo sapiens

<400> SEQUENCE: 847

Trp Val Arg Gln Ala Pro Gly Lys Gly Leu Glu Trp Val
1               5                   10
```

```
<210> SEQ ID NO 848
<211> LENGTH: 13
<212> TYPE: PRT
<213> ORGANISM: Homo sapiens

<400> SEQUENCE: 848

Trp Val Arg Gln Ala Pro Gly Lys Gly Leu Glu Trp Val
1               5                   10

<210> SEQ ID NO 849
<211> LENGTH: 14
<212> TYPE: PRT
<213> ORGANISM: Homo sapiens

<400> SEQUENCE: 849

Trp Val Arg Gln Ala Pro Gly Lys Gly Leu Glu Trp Val Ser
1               5                   10

<210> SEQ ID NO 850
<211> LENGTH: 13
<212> TYPE: PRT
<213> ORGANISM: Homo sapiens

<400> SEQUENCE: 850

Trp Val Arg Gln Ala Pro Gly Lys Gly Leu Glu Trp Val
1               5                   10

<210> SEQ ID NO 851
<211> LENGTH: 13
<212> TYPE: PRT
<213> ORGANISM: Homo sapiens

<400> SEQUENCE: 851

Trp Val Arg Gln Ala Pro Gly Lys Gly Leu Glu Trp Val
1               5                   10

<210> SEQ ID NO 852
<211> LENGTH: 14
<212> TYPE: PRT
<213> ORGANISM: Homo sapiens

<400> SEQUENCE: 852

Trp Val Arg Gln Ala Pro Gly Lys Gly Leu Glu Trp Val Ser
1               5                   10

<210> SEQ ID NO 853
<211> LENGTH: 13
<212> TYPE: PRT
<213> ORGANISM: Homo sapiens

<400> SEQUENCE: 853

Trp Val Arg Gln Ala Pro Gly Lys Gly Leu Glu Trp Val
1               5                   10

<210> SEQ ID NO 854
<211> LENGTH: 13
<212> TYPE: PRT
<213> ORGANISM: Homo sapiens

<400> SEQUENCE: 854

Trp Val Arg Gln Ala Pro Gly Lys Gly Leu Glu Trp Val
1               5                   10

<210> SEQ ID NO 855
<211> LENGTH: 13
```

```
<212> TYPE: PRT
<213> ORGANISM: Homo sapiens

<400> SEQUENCE: 855

Trp Val Arg Gln Ala Pro Gly Lys Gly Leu Glu Trp Val
1               5                   10

<210> SEQ ID NO 856
<211> LENGTH: 32
<212> TYPE: PRT
<213> ORGANISM: Homo sapiens

<400> SEQUENCE: 856

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 857
<211> LENGTH: 32
<212> TYPE: PRT
<213> ORGANISM: Homo sapiens

<400> SEQUENCE: 857

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 858
<211> LENGTH: 31
<212> TYPE: PRT
<213> ORGANISM: Homo sapiens

<400> SEQUENCE: 858

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala
            20                  25                  30

<210> SEQ ID NO 859
<211> LENGTH: 30
<212> TYPE: PRT
<213> ORGANISM: Homo sapiens

<400> SEQUENCE: 859

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 860
<211> LENGTH: 32
<212> TYPE: PRT
<213> ORGANISM: Homo sapiens

<400> SEQUENCE: 860

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

```
<210> SEQ ID NO 861
<211> LENGTH: 32
<212> TYPE: PRT
<213> ORGANISM: Homo sapiens

<400> SEQUENCE: 861

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 862
<211> LENGTH: 31
<212> TYPE: PRT
<213> ORGANISM: Homo sapiens

<400> SEQUENCE: 862

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30

<210> SEQ ID NO 863
<211> LENGTH: 30
<212> TYPE: PRT
<213> ORGANISM: Homo sapiens

<400> SEQUENCE: 863

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 864
<211> LENGTH: 32
<212> TYPE: PRT
<213> ORGANISM: Homo sapiens

<400> SEQUENCE: 864

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 865
<211> LENGTH: 32
<212> TYPE: PRT
<213> ORGANISM: Homo sapiens

<400> SEQUENCE: 865

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 866
<211> LENGTH: 31
<212> TYPE: PRT
<213> ORGANISM: Homo sapiens

<400> SEQUENCE: 866

Arg Phe Thr Ile Ser Arg Asp Asn Ser Lys Asn Thr Leu Tyr Leu Gln
1               5                   10                  15
```

Met Asn Ser Leu Arg Ala Glu Asp Thr Ala Val Tyr Tyr Cys Ala
            20                  25                  30

<210> SEQ ID NO 867
<211> LENGTH: 30
<212> TYPE: PRT
<213> ORGANISM: Homo sapiens

<400> SEQUENCE: 867

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 868
<211> LENGTH: 32
<212> TYPE: PRT
<213> ORGANISM: Homo sapiens

<400> SEQUENCE: 868

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 869
<211> LENGTH: 32
<212> TYPE: PRT
<213> ORGANISM: Homo sapiens

<400> SEQUENCE: 869

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser Arg
            20                  25                  30

<210> SEQ ID NO 870
<211> LENGTH: 31
<212> TYPE: PRT
<213> ORGANISM: Homo sapiens

<400> SEQUENCE: 870

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser
            20                  25                  30

<210> SEQ ID NO 871
<211> LENGTH: 32
<212> TYPE: PRT
<213> ORGANISM: Homo sapiens

<400> SEQUENCE: 871

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 872
<211> LENGTH: 32
<212> TYPE: PRT
<213> ORGANISM: Homo sapiens

<400> SEQUENCE: 872

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 873
<211> LENGTH: 31
<212> TYPE: PRT
<213> ORGANISM: Homo sapiens

<400> SEQUENCE: 873

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 874
<211> LENGTH: 30
<212> TYPE: PRT
<213> ORGANISM: Homo sapiens

<400> SEQUENCE: 874

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 875
<211> LENGTH: 11
<212> TYPE: PRT
<213> ORGANISM: Homo sapiens

<400> SEQUENCE: 875

Trp Gly Gln Gly Thr Leu Val Thr Val Ser Ser
1               5                   10

<210> SEQ ID NO 876
<211> LENGTH: 11
<212> TYPE: PRT
<213> ORGANISM: Homo sapiens

<400> SEQUENCE: 876

Trp Gly Gln Gly Thr Leu Val Thr Val Ser Ser
1               5                   10

<210> SEQ ID NO 877
<211> LENGTH: 11
<212> TYPE: PRT
<213> ORGANISM: Homo sapiens

<400> SEQUENCE: 877

Trp Gly Gln Gly Thr Leu Val Thr Val Ser Ser
1               5                   10

<210> SEQ ID NO 878
<211> LENGTH: 11
<212> TYPE: PRT
<213> ORGANISM: Homo sapiens

<400> SEQUENCE: 878

Trp Gly Gln Gly Thr Leu Val Thr Val Ser Ser

```
1               5                  10

<210> SEQ ID NO 879
<211> LENGTH: 11
<212> TYPE: PRT
<213> ORGANISM: Homo sapiens

<400> SEQUENCE: 879

Trp Gly Gln Gly Thr Leu Val Thr Val Ser Ser
1               5                  10

<210> SEQ ID NO 880
<211> LENGTH: 11
<212> TYPE: PRT
<213> ORGANISM: Homo sapiens

<400> SEQUENCE: 880

Trp Gly Gln Gly Thr Leu Val Thr Val Ser Ser
1               5                  10

<210> SEQ ID NO 881
<211> LENGTH: 11
<212> TYPE: PRT
<213> ORGANISM: Homo sapiens

<400> SEQUENCE: 881

Trp Gly Gln Gly Thr Leu Val Thr Val Ser Ser
1               5                  10

<210> SEQ ID NO 882
<211> LENGTH: 11
<212> TYPE: PRT
<213> ORGANISM: Homo sapiens

<400> SEQUENCE: 882

Trp Gly Gln Gly Thr Leu Val Thr Val Ser Ser
1               5                  10

<210> SEQ ID NO 883
<211> LENGTH: 11
<212> TYPE: PRT
<213> ORGANISM: Homo sapiens

<400> SEQUENCE: 883

Trp Gly Gln Gly Thr Leu Val Thr Val Ser Ser
1               5                  10

<210> SEQ ID NO 884
<211> LENGTH: 11
<212> TYPE: PRT
<213> ORGANISM: Homo sapiens

<400> SEQUENCE: 884

Trp Gly Gln Gly Thr Leu Val Thr Val Ser Ser
1               5                  10

<210> SEQ ID NO 885
<211> LENGTH: 11
<212> TYPE: PRT
<213> ORGANISM: Homo sapiens

<400> SEQUENCE: 885

Trp Gly Gln Gly Thr Leu Val Thr Val Ser Ser
1               5                  10
```

<210> SEQ ID NO 886
<211> LENGTH: 11
<212> TYPE: PRT
<213> ORGANISM: Homo sapiens

<400> SEQUENCE: 886

Trp Gly Gln Gly Thr Leu Val Thr Val Ser Ser
1               5                   10

<210> SEQ ID NO 887
<211> LENGTH: 11
<212> TYPE: PRT
<213> ORGANISM: Homo sapiens

<400> SEQUENCE: 887

Trp Gly Gln Gly Thr Leu Val Thr Val Ser Ser
1               5                   10

<210> SEQ ID NO 888
<211> LENGTH: 11
<212> TYPE: PRT
<213> ORGANISM: Homo sapiens

<400> SEQUENCE: 888

Trp Gly Gln Gly Thr Leu Val Thr Val Ser Ser
1               5                   10

<210> SEQ ID NO 889
<211> LENGTH: 11
<212> TYPE: PRT
<213> ORGANISM: Homo sapiens

<400> SEQUENCE: 889

Trp Gly Gln Gly Thr Leu Val Thr Val Ser Ser
1               5                   10

<210> SEQ ID NO 890
<211> LENGTH: 11
<212> TYPE: PRT
<213> ORGANISM: Homo sapiens

<400> SEQUENCE: 890

Trp Gly Gln Gly Thr Leu Val Thr Val Ser Ser
1               5                   10

<210> SEQ ID NO 891
<211> LENGTH: 11
<212> TYPE: PRT
<213> ORGANISM: Homo sapiens

<400> SEQUENCE: 891

Trp Gly Gln Gly Thr Leu Val Thr Val Ser Ser
1               5                   10

<210> SEQ ID NO 892
<211> LENGTH: 11
<212> TYPE: PRT
<213> ORGANISM: Homo sapiens

<400> SEQUENCE: 892

Trp Gly Gln Gly Thr Leu Val Thr Val Ser Ser
1               5                   10

<210> SEQ ID NO 893

```
<211> LENGTH: 11
<212> TYPE: PRT
<213> ORGANISM: Homo sapiens

<400> SEQUENCE: 893

Trp Gly Gln Gly Thr Leu Val Thr Val Ser Ser
1               5                   10

<210> SEQ ID NO 894
<211> LENGTH: 15
<212> TYPE: PRT
<213> ORGANISM: Homo sapiens

<400> SEQUENCE: 894

Trp Tyr Gln Gln Lys Pro Gly Lys Ala Pro Lys Leu Leu Ile Tyr
1               5                   10                  15

<210> SEQ ID NO 895
<211> LENGTH: 15
<212> TYPE: PRT
<213> ORGANISM: Homo sapiens

<400> SEQUENCE: 895

Trp Tyr Leu Gln Lys Pro Gly Gln Ser Pro Gln Leu Leu Ile Tyr
1               5                   10                  15

<210> SEQ ID NO 896
<211> LENGTH: 15
<212> TYPE: PRT
<213> ORGANISM: Homo sapiens

<400> SEQUENCE: 896

Trp Tyr Gln Gln Lys Pro Gly Gln Ala Pro Arg Leu Leu Ile Tyr
1               5                   10                  15

<210> SEQ ID NO 897
<211> LENGTH: 15
<212> TYPE: PRT
<213> ORGANISM: Homo sapiens

<400> SEQUENCE: 897

Trp Tyr Gln Gln Lys Pro Gly Gln Pro Pro Lys Leu Leu Ile Tyr
1               5                   10                  15

<210> SEQ ID NO 898
<211> LENGTH: 32
<212> TYPE: PRT
<213> ORGANISM: Homo sapiens

<400> SEQUENCE: 898

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 899
<211> LENGTH: 32
<212> TYPE: PRT
<213> ORGANISM: Homo sapiens

<400> SEQUENCE: 899

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
```

20                  25                  30

<210> SEQ ID NO 900
<211> LENGTH: 32
<212> TYPE: PRT
<213> ORGANISM: Homo sapiens

<400> SEQUENCE: 900

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 901
<211> LENGTH: 32
<212> TYPE: PRT
<213> ORGANISM: Homo sapiens

<400> SEQUENCE: 901

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 902
<211> LENGTH: 10
<212> TYPE: PRT
<213> ORGANISM: Homo sapiens

<400> SEQUENCE: 902

Phe Gly Gln Gly Thr Lys Val Glu Ile Lys
1               5                   10

<210> SEQ ID NO 903
<211> LENGTH: 10
<212> TYPE: PRT
<213> ORGANISM: Homo sapiens

<400> SEQUENCE: 903

Phe Gly Gln Gly Thr Lys Val Glu Ile Lys
1               5                   10

<210> SEQ ID NO 904
<211> LENGTH: 10
<212> TYPE: PRT
<213> ORGANISM: Homo sapiens

<400> SEQUENCE: 904

Phe Gly Gln Gly Thr Lys Val Glu Ile Lys
1               5                   10

<210> SEQ ID NO 905
<211> LENGTH: 10
<212> TYPE: PRT
<213> ORGANISM: Homo sapiens

<400> SEQUENCE: 905

Phe Gly Gln Gly Thr Lys Val Glu Ile Lys
1               5                   10

<210> SEQ ID NO 906
<211> LENGTH: 11
<212> TYPE: PRT
<213> ORGANISM: Artificial Sequence

```
<220> FEATURE:
<223> OTHER INFORMATION: Synthetic

<400> SEQUENCE: 906

Glu Tyr Tyr Arg Trp Tyr Thr Ala Ile Asp Tyr
1               5                   10
```

METHODS AND COMPOSITIONS FOR TARGETING POLYUBIQUITIN

RELATED APPLICATIONS

This application is a divisional of U.S. application Ser. No. 12/766,772, filed Apr. 23, 2010, which is a divisional of U.S. application Ser. No. 11/611,058, filed Dec. 14, 2006, now U.S. Pat. No. 7,763,245 B2, which claims priority under 35 U.S.C. §119(e) to U.S. provisional application No. 60/751,081, filed Dec. 15, 2005, and to U.S. provisional application No. 60/793,980, filed Apr. 21, 2006, the contents of each which are incorporated by reference herein in their entirety for any purpose.

FIELD OF THE INVENTION

This invention relates to the field of anti-polyubiquitin antibodies, and more particularly to anti-polyubiquitin antibodies that do not specifically bind to monoubiquitin and that can discriminate between polyubiquitins having different isopeptide linkages.

BACKGROUND

Ubiquitin is a small protein that has important regulatory roles in a wide variety of cellular pathways. The best known of these is ubiquitin's role in protein degradation, where covalent attachment of ubiquitin to a target protein enables that target protein to be recognized and destroyed by the 26S proteasome (see Wilkinson, Semin. Cell Devel. Biol. 11(3): 141-148 (2000)). Protein kinase regulation of various signaling pathways has also been correlated with ubiquitination (see Sun and Chen, Curr. Opin. Cell Biol. 16: 119-126 (2004)). For example, phosphorylation of IκB by IκB kinase permits ubiquitination of IκB and subsequent degradation by the 26S proteasome; because IκB is an inhibitor of NFκB, the degradation of IκB activates NFκB (Ghosh and Karin, Cell 109 (Suppl.): S81-S96 (2002); Palombella et al., Cell 78: 773-785 (1994)). Ubiquitination also mediates DNA repair (see Sun and Chen, Curr. Opin. Cell Biol. 16:119-126 (2004)). After DNA is damaged, monoubiquitination of proliferating cell nuclear antigen (PCNA) activates damage-tolerant polymerases which are able to synthesize DNA despite any DNA lesions (Stelter and Ulrich, Nature 425: 188-191 (2003). Other physiological processes in which ubiquitination is known to be involved include cell division, cell growth, cell movement, and apoptosis/cell death (Johnson, Nat. Cell Biol. 4:E295-E298 (2002); Pickart, Mol. Cell. 8: 499-504 (2001)).

The covalent attachment of ubiquitin, a 76 amino acid protein, to a target protein is a three-step enzymatic process (Pickart, Annu. Rev. Biochem. 70: 503-533 (2001)). First, ubiquitin-activating enzyme E1 forms an ubiquitin-E1 thioester in an ATP-dependent reaction. The ubiquitin is transferred from the ubiquitin-E1 thioester to a member of the ubiquitin-conjugating enzyme (E2) family in the second step. In the third step, with the assistance of a ubiquitin-protein ligase (E3), an isopeptide bond is formed between the carboxyl terminus of ubiquitin and the ε-amino group of a lysine residue on the target protein. Enzymes termed deubiquitinases remove ubiquitin moieties from target proteins (Guterman and Glickman, Curr. Prot. Pep. Sci. 5: 201-210 (2004)). Highlighting ubiquitin's role as an important regulatory molecule, the human genome contains many different proteins involved in ubiquitination or deubiquitination: at least 40 different E2s, 500 different E3s, and 80 different deubiquitinases have been identified thus far (Wong et al., Drug. Discov. Today 8: 746-754 (2003)).

Ubiquitin contains seven lysine residues (Lys6, Lys22, Lys27, Lys33, Lys29, Lys48, and Lys63), and thus ubiquitin itself may serve as a target protein for uqibiutination (Peng et al., Nat. Biotechnol. 21: 921-926 (2003); Pickart and Fushman, Curr. Opin. Chem. Biol. 8:610-616 (2004)). The molecule produced upon ubiquitination of a ubiquitin protein is termed a polyubiquitin molecule, and may comprise two or more ubiquitin moieties. Ubiquitination of ubiquitin may theoretically occur at any of the seven lysine residues (Peng et al., Nat. Biotechnol. 21: 921-926 (2003)), so that different species of polyubiquitins exist having isopeptide bonds to different lysine residues within ubiquitin. It is possible that a single polyubiquitin molecule with greater than two ubiquitin moieties may have more than one type of lysine linkage. Studies have shown that the E2 enzyme influences the type of lysine linkage created between one ubiquitin molecule and another (Tenno et al., Genes to Cells 9: 865-875 (2004); Deng et al. (2000); Hofmann and Pickart (2001)). Polyubiquitin and ubiquitin exist both as free molecules and in covalent attachment with a target protein.

Like ubiquitin, polyubiquitin involvement has been found in many cellular processes, including intracellular trafficking, endocytosis, gene expression/silencing, proteolysis, kinase activation, translation, and DNA repair (Hoege et al., Nature 419:135-141 (2002); Spence et al., Mol. Cell. Biol. 15:1265-1273 (1995); Hofmann and Pickart, Cell 96: 645-653 (1999). Polyubiquitin and polyubiquitination can have strikingly different physiological roles than monoubiquitin and monoubiquitination in the same pathways, however. For example, whereas monoubiquitination of PCNA after DNA damage results in the activation of error-prone DNA polymerases, polyubiquitination of PCNA at the identical residue where monoubiquitination is observed results in activation of error-free DNA repair (Stelter and Ulrich, Nature 425: 188-191 (2003); Hoege et al., Nature 419:135-141 (2002); Spence et al., Mol. Cell. Biol. 15:1265-1273 (1995); and Hofmann and Pickart, Cell 96: 645-653 (1999)).

Even polyubiquitins having different lysine linkages appear to play different physiological roles. The two best-studied are the Lys48-linked and Lys63-linked polyubiquitins, and structural studies of the two suggest that different lysine-linked polyubiquitins may adopt markedly different conformations, thus permitting different interactions with selected binding partners (Tenno et al., Genes to Cells 9: 865-875 (2004)). Covalent modification by Lys48-linked polyubiquitin typically marks the target protein for proteolytic degradation, though there is some evidence that Lys48-linked polyubiquitin may also regulate certain proteins by non-proteolytic means (Chau et al., Science 243: 1576-1583 (1989); Finley et al., Mol. Cell. Biol. 14: 5501-5509 (1994); Flick et al., Nat. Cell. Biol. 6:634-641 (2004)). Lys63-linked polyubiquitins, in contrast, have been linked to a variety of nonproteolytic intracellular pathways, including DNA repair (yeast cells expressing K63R-ubiquitin are defective in DNA repair), kinase activation, intracellular trafficking, and translation (Pickart and Fushman, Curr. Opin. Chem. Biol. 8: 610-616 (2004); Hicke and Dunn, Annu Rev. Cell Dev. Biol. 19: 141-172 (2003); Spece et al., Mol. Cell. Biol. 15: 1265-1273 (1995); Ulrich, Eukaryot. Cell 1:1-10 (2002); Spence et al., Cell 102: 67-76 (2000); Seibenhener et al., Mol. Cell. Biol. 24(18): 8055-8068 (2004)). In one specific example, synphilin-1 is normally ubiquitinated with K63-linked polyubiquitin by parkin in a proteasomal-independent manner, but synphilin-1 can alternately be targeted for destruction by ubiquitination with K48-linked polyubiquitin (Lim et al., J. Neurosci. 25(8): 2002-9 (2005)). An analysis of subjects with Parkinson's disease shows that K63-polyubiquitination of synphilin-1 may be involved in the formation of Lewy body inclusions associated with that disease (Lim et al., J. Neurosci. 25(8): 2002-9 (2005)).

Other lysine-linked polyubiquitins have not been studied extensively, largely because of the difficulty in distinguishing between them. Studies have thus far relied on cells expressing mutagenized ubiquitins in which one or more lysines have been removed, on enzymatically synthesized polyubiquitins of particular linkages, or on techniques such as mass spectrometry to distinguish between one type of polyubiquitin and another. Each of those methodologies is ill-suited or cumbersome for analysis of the normal physiological behavior of particular lysine-linked polyubiquitins. While antibodies exist that are specific for polyubiquitin as opposed to monoubiquitin (Fujimoro et al., FEBS Lett. 349: 173-180 (1994)), there are as yet no antibodies that can distinguish between polyubiquitins of different lysine linkages.

Unsurprisingly, given their important roles in a variety of cellular processes, ubiquitin and polyubiquitins have also been implicated in many diseases see (Argiles, Ubiquitin and Disease, R. G. Landes (1998)). Ubiquitin dysregulation is observed in muscle wasting (Mitch and Goldberg, New Engl. J. Med. 335: 1897-905 (1996); Bodine et al., Science 294: 1704-1708 (2001)). Several genetic diseases have been linked to aberrant ubiquitin activity, including cystic fibrosis (Ward et al., Cell 83: 121-127 (1995)), Angelman's syndrome (Kishino et al., Nature Genet. 15: 70-73 (1997)), and Liddle syndrome (Staub et al., EMBO J. 16: 6325-6336 (1997)). Ubiquitin also plays a role in immune and inflammatory responses; for example, extracellular ubiquitin has been found to act as a sort of cytokine, inhibiting the TNFα response to endotoxin in peripheral blood mononuclear cells and regulating endotoxin hyporesponsiveness (Majetschak et al., Blood 101: 1882-1890 (2003); Ciechanover, EMBO J. 17: 7151-7160 (1998)). Also, both ubiquitin and polyubiquitin have been found in human serum, with higher levels of both molecules observed in the serum of patients having parasitic and allergic disease (Takada et al., Clinical Chem. 43: 1188-1195 (1997)).

Dysregulation of several ubiquitin-mediated pathways are also involved in cancer (Spataro et al., Br. J. Cancer 77: 448-55 (1998); Beckmann et al., Hum. Mutat. 25: 507-12 (2005)). For example, mutations in the heterodimeric ubiquitin ligase BRCA1-BARD1 are correlated with breast cancer (Hashizume et al., J. Biol. Chem. 276: 14537-40 (2001)), mutations that disrupt the ability of Myc to be degraded by the ubiquitin pathway activate the oncogenic potential of c-Myc (Salghetti et al., EMBO J. 18: 717-726 (1999)), and transformed v-Jun is unable to be ubiquitinated and degraded as its non-oncogenic correlate, c-Jun, is, giving rise to uncontrolled growth (Ciechanover, EMBO J. 17: 7151-7160 (1998); Trier et al., Cell 78: 787-798 (1994)).

Ubiquitin and polyubiquitin have particularly been studied in the context of neurological diseases (Chung et al., TINS 24(11 Suppl.) S7-S14 (2001)). The inclusions, bodies, and neurofibrillary tangles that accumulate in Huntington's disease, Spinocerebellar ataxia, prion encephalopathies, Pick's disease, Lewy body disease, Parkinson's disease, and Alzheimer's disease stain immunopositively for mono and/ or polyubiquitin (Alves-Rodrigues et al., Trends Neurosci. 21: 516-520 (1998); Cammarata et al., Neurosci Lett. 156: 96-98 (1993); Kalchman et al., J. Biol. Chem. 271: 19385-94 (1996); Holmberg et al., Human Mol. Genet. 7: 913-918 (1998); Yedidia et al., EMBO J. 20: 5383-91 (2001); Mori et al., Science 235: 1641-44 (1987); Leigh et al., Acta Neuropathol. (Berl.) 79: 61-72 (1989); and Kuzuhara et al., Acta Neuropathologica 75: 345-353 (1988)). Several forms of Parkinson's disease have been linked to mutations in the ubiquitin carboxy-terminal hydrolase L1 (UCH-L1) gene, a deubiquitinase (Leroy et al., Nature 395: 451-452 (1998)), while other forms of Parkinson's have been linked to inactivating mutations in Parkin, an E2-dependent ubiquitin-protein ligase known to interact with the ubiquitin-conjugating enzyme UbCH7 and to ubiquitinate synphilin-1 (Shimura et al., Nature Genet. 25: 302-305 (2000), Zhang et al., Proc. Natl. Acad. Sci. 97: 13354-13359 (2000); Lim et al., J. Neurosci. 25(8): 2002-9 (2005)). Both types of mutations result in aberrant proteolytic processing and the inappropriate aggregation of proteins (see McNaught et al., Nature Rev. Neurosci. 2: 589-594 (2001)). UCH-L1 mutations have also been found to segregate with Huntington's disease (Naze et al., Neurosci. Lett. 328:1:1-4 (2002)). A mutant form of ubiquitin has been identified in the brains of Alzheimer's patients that is very efficiently incorporated into polyubiquitin chains, but is refractory to deubiquitination once formed, potentially leading to dominant inhibition of the normal cellular proteolytic processing system (Lam et al., Proc. Natl. Acad. Sci. 97: 9902-9906 (2000)).

It is clear that it would be beneficial not only to have compositions and methods that can distinguish between polyubiquitins of different lysine linkages, but also to have compositions and methods that are effective in targeting and modulating ubiquitin and polyubiquitin-mediated pathways. The invention provided herein relates to such compositions and methods.

All references cited herein, including patent applications and publications, are incorporated by reference in their entirety.

DISCLOSURE OF THE INVENTION

The invention provides novel antibodies capable of binding to and/or regulating biological activities associated with polyubiquitin.

In one embodiment, an isolated antibody that specifically binds to polyubiquitin is provided, wherein the antibody does not specifically bind to monoubiquitin. In one embodiment, an isolated antibody that specifically binds a first polyubiquitin comprising a first lysine linkage is provided, wherein the antibody does not specifically bind a second polyubiquitin comprising a second lysine linkage, and wherein the first lysine linkage differs from the second lysine linkage. In one aspect, the antibody further specifically binds lysine 6-linked polyubiquitin, lysine 11-linked polyubiquitin, lysine 27-linked polyubiquitin, lysine 29-linked polyubiquitin, lysine 33-linked polyubiquitin, lysine 48-linked polyubiquitin, or lysine 63-linked polyubiquitin.

In one embodiment, an isolated antibody that specifically binds a first K48-linked polyubiquitin is provided, wherein the antibody does not specifically bind a second polyubiquitin comprising a different lysine-linked form of polyubiquitin (i.e., not K48-linked polyubiquitin). In one embodiment, the second polyubiquitin is K63-linked polyubiquitin.

In one embodiment, an isolated antibody that specifically binds a first K63-linked polyubiquitin is provided, wherein the antibody does not specifically bind a second polyubiquitin comprising a different lysine-linked form of polyubiquitin (i.e., not K63-linked polyubiquitin). In one embodiment, the second polyubiquitin is K48-linked polyubiquitin.

In one embodiment, an isolated antibody that specifically binds both a first polyubiquitin comprising a first lysine linkage and a second polyubiquitin comprising a second lysine linkage is provided, wherein the first lysine linkage differs from the second lysine linkage, wherein the antibody does not specifically bind monoubiquitin, and wherein the antibody binds the second polyubiquitin with a substantially reduced binding affinity as compared to the binding affinity of the antibody for the first polyubiquitin.

In one embodiment, an isolated antibody that specifically binds lysine-48-linked polyubiquitin is provided, wherein the antibody does not specifically bind monoubiquitin. In one embodiment, the antibody further comprises at least one hypervariable (HVR) sequence selected from HVR-H1, HVR-H2, HVR-H3, and HVR-L3 of any of SEQ ID NOs: 1-25, 151-175, 265-279, 392-459, and 695-704; SEQ ID NOs: 27-51, 177-201, 281-295, 461-528, and 706-715; SEQ ID NOs: 53-77, 203-227, 297-311, 530-597, and 717-726; and SEQ ID NOs: 313-327 and 728-737, respectively. In one embodiment, the antibody further comprises at least one sequence selected from HVR-H1, HVR-H2, HVR-H3, wherein HVR-H1 comprises the amino acid sequence a b c d e f g h i j (SEQ ID NO: 825), wherein amino acid a is glycine; amino acid b is phenylalanine; amino acid c is asparagine; amino acid d is selected from valine, phenylalanine, leucine, and isoleucine; amino acid e is selected from serine and tyrosine; amino acid f is tyrosine; amino acid g is selected from serine and tyrosine; amino acid h is selected from serine and tyrosine; amino acid i is selected from isoleucine and methionine; and amino acid j is histidine; wherein HVR-H2 comprises the amino acid sequence k l m n o p q r s t u v w x y z a' (SEQ ID NO: 826), wherein amino acid k is serine; amino acid l is isoleucine; amino acid m is selected from serine and tyrosine; amino acid n is selected from proline and serine; amino acid o is tyrosine; amino acid p is tyrosine; amino acid q is selected from serine and glycine; amino acid r is selected from serine and tyrosine; amino acid s is threonine, amino acid t is selected from serine and tyrosine; amino acid u is tyrosine; amino acid v is alanine; amino acid w is aspartic acid; amino acid x is serine; amino acid y is valine; amino acid z is lysine; and amino acid a' is glycine; and wherein HVR-H3 comprises the amino acid sequence b' c' d' e' f' g' h' j' k' wherein amino acid b' is selected from glutamic acid, serine, glycine, and tyrosine; amino acid c' is selected from glycine, tyrosine, serine, and asparagine; amino acid d' is selected from tyrosine, serine, lysine, phenylalanine, and glutamic acid; amino acid e' is selected from serine, tyrosine, glycine, and tryptophan; amino acid f' is selected from glutamine, tyrosine, serine, and glycine; amino acid g' is selected from glycine, serine, tyrosine, methionine, and alanine; amino acid h' is selected from glycine, alanine, proline, and isoleucine; amino acid i' is selected from phenylalanine, isoleucine, methionine, alanine, and leucine, or is not present; amino acid j' is phenylalanine or is not present; amino acid k' is aspartic acid; and amino acid l' is tyrosine. In one embodiment, the antibody further comprises HVR-H1, HVR-H2, and HVR-H3 sequences corresponding to those set forth for clones apu01, apu02, apu03, apu04, apu05, apu06, apu07, apu08, apu09, apu10, apu11, apu12, apu13, apu14, or apu15 in FIGS. 10A and 10B.

In one embodiment, the antibody comprises at least one sequence selected from HVR-H1, HVR-H2, HVR-H3, wherein HVR-H1 comprises the amino acid sequence a b c d e f g h i j (SEQ ID NO: 827), wherein amino acid a is glycine; amino acid b is phenylalanine; amino acid c is asparagine; amino acid d is isoleucine; amino acid e is selected from serine and phenylalanine; amino acid f is tyrosine; amino acid g is selected from serine and glycine; amino acid h is selected from serine and glycine; amino acid i is selected from isoleucine and methionine; and amino acid j is histidine; wherein HVR-H2 comprises the amino acid sequence k l m n o p q r s t u v w x y z a' (SEQ ID NO: 828), wherein amino acid k is serine; amino acid l is isoleucine; amino acid m is tyrosine; amino acid n is serine; amino acid o is tyrosine; amino acid p is tyrosine; amino acid q is serine; amino acid r is tyrosine; amino acid s is threonine, amino acid t is serine; amino acid u is tyrosine; amino acid v is alanine; amino acid w is aspartic acid; amino acid x is serine; amino acid y is valine; amino acid z' is lysine; and amino acid a' is glycine; and wherein HVR-H3 comprises the amino acid sequence b' c' d' e' f' g' h' j' k' (SEQ ID NO: 829), wherein amino acid b' is selected from serine and glycine; amino acid c' is tyrosine; amino acid d' is serine; amino acid e' is selected from tyrosine and tryptophan; amino acid f' is selected from serine, tyrosine, arginine, phenylalanine, and histidine; amino acid g' is selected from glutamic acid, serine, leucine, phenylalanine, methionine, asparagine, and valine; amino acid h' is selected from alanine and glycine; amino acid i' is selected from leucine, methionine, phenylalanine, and isoleucine; amino acid j' is aspartic acid; and amino acid k' is tyrosine. In one embodiment, the antibody further comprises HVR-H1, HVR-H2, and HVR-H3 sequences corresponding to those set forth for clones apu2.01, apu2.02, apu2.03, apu2.04, apu2.05, apu2.06, apu2.07, apu2.08, apu2.09, or apu2.10 in FIG. 16A.

In one embodiment, the antibody further comprises a HVR-L3 sequence comprising the amino acid sequence m' n' o' p' q' r' s' t' u' v' w' (SEQ ID NO: 830), wherein amino acid m' is glutamine; amino acid n' is glutamine; amino acid o' is selected from serine and tyrosine; amino acid p' is selected from serine and tyrosine; amino acid q' is selected from serine and tyrosine; amino acid r' is selected from serine and tyrosine; amino acid s' is selected from serine and tyrosine; amino acid t' is selected from leucine, serine, proline, and tyrosine; amino acid u' is proline or is not present; amino acid v' is selected from phenylalanine, isoleucine, valine, and leucine; and amino acid w' is threonine. In one embodiment, the antibody further comprises an HVR-L1 sequence of SEQ ID NO: 79, an HVR-L2 sequence of SEQ ID NO: 80, and an HVR-L3 sequence corresponding to the HVR-L3 sequence set forth for clones apu01, apu02, apu03, apu04, apu05, apu06, apu07, apu08, apu09, apu10, apu11, apu12, apu13, apu14, or apu15 in FIG. 10C. In one embodiment, the antibody further comprises a HVR-L3 sequence comprising the amino acid sequence Q-Q-S-S-Y-S-S-L-I-T (SEQ ID NO: 728). In one embodiment, the antibody further comprises an HVR-L1 sequence of SEQ ID NO: 79, an HVR-L2 sequence of SEQ ID NO: 80, and an HVR-L3 sequence corresponding to the HVR-L3 sequence set forth for clones apu2.01, apu2.02, apu2.03, apu2.04, apu2.05, apu2.06, apu2.07, apu2.08, apu2.09, or apu2.10 in FIG. 16B.

In one embodiment, an isolated antibody that specifically binds lysine-48-linked polyubiquitin is provided, wherein the antibody does not specifically bind monoubiquitin, and wherein the antibody comprises an HVR-H1 sequence of SEQ ID NO: 269, an HVR-H2 sequence of SEQ ID NO: 285, an HVR-H3 sequence of SEQ ID NO: 301, an HVR-L1 sequence of SEQ ID NO: 79, an HVR-L2 sequence of SEQ ID NO: 80, and an HVR-L3 sequence of SEQ ID NO: 317. In one embodiment, an isolated antibody that specifically binds lysine-48-linked polyubiquitin is provided, wherein the antibody does not specifically bind monoubiquitin, and wherein the antibody comprises an HVR-H1 sequence of SEQ ID NO: 701, an HVR-H2 sequence of SEQ ID NO: 712, an HVR-H3 sequence of SEQ ID NO: 723, an HVR-L1 sequence of SEQ ID NO: 79, an HVR-L2 sequence of SEQ ID NO: 80, and an HVR-L3 sequence of SEQ ID NO: 734. In one embodiment, an isolated antibody that specifically binds lysine-48-linked polyubiquitin is provided, wherein the antibody does not specifically bind monoubiquitin, and wherein the antibody comprises an HVR-H1 sequence of SEQ ID NO: 701, an HVR-H2 sequence of SEQ ID NO: 712, an HVR-H3 sequence of SEQ ID NO: 723, and HVR-L1 sequence of SEQ ID NO: 79, and HVR-L2 sequence of SEQ ID NO: 80, and an HVR-L3 sequence of SEQ ID NO: 734.

In one embodiment, an isolated antibody that specifically binds to lysine-63-linked polyubiquitin is provided, wherein the antibody does not specifically bind to monoubiquitin. In one embodiment the antibody further comprises at least one hypervariable (HVR) sequence selected from HVR-H1, HVR-H2, HVR-H3, and HVR-L3 of any of SEQ ID NOs: 81-89, 229-239, 329-336, 599-629, and 739-748; SEQ ID NOs: 91-99, 241-251; 338-345, 631-661, and 750-759; SEQ ID NOs: 101-109, 253-263, 347-354, 663-693, and 761-770; and SEQ ID NOs: 356-363 and 772-781, respectively. In one embodiment, the antibody comprises at least one sequence selected from HVR-H1, HVR-H2, HVR-H3, wherein HVR-H1 comprises the amino acid sequence a b c d e f g h i j (SEQ ID NO: 831), wherein amino acid a is glycine; amino acid b is phenylalanine; amino acid c is asparagine; amino acid d is selected from valine, isoleucine, and phenylalanine; amino acid e is selected from serine and tyrosine; amino acid f is selected from serine and tyrosine; amino acid g is selected from serine and tyrosine; amino acid h is selected from serine and tyrosine; amino acid i is selected from isoleucine and methionine; and amino acid j is histidine; wherein HVR-H2 comprises the amino acid sequence k l m n o p q r s t u v w x y z a' (SEQ ID NO: 832), wherein amino acid k is selected from serine and tyrosine; amino acid l is isoleucine; amino acid m is selected from serine and tyrosine; amino acid n is selected from proline and serine; amino acid o is selected from serine and tyrosine; amino acid p is selected from serine and tyrosine; amino acid q is selected from serine and glycine; amino acid r is selected from serine and tyrosine; amino acid s is threonine, amino acid t is selected from serine and tyrosine; amino acid u is tyrosine; amino acid v is alanine; amino acid w is aspartic acid; amino acid x is serine; amino acid y is valine; amino acid z is lysine; and amino acid a is glycine; and wherein HVR-H3 comprises the amino acid sequence b' c' d' e' f' g' h' j' k' m' n' o' p' q' r' s' t' u' v', wherein amino acid b' is selected from serine, glutamic acid, glycine, and tryptophan; amino acid c' is selected from glycine, tyrosine, isoleucine, glutamine, and serine; amino acid d' is selected from tyrosine, methionine, glycine, and isoleucine; amino acid e' is selected from tyrosine, arginine, phenylalanine, tryptophan, alanine, and proline; amino acid f' is selected from tyrosine, tryptophan, serine, and glycine; amino acid g' is selected from glutamine, tyrosine, serine, phenylalanine, and valine; amino acid h' is selected from glycine, threonine, tryptophan, lysine, and proline; amino acid i' is selected from tyrosine, alanine, tryptophan, glutamic acid, proline, and serine; amino acid j' is selected from tryptophan, isoleucine, tyrosine, and alanine; amino acid k' is selected from tryptophan, tyrosine, glycine, and aspartic acid, or is not present; amino acid l' is selected from tyrosine, serine, phenylalanine, and tryptophan, or is not present; amino acid m' is selected from tyrosine, aspartic acid, and serine, or is not present; amino acid n' is selected from tyrosine and alanine, or is not present; amino acid o' is selected from threonine, serine, valine, glycine, and tyrosine, or is not present; amino acid p' is selected from glycine, aspartic acid, serine, methionine, and tyrosine, or is not present; amino acid q' is selected from tyrosine, alanine, and glycine, or is not present; amino acid r' is selected from tyrosine, leucine, and glycine, or is not present; amino acid s' is glycine or is not present; amino acid t' is selected from methionine and leucine, or is not present; amino acid u' is aspartic acid; and amino acid v' is tyrosine. In one embodiment, the antibody further comprises HVR-H1, HVR-H2, and HVR-H3 sequences corresponding to those set forth for clones apu17, apu18, apu19, apu20, apu21, apu22, apu23, and apu24 in FIGS. 11A and 11B.

In one embodiment, the antibody comprises at least one sequence selected from HVR-H1, HVR-H2, HVR-H3, wherein HVR-H1 comprises the amino acid sequence a b c d e f g h i j (SEQ ID NO: 833), wherein amino acid a is glycine; amino acid b is phenylalanine; amino acid c is asparagine; amino acid d is selected from isoleucine, valine, and leucine; amino acid e is selected from serine, lysine, and valine; amino acid f is selected from serine, tryptophan, glycine, and threonine; amino acid g is selected from serine, asparagine, and glycine; amino acid h is selected from tyrosine, isoleucine, leucine, and phenylalanine; amino acid i is selected from isoleucine and methionine; and amino acid j is histidine; wherein HVR-H2 comprises the amino acid sequence k l m n o p q r s t u v w x y z a' (SEQ ID NO: 834), wherein amino acid k is selected from tyrosine, phenylalanine, aspartic acid, histidine, and alanine; amino acid l is isoleucine; amino acid m is selected from serine, alanine, and glutamine; amino acid n is proline; amino acid o is tyrosine; amino acid p is selected from leucine, tyrosine, and phenylalanine; amino acid q is selected from serine and glycine; amino acid r is selected from serine, threonine, and tryptophan; amino acid s is threonine, amino acid t is selected from serine, asparagine, lysine, and isoleucine; amino acid u is tyrosine; amino acid v is alanine; amino acid w is aspartic acid; amino acid x is serine; amino acid y is valine; amino acid z' is lysine; and amino acid a' is glycine; and wherein HVR-H3 comprises the amino acid sequence b' c' d' e' f' g' h' j' k' (SEQ ID NO: 908), wherein amino acid b' is glutamic acid; amino acid c' is tyrosine; amino acid d' is tyrosine; amino acid e' is arginine; amino acid f' is tryptophan; amino acid g' is tyrosine; amino acid h' is threonine; amino acid i' is alanine; amino acid j' is isoleucine; amino acid k' is aspartic acid; and amino acid l' is tyrosine. In one embodiment, the antibody comprises HVR-H1, HVR-H2, and HVR-H3 sequences corresponding to those set forth for clones apu2.11, apu2.12, apu2.13, apu2.14, apu2.15, apu2.16, apu2.17, apu2.18, apu2.19, and apu2.20 in FIG. 17A.

In one embodiment, the antibody comprises at least one sequence selected from HVR-H1, HVR-H2, HVR-H3, wherein HVR-H1 comprises the amino acid sequence a b c d e f g h i j (SEQ ID NO: 835), wherein amino acid a is glycine; amino acid b is phenylalanine; amino acid c is asparagine; amino acid d is selected from isoleucine, valine, and leucine; amino acid e is selected from lysine and methionine; amino acid f is selected from threonine, methionine, asparagine, arginine, and isoleucine; amino acid g is selected from glycine, valine, and phenylalanine; amino acid h is selected from tyrosine, isoleucine, leucine, and phenylalanine; amino acid i is selected from isoleucine and methionine; and amino acid j is histidine; wherein HVR-H2 comprises the amino acid sequence k l m n o p q r s t u v w x y z a' b' (SEQ ID NO: 836), wherein amino acid k is alanine;

amino acid 1 is tyrosine; amino acid m is isoleucine; amino acid n is selected from serine, isoleucine, and threonine; amino acid o is proline; amino acid p is tyrosine; amino acid q is selected from leucine, tyrosine, aspartic acid, serine, and tryptophan; amino acid r is glycine; amino acid s is selected from tryptophan, valine, serine, asparagine, arginine, and tyrosine; amino acid t is threonine, amino acid u is selected from arginine, asparagine, valine, threonine, serine, and lysine; amino acid v is tyrosine; amino acid w is alanine; amino acid x is aspartic acid; amino acid y is serine; amino acid z is valine; amino acid a' is lysine; and amino acid b' is glycine; and wherein HVR-H3 comprises the amino acid sequence c' d' e' f' g' h' j' k' m' n' o' (SEQ ID NO: 837), wherein amino acid c' is serine; amino acid d' is arginine; amino acid e' is glutamic acid; amino acid f' is tyrosine; amino acid g' is tyrosine; amino acid h' is arginine; amino acid i' is tryptophan; amino acid j' is tyrosine; amino acid k' is threonine; amino acid l' is alanine; amino acid m' is isoleucine; amino acid n' is aspartic acid; and amino acid o' is tyrosine. In one embodiment, the antibody comprises HVR-H1, HVR-H2, and HVR-H3 sequences corresponding to those set forth for clones apu3.01, apu3.02, apu3.03, apu3.04, apu3.05, apu3.06, apu3.07, apu3.08, apu3.09, apu3.10, and 3.11 in FIGS. 23A and 23B.

In one embodiment, the antibody comprises a HVR-L3 sequence comprising the amino acid sequence w' x' y' z' A B C D E F G, wherein amino acid w' is glutamine; amino acid x' is glutamine; amino acid y' is selected from serine and tyrosine; amino acid z' is selected from serine and tyrosine; amino acid A is selected from serine and tyrosine; amino acid B is selected from serine and tyrosine; amino acid C is selected from proline, serine and leucine; amino acid D is selected from serine, proline, and tyrosine, or is not present; amino acid E is selected from leucine and phenylalanine, or is not present; amino acid F is selected from phenylalanine, valine, threonine, and isoleucine; and amino acid G is selected from arginine, threonine, and phenylalanine. In one embodiment, the antibody comprises an HVR-L1 sequence of SEQ ID NO: 79, an HVR-L2 sequence of SEQ ID NO: 80, and an HVR-L3 sequence corresponding to the HVR-L3 sequence set forth for clones apu17, apu18, apu19, apu20, apu21, apu22, apu23, and apu24 in FIG. 11C. In one embodiment, the antibody comprises a HVR-L3 sequence comprising the amino acid sequence Q-Q-Y-S-S-Y-S-S-L-F-T (SEQ ID NO: 772). In one embodiment, the antibody comprises an HVR-L1 sequence of SEQ ID NO: 79, an HVR-L2 sequence of SEQ ID NO: 80, and an HVR-L3 sequence corresponding to the HVR-L3 sequence set forth for clones apu2.11, apu2.12, apu2.13, apu2.14, apu2.15, apu2.16, apu2.17, apu2.18, apu2.19, and apu2.20 in FIG. 17B. In one embodiment, the antibody comprises an HVR-L1 sequence of SEQ ID NO: 79, an HVR-L2 sequence of SEQ ID NO: 80, and an HVR-L3 sequence corresponding to the HVR-L3 sequence of SEQ ID NO: 777.

In one embodiment, an isolated antibody that specifically binds lysine-63-linked polyubiquitin is provided, wherein the antibody does not specifically bind monoubiquitin, and wherein the antibody comprises an HVR-H1 sequence of SEQ ID NO: 330, an HVR-H2 sequence of SEQ ID NO: 339, an HVR-H3 sequence of SEQ ID NO: 348, an HVR-L1 sequence of SEQ ID NO: 79, an HVR-L2 sequence of SEQ ID NO: 80, and an HVR-L3 sequence of SEQ ID NO: 357. In one embodiment, an isolated antibody that specifically binds lysine-63-linked polyubiquitin is provided, wherein the antibody does not specifically bind monoubiquitin, and wherein the antibody comprises an HVR-H1 sequence of SEQ ID NO: 739, an HVR-H2 sequence of SEQ ID NO: 750, an HVR-H3 sequence of SEQ ID NO: 761, an HVR-L1 sequence of SEQ ID NO: 79, an HVR-L2 sequence of SEQ ID NO: 80, and an HVR-L3 sequence of SEQ ID NO: 772. In one embodiment, an isolated antibody that specifically binds lysine-63-linked polyubiquitin is provided, wherein the antibody does not specifically bind monoubiquitin, and wherein the antibody comprises an HVR-H1 sequence of SEQ ID NO: 740, an HVR-H2 sequence of SEQ ID NO: 751, an HVR-H3 sequence of SEQ ID NO: 762, an HVR-L1 sequence of SEQ ID NO: 79, an HVR-L2 sequence of SEQ ID NO: 80, and an HVR-L3 sequence of SEQ ID NO: 773. In one embodiment, an isolated antibody that specifically binds lysine-63-linked polyubiquitin is provided, wherein the antibody does not specifically bind monoubiquitin, and wherein the antibody comprises an HVR-H1 sequence of SEQ ID NO: 744, an HVR-H2 sequence of SEQ ID NO: 755, an HVR-H3 sequence of SEQ ID NO: 766, an HVR-L1 sequence of SEQ ID NO: 79, an HVR-L2 sequence of SEQ ID NO: 80, and an HVR-L3 sequence of SEQ ID NO: 777. In one embodiment, an isolated antibody that specifically binds lysine-63-linked polyubiquitin is provided, wherein the antibody does not specifically bind monoubiquitin, and wherein the antibody comprises an HVR-H1 sequence of SEQ ID NO: 795, an HVR-H2 sequence of SEQ ID NO: 807, an HVR-H3 sequence of SEQ ID NO: 819, an HVR-L1 sequence of SEQ ID NO: 79, an HVR-L2 sequence of SEQ ID NO: 80, and an HVR-L3 sequence of SEQ ID NO: 777.

In one aspect, an isolated antibody that binds to the same antigenic determinant on polyubiquitin as the antibody of any of the aforementioned antibodies is provided, wherein the antibody does not specifically bind to monoubiquitin. In one aspect, an isolated antibody that competes with any of the aforementioned antibodies for binding to polyubiquitin is provided, wherein the antibody does not specifically bind to monoubiquitin.

In one aspect, any of the aforementioned antibodies specifically binds to a polyubiquitinated protein. In one aspect, the antibody further inhibits degradation of the polyubiquitinated protein. In one aspect, the antibody further modulates at least one polyubiquitin-mediated signaling pathway. In one aspect, the antibody further inhibits at least one polyubiquitin-mediated signaling pathway. In one aspect, the antibody further stimulates at least one polyubiquitin-mediated signaling pathway.

In one aspect, a nucleic acid molecule encoding an antibody of the invention is provided. In one aspect, a vector that comprises the nucleic acid is provided. In one aspect, a host cell comprising the vector is provided. In one aspect, a cell line capable of producing an antibody of the invention is provided. In one aspect, a method of producing an antibody of the invention is provided, comprising culturing a host cell comprising a nucleic acid molecule encoding the antibody under conditions wherein the antibody is produced. In one aspect, a composition comprising an effective amount of an antibody of the invention and a pharmaceutically acceptable carrier is provided.

In one aspect, a method of identifying the presence of polyubiquitin or a polyubiquitinated protein in a sample is provided, comprising contacting the sample with at least one antibody of the invention. In one aspect, a method for the treatment of a disease or condition associated with dysregulation of polyubiquitin in a patient is provided, the method comprising administering to the patient an effective amount of at least one antibody of the invention. In one aspect, the patient is a mammalian patient. In one aspect, the patient is human. In one aspect, the disease is selected from cancer, a muscular disorder, a ubiquitin-pathway-related genetic disorder, an immune/inflammatory disorder, and a neurological disorder. In one aspect, the disease is selected from carcinoma, lymphoma, blastoma, sarcoma, leukemia, muscular dystrophy, multiple sclerosis, amyotrophic lateral sclerosis, cystic fibrosis, Angelman's syndrome, Liddle syndrome, Alzheimer's disease, Parkinson's disease, Pick's disease, and Paget's disease.

In one aspect, a method of determining the presence of a polyubiquitin or polyubiquitinated protein in a sample suspected of containing a polyubiquitin or polyubiquitinated protein is provided, comprising exposing the sample to at least one antibody of the invention and determining the binding of the at least one antibody to a polyubiquitin or polyubiquitinated protein in the sample.

In one aspect, a method of separating polyubiquitinated protein from non-polyubiquitinated protein in a sample is provided, comprising contacting the sample with at least one antibody of the invention.

In one aspect, a method of determining the function and/or activity of polyubiquitin in a cell is provided, comprising contacting the cell with at least one antibody of the invention and assessing the effect of said contacting step on the cell.

In one aspect, a method of determining the function and/or activity of polyubiquitin in a sample is provided, comprising contacting the sample with at least one antibody of the invention and assessing the effect of said contacting step on the sample.

In another embodiment, an isolated antibody that specifically binds to a lysine-63-linked polyubiquitin is provided, wherein the antibody binds to an epitope in the lysine-63-linked polyubiquitin. In one aspect, the epitope includes residues in both a first ubiquitin subunit and a second ubiquitin subunit of the lysine-63-linked polyubiquitin. In another such aspect, the epitope includes at least one residue in a first ubiquitin subunit selected from Glu-18, Pro-19, Ser-20, Asp-21, Thr-55, Leu-56, Ser-57, Asp-58, Asn-60, Ile-61, and Gln-62. In another such aspect, the epitope includes at least one residue in a second ubiquitin subunit selected from Leu-8, Thr-9, Glu-34, Gly-35, Ile-36, Pro-37, Asp-39, Gln-40, Leu-71, Arg-72, Leu-73, Arg-74, and Gly-75. In another such aspect, the epitope includes at least one residue in a first ubiquitin subunit selected from Glu-18, Pro-19, Ser-20, Asp-21, Thr-55, Leu-56, Ser-57, Asp-58, Asn-60, Ile-61, and Gln-62, and at least one residue in a second ubiquitin subunit selected from Leu-8, Thr-9, Glu-34, Gly-35, Ile-36, Pro-37, Asp-39, Gln-40, Leu-71, Arg-72, Leu-73, Arg-74, and Gly-75.

In one embodiment, an isolated antibody that specifically binds to a first polyubiquitin comprising at least one isopeptide bond to a first lysine residue at a first amino acid position of a ubiquitin molecule is provided, wherein the antibody does not specifically bind to a second polyubiquitin comprising at least one isopeptide bond to a second lysine residue at a second amino acid position of a ubiquitin molecule, and wherein the first and the second amino acid positions differ. An antibody of the invention can be in any number of forms. For example, an antibody of the invention can be a chimeric antibody, a humanized antibody or a human antibody. In one embodiment, an antibody of the invention is not a human antibody, for example it is not an antibody produced in a xenomouse (e.g., as described in WO96/33735). An antibody of the invention can be full length or a fragment thereof (e.g., a fragment comprising an antigen binding component).

In another embodiment, the invention provides an antigen-binding fragment of any of the above-described antibodies.

BRIEF DESCRIPTION OF THE DRAWINGS

FIGS. 1A-1B show the primary structure of ubiquitin and schematic views of certain polyubiquitin isopeptide linkages. FIG. 1A shows the amino acid sequence of human ubiquitin (SEQ ID NO: 377), with the lysine residues indicated in bold, underlined text. FIG. 1B shows a schematic depiction of the bond formed between the lysine-48 or lysine-63 of a first ubiquitin molecule and the C-terminal glycine residue of a second ubiquitin molecule.

FIGS. 2A-2C show heavy chain HVR loop sequences of anti-polyubiquitin antibody molecules specifically recognizing K48-linked polyubiquitin, as described in Example 1(A). The designator "48" indicates that the antibody molecule specifically recognized K48-linked polyubiquitin. The designator "both" indicates that the antibody molecule recognized both K48-linked and K63-linked polyubiquitin. The designator "all" indicates that the antibody molecule recognized both K48-linked and K63-linked polyubiquitin as well as monoubiquitin. The designator "n.p." indicates that certain clones did not have an amino acid at the indicated position. The figures show the heavy chain HVR sequences, H1, H2, and H3. Amino acid positions are numbered according to the Kabat numbering system as described below.

FIGS. 3A-3B show heavy chain HVR loop sequences of anti-polyubiquitin antibody molecules specifically recognizing K63-linked polyubiquitin, as described in Example 1(A). The designator "63" indicates that the antibody molecule specifically recognized K63-linked polyubiquitin. The designator "both" indicates that the antibody molecule recognized both K63-linked and K48-linked polyubiquitin. The designator "all" indicates that the antibody molecule recognized both K63-linked and K48-linked polyubiquitin as well as monoubiquitin. The designator "n.p." indicates that certain clones did not have an amino acid at the indicated position. The figures show the heavy chain HVR sequences, H1, H2, and H3. Amino acid positions are numbered according to the Kabat numbering system as described below.

FIGS. 4A and 4B and FIG. 5 depict exemplary acceptor human consensus framework sequences for use in practicing the instant invention with sequence identifiers as follows:

Variable Heavy (VH) Consensus Frameworks
(FIGS. 4a and 4b)

Human VH subgroup I consensus framework minus Kabat CDRs (SEQ ID NOs: 111, 839, 858, and 877)

Human VH subgroup I consensus framework minus extended hypervariable regions (SEQ ID NOs: 112-114, 840-842, 859-861, and 878-880)

Human VH subgroup II consensus framework minus Kabat CDRs (SEQ ID NOs: 115, 843, 862, and 881)

Human VH subgroup II consensus framework minus extended hypervariable regions (SEQ ID NOs: 116-118, 844-846, 863-865, and 882-884)

Human VH subgroup III consensus framework minus Kabat CDRs (SEQ ID NOs: 119, 847, 866, and 885)

Human VH subgroup III consensus framework minus extended hypervariable regions (SEQ ID NOs: 120-122, 848-850, 867-869, and 886-888)

Human VH acceptor framework minus Kabat CDRs (SEQ ID NOs: 123, 851, 870, and 889)

Human VH acceptor framework minus extended hypervariable regions (SEQ ID NOs: 124-125, 852-853, 871-872, and 890-891)

Human VH acceptor 2 framework minus Kabat CDRs (SEQ ID NOs: 126, 854, 873, and 892)

Human VH acceptor 2 framework minus extended hypervariable regions (SEQ ID NOs: 127-129, 855-857, 874-876, and 893-895)

Figure 5:
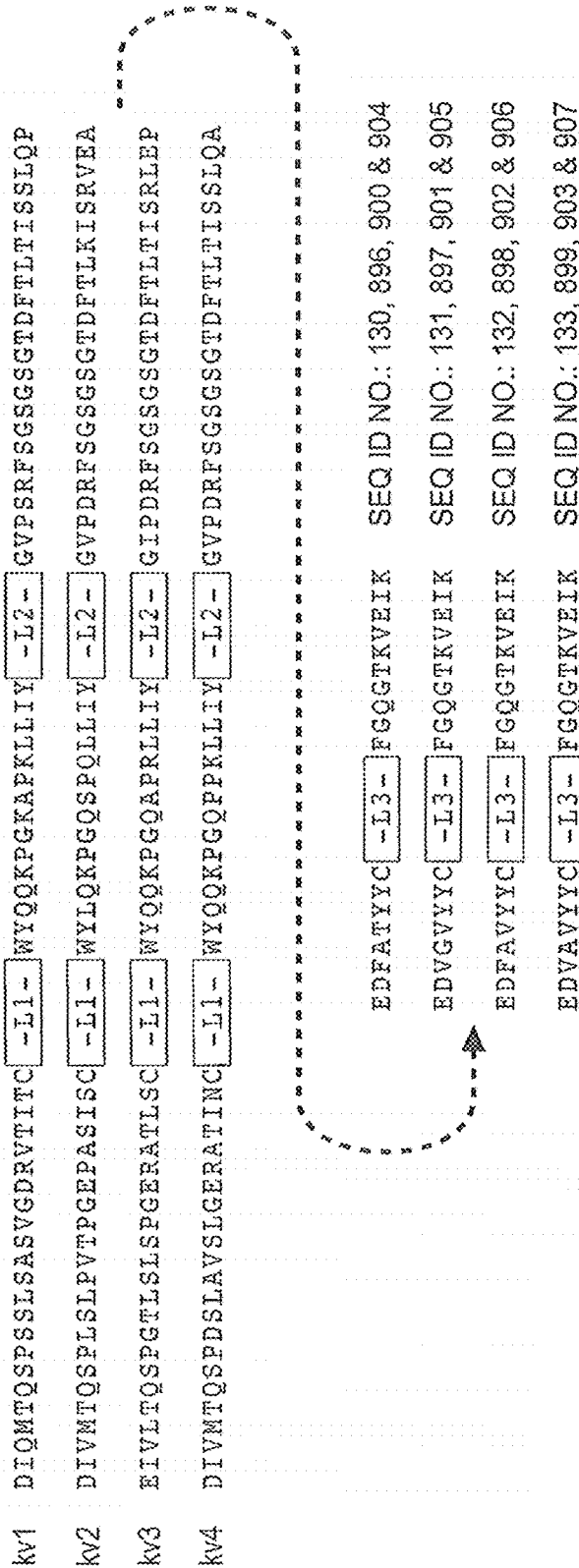

Variable Light (VL) Consensus Frameworks (FIG. 5)

Human VL kappa subgroup I consensus framework (SEQ ID NOs: 130, 896, 900, and 904)

Human VL kappa subgroup II consensus framework (SEQ ID NOs: 131, 897, 901, and 905)

Human VL kappa subgroup III consensus framework (SEQ ID NOs: 132, 898, 902, and 906)

Human VL kappa subgroup IV consensus framework (SEQ ID NOs: 133, 899, 903, and 907)

FIG. 6 depicts framework region sequences of huMAb4D5-8 light and heavy chains. Numbers in superscript/bold indicate amino acid positions according to Kabat.

FIG. 7 depicts modified/variant framework region sequences of huMAb4D5-8 light and heavy chains. Numbers in superscript/bold indicate amino acid positions according to Kabat.

FIGS. 8A-8C show heavy chain HVR loop sequences of anti-polyubiquitin antibody molecules specifically recognizing K48-linked polyubiquitin, as described in Example 1A. The figures show the heavy chain HVR sequences, H1, H2, and H3. The designator "n.p." indicates that certain clones did not have an amino acid at the indicated position Amino acid positions are numbered according to the Kabat numbering system as described below.

FIGS. 9A-9B show heavy chain HVR loop sequences of anti-polyubiquitin antibody molecules specifically recognizing K63-linked polyubiquitin, as described in Example 1A. The figures show the heavy chain HVR sequences, H1, H2, and H3. The designator "n.p." indicates that certain clones did not have an amino acid at the indicated position Amino acid positions are numbered according to the Kabat numbering system as described below.

FIGS. 10A-10C show heavy chain and light chain HVR loop sequences of anti-polyubiquitin antibody molecules apu01-apu15 that specifically recognize K48-linked polyubiquitin and which were recognized by an antibody specific for pentahistidine, as described in Example 1(B). The figure shows the heavy chain HVR sequences, H1, H2, and H3, and light chain HVR sequence, L3. The designator "n.p." indicates that certain clones did not have an amino acid at the indicated position. Amino acid positions are numbered according to the Kabat numbering system as described below.

FIGS. 11A-11C show heavy chain and light chain HVR loop sequences of anti-polyubiquitin antibody molecules apu17-apu24 that specifically recognize K63-linked polyubiquitin and which were recognized by an antibody specific for pentahistidine, as described in Example 1(B). The figures show the heavy chain HVR sequences, H1, H2, and H3, and light chain HVR sequence, L3. The designator "n.p." indicates that certain clones did not have an amino acid at the indicated position. Amino acid positions are numbered according to the Kabat numbering system as described below.

Figure 12:
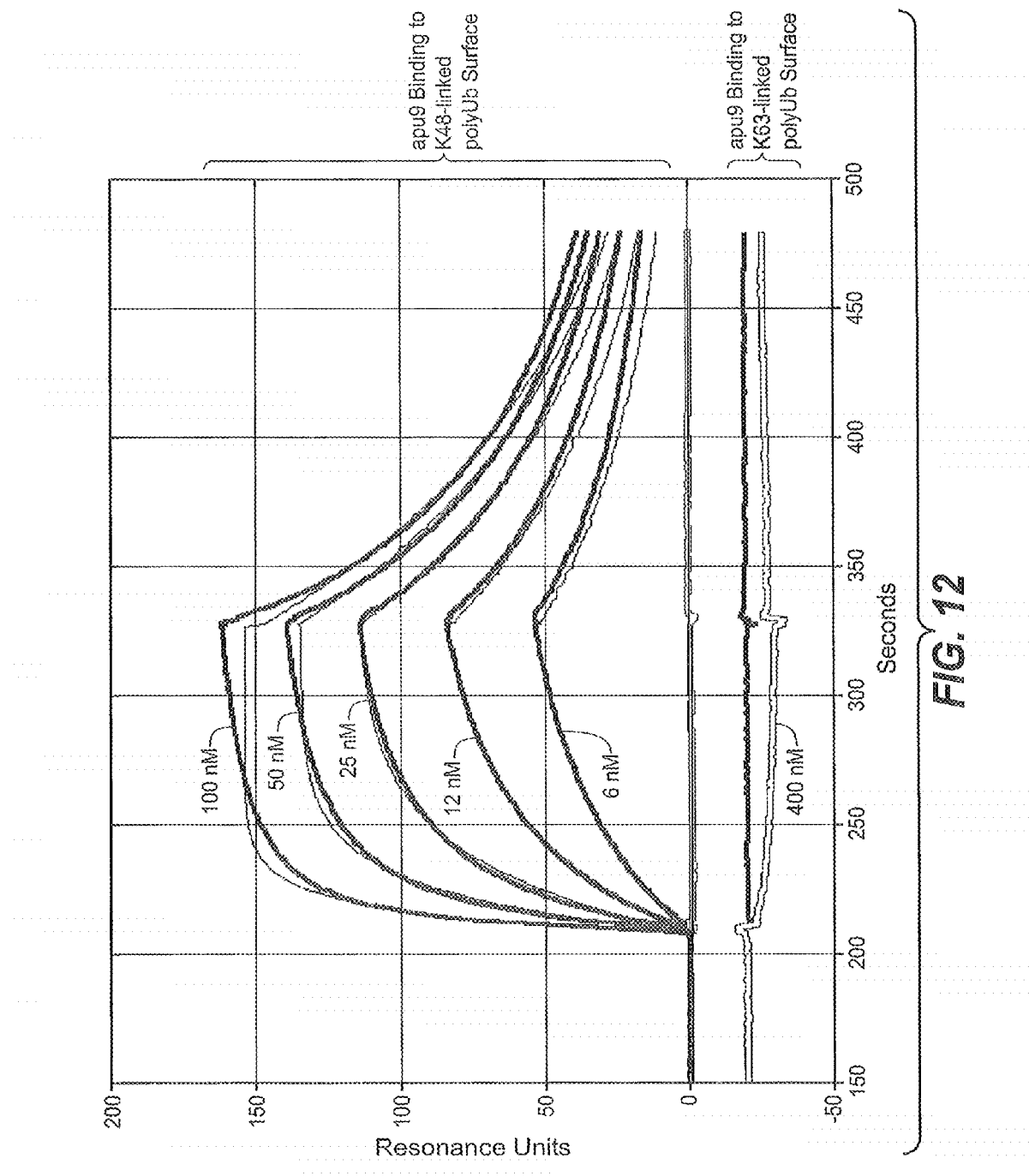

FIG. 12 depicts the binding interactions between various concentrations of the anti-polyubiquitin Fab apu09 and K48-linked or K63-linked polyubiquitin observed using BIACORE® analysis, as described in Example 1(C).

FIG. 13 depicts the binding interactions between various concentrations of the anti-polyubiquitin Fab apu18 and K48-linked or K63-linked polyubiquitin observed using BIACORE® analysis, as described in Example 1(C).

FIGS. 14A-14F show heavy chain HVR loop sequences of second generation anti-polyubiquitin antibody molecules based on the sequence of Fab apu05, which specifically recognize K48-linked polyubiquitin, as described in Example 2. The figures show the heavy chain HVR sequences, H1, H2, and H3. The designator "n.p." indicates that certain clones did not have an amino acid at the indicated position. Amino acid positions are numbered according to the Kabat numbering system as described below. Shaded text indicates that the sequence is identical to the amino acid sequence of the corresponding HVR sequence in the Fab apu05. Bold text indicates that the antibody demonstrated strong binding in the phage ELISA assay described in Example 2.

FIGS. 15A-15C show heavy chain HVR loop sequences of second generation anti-polyubiquitin antibody molecules based on the sequence of Fab apu18, which specifically recognize K63-linked polyubiquitin, as described in Example 2. The figures show the heavy chain HVR sequences, H1, H2, and H3. The designator "n.p." indicates that certain clones did not have an amino acid at the indicated position. Amino acid positions are numbered according to the Kabat numbering system as described below. Shaded text indicates that the sequence is identical to the amino acid sequence of the corresponding HVR sequence in the Fab apu18. Bold text indicates that the antibody demonstrated strong binding in the phage ELISA assay described in Example 2.

FIGS. 16A and 16B show the amino acid sequences of the heavy chain hypervariable regions of Fab molecules derived from mutagenized apu05 which specifically recognized K48-linked polyubiquitin (apu2.01-apu2.10) and which were recognized by an antibody specific for pentahistidine, as described in Example 2. The figures show the heavy chain HVR sequences, H1, H2, and H3, and light chain HVR sequence, L3. The designator "n.p." indicates that certain clones did not have an amino acid at the indicated position. Amino acid positions are numbered according to the Kabat numbering system as described below. Shaded text indicates that the sequence is identical to the amino acid sequence of the corresponding HVR sequence in the Fab apu05.

FIGS. 17A and 17B show the amino acid sequences of the heavy chain hypervariable regions of Fab molecules derived from mutagenized apu18 which specifically recognized K63-linked polyubiquitin (apu2.11-apu2.20) and which were recognized by an antibody specific for pentahistidine, as described in Example 2. The figures show the heavy chain HVR sequences, H1, H2, and H3, and light chain HVR sequence, L3. The designator "n.p." indicates that certain clones did not have an amino acid at the indicated position. Amino acid positions are numbered according to the Kabat numbering system as described below. Shaded text indicates that the sequence is identical to the amino acid sequence of the corresponding HVR sequence in the Fab apu18.

Figure 18:
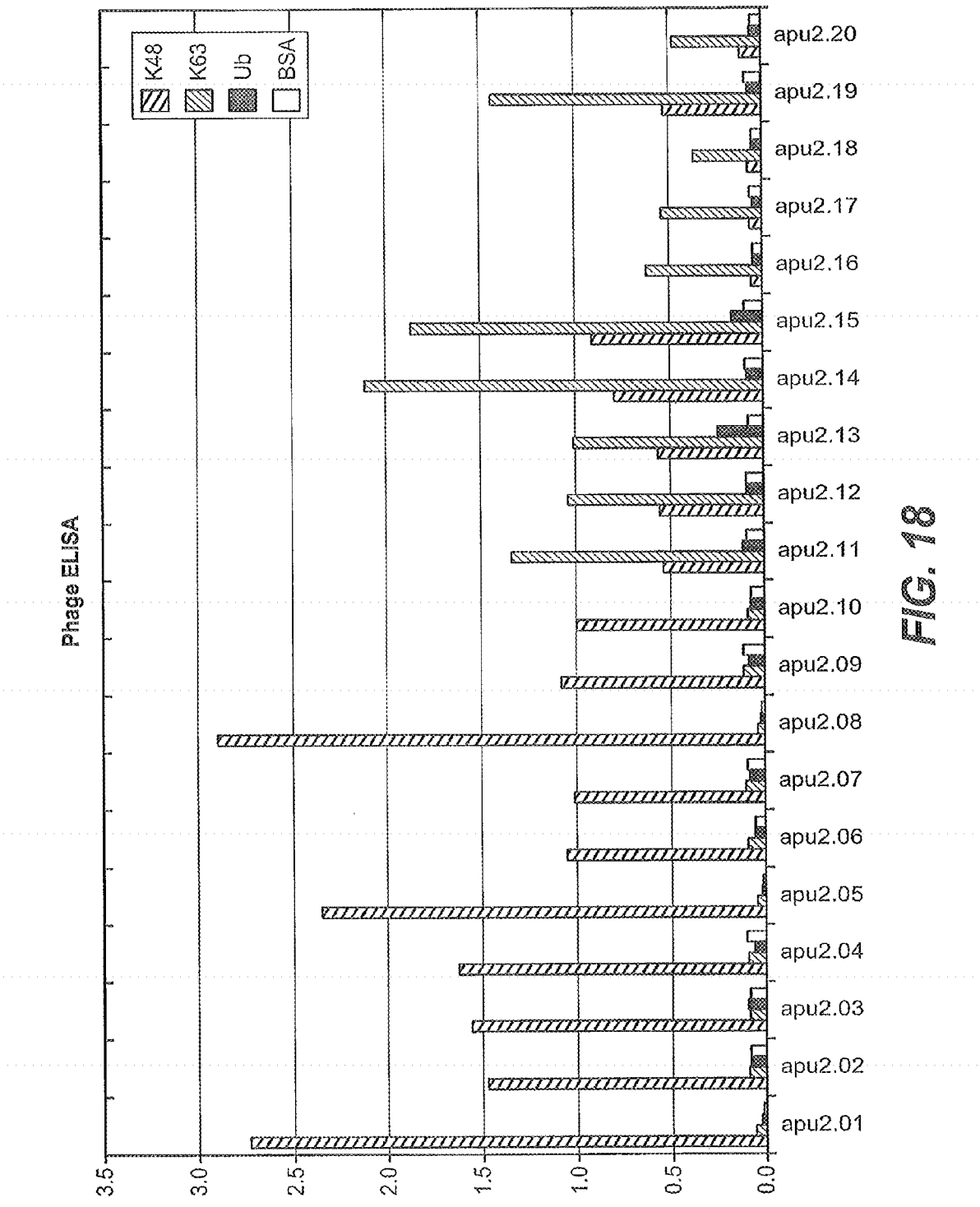

FIG. 18 depicts the results of the phage ELISA assay described in Example 2 where the binding of each of second-generation Fabs apu2.01-2.20 to K48-linked polyubiquitin, K63-linked polyubiquitin, monoubiquitin, and bovine serum albumin was assessed.

FIGS. 19A and 19B depict the results of western blotting experiments described in Example 1. FIG. 19A shows the binding of the Fabs produced from clones apu01 to apu15 to immobilized K48-linked tetraubiquitin. FIG. 19B shows an absence of binding of the Fabs produced from clones apu18 to apu24 to immobilized K63-linked polyubiquitin.

Figure 20A:
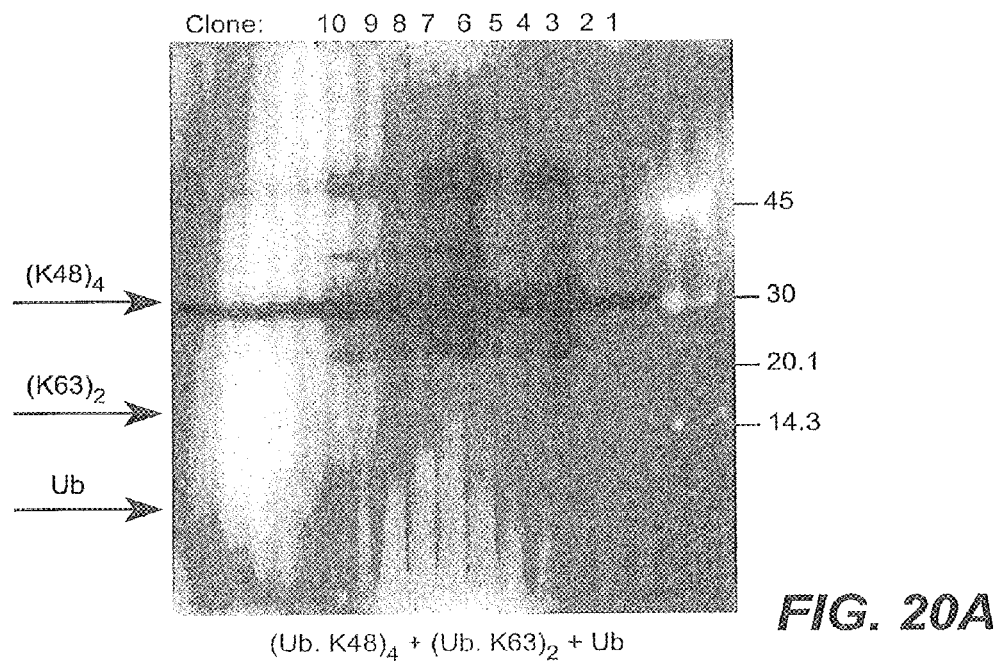
Figure 20B:
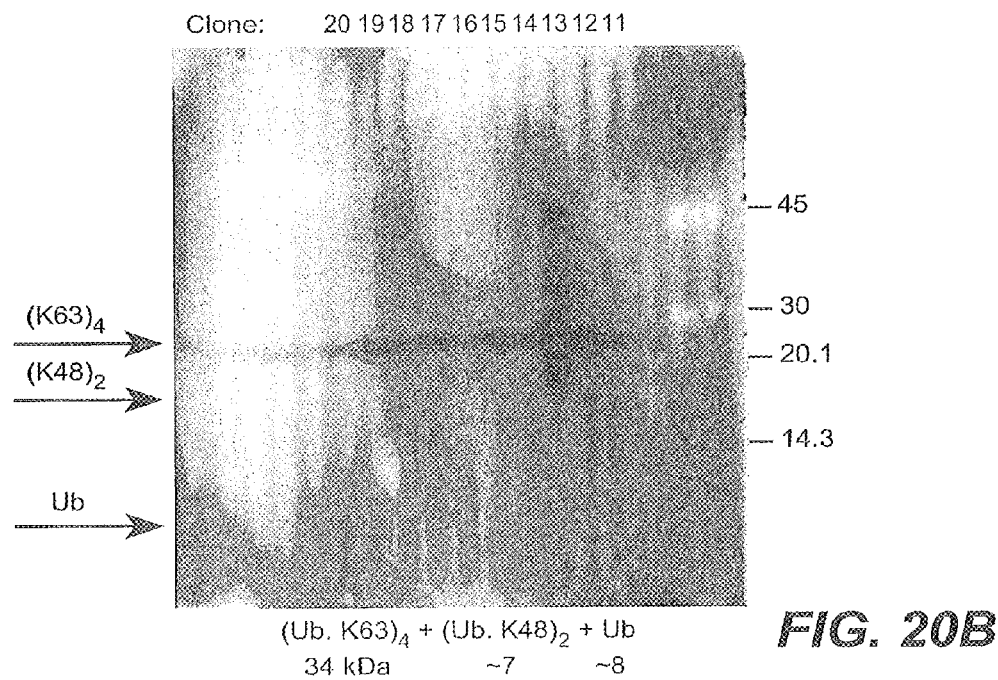

FIGS. 20A and 20B depict the results of western blotting experiments described in Example 2. FIG. 20A shows the binding of apu2.01-apu2.10 to immobilized K48-linked tetraubiquitin and the absence of binding to immobilized K63-linked diubiquitin. FIG. 20B shows the binding of apu2.11-apu2.20 to immobilized K63-linked tetraubiquitin and the absence of binding to immobilized K48-linked diubiquitin.

Figure 21A:
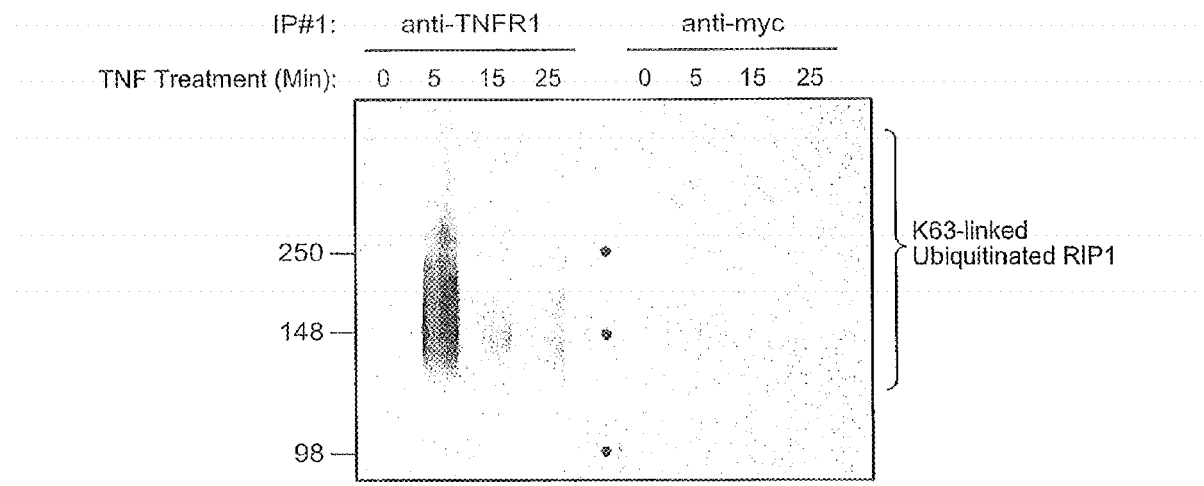
Figure 21B:
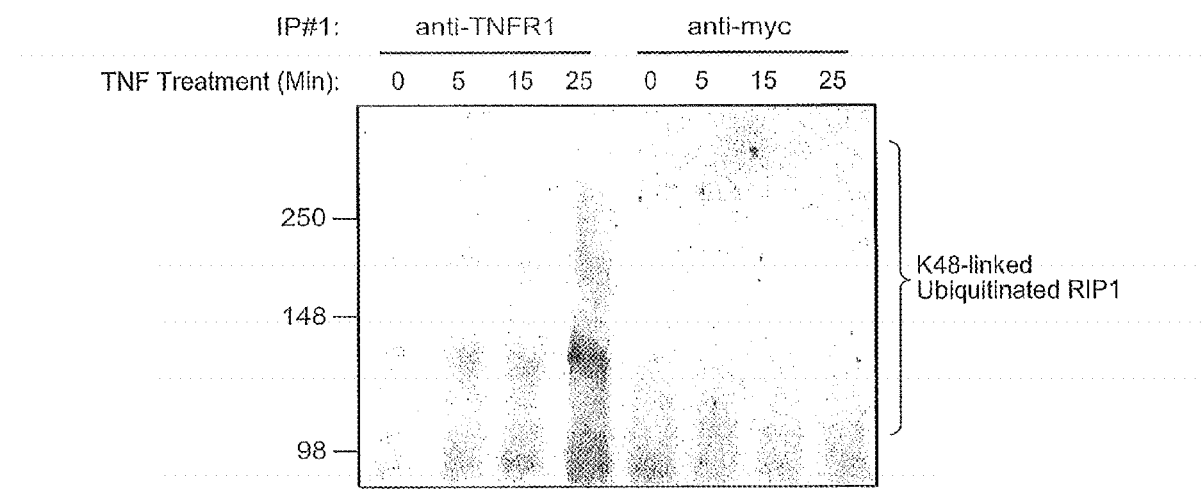

FIGS. 21A and 21B show Western blots from immunoprecipitation experiments to detect the ubiquitination state of RIP, as described in Example 3. The blot in FIG. 21A includes samples that were immunoprecipitated with apu2.16 IgG to capture K63-linked polyubiquitinated proteins. The blot in FIG. 21B includes samples that were immunoprecipitated with apu2.07 IgG to capture K48-linked polyubiquitinated proteins. Both blots were stained with an anti-RIP antibody.

Figure 22:
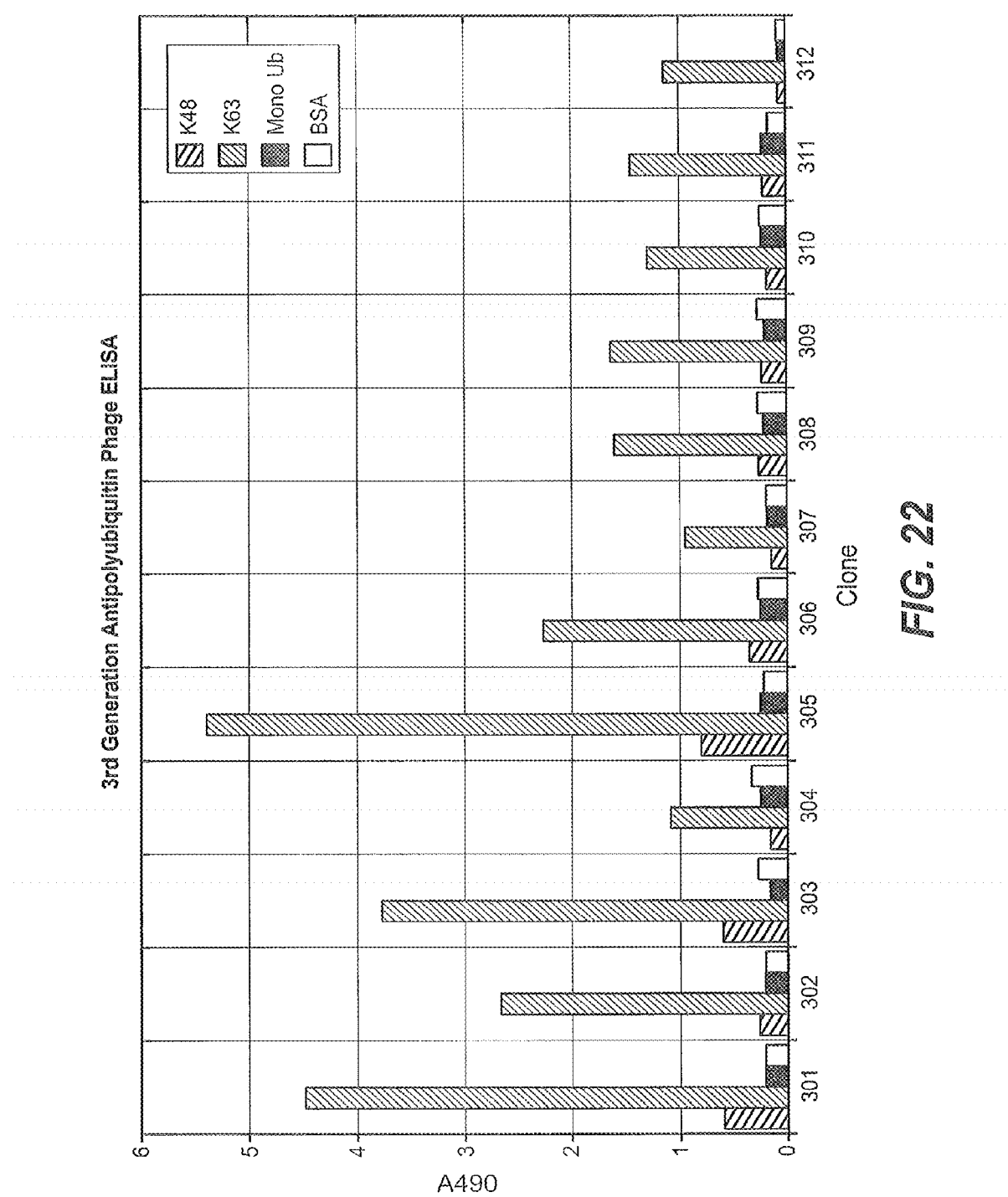

FIG. 22 depicts the results of the phage ELISA assay described in Example 4 where the binding of each of third-generation clones apu3.01-3.12 to K48-linked polyubiquitin, K63-linked polyubiquitin, monoubiquitin, and bovine serum albumin was assessed.

FIGS. 23A and 23B show the amino acid sequences of the heavy chain hypervariable regions of clones derived from mutagenized apu2.16 which specifically recognized K63-linked polyubiquitin (apu3.01-apu3.12), as described in Example 4. The figures show the heavy chain HVR sequences, H1, H2, and H3. The designator "ND." indicates that the sequence was not determined Amino acid positions are numbered according to the Kabat numbering system as described below. Shaded text indicates that the sequence is identical to the amino acid sequence of the corresponding HVR sequence in apu2.16.

Figure 24A:
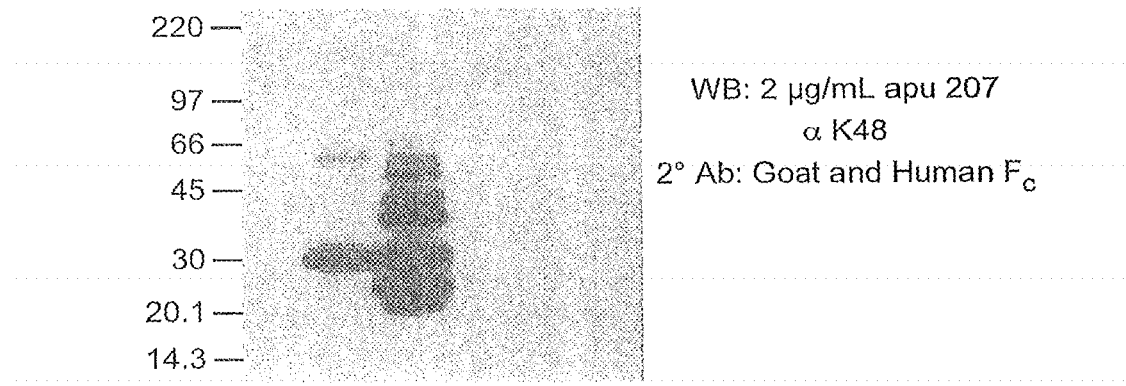
Figure 24B:
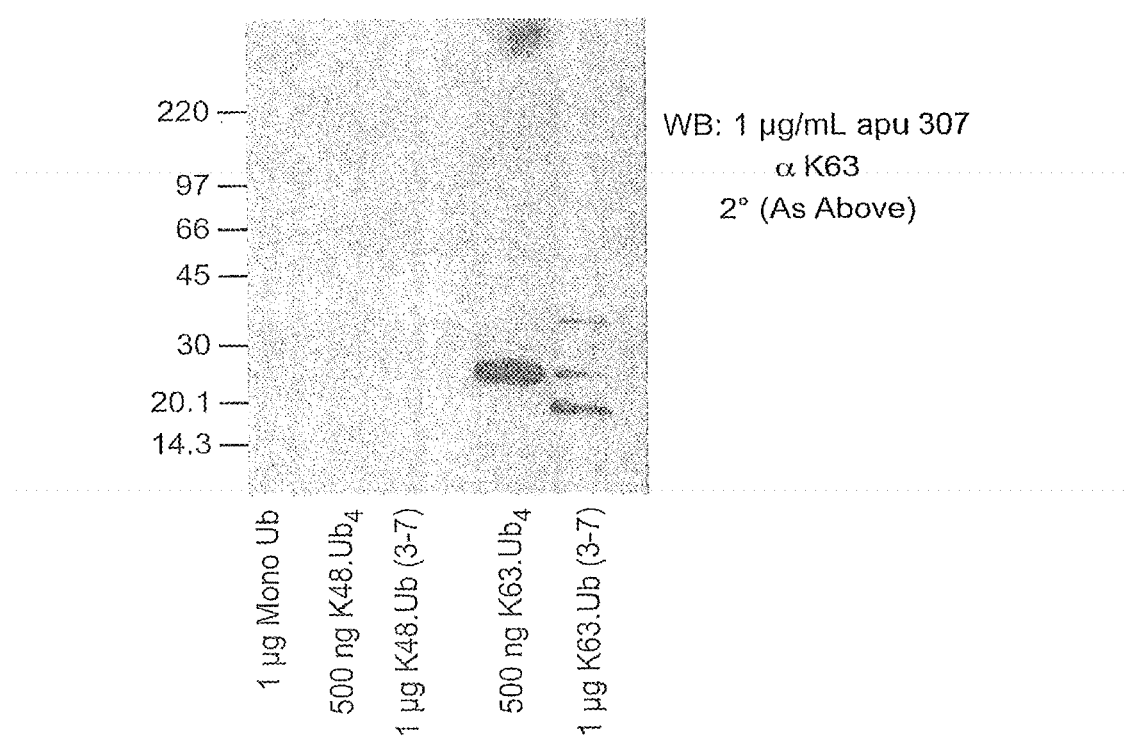
Figure 24C:
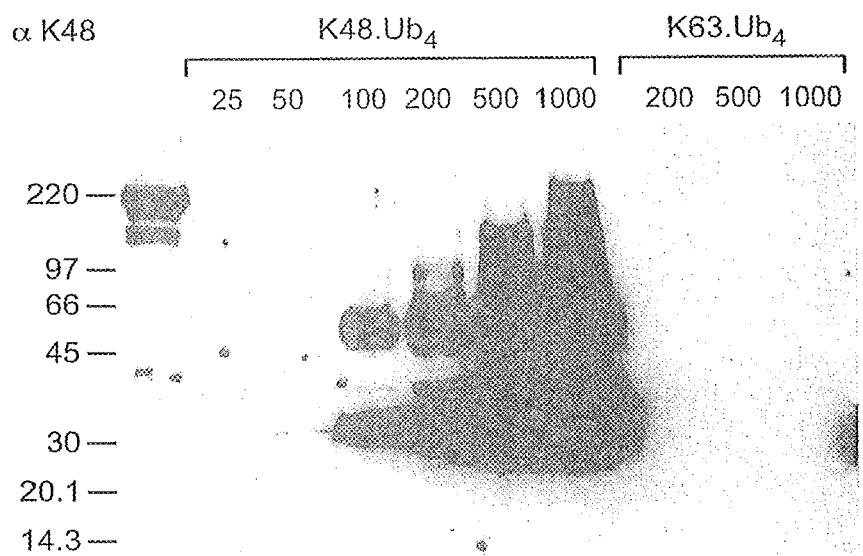
Figure 24D:
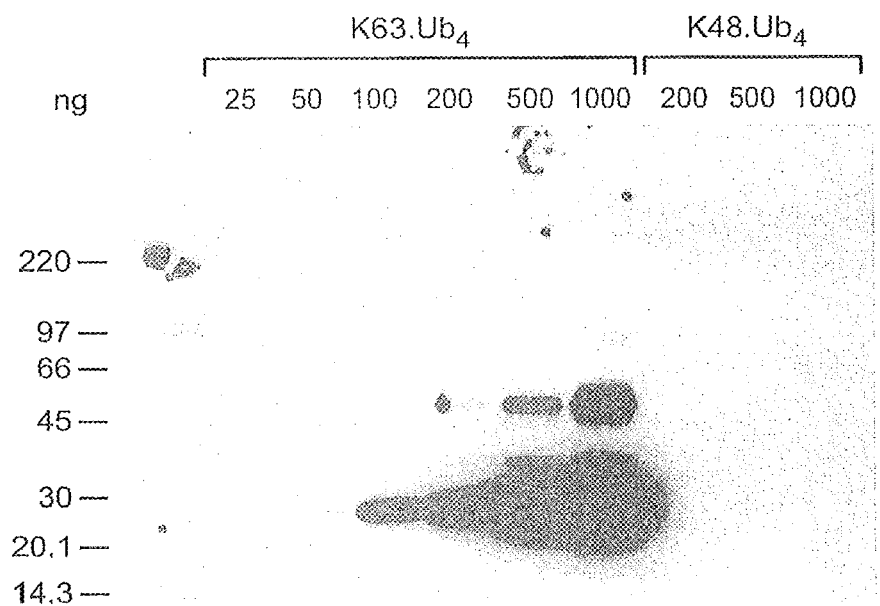

FIGS. 24A-24D depict the results of western blotting experiments described in Example 4. FIG. 24A shows the binding of apu2.07 IgG to immobilized K48-linked tri- to heptaubiquitin and the absence of binding to immobilized K63-linked tri- to heptaubiquitin or monoubiquitin. FIG. 24B shows the binding of apu3.07 IgG to immobilized K63-linked tri- to heptaubiquitin and the absence of binding to immobilized K48-linked tri- to heptaubiquitin or monoubiquitin. FIG. 24C shows concentration-dependent binding of apu2.07 IgG to immobilized K48-linked tetraubiquitin and the absence of binding to immobilized K63-linked tetraubiquitin. FIG. 24D shows concentration-dependent binding of apu3.07 IgG to immobilized K63-linked tetraubiquitin and the absence of binding to immobilized K48-linked tetraubiquitin.

Figure 25:
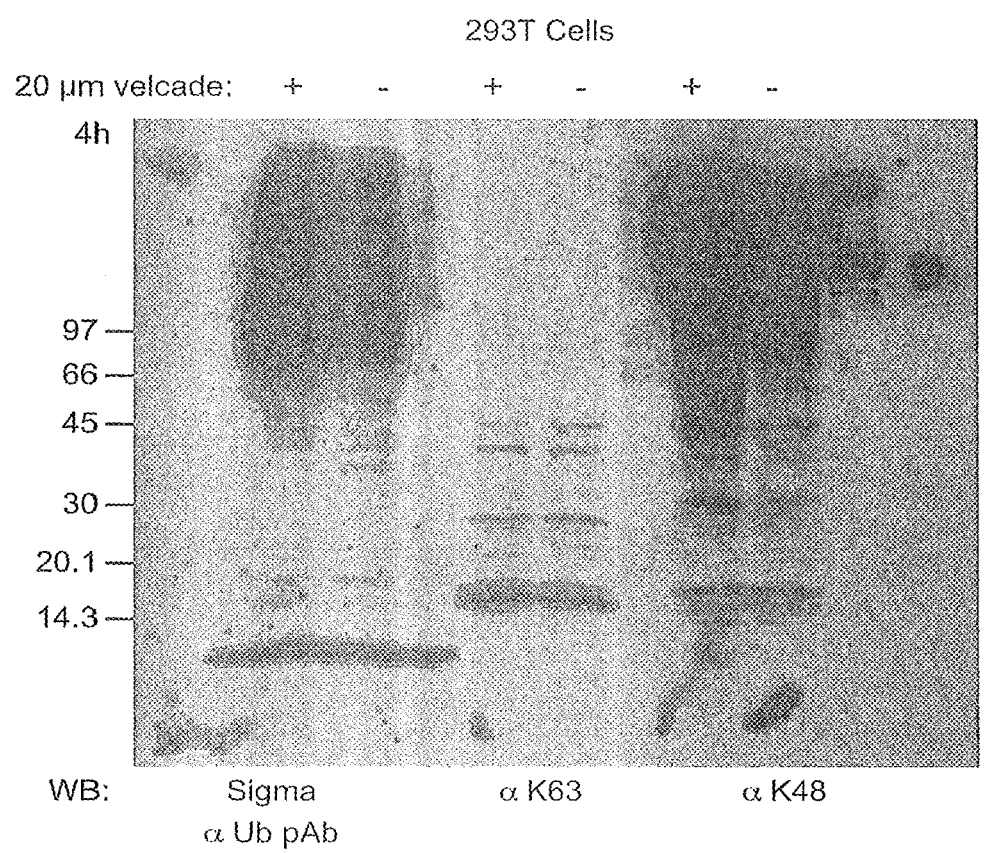

FIG. 25 depicts the results of a western blotting experiment described in Example 4. The figure shows the binding of an anti-ubiquitin polyclonal antibody, apu2.07 IgG, and apu3.07 IgG to immobilized lysates from 293T cells treated (+) or untreated (−) with Velcade®.

Figure 26B:
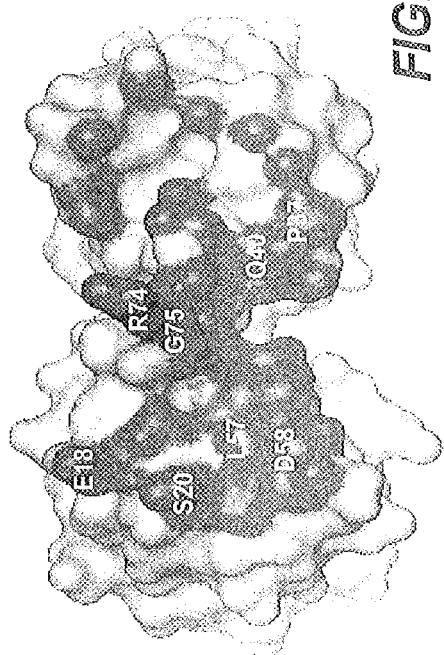
Figure 26C:
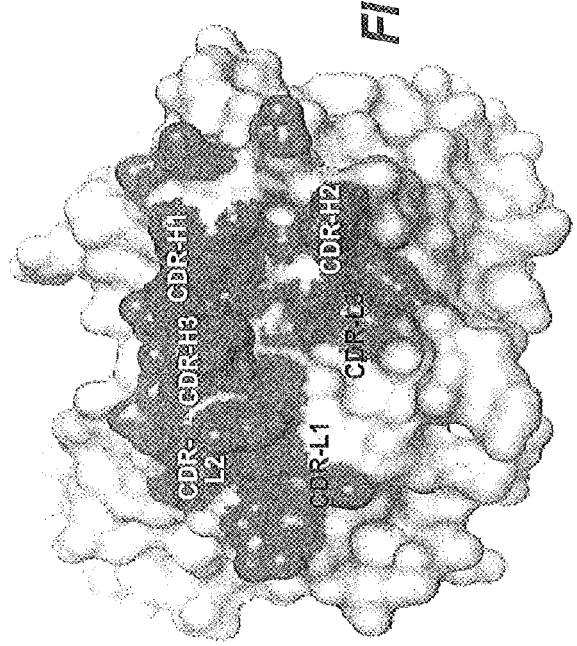
Figure 26A:

FIGS. 26A-26C show the interactions between a K63-linked polyubiquitin-specific fab of the invention and K63-linked polyubiquitin as determined by crystallographic analysis. FIG. 26A depicts the complex formed between K63-linked polyubiquitin-specific fab apu2.16 and a K63-linked diubiquitin. Apu2.16 is shown in ribbon diagram at the bottom of the figure while K63-linked diubiquitin is shown in globular form at the top of the figure. FIG. 26B depicts the surface of K63-linked diubiquitin, with those residues within 4.5 Å of the fab colored dark grey and residues of interest labeled. FIG. 26C depicts the surface of apu2.16, with those residues within 4.5 Å of the K63-linked ubiquitin dimer colored dark grey. The CDRs are labeled.

MODES FOR CARRYING OUT THE INVENTION

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", third edition (Sambrook et al., 2001); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); PCR 2: A Practical Approach (M. J. MacPherson, B. D. Hames and G. R. Taylor eds. (1995)); Harlow and Lane, eds. (1988) Antibodies, A Laboratory Manual; "A Practical Guide to Molecular Cloning" (Perbal Bernard V., 1988); and "Phage Display: A Laboratory Manual" (Barbas et al., 2001).

Definitions

As used herein, the terms "ubiquitin" and "monoubiquitin" are used interchangeably, and are defined as all species of native human and synthetic ubiquitin substantially similar to a 76-amino acid protein having at least one lysine residue at amino acid 6, amino acid 22, amino acid 27, amino acid 29, amino acid 33, amino acid 48, and/or amino acid 63.

As used herein, the term "polyubiquitin" is defined as all species of native human and synthetic polymeric chains of ubiquitin which fall within human and synthetic classes of different polymeric linkages of ubiquitin, including, but not limited to, K6-linked polyubiquitin, K22-linked polyubiquitin, K27-linked polyubiquitin, K29-linked polyubiquitin, K33-linked polyubiquitin, K48-linked polyubiquitin and K63-linked polyubiquitin. Polyubiquitin may be of any length, and includes at least two ubiquitin moieties. Polyubiquitin is distinguished from tandem repeats of ubiquitin that are originally expressed as a single protein.

As used herein, the terms "K*-linked polyubiquitin" and "Lys*-linked polyubiquitin" are interchangeable, and refer to a polyubiquitin molecule comprising at least one isopeptide bond between the C-terminus of one ubiquitin moiety and a lysine at position * in another ubiquitin moiety. For example, a "K63-linked polyubiquitin" is used interchangeably with a "Lys63-linked polyubiquitin", and both terms refer to a polyubiquitin molecule comprising an isopeptide bond between the C-terminus of one of the ubiquitin moieties in the molecule and the lysine at position 63 in another ubiquitin moiety in the molecule.

As used herein, a statement that a first lysine linkage "differs" from a second lysine linkage indicates that the first lysine linkage between one ubiquitin moiety and another ubiquitin moiety involves a different lysine residue (e.g., K6, K22, K27, K29, K33, K48, and/or K63) than the second lysine linkage between one ubiquitin moiety and another ubiquitin moiety.

As used herein, the term "ubiquitin pathway" refers to a biochemical pathway in a cell or reconstituted in vitro that includes ubiquitin and/or polyubiquitin.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In one embodiment, the antibody will be purified (1) to greater than 95% by weight of antibody as determined by, for example, the Lowry method, and in some embodiments more than 99% by weight, (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

As used herein, the terms "anti-ubiquitin antibody" and "anti-monoubiquitin antibody" are used interchangeably, and refer to an antibody that is capable of specifically binding to a ubiquitin molecule.

As used herein, the term "anti-polyubiquitin antibody" refers to an antibody that is capable of specifically binding to a polyubiquitin molecule.

As used herein, the term "anti-K48-linked polyubiquitin antibody" refers to an antibody that is capable of specifically binding to K48-linked polyubiquitin.

As used herein, the term "anti-K63-linked polyubiquitin antibody" refers to an antibody that is capable of binding to K63-linked polyubiquitin.

The phrase "substantially similar," "substantially the same", "equivalent", or "substantially equivalent", as used herein, denotes a sufficiently high degree of similarity between two numeric values (for example, one associated with a molecule and the other associated with a reference/comparator molecule) such that one of skill in the art would consider the difference between the two values to be of little or no biological and/or statistical significance within the context of the biological characteristic measured by said values (e.g., Kd values, anti-viral effects, etc.). The difference between said two values is, for example, less than about 50%, less than about 40%, less than about 30%, less than about 20%, and/or less than about 10% as a function of the value for the reference/comparator molecule.

The phrase "substantially reduced," or "substantially different", as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) *J. Mol Biol* 293:865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (~0.2 μM) before injection at a flow rate of 5 μl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneously fitting the association and dissociation sensorgrams. The equilibrium dissociation constant (Kd) is calculated as the ratio $k_{off}/k_{on}$. See, e.g., Chen, Y., et al., (1999) *J. Mal Biol* 293:865-881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 Association rates ($k_{on}$) and dissociation rates ($k_{off}$) are calculated using a simple one-to-one Langmuir binding model (BIAcore Evaluation Software version 3.2) by simultaneously fitting the association and dissociation sensorgram. The equilibrium dissociation constant (Kd) was calculated as the ratio $k_{off}/k_{on}$. See, e.g., Chen, Y., et al., (1999) J. Mol Biol 293:865-881. However, if the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semisolid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single-stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Antibodies" (Abs) and "immunoglobulins" (Igs) are glycoproteins having the same structural characteristics.

While antibodies exhibit binding specificity to a specific antigen, immunoglobulins include both antibodies and other antibody-like molecules which generally lack antigen specificity. Polypeptides of the latter kind are, for example, produced at low levels by the lymph system and at increased levels by myelomas.

The terms "antibody" and "immunoglobulin" are used interchangeably in the broadest sense and include monoclonal antibodies (e.g., full length or intact monoclonal antibodies), polyclonal antibodies, monovalent, multivalent antibodies, multispecific antibodies (e.g., bispecific antibodies so long as they exhibit the desired biological activity) and may also include certain antibody fragments (as described in greater detail herein). An antibody can be chimeric, human, humanized and/or affinity matured.

The "variable region" or "variable domain" of an antibody refers to the amino-terminal domains of heavy or light chain of the antibody. These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol Immunology, 4th ed. (2000). An antibody may be part of a larger fusion molecule, formed by covalent or non-covalent association of the antibody with one or more other proteins or peptides.

The terms "full length antibody," "intact antibody" and "whole antibody" are used herein interchangeably, to refer to an antibody in its substantially intact form, not antibody fragments as defined below. The terms particularly refer to an antibody with heavy chains that contain the Fc region.

"Antibody fragments" comprise only a portion of an intact antibody, wherein the portion retains at least one, and as many as most or all, of the functions normally associated with that portion when present in an intact antibody. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For example, such an antibody fragment may comprise on antigen binding arm linked to an Fc sequence capable of conferring in vivo stability to the fragment.

The term "monoclonal antibody" as used herein refers to an antibody obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. Such monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones or recombinant DNA clones. It should be understood that the selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations which typically include different antibodies directed against different determinants (epitopes), each monoclonal antibody of a monoclonal antibody preparation is directed against a single determinant on an antigen. In addition to their specificity, the monoclonal antibody preparations are advantageous in that they are typically uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler et al., Nature, 256: 495 (1975); Harlow et al., Antibodies: A Laboratory Manual, (Cold Spring Harbor Laboratory Press, 2$^{nd}$ ed. 1988); Hammerling et al., in: Monoclonal Antibodies and T-Cell hybridomas 563-681 (Elsevier, N.Y., 1981)), recombinant DNA methods (see, e.g., U.S. Pat. No. 4,816,567), phage display technologies (See, e.g., Clackson et al., Nature, 352: 624-628 (1991); Marks et al., J. Mol. Biol. 222: 581-597 (1992); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004), and technologies for producing human or human-like antibodies in animals that have parts or all of the human immunoglobulin loci or genes encoding human immunoglobulin sequences (see, e.g., WO98/24893; WO96/34096; WO96/33735; WO91/10741; Jakobovits et al., Proc. Natl. Acad. Sci. USA 90: 2551 (1993); Jakobovits et al., Nature 362: 255-258 (1993); Bruggemann et al., Year in Immunol. 7:33 (1993); U.S. Pat. Nos. 5,545,807; 5,545,806; 5,569,825; 5,625,126; 5,633,425; 5,661,016; Marks et al., Bio. Technology 10: 779-783 (1992); Lonberg et al., Nature 368: 856-859 (1994); Morrison, Nature 368: 812-813 (1994); Fishwild et al., Nature Biotechnol. 14: 845-851 (1996); Neuberger, Nature Biotechnol. 14: 826 (1996) and Lonberg and Huszar, Intern. Rev. Immunol. 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region of the recipient are replaced by residues from a hypervariable region of a non-human species (donor antibody) such as mouse, rat, rabbit or nonhuman primate having the desired specificity, affinity, and/or capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

The term "hypervariable region", "HVR", or "HV", when used herein refers to the regions of an antibody variable domain which are hypervariable in sequence and/or form structurally defined loops. Generally, antibodies comprise six hypervariable regions; three in the VH(H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B (Kabat Numbering) | H26-H32 | H30-H35B |
| H1 | H31-H35 | H26-H35 (Chothia Numbering) | H26-H32 | H30-H35 |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the hypervariable region residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5$^{th}$ Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO93/1161; and Hollinger et al., Proc. Natl. Acad. Sci. USA 90: 6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it binds. Certain blocking antibodies or antagonist antibodies substantially or completely inhibit the biological activity of the antigen.

An "agonist antibody", as used herein, is an antibody which mimics at least one of the functional activities of a polypeptide of interest.

A "disorder" is any condition that would benefit from treatment with an antibody of the invention. This includes chronic and acute disorders or diseases including those pathological conditions which predispose the mammal to the disorder in question. Non-limiting examples of disorders to be treated herein include cancer, muscular disorders, ubiquitin-pathway-related genetic disorders, immune/inflammatory disorders, neurological disorders, and other ubiquitin pathway-related disorders.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, leukemia and other lymphoproliferative disorders, and various types of head and neck cancer.

The term "muscular disorder" refers to or describes the physiological condition in muscle-containing animals that is typically characterized by deterioration or weakening of skeletal and/or smooth muscle such that normal muscular function is significantly reduced. Examples of muscular disorders include, but are not limited to, muscular dystrophy, multiple sclerosis, amyotrophic lateral sclerosis, Isaac's syndrome; stiff-person syndrome; familiar periodic paralyses, myopathy, myotonia, rhabdomyolyses, muscle atrophy, and various types of muscle weakness and muscle rigidity.

The term "ubiquitin pathway-related genetic disorder" refers to or describes a genetically-based disorder that is typically characterized by or contributed to by aberrant functioning of the ubiquitin pathway. Examples of ubiquitin pathway-related genetic disorders include, but are not limited to, cystic fibrosis, Angelman's syndrome, and Liddle syndrome.

The terms "neurological disorder" or "neurological disease" refer to or describe a disease or disorder of the central and/or peripheral nervous system in mammals that is typically characterized by deterioration of nervous tissue or deterioration of communication between cells in nervous tissue. Examples of neurological disorders include, but are not limited to, neurodegenerative diseases (including, but not limited to, Lewy body disease, postpoliomyelitis syndrome, Shy-Draeger syndrome, olivopontocerebellar atrophy, Parkinson's disease, multiple system atrophy, striatonigral degeneration, tauopathies (including, but not limited to, Alzheimer disease and supranuclear palsy), prion diseases (including, but not limited to, bovine spongiform encephalopathy, scrapie, Creutzfeldt-Jakob syndrome, kuru, Gerstmann-Straussler-Scheinker disease, chronic wasting disease, and fatal familial insomnia), bulbar palsy, motor neuron disease, and nervous system heterodegenerative disorders (including, but not limited to, Canavan disease, Huntington's disease, neuronal ceroid-lipofuscinosis, Alexander's disease, Tourette's syndrome, Menkes kinky hair syndrome, Cockayne syndrome, Halervorden-Spatz syndrome, lafora disease, Rett syndrome, hepatolenticular degeneration, Lesch-Nyhan syndrome, and Unverricht-Lundborg syndrome), dementia (including, but not limited to, Pick's disease, and spinocerebellar ataxia.

The terms "inflammatory disorder" and "immune disorder" refer to or describe disorders caused by aberrant immunologic mechanisms and/or aberrant cytokine signaling. Examples of inflammatory and immune disorders include, but are not limited to, autoimmune diseases, immunologic deficiency syndromes, and hypersensitivity. An "autoimmune disease" herein is a non-malignant disease or disorder arising from and directed against an individual's own tissues. The autoimmune diseases herein specifically exclude malignant or cancerous diseases or conditions, especially excluding B cell lymphoma, acute lymphoblastic leukemia (ALL), chronic lymphocytic leukemia (CLL), Hairy cell leukemia and chronic myeloblastic leukemia. Examples of autoimmune diseases or disorders include, but are not limited to, inflammatory responses such as inflammatory skin diseases including psoriasis and dermatitis (e.g. atopic dermatitis); systemic scleroderma and sclerosis; responses associated with inflammatory bowel disease (such as Crohn's disease and ulcerative colitis); respiratory distress syndrome (including adult respiratory distress syndrome; ARDS); dermatitis; meningitis; encephalitis; uveitis; colitis; glomerulonephritis; allergic conditions such as eczema and asthma and other conditions involving infiltration of T cells and chronic inflammatory responses; atherosclerosis; leukocyte adhesion deficiency; rheumatoid arthritis; systemic lupus erythematosus (SLE) (including but not limited to lupus nephritis, cutaneous lupus); diabetes mellitus (e.g. Type I diabetes mellitus or insulin dependent diabetes mellitus); multiple sclerosis; Reynaud's syndrome; autoimmune thyroiditis; Hashimoto's thyroiditis; allergic encephalomyelitis; Sjogren's syndrome; juvenile onset diabetes; and immune responses associated with acute and delayed hypersensitivity mediated by cytokines and T-lymphocytes typically found in tuberculosis, sarcoidosis, polymyositis, granulomatosis and vasculitis; pernicious anemia (Addison's disease); diseases involving leukocyte diapedesis; central nervous system (CNS) inflammatory disorder; multiple organ injury syndrome; hemolytic anemia (including, but not limited to cryoglobinemia or Coombs positive anemia); myasthenia gravis; antigen-antibody complex mediated diseases; anti-glomerular basement membrane disease; antiphospholipid syndrome; allergic neuritis; Graves' disease; Lambert-Eaton myasthenic syndrome; pemphigoid bullous; pemphigus; autoimmune polyendocrinopathies; Reiter's disease; stiff-man syndrome; Behcet disease; giant cell arteritis; immune complex nephritis; IgA nephropathy; IgM polyneuropathies; immune thrombocytopenic purpura (ITP) or autoimmune thrombocytopenia, etc.

Examples of immunologic deficiency syndromes include, but are not limited to, ataxia telangiectasia, leukocyte-adhesion deficiency syndrome, lymphopenia, dysgammaglobulinemia, HIV or deltaretrovirus infections, common variable immunodeficiency, severe combined immunodeficiency, phagocyte bactericidal dysfunction, agammaglobulinemia, DiGeorge syndrome, and Wiskott-Aldrich syndrome. Examples of hypersensitivity include, but are not limited to, allergies, asthma, dermatitis, hives, anaphylaxis, Wissler's syndrome, and thrombocytopenic purpura.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or decreasing inflammation and/or tissue/organ damage, decreasing the rate of disease progression, amelioration or palliation of the disease state, and remission or improved prognosis. In some embodiments, antibodies of the invention are used to delay development of a disease or disorder.

An "individual" is a vertebrate. In certain embodiments, the vertebrate is a mammal. Mammals include, but are not limited to, farm animals (such as cows), sport animals, pets (such as cats, dogs, and horses), primates, mice and rats. In certain embodiments, the vertebrate is a human.

"Mammal" for purposes of treatment refers to any animal classified as a mammal, including humans, domestic and farm animals, and zoo, sports, or pet animals, such as dogs, horses, cats, cows, etc. In certain embodiments, the mammal is human.

An "effective amount" refers to an amount effective, at dosages and for periods of time necessary, to achieve the desired therapeutic or prophylactic result.

A "therapeutically effective amount" of a substance/molecule of the invention may vary according to factors such as the disease state, age, sex, and weight of the individual, and the ability of the substance/molecule, to elicit a desired response in the individual. A therapeutically effective amount is also one in which any toxic or detrimental effects of the substance/molecule are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount would be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu), chemotherapeutic agents (e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolyticenzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

Compositions and Methods of Making Same

The present invention provides antibodies that bind specifically to polyubiquitin, but not to monoubiquitin. More specifically, antibodies that are capable of binding specifically to a polyubiquitin comprising a first lysine linkage but not to a polyubiquitin comprising a second, different, lysine linkage are provided.

In one aspect, the invention provides an antibody comprising an HVR-H1 region comprising the sequence of at least one of SEQ ID NOs: 1-25, 81-89, 151-175, 229-239, 265-279, 329-336, 392-459, 599-629, 695-704, 739-748, and 789-799. In one aspect, the invention provides an antibody comprising a HVR-H1 region consensus sequence selected from SEQ ID NOs: 26, 90, 176, 240, 280, 337, 460, 630, 705, 749, and 800. In one aspect, the invention provides an antibody comprising a HVR-H2 region comprising the sequence of at least one of SEQ ID NOs: 27-51, 91-99, 177-201, 241-251, 281-295, 338-345, 461-528, 631-661, 706-715, 750-759, and 801-811. In one aspect, the invention provides an antibody comprising a HVR-H2 region consensus sequence selected from SEQ ID NOs: 52, 100, 202, 252, 296, 346, 529, 662, 716, 760, and 812. In one aspect, the invention provides an antibody comprising a HVR-H3 region comprising the sequence of at least one of SEQ ID NOs: 53-77, 101-109, 203-227, 253-263, 297-311, 347-354, 530-597, 663-693, 717-726, 761-770, and 813-823. In one aspect, the invention provides an antibody comprising a HVR-H3 region consensus sequence selected from SEQ ID NOs: 78, 110, 228, 264, 312, 355, 598, 694, 727, 771, and 824.

In one aspect, the invention provides an antibody comprising a HVR-H1 region comprising the sequence of at least one of SEQ ID NOs: 1-26, 81-90, 151-176, 229-240, 265-280, 329-337, 392-460, 599-630, 695-705, 739-749, and 789-800, and an HVR-H2 region comprising the sequence of at least one of SEQ ID NOs: 27-52, 91-100, 177-202, 241-252, 281-296, 338-346, 461-529, 631-662, 706-716, 750-760, and 801-812. In one aspect, the invention provides an antibody comprising a HVR-H1 region comprising the sequence of at least one of SEQ ID NOs: 1-26, 81-90, 151-176, 229-240, 265-280, 329-337, 392-460, 599-630, 695-705, 739-749, and 789-800, and an HVR-H3 region comprising the sequence of at least one of SEQ ID NOs: 53-78, 101-110, 203-228, 253-264, 297-312, 347-355, 530-598, 663-694, 717-727, 761-771, and 813-824. In one aspect, the invention provides an antibody comprising a HVR-H2 region comprising the sequence of at least one of SEQ ID NO: 27-52, 91-100, 177-202, 241-252, 281-296, 338-346, 461-529, 631-662, 706-716, 750-760, and 801-812, and an HVR-H3 region comprising the sequence of at least one of SEQ ID NOs: 53-78, 101-110, 203-228, 253-264, 297-312, 347-355, 530-598, 663-694, 717-727, 761-771, and 813-824.

In one aspect, the invention provides an antibody comprising a HVR-L3 region comprising the sequence of at least one of SEQ ID NOs: 313-327, 356-363, 728-737, and 772-781. In one aspect, the invention provides an antibody comprising a HVR-L3 region consensus sequence selected from SEQ ID NOs: 328, 364, 738, and 782. In one embodiment, the invention provides an antibody comprising a HVR-L3 region comprising the sequence of at least one of SEQ ID NOs: 313-328, 356-364, 728-738, and 772-782, and further comprising at least one HVR-H1, HVR-H2 or HVR-H3 sequence selected from SEQ ID NOs: 1-26, 81-90, 151-176, 229-240, 265-280, 329-337, 392-460, 599-630, 695-705, 739-749, and 789-800; SEQ ID NOs: 27-52, 91-100, 177-202, 241-252, 281-296, 338-346, 461-529, 631-662, 706-716, 750-760, and 801-812; and SEQ ID NOs: 53-78, 101-110, 203-228, 253-264, 297-312, 347-355, 530-598, 663-694, 717-727, 761-771, and 813-824, respectively.

In one aspect, the invention provides an antibody comprising at least one, at least two, at least three, or all four of the following:
(i) an HVR-H1 sequence comprising at least one sequence of SEQ ID NOs: 1-26, 81-90, 151-176, 229-240, 265-280, 329-337, 392-460, 599-630, 695-705, 739-749, and 789-800;
(ii) an HVR-H2 sequence comprising at least one sequence of SEQ ID NOs: 27-52, 91-100, 177-202, 241-252, 281-296, 338-346, 461-529, 631-662, 706-716, 750-760, and 801-812;
(iii) an HVR-H3 sequence comprising at least one sequence of SEQ ID NOs: 53-78, 101-110, 203-228, 253-264, 297-312, 347-355, 530-598, 663-694, 717-727, 761-771, and 813-824;
(iv) an HVR-L3 sequence comprising at least one sequence of SEQ ID NOs: 313-328, 356-364, 728-738, and 772-782.

In one aspect, the invention provides an antibody that specifically binds K48-linked polyubiquitin with high affinity but binds K63-linked polyubiquitin with substantially reduced affinity, comprising at least one, at least two, at least three, or all four of the following:
(i) an HVR-H1 sequence comprising at least one sequence of SEQ ID NOs: 1-26, 151-176, 265-280, 392-460, and 695-705;
(ii) an HVR-H2 sequence comprising at least one sequence of SEQ ID NOs: 27-52, 177-202, 281-296, 461-529, and 706-716;
(iii) an HVR-H3 sequence comprising at least one sequence of SEQ ID NOs: 53-78, 203-228, 297-312, 530-598, and 717-727; and
(iv) an HVR-L3 sequence comprising at least one sequence of SEQ ID NOs: 313-328 and 728-738.

In one aspect, the invention provides an antibody that specifically binds K63-linked polyubiquitin with high affinity but binds K48-linked polyubiquitin with substantially reduced affinity, comprising at least one, at least two, at least three, or all four of the following:
(i) an HVR-H1 sequence comprising at least one sequence of SEQ ID NOs: 81-90, 229-240, 329-337, 599-630, 739-749, and 789-800;
(ii) an HVR-H2 sequence comprising at least one sequence of SEQ ID NOs: 91-100, 241-252, 338-346, 631-662, 750-760, and 801-812;
(iii) an HVR-H3 sequence comprising at least one sequence of SEQ ID NOs: 101-110, 253-264, 347-355, 663-694, 761-771, and 813-824;
(iv) an HVR-L3 sequence comprising at least one sequence of SEQ ID NOs: 356-364 and 772-782.

The amino acid sequences of SEQ ID NOs: 1-78, 81-106-149, 151-364, 392-782, and 789-824 are numbered with respect to individual HVR (i.e., H1, H2, H3, L3) as indicated in FIGS. 2, 3, 8, 9, 10, 11, 14, 15, 16, 17, and 22, the numbering being consistent with the Kabat numbering system as described below. In one embodiment, an antibody of the invention comprises one, two, three, or all of the HVR sequences of (i)-(iv) above, and HVR-L1 and/or HVR-L2 comprising a Kabat consensus sequence (e.g., SEQ ID NO: 79 (HVR-L1) and 80 (HVR-L2)).

In one aspect, the invention provides antibodies comprising heavy chain HVR sequences as depicted in FIGS. 2, 3, 8, 9, 10, 11, 14, 15, 16, 17, and 22. In one embodiment, the antibodies further comprise light chain HVR sequences as depicted in FIGS. 10, 11, 16, and 17.

Some embodiments of antibodies of the invention comprise a light chain variable domain of humanized 4D5 antibody (huMAb4D5-8) (HERCEPTIN®, Genentech, Inc., South San Francisco, Calif., USA) (also referred to in U.S. Pat. No. 6,407,213 and Lee et al., *J. Mol. Biol.* (2004), 340(5):1073-93) as depicted in SEQ ID NO: 783 below.

1 Asp Ile Gln Met Thr Gln Ser Pro Ser Ser Leu Ser Ala Ser Val Gly Asp Arg Val Thr Ile Thr Cys argalaserglnaspvalasnthralavalala Trp Tyr Gln Gln Lys Pro Gly Lys Ala Pro Lys Leu Leu Ile Tyr SerAlaSerPheLeuTyrSer Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys GlnGlnHisTyrThrThrProProThr Phe Gly Gln Gly Thr Lys Val Glu Ile Lys 107 (SEQ ID NO: 783) (HVR residues are underlined)

In one embodiment, the huMAb4D5-8 light chain variable domain sequence is modified at one or more of positions 28, 30, 31, 53, 66, and 91 (Asp, Asn, Thr, Phe, Arg, and His as indicated in bold/italics above, respectively). In one embodiment, the modified huMAb4D5-8 sequence comprises Ser in position 28, Ser in position 30, Ser in position 31, Ser in position 53, Gly in position 66, and/or Ser in position 91. Accordingly, in one embodiment, an antibody of the invention comprises a light chain variable domain comprising the sequence depicted in SEQ ID NO: 784 below:

1 Asp Ile Gln Met Thr Gln Ser Pro Ser Ser Leu Ser Ala Ser Val Gly Asp Arg Val Thr Ile Thr Cys ArgAlaSerGlnSerValSerSerAlaVal Ala Trp Tyr Gln Gln Lys Pro Gly Lys Ala Pro Lys Leu Leu Ile Tyr SerAlaSerSerLeuTyrSer Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys GlnGlnSerTyrThrThrProProThr Phe Gly Gln Gly Thr Lys Val Glu Ile Lys 107 (SEQ ID NO: 784) (HVR residues are underlined)

Substituted residues with respect to huMAb4D5-8 are indicated in bold/italics above.

Antibodies of the invention can comprise any suitable framework variable domain sequence, provided binding activity to polyubiquitin including a particular lysine linkage is substantially retained. For example, in some embodiments, antibodies of the invention comprise a human subgroup III heavy chain framework consensus sequence. In one embodiment of these antibodies, the framework consensus sequence comprises substitution at position 71, 73 and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. Nos. 6,407,213 & 5,821,337, and Lee et al., *J. Mol. Biol.* (2004), 340(5):1073-93). In one embodiment, these antibodies further comprise a human id light chain framework consensus sequence. In one embodiment, these antibodies comprise at least one, two or all of the light chain HVR sequences of SEQ ID NOs: 79, 80, 313-328, 356-364, 728-738, and 772-78. In one embodiment, these antibodies comprise light chain HVR sequences of huMAb4D5-8 as described in U.S. Pat. Nos. 6,407,213 & 5,821,337.) In one embodiment, these antibodies comprise light chain variable domain sequences of huMAb4D5-8 (SEQ ID NO: 783 and 784) (HERCEPTIN®, Genentech, Inc., South San Francisco, Calif., USA) (also referred to in U.S. Pat. Nos. 6,407,213 & 5,821,337, and Lee et al., *J. Mol. Biol.* (2004), 340(5):1073-93).

In one embodiment, an antibody of the invention comprises a heavy chain variable domain, wherein the framework sequence comprises the sequence of at least one of SEQ ID NOs: 111-129, 138-141, 146-149, and 839-895, and HVR H1, H2 and H3 sequences are selected from at least one of SEQ ID NOs: 1-26, 81-90, 151-176, 229-240, 265-280, 329-337, 392-460, 599-630, 695-705, 739-749, and 789-800; 27-52, 91-100, 177-202, 241-252, 281-296, 338-346, 461-529, 631-662, 706-716, 750-760, and 801-812; and 53-78, 101-110, 203-228, 253-264, 297-312, 347-355, 530-598, 663-694, 717-727, 761-771, and 813-824, respectively.

In one embodiment, an antibody of the invention comprises a light chain variable domain, wherein the framework sequence comprises the sequence of at least one of SEQ ID NOs: 130-133, 134-137, 142-145, and 896-907, the HVR-L1 sequence is SEQ ID NO: 79, the HVR-L2 sequence is SEQ ID NO: 80, and the HVR-L3 sequence is selected from at least one of SEQ ID NOs: 313-328, 356-364, 728-738, and 772-782.

In one embodiment, an antibody of the invention comprises a heavy chain variable domain, wherein the framework sequence comprises at least one sequence of SEQ ID NOs: 111-129 and 839-895, and HVR H1, H2 and H3 sequences are SEQ ID NO: 1, 27, and 53, respectively (clone 48-1). Similarly, in other embodiments, antibodies of each of clones 48-2 through 48-118, clones 63-1 through 63-51, Fabs apu01 through apu24, Fabs apu2.01 through apu2.20, and clones apu3.01 through 3.11 comprise a heavy chain variable domain, wherein the framework sequence comprises at least one sequence of SEQ ID NOs: 111-129 and 839-895, and HVR-H1, HVR-H2, and HVR-H3 sequences are those sequences specifically enumerated for each clone or Fab in FIGS. 2, 3, 8-11, 14-17, and 22. In one embodiment, an antibody of the invention comprises a light chain variable domain, wherein the framework sequence comprises at least one sequence of SEQ ID NOs: 130-133 and 896-907, and HVR L1, L2 and L3 sequences are SEQ ID NOs: 79, 80, and 313, respectively (Fab apu01). Similarly, in other embodiments, antibodies of each of Fabs apu01 through apu24 and Fabs apu2.01 through apu2.20 comprise a light chain variable domain, wherein the framework sequence comprises at least one sequence of SEQ ID NOs: 130-133 and 896-907, and HVR-L1 is SEQ ID NO: 79, HVR-L2 is SEQ ID NO: 80, and HVR-L3 sequences are those sequences specifically enumerated for each Fab in FIGS. 10, 11C, 16B, and 17B.

In one embodiment, an antibody of the invention comprises a heavy chain variable domain, wherein the framework sequence comprises at least one sequence of SEQ ID NOs: 138-141, and HVR H1, H2 and H3 sequences are SEQ ID NO: 1, 27, and 53, respectively (clone 48-1). Similarly, in other embodiments, antibodies of each of clones 48-2 through 48-118, clones 63-1 through 63-51, Fabs apu01 through apu24, Fabs apu2.01 through apu2.20, and clones apu3.01-3.11 comprise a heavy chain variable domain, wherein the framework sequence comprises at least one sequence of SEQ ID NOs: 138-141, and HVR-H1, HVR-H2, and HVR-H3 sequences are those sequences specifically enumerated for each clone or Fab in FIGS. 2, 3, 8-11, 14-17, and 22. In one embodiment, an antibody of the invention comprises a light chain variable domain, wherein the framework sequence comprises at least one sequence of SEQ ID NOs: 134-137, and HVR L1, L2 and L3 sequences are SEQ ID NOs: 79, 80, and 313, respectively (Fab apu01). Similarly, in other embodiments, antibodies of each of Fabs apu01 through apu24 and Fabs apu2.01 through apu2.20 comprise a light chain variable domain, wherein the framework sequence comprises at least one sequence of SEQ ID NOs: 134-137, and HVR-L1 is SEQ ID NO: 79, HVR-L2 is SEQ ID NO: 80, and HVR-L3 sequences are those sequences specifically enumerated for each Fab in FIGS. 10, 11C, 16B, and 17B.

In one embodiment, an antibody of the invention comprises a heavy chain variable domain, wherein the framework sequence comprises at least one sequence of SEQ ID NOs: 146-149, and HVR H1, H2 and H3 sequences are SEQ ID NO: 1, 27, and 53, respectively (clone 48-1). Similarly, in other embodiments, antibodies of each of clones 48-2 through 48-118, clones 63-1 through 63-51, Fabs apu01 through apu24, Fabs apu2.01 through apu2.20, and clones apu3.01 through 3.11 comprise a heavy chain variable domain, wherein the framework sequence comprises at least one sequence of SEQ ID NOs: 146-149, and HVR-H1, HVR-H2, and HVR-H3 sequences are those sequences specifically enumerated for each clone or Fab in FIGS. 2, 3, 8-11, 14-17, and 22. In one embodiment, an antibody of the invention comprises a light chain variable domain, wherein the framework sequence comprises at least one sequence of SEQ ID NOs: 142-145, and HVR L1, L2 and L3 sequences are SEQ ID NOs: 79, 80, and 313, respectively (Fab apu01). Similarly, in other embodiments, antibodies of each of Fabs apu01 through apu24 and Fabs apu2.01 through apu2.20 comprise a light chain variable domain, wherein the framework sequence comprises at least one sequence of SEQ ID NOs: 142-145, and HVR-L1 is SEQ ID NO: 79, HVR-L2 is SEQ ID NO: 80, and HVR-L3 sequences are those sequences specifically enumerated for each Fab in FIGS. 10, 11C, 16B, and 17B.

In one embodiment, an antibody of the invention is affinity matured to obtain the target binding affinity desired. In one example, an affinity matured antibody of the invention which specifically binds to K48-linked polyubiquitin with high affinity but binds to K63-linked polyubiquitin with substantially reduced affinity comprises substitution at HVR-H1 amino acid positions 29, 30, 33, and 34. In another example, an affinity matured antibody of the invention which specifically binds to K48-linked polyubiquitin with high affinity but binds to K63-linked polyubiquitin with substantially reduced affinity comprises substitution at HVR-H2 amino acid positions 52 and 52a. In another example, an affinity matured antibody of the invention which specifically binds to K48-linked polyubiquitin with high affinity but binds to K63-linked polyubiquitin with substantially reduced affinity comprises substitution at HVR-H3 amino acid positions 99, 100, 100a, and 100b. In another example, an affinity matured antibody of the invention which specifically binds to K48-linked polyubiquitin with high affinity but binds to K63-linked polyubiquitin with substantially reduced affinity comprises substitution at HVR-H3 amino acid positions 95-100, 100a, and 100b. In another example, an affinity matured antibody of the invention which specifically binds to K48-linked polyubiquitin with high affinity but binds to K63-linked polyubiquitin with substantially reduced affinity comprises substitution at HVR-L3 amino acid positions 91 and 96. In another example, an affinity matured antibody of the invention which specifically binds to K63-linked polyubiquitin with high affinity but binds to K48-linked polyubiquitin with substantially reduced affinity comprises substitution at HVR-H1 amino acid positions 29-34. In another example, an affinity matured antibody of the invention which specifically binds to K63-linked polyubiquitin with high affinity but binds to K48-linked polyubiquitin with substantially reduced affinity comprises substitution at HVR-H2 amino acid positions 50, 52, 52a, 53-56, and 58. In another example, an affinity matured antibody of the invention which specifically binds to K63-linked polyubiquitin with high affinity but binds to K48-linked polyubiquitin with substantially reduced affinity comprises substitution at HVR-H3 amino acid positions 95-100, 100a, 100b, and 100c. In another example, an affinity matured antibody of the invention which specifically binds to K63-linked polyubiquitin with high affinity but binds to K48-linked polyubiquitin with substantially reduced affinity comprises substitution at HVR-L3 amino acid positions 91-95, 95a, and 95b.

In another example, an affinity matured antibody of the invention which specifically binds to K63-linked polyubiquitin with high affinity but binds to K48-linked polyubiquitin with substantially reduced affinity comprises substitution at HVR-H1 amino acid positions 29-34. In another example, an affinity matured antibody of the invention which specifically binds to K63-linked polyubiquitin with high affinity but binds to K48-linked polyubiquitin with substantially reduced affinity comprises substitution at HVR-H2 amino acid positions 50, 52, 54, 56, and 58. In another example, an affinity matured antibody of the invention which specifically binds to K63-linked polyubiquitin with high affinity but binds to K48-linked polyubiquitin with substantially reduced affinity comprises substitution at HVR-H3 amino acid positions 95-100, 100a, 100b, and 100c.

In one embodiment, an antibody of the invention comprises a heavy chain variable domain comprising the sequence of SEQ ID NOs: 265, 281, and 297. In one embodiment, an antibody of the invention comprises a light chain variable domain comprising the sequence of SEQ ID NOs: 79, 80, and 313. In one embodiment, an antibody of the invention comprises a heavy chain variable domain comprising the sequence of SEQ ID NOs: 265, 281, and 297 and also comprises a light chain variable domain comprising the sequence of SEQ ID NOs: 79, 80, and 313. In other embodiments, an antibody of the invention corresponding to a particular clone number comprises a heavy chain variable domain comprising an HVR-H1, HVR-H2, and HVR-H3 sequence as set forth in FIGS. 2, 3, 8, 9, 10, 11, 14-17, and 22 for that clone number. In other embodiments, an antibody of the invention corresponding to a particular clone number comprises a light chain variable domain comprising an HVR-L1 sequence of SEQ ID NO: 79, an HVR-L2 sequence of SEQ ID NO: 80, and an HVR-L3 sequence as set forth in FIGS. 10, 11, 16, and 17 for that clone number. In other embodiments, an antibody of the invention corresponding to a particular clone number comprises a heavy chain variable domain comprising an HVR-H1, HVR-H2, and HVR-H3 sequence as set forth in FIGS. 2, 3, 8, 9, 10, 11, 14-17, and 22 for that clone number and also comprises a light chain variable domain comprising an HVR-L1 sequence of SEQ ID NO: 79, an HVR-L2 sequence of SEQ ID NO: 80, and an HVR-L3 sequence as set forth in FIGS. 10, 11, 16, and 17 for that clone number.

In one aspect, the invention provides an antibody that competes with any of the above-mentioned antibodies for binding to polyubiquitin. In one aspect, the invention provides an antibody that binds to the same antigenic determinant on polyubiquitin as any of the above-mentioned antibodies.

As shown herein, the antibodies of the invention specifically bind to an isolated polyubiquitin having a specific lysine linkage. As shown herein, the antibodies of the invention also specifically bind to polyubiquitin having a specific lysine linkage when that polyubiquitin is attached to a heterologous protein (see, e.g., Examples 3 and 4).

Compositions comprising at least one anti-polyubiquitin antibody or at least one polynucleotide comprising sequences encoding an anti-polyubiquitin antibody are provided. In certain embodiments, a composition may be a pharmaceutical composition. As used herein, compositions comprise one or more antibodies that bind to one or more polyubiquitin and/or one or more polynucleotides comprising sequences encoding one or more antibodies that bind to one or more polyubiquitin. These compositions may further comprise suitable carriers, such as pharmaceutically acceptable excipients including buffers, which are well known in the art.

Isolated antibodies and polynucleotides are also provided. In certain embodiments, the isolated antibodies and polynucleotides are substantially pure.

In one embodiment, anti-polyubiquitin antibodies are monoclonal. In another embodiment, fragments of the anti-polyubiquitin antibodies (e.g., Fab, Fab'-SH and F(ab')2 fragments) are provided. These antibody fragments can be created by traditional means, such as enzymatic digestion, or may be generated by recombinant techniques. Such antibody fragments may be chimeric, humanized, or human. These fragments are useful for the diagnostic and therapeutic purposes set forth below.

Generation of Anti-Polyubiquitin Antibodies Using a Phage Display Library

A variety of methods are known in the art for generating phage display libraries from which an antibody of interest can be obtained. One method of generating antibodies of interest is through the use of a phage antibody library as described in Lee et al., J. Mol. Biol. (2004), 340(5):1073-93.

The anti-polyubiquitin antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the nonbinding clones in the library. The binding clones are then eluted from the antigen, and can be further enriched by additional cycles of antigen adsorption/elution. Any of the anti-polyubiquitin antibodies of the invention can be obtained by designing a suitable antigen screening procedure to select for the phage clone of interest followed by construction of a full length anti-polyubiquitin antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g. as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g. as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-polyubiquitin clones is desired, the subject is immunized with polyubiquitin to generate an antibody response, and spleen cells and/or circulating B cells or other peripheral blood lymphocytes (PBLs) are recovered for library construction. In one embodiment, a human antibody gene fragment library biased in favor of anti-human polyubiquitin clones is obtained by generating an anti-human polyubiquitin antibody response in transgenic mice carrying a functional human immunoglobulin gene array (and lacking a functional endogenous antibody production system) such that polyubiquitin immunization gives rise to B cells producing human antibodies against polyubiquitin. The generation of human antibody-producing transgenic mice is described in Section (III)(b) below.

Additional enrichment for anti-polyubiquitin reactive cell populations can be obtained by using a suitable screening procedure to isolate B cells expressing polyubiquitin-specific membrane bound antibody, e.g., by cell separation with polyubiquitin affinity chromatography or adsorption of cells to fluorochrome-labeled polyubiquitin followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which polyubiquitin is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci. (USA)*, 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci. (USA)*, 86: 5728-5732 (1989). To maximize complementarity, degeneracy can be incorporated in the primers as described in Orlandi et al. (1989) or Sastry et al. (1989). In certain embodiments, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128: 119-126 (1993), or in vivo by combinatorial infection, e.g., the loxP system described in Waterhouse et al., *Nucl. Acids Res.*, 21: 2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g. as described in Barbas et al., *Proc. Natl. Acad. Sci. USA*, 88: 7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20: 3831-3837 (1992).

Screening of the libraries can be accomplished by any art-known technique. For example, polyubiquitin can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized polyubiquitin under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA*, 88: 7978-7982 (1991), or by alkali, e.g. as described in Marks et al., *J. Mol. Biol.*, 222: 581-597 (1991), or by polyubiquitin antigen competition, e.g. in a procedure similar to the antigen competition method of Clackson et al., *Nature*, 352: 624-628 (1991). Phages can be enriched 20-1,000-fold in a single round of selection. Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins*, 8: 309-314 (1990) and in WO 92/09690, and a low coating density of antigen as described in Marks et al., *Biotechnol.*, 10: 779-783 (1992).

It is possible to select between phage antibodies of different affinities, even with affinities that differ slightly, for polyubiquitin. However, random mutation of a selected antibody (e.g. as performed in some of the affinity maturation techniques described above) is likely to give rise to many mutants, most binding to antigen, and a few with higher affinity. With limiting polyubiquitin, rare high affinity phage could be competed out. To retain all the higher affinity mutants, phages can be incubated with excess biotinylated polyubiquitin, but with the biotinylated polyubiquitin at a concentration of lower molarity than the target molar affinity constant for polyubiquitin. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-polyubiquitin clones may be activity selected. In one embodiment, the invention provides anti-polyubiquitin antibodies that block the binding between a polyubiquitin ligand and polyubiquitin, but do not block the binding between a polyubiquitin ligand and a second protein. Fv clones corresponding to such anti-polyubiquitin antibodies can be selected by (1) isolating anti-polyubiquitin clones from a phage library as described in Section B(I)(2) above, and optionally amplifying the isolated population of phage clones by growing up the population in a suitable bacterial host; (2) selecting polyubiquitin and a second protein against which blocking and non-blocking activity, respectively, is desired; (3) adsorbing the anti-polyubiquitin phage clones to immobilized polyubiquitin; (4) using an excess of the second protein to elute any undesired clones that recognize polyubiquitin-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.*, 5: 256 (1993) and Pluckthun, *Immunol. Revs*, 130: 151 (1992).

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid", full length heavy chain and/or light chain is included in the definition of "chimeric" and "hybrid" antibody as used herein. In one embodiment, a Fv clone derived from human variable DNA is fused to human constant region DNA to form coding sequence(s) for all human, full or partial length heavy and/or light chains.

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutation can be introduced at random in vitro by using error-prone polymerase (reported in Leung et al., *Technique*, 1: 11-15 (1989)) in the method of Hawkins et al., *J. Mol. Biol.*, 226: 889-896 (1992) or in the method of Gram et al., *Proc. Natl. Acad. Sci. USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 9607754 (published 14 Mar. 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10: 779-783 (1992). This technique allows the production of antibodies and antibody fragments with affinities in the $10^{-9}$ M range.

Other Methods of Generating Anti-Polyubiquitin Antibodies

Other methods of generating and assessing the affinity of antibodies are well known in the art and are described, e.g., in Kohler et al., *Nature* 256: 495 (1975); U.S. Pat. No. 4,816,567; Goding, Monoclonal Antibodies: Principles and Practice, pp. 59-103 (Academic Press, 1986; Kozbor, *J. Immunol.*, 133:3001 (1984); Brodeur et al., *Monoclonal Antibody Production Techniques and Applications*, pp. 51-63 (Marcel Dekker, Inc., New York, 1987; Munson et al., *Anal. Biochem.*, 107:220 (1980); Engels et al., *Agnew. Chem. Int. Ed. Engl.*, 28: 716-734 (1989); Abrahmsen et al., *EMBO J.*, 4: 3901 (1985); Methods in Enzymology, vol. 44 (1976); Morrison et al., *Proc. Natl. Acad. Sci. USA*, 81: 6851-6855 (1984).

General Methods

In general, the invention provides anti-polyubiquitin antibodies that are useful for treatment of polyubiquitin-mediated disorders in which a partial or total blockade of one or more polyubiquitin activities is desired. In one embodiment, the anti-polyubiquitin antibodies of the invention are used to treat cancer. In another embodiment, the anti-polyubiquitin antibodies provided herein are used to treat muscular disorders, such as those indicated above. In another embodiment, the anti-polyubiquitin antibodies provided herein are used to treat neurological disorders, such as those indicated above. In another embodiment, the anti-polyubiquitin antibodies provided herein are used to treat genetic disease. In another embodiment, the anti-polyubiquitin antibodies provided herein are used to treat immune/inflammatory disorders.

The unique properties of the anti-polyubiquitin antibodies of the invention make them particularly useful for distinguishing between different lysine-linked forms of polyubiquitin in a cellular system without resorting to cumbersome and expensive genetic manipulation or biophysical methods such as mass spectrometry. The anti-polyubiquitin antibodies of the invention can be used to characterize the function(s) and activities of specific lysine-linked polyubiquitins both in vitro and in vivo. The anti-polyubiquitin antibodies of the invention can also be used to determine the role of specific lysine-linked polyubiquitins in the development and pathogenesis of disease. The anti-polyubiquitin antibodies of the invention can further be used to treat diseases in which one or more specific lysine-linked polyubiquitins are aberrantly regulated or aberrantly functioning without interfering with the normal activity of polyubiquitins for which the anti-polyubiquitin antibodies are not specific.

In another aspect, the anti-polyubiquitin antibodies of the invention find utility as reagents for detection and isolation of polyubiquitin of specific lysine linkages, such as detection of polyubiquitin in various cell types and tissues, including the determination of polyubiquitin density and distribution in cell populations and within a given cell, and cell sorting based on the presence or amount of polyubiquitin.

In yet another aspect, the present anti-polyubiquitin antibodies are useful for the development of polyubiquitin antagonists with blocking activity patterns similar to those of the subject antibodies of the invention. For example, anti-K48-linked polyubiquitin antibodies of the invention can be used to determine and identify other antibodies that have the same K48-linked polyubiquitin binding characteristics and/or capabilities of blocking K48-linked polyubiquitin-mediated pathways. Similarly, anti-K63-linked polyubiquitin antibodies of the invention can be used to determine and identify other antibodies that have the same K63-linked polyubiquitin binding characteristics and/or capabilities of blocking K63-linked polyubiquitin-mediated pathways.

As a further example, anti-polyubiquitin antibodies of the invention can be used to identify other anti-polyubiquitin antibodies that bind substantially the same antigenic determinant(s) of polyubiquitin as the antibodies exemplified herein, including linear and conformational epitopes.

The anti-polyubiquitin antibodies of the invention can be used in assays based on the physiological pathways in which polyubiquitin is involved to screen for small molecule antagonists of polyubiquitin having one or more specific lysine linkages which will exhibit similar pharmacological effects in blocking the binding of one or more binding partners to polyubiquitin having those one or more lysine linkages. For example, K48-linked polyubiquitin is known to be involved in targeted proteasomal degradation of certain proteins (see, e.g., Chau et al., Science 243: 1576-1583 (1989); Finley et al., Mol. Cell. Biol. 14: 5501-5509 (1994); Flick et al., Nat. Cell. Biol. 6:634-641 (2004)); thus anti-K48-linked polyubiquitin antibodies may be used in screens to identify small molecule antagonists of K48-linked polyubiquitin-mediated targeted proteasomal degradation by comparing the activity of one or more potential small molecule antagonists to the activity of the anti-K48-linked polyubiquitin antibodies in that pathway. Similarly, in another example, K63-linked polyubiquitin is known to be involved in DNA repair (see, e.g., Pickart and Fushman, Curr. Opin. Chem. Biol. 8: 610-616 (2004)), and thus the activity of anti-K63-linked polyubiquitin antibodies to antagonize a DNA repair pathway may be compared to the activity of one or more potential small molecule antagonists of K63-linked polyubiquitin in that same DNA repair pathway. Similarly, in another example, K63-linked polyubiquitin is known to be involved in formation of Lewy bodies in Parkinson's disease (see, e.g., Lim et al., J. Neurosci. 25(8): 2002-9 (2005)), and thus the activity of anti-K63-linked polyubiquitin antibodies to antagonize the formation of Lewy bodies may be compared to the activity of one or more potential small molecule antagonists of K63-linked polyubiquitin in antagonizing the formation of Lewy bodies.

Generation of candidate antibodies can be achieved using routine skills in the art, including those described herein, such as the hybridoma technique and screening of phage displayed libraries of binder molecules. These methods are well-established in the art.

Briefly, the anti-polyubiquitin antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the nonbinding clones in the library. The binding clones are then eluted from the antigen, and can be further enriched by additional cycles of antigen adsorption/elution. Any of the anti-polyubiquitin antibodies of the invention can be obtained by designing a suitable antigen screening procedure to select for the phage clone of interest followed by construction of a full length anti-polyubiquitin antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3. See also PCT Pub. WO03/102157, and references cited therein.

In one embodiment, anti-polyubiquitin antibodies of the invention are monoclonal. Also encompassed within the scope of the invention are antibody fragments such as Fab, Fab', Fab'-SH and F(ab')$_2$ fragments, and variations thereof, of the anti-polyubiquitin antibodies provided herein. These antibody fragments can be created by traditional means, such as enzymatic digestion, or may be generated by recombinant techniques. Such antibody fragments may be chimeric, human or humanized. These fragments are useful for the experimental, diagnostic, and therapeutic purposes set forth herein.

Monoclonal antibodies can be obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-polyubiquitin monoclonal antibodies of the invention can be made using a variety of methods known in the art, including the hybridoma method first described by Kohler et al., *Nature,* 256:495 (1975), or alternatively they may be made by recombinant DNA methods (e.g., U.S. Pat. No. 4,816,567).

Vectors, Host Cells and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Host cells include, but are not limited to, cells of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells

Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, lpp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxB⁻ strains) provide cytoplasm conditions that are favorable for disulfide bond formation, thereby permitting proper folding and assembly of expressed protein subunits. Proba and Pluckthun *Gene*, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kan$^R$ (U.S. Pat. No. 5,639,635). Other strains and derivatives thereof, such as *E. coli* 294 (ATCC 31,446), *E. coli* B, *E. coli*$_\lambda$ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli*, *Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, growth occurs at a temperature range including, but not limited to, about 20° C. to about 39° C., about 25° C. to about 37° C., and at about 30° C. The pH of the medium may be any pH ranging from about 5 to about 9, depending mainly on the host organism. For *E. coli*, the pH can be from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In one embodiment, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, for example about 1,000 to 100,000 liters of capacity. These fermentors use agitator impellers to distribute oxygen and nutrients, especially glucose (a common carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD$_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275: 17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., *Microbial Drug Resistance,* 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al (1983) *J. Immunol. Meth.* 62:1-13. The solid phase to which Protein A is immobilized can be a column comprising a glass or silica surface, or a controlled pore glass column or a silicic acid column. In some applications, the column is coated with a reagent, such as glycerol, to possibly prevent nonspecific adherence of contaminants.

As the first step of purification, the preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected generally is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II (e.g., primate metallothionein genes), adenosine deaminase, ornithine decarboxylase, etc.

For example, cells transformed with the DHFR selection gene may first be identified by culturing all of the transformants in a culture medium that contains methotrexate (Mtx), a competitive antagonist of DHFR. Appropriate host cells when wild-type DHFR is employed include, for example, the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to nucleic acid encoding a polypeptide of interest (e.g., an antibody). Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells can be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding an antibody polypeptide of the invention by higher eukaryotes can often be increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody polypeptide-encoding sequence, but is generally located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/–DHFR(CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are generally removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a generally acceptable purification technique. The suitability of affinity reagents such as protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification steps, as necessary, for example by low pH hydrophobic interaction chromatography using an elution buffer at a pH between about 2.5-4.5, generally performed at low salt concentrations (e.g., from about 0-0.25M salt).

It should be noted that, in general, techniques and methodologies for preparing antibodies for use in research, testing and clinical use are well-established in the art, consistent with the above and/or as deemed appropriate by one skilled in the art for the particular antibody of interest.

Activity Assays

Antibodies of the invention can be characterized for their physical/chemical properties and biological functions by various assays known in the art.

Purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

Where necessary, antibodies are analyzed for their biological activity. In some embodiments, antibodies of the invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays.

In one embodiment, the invention contemplates an altered antibody that possesses some but not all effector functions, which make it a desirable candidate for many applications in which the half life of the antibody in vivo is important yet certain effector functions (such as complement and ADCC) are unnecessary or deleterious. In certain embodiments, the Fc activities of the antibody are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *PNAS* (USA) 95:652-656 (1998). C1q binding assays may also be carried out to confirm that the antibody is unable to bind C1q and hence lacks CDC activity. To assess complement activation, a CDC assay, e.g. as described in Gazzano-Santoro et al., *J. Immunol. Methods* 202:163 (1996), may be performed. FcRn binding and in vivo clearance/half life determinations can also be performed using methods known in the art.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form $F(ab')_2$ fragments (Carter et al., Bio/Technology 10:163-167 (1992)). According to another approach, $F(ab')_2$ fragments can be isolated directly from recombinant host cell culture. Fab and $F(ab')_2$ fragment with increased in vivo half-life comprising salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. Nos. 5,571,894; and 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody", e.g., as described in U.S. Pat. No. 5,641,870 for example. Such linear antibody fragments may be monospecific or bispecific.

Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA*, 89:4285; Presta et al. (1993) *J. Immunol.*, 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-polyubiquitin antibodies of the invention can be constructed by combining Fv clone variable domain sequence(s) selected from human-derived phage display libraries with known human constant domain sequences(s) as described above. Alternatively, human monoclonal anti-polyubiquitin antibodies of the invention can be made by the hybridoma method. Human myeloma and mouse-human heteromyeloma cell lines for the production of human monoclonal antibodies have been described, for example, by Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., *J. Immunol.*, 147: 86 (1991).

It is now possible to produce transgenic animals (e.g. mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germline mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90: 2551 (1993); Jakobovits et al., *Nature*, 362: 255 (1993); Bruggermann et al., *Year in Immunol.*, 7: 33 (1993).

Gene shuffling can also be used to derive human antibodies from non-human, e.g. rodent, antibodies, where the human antibody has similar affinities and specificities to the starting non-human antibody. According to this method, which is also called "epitope imprinting", either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for polyubiquitin including a specific lysine linkage and the other is for any other antigen. In certain embodiments, bispecific antibodies may bind to two different polyubiquitins having two different lysine linkages. Bispecific antibodies can be prepared as full length antibodies or antibody fragments (e.g. F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature*, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.*, 10: 3655 (1991).

According to a different embodiment, antibody variable domains with the desired binding specificities (antibody-antigen combining sites) are fused to immunoglobulin constant domain sequences. The fusion, for example, is with an immunoglobulin heavy chain constant domain, comprising at least part of the hinge, CH2, and CH3 regions. In certain embodiments, the first heavy-chain constant region (CH1), containing the site necessary for light chain binding, is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The dimerization domain comprises (or consists of), for example, an Fc region or a hinge region. In this scenario, the antibody will comprise an Fc region and three or more antigen binding sites amino-terminal to the Fe region. In one embodiment, a multivalent antibody comprises (or consists of), for example, three to about eight, or four antigen binding sites. The multivalent antibody comprises at least one polypeptide chain (for example, two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein may further comprise at least two (for example, four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table A under the heading of "preferred substitutions". If such substitutions result in a change in biological activity, then more substantial changes, denominated "exemplary substitutions" in Table A, or as further described below in reference to amino acid classes, may be introduced and the products screened.

TABLE A

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu; Asn | Glu |
| Cys (C) | Ser; Ala | Ser |
| Gln (Q) | Asn;Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine, Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):

(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (O)
(3) acidic: Asp (D), Glu (E)
(4) basic: Lys (K), Arg (R), His(H)

Alternatively, naturally occurring residues may be divided into groups based on common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g. a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g. binding affinity) as herein disclosed. In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter *Nature* 322:738-40 (1988); U.S. Pat. No. 5,648,260; U.S. Pat. No. 5,624,821; and WO94/29351 concerning other examples of Fc region variants.

In one aspect, the invention provides antibodies comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

Immunoconjugates

In another aspect, the invention provides immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) *Bioconjugate Chem.* 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10): 2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5585089; 5606040; 5693762; 5739116; 5767285; 5773001). Cantuzumab mertansine (Immunogen, Inc.), an antibody drug conjugate composed of the huC242 antibody linked via the disulfide linker SPP to the maytansinoid drug moiety, DM1, is tested for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is tested for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of immunoconjugates are described herein (above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolostatins, aurostatins, a trichothecene, and CC1065, and the derivatives of these toxins that have toxin activity, are also contemplated herein.

Maytansine and Maytansinoids

In some embodiments, the immunoconjugate comprises an antibody of the invention conjugated to one or more maytansinoid molecules.

Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Exemplary embodiments of maytansinoid drug moieties include: DM1; DM3; and DM4. Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates can be prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Maytansinoids include, but are not limited to, maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents. Additional linking groups are described and exemplified herein.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). Coupling agents include, but are not limited to, N-succinimidyl-3-(2-pyridyldithio)propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In one embodiment, the linkage is formed at the C-3 position of maytansinol or a maytansinol analogue.

Auristatins and Dolostatins

In some embodiments, the immunoconjugate comprises an antibody of the invention conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. 5663149) and antifungal activity (Pettit et al (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands", U.S. Ser. No. 10/983,340, filed Nov. 5, 2004, the disclosure of which is expressly incorporated by reference in its entirety.

Exemplary auristatin embodiments include MMAE and MMAF. Additional exemplary embodiments comprising MMAE or MMAF and various linker components (described further herein) include Ab-MC-vc-PAB-MMAF, Ab-MC-vc-PAB-MMAE, Ab-MC-MMAE and Ab-MC-MMAF.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry. The auristatin/dolastatin drug moieties may be prepared according to the methods of: U.S. Pat. No. 5,635,483; U.S. Pat. No. 5,780,588; Pettit et al (1989) J. Am. Chem. Soc. 111:5463-5465; Pettit et al (1998) Anti-Cancer Drug Design 13:243-277; Pettit, G. R., et al. Synthesis, 1996, 719-725; and Pettit et al (1996) J. Chem. Soc. Perkin Trans. 15:859-863. See also Doronina (2003) Nat Biotechnol 21(7):778-784; "Monomethylvaline Compounds Capable of Conjugation to Ligands", U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

Calicheamicin

In other embodiments, the immunoconjugate comprises an antibody of the invention conjugated to one or more calicheamicin molecules. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another anti-tumor drug to which the antibody can be conjugated is QFA, which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $Tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun 80: 49-57) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab-(L-D)_p \qquad \qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-1 carboxylate ("SMCC'), and N-Succinimidyl (4-iodo-acetyl)aminobenzoate ("SIAB"). Additional linker components are known in the art and some are described herein. See also "Monomethylvaline Compounds Capable of Conjugation to Ligands", U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzyme, for example, a tumor-associated protease, cathepsin B, C and D, or a plasmin protease.

Exemplary linker component structures are shown below (wherein the wavy line indicates sites of covalent attachment to other components of the ADC):

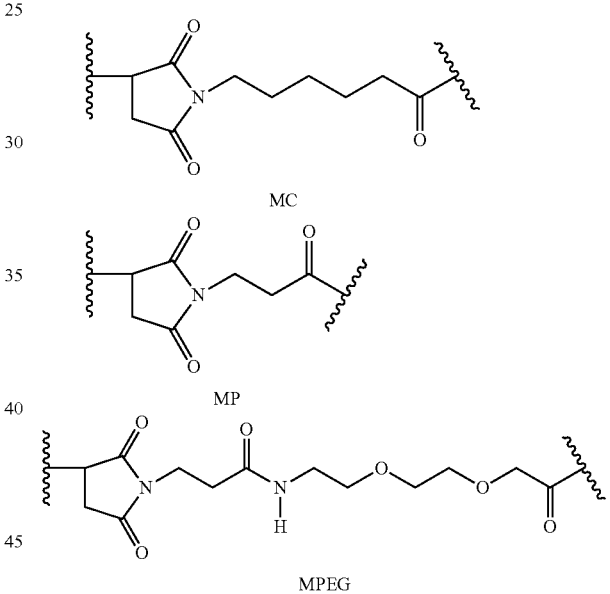

Additional exemplary linker components and abbreviations include (wherein the antibody (Ab) and linker are depicted, and p is 1 to about 8):

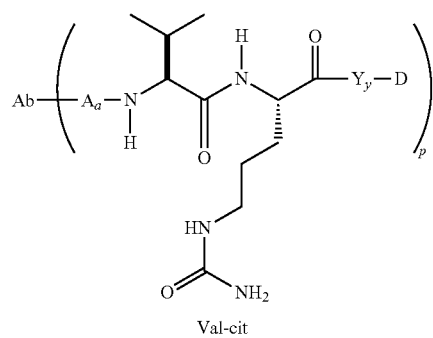

Val-cit

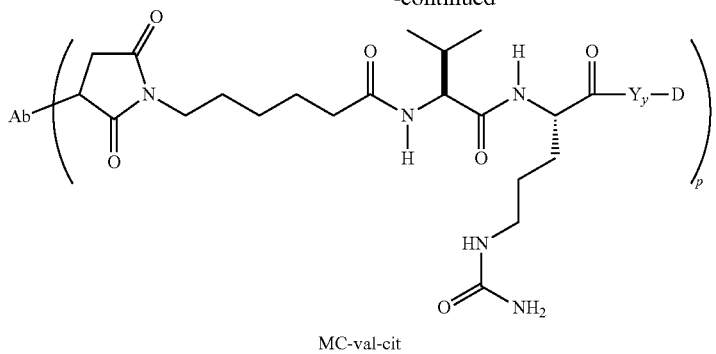
MC-val-cit

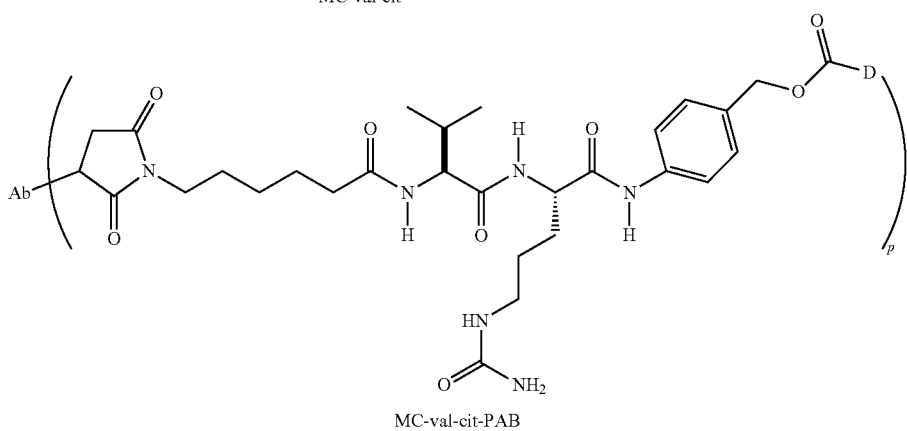
MC-val-cit-PAB

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. 5362852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent to one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody (Ab)-MC-MMAE may be prepared by conjugation of any of the antibodies provided herein with MC-MMAE as follows. Antibody, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice. The drug linker reagent, maleimidocaproyl-monomethyl auristatin E (MMAE), i.e. MC-MMAE, dissolved in DMSO, is diluted in acetonitrile and water at known concentration, and added to the chilled reduced antibody 2H9 in PBS. After about one hour, an excess of maleimide is added to quench the reaction and cap any unreacted antibody thiol groups. The reaction mixture is concentrated by centrifugal ultrafiltration and 2H9-MC-MMAE is purified and desalted by elution through G25 resin in PBS, filtered through 0.2 μm filters under sterile conditions, and frozen for storage.

Antibody-MC-MMAF may be prepared by conjugation of any of the antibodies provided herein with MC-MMAF following the protocol provided for preparation of Ab-MC-MMAE.

Antibody-MC-val-cit-PAB-MMAE is prepared by conjugation of any of the antibodies provided herein with MC-val-cit-PAB-MMAE following the protocol provided for preparation of Ab-MC-MMAE.

Antibody-MC-val-cit-PAB-MMAF is prepared by conjugation of any of the antibodies provided herein with MC-val-cit-PAB-MMAF following the protocol provided for preparation of Ab-MC-MMAE.

Antibody-SMCC-DM1 is prepared by conjugation of any of the antibodies provided herein with SMCC-DM1 as follows. Purified antibody is derivatized with (Succinimidyl 4-(N-maleimidomethyl)cyclohexane-1-carboxylate (SMCC, Pierce Biotechnology, Inc) to introduce the SMCC linker. Specifically, antibody is treated at 20 mg/mL in 50 mM potassium phosphate/50 mM sodium chloride/2 mM EDTA, pH 6.5 with 7.5 molar equivalents of SMCC (20 mM in DMSO, 6.7 mg/mL). After stirring for 2 hours under argon at ambient temperature, the reaction mixture is filtered through a Sephadex G25 column equilibrated with 50 mM potassium phosphate/50 mM sodium chloride/2 mM EDTA, pH 6.5. Antibody-containing fractions are pooled and assayed.

Antibody-SMCC prepared thusly is diluted with 50 mM potassium phosphate/50 mM sodium chloride/2 mM EDTA, pH 6.5, to a final concentration of about 10 mg/ml, and reacted with a 10 mM solution of DM1 in dimethylacetamide. The reaction is stirred at ambient temperature under argon for 16.5 hours. The conjugation reaction mixture is filtered through a Sephadex G25 gel filtration column (1.5× 4.9 cm) with 1×PBS at pH 6.5. The DM1 drug to antibody ratio (p) may be about 2 to 5, as measured by the absorbance at 252 nm and at 280 nm.

Ab-SPP-DM1 is prepared by conjugation of any of the antibodies provided herein with SPP-DM1 as follows. Purified antibody is derivatized with N-succinimidyl-4-(2-pyridylthio)pentanoate to introduce dithiopyridyl groups. Antibody (376.0 mg, 8 mg/mL) in 44.7 mL of 50 mM potassium phosphate buffer (pH 6.5) containing NaCl (50 mM) and EDTA (1 mM) is treated with SPP (5.3 molar equivalents in 2.3 mL ethanol). After incubation for 90 minutes under argon at ambient temperature, the reaction mixture is gel filtered through a Sephadex G25 column equilibrated with a 35 mM sodium citrate, 154 mM NaCl, 2 mM EDTA buffer. Antibody-containing fractions were pooled and assayed. The degree of modification of the antibody is determined as described above.

Antibody-SPP-Py (about 10 μmoles of releasable 2-thiopyridine groups) is diluted with the above 35 mM sodium citrate buffer, pH 6.5, to a final concentration of about 2.5 mg/mL. DM1 (1.7 equivalents, 17 μmoles) in 3.0 mM dimethylacetamide (DMA, 3% v/v in the final reaction mixture) is then added to the antibody solution. The reaction proceeds at ambient temperature under argon for about 20 hours. The reaction is loaded on a Sephacryl S300 gel filtration column (5.0 cm×90.0 cm, 1.77 L) equilibrated with 35 mM sodium citrate, 154 mM NaCl, pH 6.5. The flow rate may be about 5.0 mL/min and 65 fractions (20.0 mL each) are collected. The number of DM1 drug molecules linked per antibody molecule (p') is determined by measuring the absorbance at 252 nm and 280 nm, and may be about 2 to 4 DM1 drug moieties per 2H9 antibody.

Antibody-BMPEO-DM1 is prepared by conjugation of any of the antibodies provided herein with BMPEO-DM1 as follows. The antibody is modified by the bis-maleimido reagent BM(PEO)$_4$ (Pierce Chemical), leaving an unreacted maleimido group on the surface of the antibody. This may be accomplished by dissolving BM(PEO)$_4$ in a 50% ethanol/water mixture to a concentration of 10 mM and adding a tenfold molar excess to a solution containing antibody in phosphate buffered saline at a concentration of approximately 1.6 mg/ml (10 micromolar) and allowing it to react for 1 hour to form an antibody-linker intermediate, 2H9-BMPEO. Excess BM(PEO)$_4$ is removed by gel filtration (HiTrap column, Pharmacia) in 30 mM citrate, pH 6 with 150 mM NaCl buffer. An approximate 10 fold molar excess DM1 is dissolved in dimethyl acetamide (DMA) and added to the 2H9-BMPEO intermediate. Dimethyl formamide (DMF) may also be employed to dissolve the drug moiety reagent. The reaction mixture is allowed to react overnight before gel filtration or dialysis into PBS to remove unreacted DM1. Gel filtration on S200 columns in PBS is used to remove high molecular weight aggregates and to furnish purified 2H9-BMPEO-DM1.

Antibody Derivatives

Antibodies of the invention can be further modified to contain additional nonproteinaceous moieties that are known in the art and readily available. In one embodiment, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, the polymers can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., Proc. Natl. Acad. Sci. 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Pharmaceutical Formulations

Therapeutic formulations comprising an antibody of the invention are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, including, but not limited to those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the invention may be used in, for example, in vitro, ex vivo and in vivo therapeutic methods. Antibodies of the invention can be used as an antagonist to partially or fully block the specific antigen activity in vitro, ex vivo and/or in vivo. Moreover, at least some of the antibodies of the invention can neutralize antigen activity from other species. Accordingly, antibodies of the invention can be used to inhibit a specific antigen activity, e.g., in a cell culture containing the antigen, in human subjects or in other mammalian subjects having the antigen with which an antibody of the invention cross-reacts (e g chimpanzee, baboon, marmoset, cynomolgus and rhesus, pig or mouse). In one embodiment, an antibody of the invention can be used for inhibiting antigen activities by contacting the antibody with the antigen such that antigen activity is inhibited. In one embodiment, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. In one embodiment, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Antibodies of the invention can be used to treat, inhibit, delay progression of, prevent/delay recurrence of, ameliorate, or prevent diseases, disorders or conditions associated with abnormal expression and/or activity of polyubiquitins and polyubiquitinated proteins, including but not limited to cancer, muscular disorders, ubiquitin-pathway-related genetic disorders, immune/inflammatory disorders, neurological disorders, and other ubiquitin pathway-related disorders.

In one aspect, a blocking antibody of the invention is specific for a polyubiquitin having a particular lysine linkage, and inhibits normal polyubiquitin activity by blocking or interfering with the interaction between a polyubiquitin having a particular lysine linkage and a protein that interacts with that polyubiquitin, thereby inhibiting the corresponding signal pathway and other associated molecular or cellular events.

In certain embodiments, an immunoconjugate comprising an antibody conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, and/or adjuvant/therapeutic agents (e.g., steroids). For instance, an antibody of the invention may be combined with an anti-inflammatory and/or antiseptic in a treatment scheme, e.g. in treating any of the diseases described herein, including cancer, muscular disorders, ubiquitin-pathway-related genetic disorders, immune/inflammatory disorders, neurological disorders, and other ubiquitin pathway-related disorders. Such combined therapies noted above include combined administration (where the two or more agents are included in the same or separate formulations), and separate administration, in which case, administration of the antibody of the invention can occur prior to, and/or following, administration of the adjunct therapy or therapies.

An antibody of the invention (and adjunct therapeutic agent) can be administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The location of the binding target of an antibody of the invention may be taken into consideration in preparation and administration of the antibody. When the binding target is an intracellular molecule, certain embodiments of the invention provide for the antibody or antigen-binding fragment thereof to be introduced into the cell where the binding target is located. In one embodiment, an antibody of the invention can be expressed intracellularly as an intrabody. The term "intrabody," as used herein, refers to an antibody or antigen-binding portion thereof that is expressed intracellularly and that is capable of selectively binding to a target molecule, as described in Marasco, Gene Therapy 4: 11-15 (1997); Kontermann, Methods 34: 163-170 (2004); U.S. Pat. Nos. 6,004,940 and 6,329,173; U.S. Patent Application Publication No. 2003/0104402, and PCT Publication No. WO2003/077945. Intracellular expression of an intrabody is effected by introducing a nucleic acid encoding the desired antibody or antigen-binding portion thereof (lacking the wild-type leader sequence and secretory signals normally associated with the gene encoding that antibody or antigen-binding fragment) into a target cell. Any standard method of introducing nucleic acids into a cell may be used, including, but not limited to, microinjection, ballistic injection, electroporation, calcium phosphate precipitation, liposomes, and transfection with retroviral, adenoviral, adeno-associated viral and vaccinia vectors carrying the nucleic acid of interest. One or more nucleic acids encoding all or a portion of an anti-polyubiquitin antibody of the invention can be delivered to a target cell, such that one or more intrabodies are expressed which are capable of intracellular binding to a polyubiquitin and modulation of one or more polyubiquitin-mediated cellular pathways.

In another embodiment, internalizing antibodies are provided. Antibodies can possess certain characteristics that enhance delivery of antibodies into cells, or can be modified to possess such characteristics. Techniques for achieving this are known in the art. For example, cationization of an antibody is known to facilitate its uptake into cells (see, e.g., U.S. Pat. No. 6,703,019). Lipofections or liposomes can also be used to deliver the antibody into cells. Where antibody fragments are used, the smallest inhibitory fragment that specifically binds to the binding domain of the target protein is generally advantageous. For example, based upon the variable-region sequences of an antibody, peptide molecules can be designed that retain the ability to bind the target protein sequence. Such peptides can be synthesized chemically and/or produced by recombinant DNA technology. See, e.g., Marasco et al., *Proc. Natl. Acad. Sci. USA*, 90: 7889-7893 (1993).

Entry of modulator polypeptides into target cells can be enhanced by methods known in the art. For example, certain sequences, such as those derived from HIV Tat or the Antennapedia homeodomain protein are able to direct efficient uptake of heterologous proteins across cell membranes. See, e.g., Chen et al., *Proc. Natl. Acad. Sci. USA* (1999), 96:4325-4329.

When the binding target is located in the brain, certain embodiments of the invention provide for the antibody or antigen-binding fragment thereof to traverse the blood-brain barrier. Certain neurodegenerative diseases are associated with an increase in permeability of the blood-brain barrier, such that the antibody or antigen-binding fragment can be readily introduced to the brain. When the blood-brain barrier remains intact, several art-known approaches exist for transporting molecules across it, including, but not limited to, physical methods, lipid-based methods, and receptor and channel-based methods.

Physical methods of transporting the antibody or antigen-binding fragment across the blood-brain barrier include, but are not limited to, circumventing the blood-brain barrier entirely, or by creating openings in the blood-brain barrier. Circumvention methods include, but are not limited to, direct injection into the brain (see, e.g., Papanastassiou et al., Gene Therapy 9: 398-406 (2002)), interstitial infusion/convection-enhanced delivery (see, e.g., Bobo et al., Proc. Natl. Acad. Sci. USA 91: 2076-2080 (1994)), and implanting a delivery device in the brain (see, e.g., Gill et al., Nature Med. 9: 589-595 (2003); and Gliadel Wafers™, Guildford Pharmaceutical). Methods of creating openings in the barrier include, but are not limited to, ultrasound (see, e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding the antibody or antigen-binding fragment (see, e.g., U.S. Patent Publication No. 2003/0083299).

Lipid-based methods of transporting the antibody or antigen-binding fragment across the blood-brain barrier include, but are not limited to, encapsulating the antibody or antigen-binding fragment in liposomes that are coupled to antibody binding fragments that bind to receptors on the vascular endothelium of the blood-brain barrier (see, e.g., U.S. Patent Application Publication No. 20020025313), and coating the antibody or antigen-binding fragment in low-density lipoprotein particles (see, e.g., U.S. Patent Application Publication No. 20040204354) or apolipoprotein E (see, e.g., U.S. Patent Application Publication No. 20040131692).

Receptor and channel-based methods of transporting the antibody or antigen-binding fragment across the blood-brain barrier include, but are not limited to, using glucocorticoid blockers to increase permeability of the blood-brain barrier (see, e.g., U.S. Patent Application Publication Nos. 2002/0065259, 2003/0162695, and 2005/0124533); activating potassium channels (see, e.g., U.S. Patent Application Publication No. 2005/0089473), inhibiting ABC drug transporters (see, e.g., U.S. Patent Application Publication No. 2003/0073713); coating antibodies with a transferrin and modulating activity of the one or more transferrin receptors (see, e.g., U.S. Patent Application Publication No. 2003/0129186), and cationizing the antibodies (see, e.g., U.S. Pat. No. 5,004,697).

The antibody composition of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Example 1

Isolation and Characterization of First Generation Anti-Polyubiquitin Antibodies A) Library Sorting Phage from naïve antibody libraries were subjected to binding selection against immobilized synthetic peptides including an isopeptide bond mimicking either K48-linked polyubiquitin or K63-linked polyubiquitin. No enrichment was observed after six rounds of selection. The synthetic peptides were lengthened, and the naïve antibody libraries were again screened. Once again, no enrichment was observed after six rounds of binding selection.

Phage from the naive YS-B antibody library were subjected to four rounds of binding selection against polyubiquitin chains having different known ubiquitin isopeptide linkages. The YS-B antibody library contains randomized amino acids in all three heavy chain CDRs and light chain CDR3 (see U.S. Published Patent Application No. 2005-0106667), and is based on humanized antibody 4D5.

Enzymatically synthesized full-length K48-linked or K63-linked polyubiquitin chains of 3 to 7 units in length (Boston Biochem) were immobilized on 96-well Maxisorp immunoplates (NUNC). The plates were coated overnight with 5 µg/ml of K48- or K63-linked polyubiquitin in 50 mM carbonate buffer, pH 9.6. The coated plates were washed with phosphate buffered saline (PBS) and blocked with either bovine serum albumin (BSA) or casein, at a concentration of 0.2% in PBS. The plates were subsequently washed with PBS containing 0.05% Tween 20 (PBST) at 25° C. Each well was incubated with 100 µl of $10^{12}$ phage/ml in sorting buffer (BSA or casein, 0.2% in PBST) for 2 hours at room temperature. Each well was washed eight times in PBST to remove unbound phage. Bound phage were eluted by incubation with 0.1 M HCl for 10 minutes, and the eluant was neutralized with 2 M Tris base. The eluted phage were propagated in *Escherichia coli* XL1-blue (Stratagene) with the addition of M13-K07 helper phage (New England Biolabs).

Amplified phage were used for additional rounds of selection against the same target that was used in the previous round. For selection rounds two to four, 10 µg/ml ubiquitin was included in the sorting buffer as a counterselection. Rounds three and four were also sorted both with and without additional counterselection: either 10 µg/ml K63-linked polyubiquitin in the K48-linked polyubiquitin selection or 10 µg/ml K48-linked polyubiquitin in the K63-linked polyubiquitin selection.

For those clones where selection rounds two to four lacked polyubiquitin counterselection, individual clones were grown in a 96-well format in 400 µl of 2YT broth supplemented with carbenicillin and M13-K07 helper phage. Supernatants from those cultures were used in high-throughput phage ELISAs to screen clones for binding to K48-linked polyubiquitin, K63-linked polyubiquitin, ubiquitin and BSA. All clones were subjected to DNA sequence analysis. A portion of the heavy chain that includes the HVR was sequenced, allowing for analysis of the heavy chain hypervariable regions. The heavy chain hypervariable regions for the clones recognizing K48-linked polyubiquitin or both K48-linked and K63-linked polyubiquitin are shown in FIGS. 2A-C. The heavy chain hypervariable regions for the clones recognizing K63-linked polyubiquitin or both K48-linked and K63-linked polyubiquitin are shown in FIGS. 3A and 3B. The light chain HVR for each clone was not sequenced, but based on the nature of the YS-B library, the sequences of HVR-L1 and HVR-L2 were expected to be invariant, while the HVR-L3 sequence was expected to be clone-specific. The HVR-L1 sequence is RASQSVSSAVA (SEQ ID NO: 79) and the HVR-L2 sequence is SASSLYS (SEQ ID NO: 80), according to the library design. All clones had the same heavy chain and light chain framework sequences (see FIG. 6).

A different set of clones included counterselection with 10 µg/ml of polyubiquitin of a different lysine linkage (either K48-linked polyubiquitin or K63-linked polyubiquitin) in selection rounds two to four. Ten µl of the phage eluted from the fourth selection round was used to infect growing *E. coli* CJ236 for 20 minutes, which were then grown overnight on solid agar containing carbenicillin. Fifteen milliliters of 2YT broth supplemented with carbenicillin and chloramphenicol was added to the plate to resuspend the phagemid-containing CJ236 cells. M13-K07 helper phage was added. After incubation for one hour at 37° C. with agitation, 2.5 ml of the suspension was added to 250 ml of 2YT broth supplemented with carbenicillin and kanamycin. The suspension was allowed to grow overnight.

The phage were harvested by polyethylene glycol precipitation, and the Kunkel DNA was isolated using an M13 spin kit (Qiagen). One microgram of Kunkel template was used for Kunkel mutagenesis (see Kunkel, Proc. Natl. Acad. Sci. USA 82:488 (1985)) with the oligonucleotide F1560-2 (TCTTGTGACAAAACTCACCATCACCATCACCAT-CACTA GGGCGGTGGCTCTGGTTCCGGTGATTTT) (SEQ ID NO: 150). The mutagenesis reaction was transformed in *E. coli* XL1-blue and grown on solid agar containing carbenicillin overnight. Individual clones were then picked and grown as above and screened against K48- and K63-linked polyubiquitin, monoubiquitin, BSA and anti-pentaHis antibody (Qiagen) in a phage ELISA as described above. Clones identified to be specific for K48-linked polyubiquitin or for K63-linked polyubiquitin were subjected to DNA sequence analysis. The amino acid sequences of hypervariable regions HVR-H1, HVR-H2, and HVR-H3 are shown in FIGS. 8A-C (specific for K48-linked polyubiquitin) and 9A and 9B (specific for K63-linked polyubiquitin). The light chain HVR for each clone was not sequenced, but based on the nature of the YS-B library, the sequences of HVR-L1 and HVR-L2 were expected to be invariant, while the HVR-L3 sequence was expected to be clone-specific. The HVR-L1 sequence is RASQSVSSAVA (SEQ ID NO: 79) and the HVR-L2 sequence is SASSLYS (SEQ ID NO: 80), according to the library design. All clones had the same heavy chain and light chain framework sequences (see FIG. 6).

(B) Fab Production

For Fab production, phage supernatants from unique clones positive for the pentahistidine tag were used to infect *E. coli* FF34B8, a cell line in which the F' episome was added to the 34B8 strain by mating with XL1 and culturing in selective solid media. Infected cells were streaked on solid agar containing carbenicillin and grown overnight. Single colonies of FF34B8 containing phagemid were picked from the plates and grown overnight at 37° C. in LB containing carbenicillin. Those cultures were then used to inoculate 500 ml complete CRAP media (3.57 g $(NH_4)_2SO_4$, 0.71 g sodium citrate $2H_2O$, 1.07 g KCl, 5.36 g yeast extract (certified), 5.36 g Hycase SF (Sheffield), pH adjusted to 7.3 by addition of KOH and volume adjusted to 872 mL with ultrapure water, autoclaved, cooled to 55° C., to which was added (per L) 110 mL 1 M MOPS pH 7.3, 11 mL 50% glucose, and 7 mL 1 M $MgSO_4$) containing carbenicillin, and grown for 24 hours at 30° C. with agitation. Cells were harvested by centrifugation and the cell pellets were stored at −20° C. Fabs were purified by resuspending each cell pellet in 35 ml cold wash buffer (PBS+150 mM NaCl) containing 0.2 mg/ml lysozyme and 0.3 U/mL Dnase I.

Resuspended cell pellets were transferred to 50 ml centrifuge tubes and vortexed rapidly at 25° C. for 45 minutes. The pellets were centrifuged and the lysate was loaded on 1 ml protein G-sepharose columns preequilibrated with wash buffer at 4° C. The columns were washed with 50 ml cold wash buffer, eluted with 3 ml 0.1 M acetic acid, and neutralized with 150 µl of 2 M Tris base. The eluted Fabs were buffer-exchanged into PBS and concentrated using Centriprep 10 centrifuge filters (Millipore). The resulting Fab concentrations were determined spectrophotometrically (1 $OD_{280nm}$=1.55 mg/mL). The concentrated Fabs were stored at 4° C.

Each Fab was included in an ELISA protein assay, as described above, to determine its relative affinity for K48-linked and K63-linked polyubiquitin, and to confirm that the Fab was not reactive with monoubiquitin or BSA. The Fabs apu01-15 had greater specificity for K48-linked polyubiquitin than for K63-linked polyubiquitin. Fabs apu17-apu24 demonstrated greater specificity for K63-linked polyubiquitin than for K48-linked polyubiquitin in the ELISA. Apu16 was not produced as a Fab.

All Fabs were subjected to DNA sequence analysis. The amino acid sequences of hypervariable regions HVR-H1, HVR-H2, HVR-H3, and HVR-L3 for each Fab that bound specifically to K48-linked polyubiquitin are shown in FIGS. 10A-C. The amino acid sequences of hypervariable regions HVR-H1, HVR-H2, HVR-H3, and HVR-L3 for each Fab that bound specifically to K63-linked polyubiquitin are shown in FIGS. 11A-C. The heavy chain and light chain framework sequences for each Fab appear in FIG. 6. The first two light chain hypervariable regions, HVR-L1 and HVR-L2, were identical for each clone, according to the library design (see SEQ ID NOs: 79 and 80, above).

(C) Affinity Analysis of Isolated Fabs

Figure 13A:
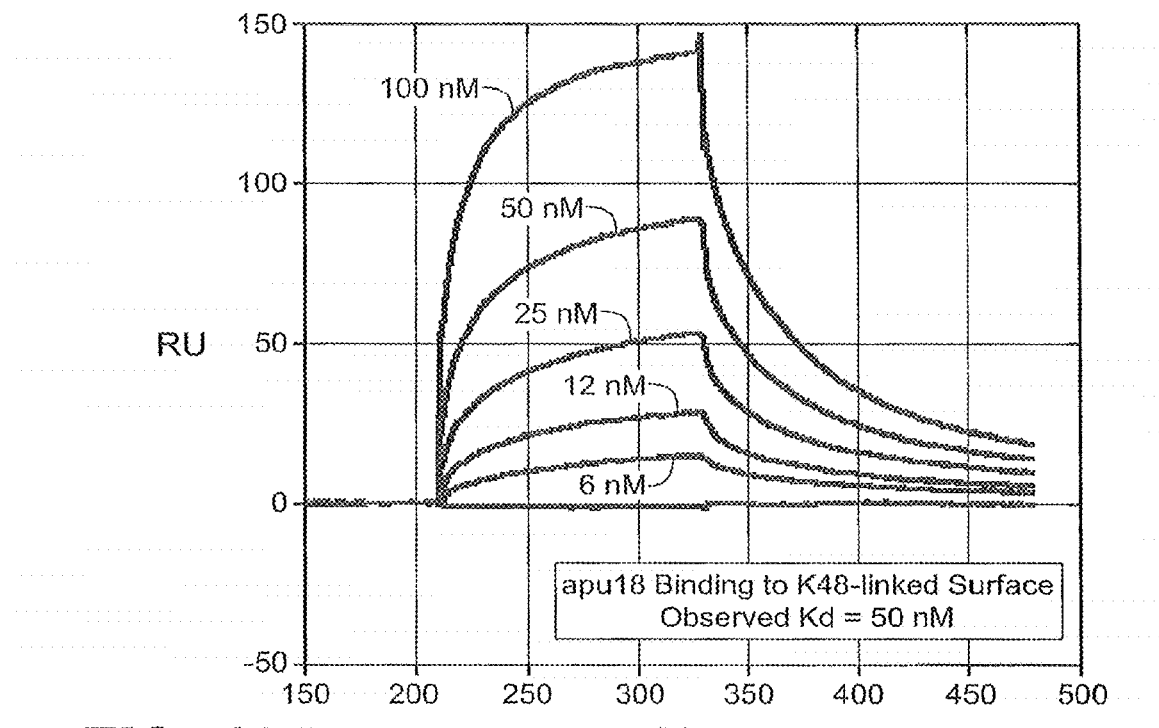
Figure 13B:
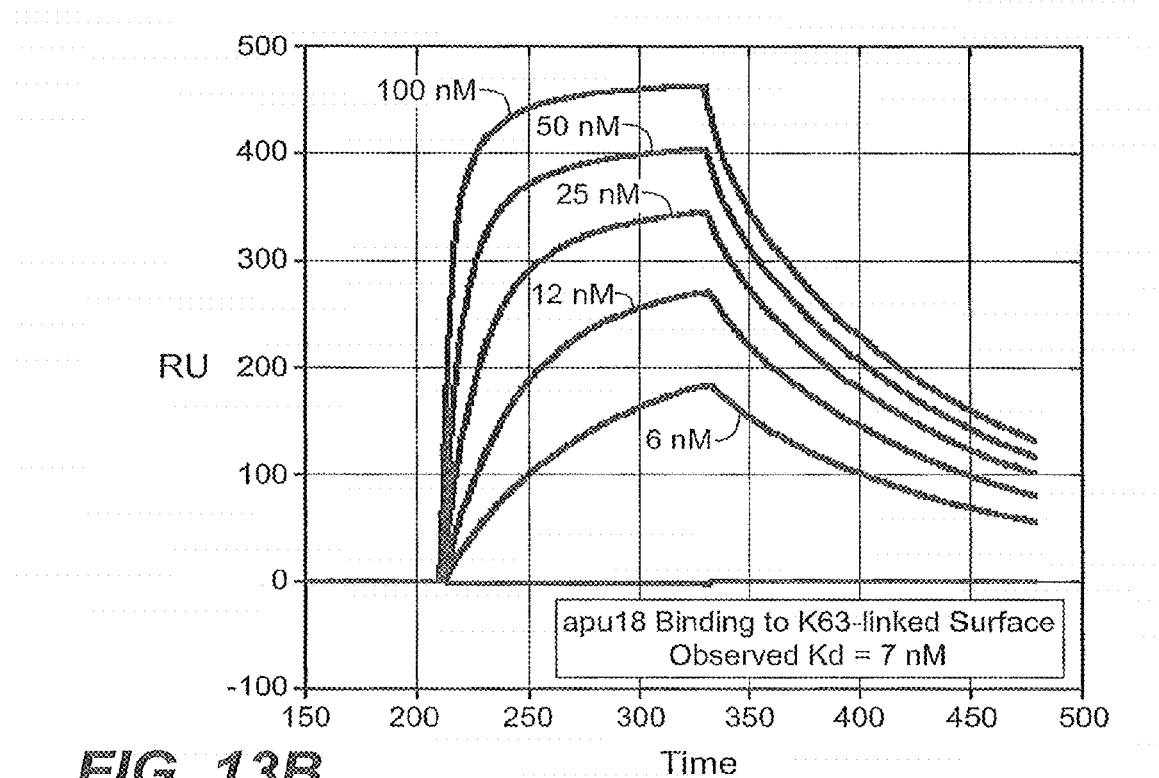

The affinities of selected Fabs (see section (B), above) for ubiquitin and its lysine-linked forms were determined by surface plasmon resonance using a BIACORE® 3000 system (Biacore). Approximately 100 resonance units of ubiquitin, K48- or K63-linked diubiquitin, or K48- or K63-linked polyubiquitin (chain lengths 3 to 7) were immobilized on different flow cells of CM5 chips using the amine coupling protocol supplied by the manufacturer. In each experiment, flow cell 1 was activated and ethanolamine-blocked without immobilizing protein, to be used for reference subtraction. Serial dilutions of Fab proteins (1.6-100 nM) of each of apu01 to apu24 were injected (50 µl total at a flow rate of 25 µl/minute) over each flow cell. The signal for each flow cell was recorded and the reference signal was subtracted. Following a dissociation period (5 minutes), the chip surface was regenerated with 13 µl of 20 mM HCl. Exemplary binding curves for the Fabs apu09 and apu18 are shown in FIGS. 12 and 13. Apu09 binds to K48-linked polyubiquitin, but not to K63-linked polyubiquitin, as shown in FIG. 12. FIG. 13A shows the binding curves for apu18 to K48-linked polyubiquitin. While some binding is observed, it is substantially less than the binding observed to K63-linked polyubiquitin (FIG. 13B). Similar analyses were performed for each Fab.

Kinetic constants and binding constants were simultaneously calculated by nonlinear regression analysis using software provided by the manufacturer, and are shown in Table B. The language "NB" in Table B indicates that no binding was detected for the indicated interaction. The language "nd" in Table B indicates that no data was measured for the indicated interaction. The results show that the kinetic constants of a particular Fab for binding to diubiquitin are very similar to those for binding to a polyubiquitin. Thus, the Fabs appear to recognize a particular isopeptide linkage between two ubiquitin moieties.

TABLE B

Kinetic Constants of Anti-Polyubiquitin Fabs as Measured by BIACORE ® Analysis

| | K48-linked polyubiquitin | | | K63-linked polyubiquitin | | | K48-linked diubiquitin |
|---|---|---|---|---|---|---|---|
| | $k_{on}$ (1/M·s) | $k_{off}$ (1/s) | $K_d$ (nM) | $k_{on}$ (1/M·s) | $k_{off}$ (1/s) | $K_d$ (nM) | $k_{on}$ (1/M·s) |
| Apu01 | $1.92 \times 10^6$ | $3.49 \times 10^{-3}$ | 1.82 | | | NB | $3.28 \times 10^6$ |
| Apu02 | nd | nd | nd | nd | nd | nd | $5.46 \times 10^5$ |
| Apu03 | nd | nd | nd | nd | nd | nd | $4.79 \times 10^5$ |
| Apu04 | nd | nd | nd | nd | nd | nd | $5.38 \times 10^5$ |
| Apu05 | $1.69 \times 10^6$ | $4.16 \times 10^{-3}$ | 2.46 | | | NB | $3.70 \times 10^6$ |
| Apu06 | $1.04 \times 10^6$ | $6.58 \times 10^{-3}$ | 6.31 | | | NB | $2.60 \times 10^6$ |
| Apu07 | nd | nd | nd | nd | nd | nd | $1.05 \times 10^6$ |
| Apu08 | $9.04 \times 10^5$ | $8.71 \times 10^{-3}$ | 9.64 | | | NB | $1.12 \times 10^6$ |
| Apu09 | $1.05 \times 10^6$ | $9.79 \times 10^{-3}$ | 9.36 | | | NB | $1.81 \times 10^6$ |
| Apu 10 | $8.45 \times 10^5$ | $5.62 \times 10^{-3}$ | 6.65 | | | NB | $1.12 \times 10^6$ |
| Apu 11 | nd | nd | nd | nd | nd | nd | $9.04 \times 10^5$ |
| Apu 12 | $5.73 \times 10^5$ | $7.07 \times 10^{-3}$ | 12.30 | | | NB | $3.13 \times 10^5$ |
| Apu 13 | nd | nd | nd | nd | nd | nd | $1.15 \times 10^5$ |
| Apu 14 | $1.58 \times 10^6$ | $1.08 \times 10^{-2}$ | 6.85 | | | NB | $3.18 \times 10^6$ |
| Apu 15 | nd | nd | nd | nd | nd | nd | $6.91 \times 10^5$ |
| Apu 16 | nd | nd | nd | nd | nd | nd | nd |
| Apu 17 | nd | nd | nd | nd | nd | nd | |
| Apu 18 | $2.32 \times 10^5$ | 0.0169 | 72.80 | $1.09 \times 10^6$ | $8.17 \times 10^{-3}$ | 7.53 | $1.73 \times 10^6$ |
| Apu 18* | | | | | | | $3.16 \times 10^5$ |
| Apu 19 | | | NB | | | NB | |
| Apu 20 | nd | nd | nd | nd | nd | nd | |
| Apu21 | nd | nd | nd | nd | nd | nd | |
| Apu22 | nd | nd | nd | $1.53 \times 10^5$ | 0.0191 | 125.00 | $6.19 \times 10^5$ |
| Apu23 | nd | nd | nd | nd | nd | nd | |
| Apu24 | nd | nd | nd | nd | nd | nd | |

TABLE B-continued

Kinetic Constants of Anti-Polyubiquitin Fabs as Measured by BIACORE ® Analysis

|  | K48-linked diubiquitin | | K63-linked diubiquitin | | |
| --- | --- | --- | --- | --- | --- |
|  | $k_{off}$ (1/s) | $K_d$ (nM) | $k_{on}$ (1/M·s) | $k_{off}$ (1/s) | $K_d$ (nM) |
| Apu01 | $1.38 \times 10^{-2}$ | 4.20 | | | NB |
| Apu02 | $6.96 \times 10^{-3}$ | 12.70 | | | NB |
| Apu03 | $5.33 \times 10^{-3}$ | 11.10 | $8.27 \times 10^4$ | 0.0112 | 135.00 |
| Apu04 | $5.89 \times 10^{-3}$ | 10.90 | $3.70 \times 10^5$ | 0.0232 | 62.70 |
| Apu05 | $1.46 \times 10^{-2}$ | 3.94 | | | NB |
| Apu06 | $2.20 \times 10^{-2}$ | 8.5 | | | NB |
| Apu07 | $9.93 \times 10^{-3}$ | 9.49 | | | NB |
| Apu08 | 0.0127 | 11.30 | | | NB |
| Apu09 | 0.0169 | 9.32 | | | NB |
| Apu 10 | 0.016 | 14 | | | NB |
| Apu 11 | 0.0177 | 19.60 | | | NB |
| Apu 12 | 0.0108 | 34.50 | | | NB |
| Apu 13 | 0.016 | 139.00 | | | NB |
| Apu 14 | $2.66 \times 10^{-2}$ | 8.35 | | | NB |
| Apu 15 | $7.31 \times 10^{-3}$ | 10.60 | 1.28 | 0.0212 | 1650.00 |
| Apu 16 | nd | nd | nd | nd | nd |
| Apu 17 | | NB | | | NB |
| Apu 18 | $1.95 \times 10^{-2}$ | 11.30 | $1.69 \times 10^6$ | $1.75 \times 10^{-2}$ | 10.40 |
| Apu 18* | $1.48 \times 10^{-2}$ | 46.90 | $1.01 \times 10^6$ | $1.54 \times 10^{-2}$ | 15.30 |
| Apu 19 | | NB | | | NB |
| Apu 20 | | NB | | | NB |
| Apu21 | | NB | | | NB |
| Apu22 | $1.28 \times 10^{-2}$ | 20.70 | nd | nd | nd |
| Apu23 | | NB | | | NB |
| Apu24 | | NB | | | NB |

*A second Biacore analysis of Apu18 confirmed the previously obtained kinetic constants for the K63-linked diubiquitin interaction.

(D) Western Blot

Tetraubiquitin (K48-linked or K63-linked as appropriate) and diubiquitin (either K48-linked or K63-linked) (Boston Biochem) were separated in polyacrylamide gels and transferred by electroblotting to nitrocellulose membranes. Nonspecific binding sites on the membranes were blocked by incubating the membranes overnight at 4° C. in 0.5% Qiagen blocking reagent (Qiagen). The blocked membranes were placed in a miniblotter apparatus. Fab clones (1 µg/ml) were applied to serial sections of the membrane in 0.5% Qiagen blocking reagent (Qiagen). After a one hour incubation period, the membranes were washed. Anti-ubiquitin antibodies bound to the membrane were revealed using HRP-conjugated anti-penta-histidine antibody (Qiagen) according to the manufacturer's instructions.

The K48-linked polyubiquitin-specific Fabs produced from clones apu01 to apu15 specifically bound to K48-linked tetraubiquitin immobilized to nitrocellulose (see FIG. 19B). No binding of the K63-linked polyubiquitin-specific Fabs produced from clones apu17 to apu24 was observed to K63-linked polyubiquitin immobilized on nitrocellulose membranes (see FIG. 19A).

Example 2

Isolation and Characterization of Second Generation Anti-Polyubiquitin Antibodies Second generation libraries for Fab display were constructed from the phagemids encoding the previously identified clones apu05 (K48-linked polyubiquitin-selective) and apu18 (K63-linked polyubiquitin-selective) (see FIGS. 10 and 11). Phage from those clones were used to infect CJ236 cells to prepare Kunkel DNA templates. Those templates were subsequently mutagenized to insert stop codons, and the stop-containing templates were used in library construction as follows.

The Fab apu05 was mutagenized according to two different schemes to create two different apu05-derived libraries. In the first library, only HVR-H3 was mutagenized. HVR-H3 was first modified to include a stop codon in the Kunkel template, followed by a mutagenesis utilizing four mutagenic oligonucleotides. The stop codon-encoding oligonucleotide in all cases was CGTCTATTATTGT-GCTCGCTAATAAGACTACTGGGGTCAAGG (SEQ ID NO: 365). The first three mutagenic oligonucleotides were three permutations of the same desired sequence, in which one tyrosine residue was fixed and each remaining tyrosine residue was randomized using the NNS mixed codon set (where N corresponds to G, C, A, or T and S corresponds to G or C); the amino acid at position 100b was selected from phenylalanine, methionine, leucine, and isoleucine; the amino acid at position 100a was selected from glycine and alanine; and the remaining amino acids were soft randomized. Soft randomization in this context indicates that certain nucleotide positions were 70% of the time occupied by the indicated base and 10% of the time occupied by one of the other three bases. For those oligonucleotides that follow, where such soft randomization was included at a particular base, the presence of the soft randomization is indicated by the presence of a number at that base position. The number "5" indicates that the base adenine is present 70% of the time at that position, while the bases guanine, cytosine, and thymine are each present 10% of the time. Similarly, the number "6" refers to guanine, "7" to cytosine, and "8" to thymine, where in each case, each of the other three bases is present only 10% of the time. The first three mutagenic oligonucleotide sequences were: CGTCTATTATTG-TGCTCGC567TAC567NNSNNS567GSTWTSGACTA CTGGGGTCAAGG (SEQ ID NO: 367), CGTCTATTATTGTGCTCGC567NNS567TACNNS567 GSTWTSGACTACTGGGGTCAAGG (SEQ ID NO: 368), and CGTCTATTATTGTGCTCGC567

NNS567NNSTAC567GSTWTSGACTACTGGGGTCAAGG (SEQ ID NO: 369). The fourth mutagenic oligonucleotide included randomization of the tyrosines at positions 96, 98, and 99 using the NNS mixed codon set; selection of the amino acid at position 100b from phenylalanine, methionine, leucine, and isoleucine; selection of the amino acid at position 100a from glycine and alanine, and soft randomization at every other position, in keeping with the soft randomization nomenclature described above. The sequence of the fourth oligonucleotide was CGTCTATTATTGTGCTCGC567NNS567NNSNNS5-67GSTWTSGACTACTGGGGTCAAGG (SEQ ID NO: 370).

In the second apu05 library, HVR-H1, HVR-H2, HVR-H3, and HVR-L3 were mutagenized. HVR-H1 was modified such that the serines at positions 30 and 33 were randomized using the NNS mixed codon set (where N corresponds to G, C, A, or T and S corresponds to G or C); the amino acid at position 29 was selected from amino acids phenylalanine, leucine, isoleucine, and valine; and the amino acid at position 34 was selected from isoleucine and methionine. The oligonucleotides used to mutagenize apu05 HVR-H1 were GCAGCTTCTGGCTTCAACTAATAACACTGGGT-GCGTCAGG (SEQ ID NO: 371) and GCAGCTTCTGGCT-TCAACNTCNNSTACTCTNNSATSCACTGGGTGC GTCAGG (SEQ ID NO: 372). HVR-H2 was modified such that the tyrosine at position 52 was randomized using the NNS mixed codon set and the amino acid at position 52a was selected from proline and serine. The oligonucleotides used to mutagenize HVR-H2 were GGCCTGGAATGGGT-TGCATAATAATATGCCGATAGCGTCAAGG (SEQ ID NO: 373) and GGCCTGGAATGGGTTGCATC-TATCNNSYCTTACTACTCTTACACCTCTTATGCCGA-TAGCG TCAAGG (SEQ ID NO: 374). HVR-H3 was modified such that the tyrosine at position 99 and the serine at position 100 were randomized using the NNS mixed codon set; the amino acid at position 100a was selected from glycine and alanine; and the amino acid at position 100b was selected from phenylalanine, methionine, leucine, and isoleucine. The oligonucleotides used to mutagenize HVR-H3 were CGTCTATTATTGTGCTCGCTAATAAGAC-TACTGGGGTCAAGG (SEQ ID NO: 365) and CGTCTAT-TATTGTGCTCGCTCTTACTCTTACNNSNNSGSTWTS-GACTACTGGGGTCA AGG (SEQ ID NO: 375). HVR-L3 was modified such that position S91 was randomized according to the NNS mixed codon set and position I96 was selected from phenylalanine, isoleucine, and valine. The oligonucleotides used to mutagenize HVR-L3 were CGCAACTTATTACTGTCAGCAATAATAAACGTTCG-GACAGGGTACC (SEQ ID NO: 376) and CGCAACTT-ATTACTGTCAGCAANNSTCTTACTCTTCTCTGDT-TACGTTCGGACAGGGTACC (SEQ ID NO: 378).

Six different apu18-derived libraries were made by six different mutagenesis schemes of apu18. In the first library, only HVR-H3 was mutagenized. HVR-H3 was first modified to include a stop codon in the Kunkel template, followed by a mutagenesis methodology utilizing seven mutagenic oligonucleotides. The stop-codon-encoding oligonucleotide in all cases was CGTCTATTATTGT-GCTCGCTAATAAGACTACTGGGGTCAAGG (SEQ ID NO: 366). The first six mutagenic oligonucleotides were six permutations of the same desired sequence, in which two tyrosine or tryptophan residues were fixed and each remaining tyrosine and tryptophan residue was randomized using the NNS mixed codon set (where N corresponds to G, C, A, or T and S corresponds to G or C); the amino acid at position 100c was selected from phenylalanine, methionine, leucine, and isoleucine; the amino acid at position 100b was selected from glycine and alanine; and the remaining amino acids were soft randomized in keeping with the soft randomization nomenclature described above. The first six mutagenic oligonucleotide sequences were:
CGTCTATTATTGTGCTCGC655TACTAC565NNSNN-S577GSTWTSGACTACTGGGGTCAAGG (SEQ ID NO: 379),
CGTCTATTATTGTGCTCGC655NNSNNS565TGGTA-C577GSTWTSGACTACTGGGGTCAAGG (SEQ ID NO: 380),
CGTCTATTATTGTGCTCGC655TACBBS565NNSTA-C577GSTWTSGACTACTGGGGTCAAGG (SEQ ID NO: 381),
CGTCTATTATTGTGCTCGC655NNSTAC565TGGNN-S577GSTWTSGACTACTGGGGTCAAGG (SEQ ID NO: 382),
CGTCTATTATTGTGCTCGC655TACNNS565TGGNN-S577GSTWTSGACTACTGGGGTCAAGG (SEQ ID NO: 383), and
CGTCTATTATTGTGCTCGC655NNSTAC565NNSTA-C577GSTWTSGACTACTGGGGTCAAGG (SEQ ID NO: 384). The seventh mutagenic oligonucleotide included randomization of the tyrosines at positions 96, 97, and 100 and the tryptophan at position 99 using the NNS mixed codon set; selection of the amino acid at position 100b from phenylalanine, methionine, leucine, and isoleucine; selection of the amino acid at position 100c from phenylalanine, methionine, leucine, and isoleucine; selection of the amino acid at position 100b from glycine and alanine, and soft randomization at every other position, in keeping with the soft randomization nomenclature described above. The sequence of the seventh oligonucleotide was:
CGTCTATTATTGTGCTCGC655NNSNNS565NNSNNS-577GSTWTSGACTACTGGGGTCAAGG (SEQ ID NO: 385).

In the second apu18 library, only HVR-H2 was mutagenized. HVR-H2 was first modified to include a stop codon in the Kunkel template, followed by a mutagenesis methodology utilizing four mutagenic oligonucleotides. The stop codon-encoding oligonucleotide in all cases was GGCCTG-GAATGGGTTGCATAATAATATGCCGATAGCGT-CAAGG (SEQ ID NO: 373). The first three mutagenic oligonucleotides were three permutations of the same desired sequence, in which one tyrosine residue was fixed and each remaining tyrosine and the serine at position 52 were randomized using the NNS mixed codon set (where N corresponds to G, C, A, or T and S corresponds to G or C); the amino acid at position 52a was selected from proline and serine; the amino acid at position 55 was selected from glycine and serine; the isoleucine and position 51 and the threonine at position 57 were fixed; and the remaining amino acids were soft randomized in keeping with the soft randomization nomenclature described above. The first three mutagenic oligonucleotide sequences were:
GGCCTGGAATGGGTTGCATACATCNNSYCTNNSN-NSRGC567ACC567TATGCCGATAGCGT CAAGG (SEQ ID NO: 386),
GGCCTGGAATGGGTTGCANNSATCNNSYCTTACN-NSRGC567ACC567TATGCCGATAGCGT CAAGG (SEQ ID NO: 387), and
GGCCTGGAATGGGTTGCANNSATCNNSYCTNNST-ACRGC567ACC567TATGCCGATAGCGT CAAGG (SEQ ID NO: 388). The fourth mutagenic oligonucleotide included randomization of the tyrosines at positions 50, 53, and 54 using the NNS mixed codon set; selection of the amino acid at position 52a from phenylalanine and serine;

selection of the amino acid at position 55 from glycine and serine; fixing the isoleucine and threonine residues at positions 51 and 57, respectively; and soft randomization at every other position, in keeping with the soft randomization nomenclature described above. The sequence of the fourth oligonucleotide was:
GGCCTGGAATGGGTTGCANNSATCNNSYCTNNSNN-SRGC567ACC567TATGCCGATAGCGT CAAGG (SEQ ID NO: 389).

In the third apu18 library, HVR-H2 and HVR-H3 were mutagenized. HVR-H2 was modified identically to the modifications made to HVR-H2 in the second apu18 library, using the same four mutagenic oligonucleotides. HVR-H3 was modified identically to the modifications made to HVR-H3 in the first apu18 library, using the same first six mutagenic oligonucleotides.

In the fourth apu18 library, HVR-H3 and HVR-L3 were mutagenized. HVR-H3 was modified identically to the modifications made to HVR-H3 in the first apu18 library, using the same first six mutagenic oligonucleotides. HVR-L3 was first modified to include a stop codon in the Kunkel template, followed by a mutagenesis using a mutagenic oligonucleotide. Within HVR-L3, the tyrosines at positions 91 and 94 and the serine at position 95a were randomized using the NNS mixed codon set; the leucine at position 95b was selected from phenylalanine, isoleucine, and valine; and the serines at positions 92, 93, and 95 were soft randomized in keeping with the soft randomization nomenclature described above. The oligonucleotides used for the mutagenesis of HVR-L3 were CGCAACTTATTACTGTCAG-CAATAATAAACGTTCGGACAGGGTACC (SEQ ID NO: 376) and CGCAACTTATTACTGTCAGCAANN-S567567NNS567NNSCTGDTTACGTTCGGACAGGGTACC (SEQ ID NO: 390).

In the fifth apu18 library, HVR-H1 and HVR-H2 were mutagenized. HVR-H2 was modified identically to the modifications made to HVR-H2 in the second apu18 library, using the same four mutagenic oligonucleotides. HVR-H1 was modified to include a stop codon; the serine at position 30 and the tyrosine at position 33 were randomized using the NNS mixed codon set; the amino acid at position 29 was selected from phenylalanine, leucine, isoleucine, and valine; the amino acid at position 34 was selected from isoleucine and methionine, and the amino acids at positions 31 and 32 were soft randomized in keeping with the soft randomization nomenclature described above. The oligonucleotides used for the mutagenesis of HVR-H1 were:
GCAGCTTCTGGCTTCAACTAATAACACTGGGT-GCGTCAGG (SEQ ID NO: 371) and
GCAGCTTCTGGCTTCAACNTCNNS567567NNSA-TSCACTGGGTGCGTCAGG (SEQ ID NO: 391).

In the sixth apu18 library, HVR-H1, HVR-H2 and HVR-L3 were mutagenized. HVR-H1 was modified identically to the modifications made to HVR-H1 in the fifth apu18 library, using the same mutagenic oligonucleotide. HVR-H2 was modified identically to the modifications made to HVR-H2 in the second apu18 library, using the same four mutagenic oligonucleotides. HVR-L3 was modified identically to the modifications made to HVR-L3 in the fourth apu18 library, using the same mutagenic oligonucleotide.

Mutagenesis reactions for each of the two apu5-derived libraries and each of the six apu18-derived libraries were transformed into electrocompetent *E. coli* XL-1 by electroporation. Cells were allowed to recover for 30 minutes at 37° C. with agitation in SOC medium. Twenty microliters of the cell-containing SOC medium was reserved to determine the number of transformants, and the remainder was then transferred to 500 ml 2YT containing carbenicillin and $10^{10}$ M13K07 helper phage per milliliter. After 45 minutes at 37° C. with agitation, the broth was supplemented with kanamycin and grown overnight at 37° C. with agitation. The number of transformants for each library was >$10^9$. Phage were harvested and concentrated from the broth by centrifugation and PEG precipitation, and subsequently used in rounds of selection.

K48-linked polyubiquitin and K63-linked polyubiquitin were immobilized on different Maxisorp plates (NUNC) as described above in Example 1(A). Each library was sorted separately against its respective target (K48-linked polyubiquitin for the two apu05-derived libraries, K63-linked polyubiquitin for the six apu18-derived libraries) for one round with the addition of 3 μM monoubiquitin in the sorting buffer. The eluted phage were amplified and pooled (two pools, one for each lysine-linked polyubiquitin target) for further rounds of sorting.

Subsequent selection rounds were solution-phase sorted. Phage pools were incubated with biotinylated (Sulfo-NHS-biotin, Pierce) polyubiquitin chains for one to two hours at room temperature in solution-sorting buffer (PBST with 0.5% Superblock (Pierce)). The mixture was diluted five- to ten-fold in solution-sorting buffer and added to neutravidin-coated wells for a brief (5 minute) capture of biotinylated polyubiquitin. A reaction containing unbiotinylated polyubiquitin chains served as a control to monitor background phage binding. The plates were washed with PBST and eluted with 0.1 M HCl for 10 minutes.

Stringency was modulated in three ways: by the concentration of biotinylated polyubiquitin; by the addition of excess unbiotinylated polyubiquitin to compete for binding before capture on neutravidin-coated wells; and by the duration of the competition. For each round of sorting, monoubiquitin and polyubiquitin of the other linkage was added at a concentration of 30 μg/ml to the sorting buffer during the first incubation step. The first round of solution sorting employed 20 nM biotinylated polyubiquitin incubated with phage for one hour at room temperature. The mixture was then diluted tenfold in solution-sorting buffer, and captured using neutravidin-coated wells for five minutes. For the second round phage was equilibrated with 20 nM biotinylated polyubiquitin, as in round 1, but was diluted tenfold in solution-sorting buffer containing 30 μg/ml of unbiotinylated polyubiquitin (K48-linked for K48 selection, K63-linked for K63 selection) for fifteen minutes of off-rate selection followed by capture on neutravidin coated wells. The third round of solution sorting was as described for the second round, but further included 5 nM biotinylated polyubiquitin and 30 minutes of off-rate selection. After one round of plate sorting and three rounds of solution sorting, individual clones selected from the second generation were grown in a 96 well format as described. Individual clones were screened by phage ELISA and sequenced.

After the first round of solution sorting, up to 40 times enrichment was observed for the libraries based on apu05 and up to 7-fold enrichment for the libraries based on apu18 (see Table C). An additional 11-fold enrichment was obtained for the K48-specific clones and an additional 3-fold enrichment for the K63-specific clones after the second selection (solution sort for slow off rate) (see Table C). The third selection (both affinity sorting and off-rate sorting) resulted in an 18-fold enrichment for the K48-specific clones and a four-fold enrichment for the K63-specific clones (see Table C).

TABLE C

Results from Second Generation Anti-Polyubiquitin Antibody Library Solution Sorting First Selection (solution sort for affinity)

| | 5 nM | | 10 nM | | 20 nM | |
| --- | --- | --- | --- | --- | --- | --- |
| | Size | Enrichment | Size | Enrichment | Size | Enrichment |
| Based on apu05 | $2.00 \times 10^4$ | 20.00 | $3.00 \times 10^4$ | 30.00 | $4.00 \times 10^4$ | 40 |
| Based on apu18 | $2.20 \times 10^3$ | 1.83 | $2.00 \times 10^3$ | 1.67 | $8.40 \times 10^3$ | 7 |

Second Selection (solution sort for slow off rate)

| | 5 min | | 10 min | | 15 min | |
| --- | --- | --- | --- | --- | --- | --- |
| | Size | Enrichment | Size | Enrichment | Size | Enrichment |
| Based on apu05 | $4.00 \times 10^4$ | 17.78 | $4.00 \times 10^4$ | 17.78 | $2.50 \times 10^4$ | 11.11 |
| Based on apu18 | $5.50 \times 10^3$ | 4.07 | $7.00 \times 10^3$ | 5.19 | $4.50 \times 10^3$ | 3.33 |

Third Selection (solution sort for both affinity and slow off rate)

| | 5 nM and 30 min | |
| --- | --- | --- |
| | Size | Enrichment |
| Based on apu05 | $4.70 \times 10^3$ | 18.60 |
| Based on apu18 | $1.00 \times 10^2$ | 4.25 |

Sixty-eight unique clones were identified which bound specifically to K48-linked polyubiquitin; those clones were subjected to DNA sequence analysis. The HVR-H1, HVR-H2, and HVR-H3 sequences of those clones are shown in FIGS. 14A-F. Thirty-one unique clones were identified which bound specifically to K63-linked polyubiquitin; those clones were also subjected to sequence analysis. The HVR-H1, HVR-H2, and HVR-H3 sequences of those clones are shown in FIGS. 15A-C. The light chain HVR for each of the K48-linked polyubiquitin and K63-linked polyubiquitin-specific clones were not sequenced, but, as with apu05 and apu18, the sequences of HVR-L1 and HVR-L2 were expected to be invariant, while the HVR-L3 sequence was expected to be clone-specific. The HVR-L1 sequence is RASQSVSSAVA (SEQ ID NO: 79) and the HVR-L2 sequence is SASSLYS (SEQ ID NO: 80), according to the library design. All clones had the same heavy chain and light chain framework sequences (see FIG. 6).

The twenty clones with the greatest observed binding (ten K48-linked polyubiquitin-specific and ten K63-linked polyubiquitin-specific) were produced as Fabs as described in Example 1. Fabs apu2.01 through apu2.20 were subjected to DNA sequence analysis. The HVR-H1, HVR-H2, HVR-H3, and HVR-L3 sequences of those clones are shown in FIGS. 16A and B (K48-specific Fabs) and 17A and B (K63-specific Fabs).

Fabs apu2.01 through apu2.20 were included in an ELISA protein assay to determine their relative affinities for K48-linked and K63-linked polyubiquitin, and to confirm that the Fabs was not reactive with monoubiquitin or BSA (see FIG. 18). Apu clones 2.11 and 2.12 each demonstrated about 300 times greater affinity for K63-linked polyubiquitin than for K48-linked polyubiquitin in that assay. Apu2.20 and 2.16 had lesser, but still marked differences (about 30 times greater and about 10 times greater, respectively) in affinity for K63-linked polyubiquitin as compared to K48-linked polyubiquitin. No binding of clones apu2.01-apu2.10 to K63-linked poly- or diubiquitin was detected.

Each Fab was also analyzed by BIAcore as described previously in Example 1(C). The obtained kinetic constants and binding constants are shown in Table D. The language "NB" in Table D indicates that no binding was detected for the indicated interaction.

TABLE D

Kinetic Constants of Anti-Polyubiquitin Fabs as Measured by BIAcore Analysis

| | K63-linked polyubiquitin | | | K48-linked diubiquitin | | | K63-linked diubiquitin | | |
| --- | --- | --- | --- | --- | --- | --- | --- | --- | --- |
| | $k_{on}$ (1/M·s) | $k_{off}$ (1/s) | $K_d$ (nM) | $k_{on}$ (1/M·s) | $k_{off}$ (1/s) | $K_d$ (nM) | $k_{on}$ (1/M·s) | $k_{off}$ (1/s) | $K_d$ (nM) |
| Apu2.01 | | | NB | $6.33 \times 10^5$ | $1.49 \times 10^{-2}$ | 23.5 | | | NB |
| Apu2.02 | | | NB | $1.11 \times 10^6$ | $1.01 \times 10^{-2}$ | 9.16 | | | NB |
| Apu2.03 | | | NB | $8.67 \times 10^5$ | $2.66 \times 10^{-3}$ | 3.07 | | | NB |
| Apu2.04 | | | NB | $6.22 \times 10^5$ | $9.39 \times 10^{-3}$ | 15.10 | | | NB |
| Apu2.05 | | | NB | $1.20 \times 10^6$ | $6.09 \times 10^{-3}$ | 5.06 | | | NB |
| Apu2.06 | | | NB | $1.28 \times 10^6$ | $2.40 \times 10^{-3}$ | 1.87 | | | NB |
| Apu2.07 | | | NB | $2.70 \times 10^6$ | $3.18 \times 10^{-3}$ | 1.18 | | | NB |
| Apu2.08 | | | NB | $1.25 \times 10^6$ | $7.21 \times 10^{-3}$ | 5.76 | | | NB |
| Apu2.09 | | | NB | $7.15 \times 10^5$ | $4.78 \times 10^{-3}$ | 6.69 | | | NB |
| Apu2.10 | | | NB | $3.28 \times 10^6$ | $3.99 \times 10^{-3}$ | 1.21 | | | NB |
| Apu05 | | | NB | $2.44 \times 10^6$ | $1.07 \times 10^{-2}$ | 4.37 | | | NB |
| Apu2.11 | $2.49 \times 10^5$ | $7.11 \times 10^{-3}$ | 28.6 | $1.68 \times 10^4$ | $1.24 \times 10^{-2}$ | 738 | $3.12 \times 10^5$ | $1.02 \times 10^{-2}$ | 32.7 |
| Apu2.12 | $4.76 \times 10^5$ | $9.68 \times 10^{-3}$ | 20.3 | $5.66 \times 10^3$ | $7.88 \times 10^{-3}$ | 1390 | $5.49 \times 10^5$ | $1.51 \times 10^{-2}$ | 27.5 |
| Apu2.13 | $4.89 \times 10^5$ | $2.41 \times 10^{-3}$ | 4.93 | $2.08 \times 10^5$ | $2.15 \times 10^{-2}$ | 103 | $5.83 \times 10^5$ | $4.11 \times 10^{-3}$ | 7.05 |
| Apu2.14 | $2.09 \times 10^5$ | $7.08 \times 10^{-3}$ | 34.0 | $4.97 \times 10^3$ | $1.15 \times 10^{-2}$ | 2310 | $2.14 \times 10^5$ | $1.06 \times 10^{-2}$ | 49.6 |
| Apu2.15 | $9.07 \times 10^5$ | $9.98 \times 10^{-3}$ | 11.0 | $1.43 \times 10^4$ | $1.23 \times 10^{-2}$ | 856 | $1.10 \times 10^6$ | $1.55 \times 10^{-2}$ | 14.0 |
| Apu2.16 | $1.68 \times 10^5$ | $1.80 \times 10^{-2}$ | 107 | $4.11 \times 10^1$ | $1.73 \times 10^{-3}$ | 42000 | $1.38 \times 10^5$ | $1.27 \times 10^{-2}$ | 92.1 |
| Apu2.17 | $1.19 \times 10^6$ | $1.35 \times 10^{-2}$ | 11.3 | $6.90 \times 10^3$ | $2.73 \times 10^{-3}$ | 396 | $1.13 \times 10^6$ | $2.89 \times 10^{-2}$ | 25.6 |
| Apu2.18 | $1.48 \times 10^5$ | $1.89 \times 10^{-2}$ | 128 | $4.98 \times 10^3$ | $5.36 \times 10^{-3}$ | 1080 | $2.66 \times 10^5$ | $2.53 \times 10^{-2}$ | 95.0 |
| Apu2.19 | $8.97 \times 10^5$ | $8.47 \times 10^{-3}$ | 9.44 | $2.54 \times 10^5$ | $1.24 \times 10^{-2}$ | 48.9 | $8.76 \times 10^5$ | $1.41 \times 10^{-2}$ | 16.1 |
| Apu2.20 | $2.93 \times 10^5$ | $1.77 \times 10^{-2}$ | 60.7 | $4.02 \times 10^3$ | $3.77 \times 10^{-3}$ | 939 | $4.19 \times 10^5$ | $2.50 \times 10^{-2}$ | 59.7 |
| Apu18 | $1.09 \times 10^6$ | $8.17 \times 10^{-3}$ | 7.53 | $3.16 \times 10^5$ | $1.48 \times 10^{-2}$ | 46.9 | $1.01 \times 10^6$ | $1.54 \times 10^{-2}$ | 15.3 |

Several of the Fabs based on apu05 had $K_d$s lower than that of the Fab corresponding to apu05 for K48-linked diubiquitin, representing tighter binding to polyubiquitin. Each of the apu2.11-2.20 Fabs bound not only to K63-linked polyubiquitin but also, to a lesser extent, to K48-linked diubiquitin. While only apu2.13 had a lower Kd than apu18, its Kd for K48-linked diubiquitin was larger than that of apu18. Each of apu 2.11, 2.12, 2.16, and 2.20 had better ratios of Kd for K63-linked polyubiquitin to Kd for K48-linked diubiquitin than apu18. The observed kinetic constants for binding of the apu18-based Fabs to K63-linked polyubiquitin were similar to those observed for binding to K63-linked diubiquitin.

The ability of each Fab to specifically bind to polyubiquitin immobilized to a nitrocellulose membrane was also assessed by Western blot as previously described in Example 1(D). Tetraubiquitin containing either a K48 or K63 linkage, diubiquitin containing the opposite lysine linkage from that of the tetraubiquitin (e.g., K63-linked diubiqitin when K48-linked tetraubiquitin was used, or K48-linked diubiquitin when K63-linked tetraubiquitin was used), and monoubiquitin were immobilized to nitrocellulose membranes, and Fabs apu2.01-2.20 were assessed for their abilities to recognize all three immobilized molecules (FIGS. 20A and 20B). None of the Fabs specifically recognized monoubiquitin. Apu2.01-apu2.10 each specifically recognized immobilized K48-linked tetraubiquitin but did not recognize immobilized K63-linked diubiquitin (see FIG. 20A). Several other bands appeared on the blot which represent contaminant tri-, penta-, and octaubiquitin species in the K48-linked tetraubiquitin preparation. Apu2.11-apu2.20 specifically recognized immobilized K63-linked tetraubiquitin and did not recognize immobilized K48-linked diubiquitin (see FIG. 20B).

Example 3

Binding of Anti-Polyubiquitin Antibodies to Endogenously Polyubiquitinated Proteins Previous experiments had demonstrated that the activity of Receptor Interacting Protein (RIP), a 140 kD essential mediator of the proximal TNF receptor 1 (TNFR1) signaling complex, is modulated by polyubiquitination (Wertz et al., Nature 430: 694-699 (2004)). When RIP is polyubiquitinated with K63-linked polyubiquitin chains, signaling through TNFR1 is facilitated. Removal of the K63-linked polyubiquitin chains from RIP by the de-ubiquitinating N-terminus of A20 and replacement with K48-linked polyubiquitin chains by the ubiquitin ligase function of the A20 C terminus inactivates RIP and targets it for proteasomal degradation. That mechanism had been elucidated using cell lines expressing mutant ubiquitin capable of forming only K48-linked or K63-linked polyubiquitin.

The ability of two of the anti-K48 and anti-K63-linked polyubiquitin binding proteins of the invention to specifically recognize the differently polyubiquitinated forms of RIP that exist in HeLa S3 cells at different time points after TNF treatment was assessed. Four liters of HeLa S3 cells at approximately $1.5 \times 10^6$ cells/mL were treated with 21 µM MG-132. Immediately after treatment, one liter of cells was removed from the main culture, harvested by centrifugation, washed with 200 mL PBS, and recentrifuged. This sample was used as the time zero time point. The remaining three liters of cell culture were treated with 100 ng/mL TNF. One liter of cells were removed, harvested, washed with 200 mL PBS, and recentrifuged at each of 5, 15, and 25 minutes after treatment with TNF. The cells from each time point were lysed in 30 mL of IP lysis buffer (LB) (20 mM Tris pH 7.5, 150 mM NaCl, 1% Triton x-100, 1 mM EDTA, 25 µM MG-132, 10 mM NEM, 30 µL of each of phosphatase inhibitor cocktails 1 and 2 (Sigma), and 1 Complete protease inhibitor tablet (Roche)) and incubated with rotation at 4° C. for 20-60 minutes. Each lysate was transferred to a 50 mL centrifuge tube and pelleted twice for five minutes at 10,000×g. The protein concentration of the lysate from each time point was estimated. Each lysate (30 mL for each time point with normalized protein concentrations) was incubated for 1.25-1.5 hours with 1 mL unblocked Protein A/G beads at 4° C. The beads and debris were separated from the lysate by centrifugation at 2000 rpm for 5 minutes. A sample was taken from each lysate for direct Western blot analysis, and the remaining volume was frozen at −80° C.

Four 16 mL samples of each lysate were taken. To each sample was added 25 mM MG-132 and 20 µL NEM. Two samples were each combined with 2.4 µg/mL of an anti-TNFR1 antibody. Two other samples were each combined with 2.4 µg/mL of a control antibody (anti-myc). All samples were incubated for two hours at 4° C. with rotation, followed by the addition of 150 µL of a 50% slurry of unblocked protein A beads. The samples were incubated at 4° C. for an additional 5 hours with rotation. The samples were pelleted by centrifugation, and the beads were washed once with 15 mL LB, twice with 10 mL LB containing 1 M NaCl, and twice with 10 mL LB. The washed beads were resuspended in 1.25 mL LB and transferred to microfuge tubes. Each sample was aspirated such that the tube contained a total volume of 950 µL, and 360 mg solid urea was added to each sample for a final concentration in each sample of 6M in urea. The samples were incubated for 15 minutes at room temperature with gentle agitation. The beads in each sample were pelleted by centrifugation. A portion of each supernatant was reserved for Western blot analysis, and the remaining supernatant from each sample (approximately 1 mL per sample) was diluted to 10 mL with dissociation dilution buffer (1% Triton-X100, 0.5% deoxycholate, 120 mM NaCl, 50 mM HEPES pH 7.2, and Complete protease inhibitor cocktail (Roche)).

Each sample was split into two five mL portions. One portion was treated with 2.5 µg apu2.16 that had been reformatted from the fab form to the IgG form, and the other was treated with 2.5 µg apu2.07 that had been reformatted from the fab form to the IgG form. To both samples were added 50 µL protein A beads, and the samples were incubated for 5 hours at 4° C. The protein A beads were pelleted and washed three times in TNFR1 LB, having been transferred to microfuge tubes during the washing process. Sample buffer was added to all samples, and each sample (including the samples previously reserved for Western blot analysis) was reduced and run on 10% tris/gly 1.5 mm 10-well Novex® gels (Invitrogen). After running, the proteins in the gels were transferred to Invitrolon™ PVDF membranes (Invitrogen) according to the manufacturer's instructions. The membranes were blocked with 5% PBS-T and probed with an anti-RIP monoclonal antibody (Becton Dickinson) overnight at room temperature. The blots were then washed, probed with HRP-conjugated goat anti-mouse secondary antibody (Cappel), washed, exposed to the reagent to activate chemiluminescence, and exposed to film. The results are shown in FIGS. 21A and 21B. FIG. 21A depicts the blot containing the samples first immunoprecipitated with TNFR1 or anti-myc and then immunoprecipitated with the apu2.16 IgG (K63-linked polyubiquitin selective). As shown in FIG. 21A, RIP is not visible in either the anti-myc control samples or in the zero time sample. The RIP band was strongest in the 5 minute sample, and then decreased significantly in the 15 and 25 minute samples. FIG. 21B depicts the blot containing the samples first immunoprecipitated with TNFR1 or anti-myc and then immunoprecipitated with the apu2.07 IgG (K48-linked polyubiquitin selective). As shown in FIG. 21B, no RIP was observed in the anti-myc control lanes. RIP levels in this blot increased over time, and were strongest in the 25 minute time point sample. This data correlates with the earlier findings that upon signaling through the TNFR1, RIP is first K63-linked polyubiquitinated, and then subsequently deubiquitinated and K48-linked polyubiquitinated by A20. Thus, the antibodies of the invention were able to specifically bind to and discriminate between a K63-linked polyubiquitinated polypeptide and a K48-linked polyubiquitinated polypeptide that had been polyubiquitinated in cells.

Example 4

Isolation and Characterization of Third Generation Anti-Polyubiquitin Antibodies Third generation libraries for Fab display were constructed from the phagemid encoding the previously identified clone apu2.16 (K63-linked polyubiquitin-selective) (see Example 2 and FIGS. 17A and 17B). Phage from that clone was used to infect CJ236 cells to prepare a Kunkel DNA template. That template was subsequently mutagenized to insert stop codons, and the stop-containing templates were used in library construction as follows.

The Fab apu2.16 was mutagenized according to three different schemes to create three different apu2.16-derived libraries. In the first library, HVR-H1 and HVR-H2 were mutagenized. HVR-H1 was mutagenized to include a stop codon in the Kunkel template, followed by a mutagenesis methodology utilizing one mutagenic oligonucleotide. The stop codon-encoding oligonucleotide sequence was: GCAGCTTCTGGCTTCAACTAATAACACTGGGTGCGTCAGG (SEQ ID NO: 371). The mutagenic oligonucleotide permitted the isoleucine at position 29 to be selected from phenylalanine, leucine, isoleucine, and valine; the isoleucine at position 34 to be selected from methionine and isoleucine using the NNS mixed codon set (where N corresponds to G, C, A, or T and S corresponds to G or C); and the soft-randomization of amino acids K30, T31, G32, and L33. Soft randomization in this context indicated that certain nucleotide positions were 70% of the time occupied by the indicated base and 10% of the time occupied by one of the other three bases. For those oligonucleotides that follow, where such soft randomization was included at a particular base, the presence of the soft randomization is indicated by the presence of a number at that base position. The number "5" indicates that the base adenine was present 70% of the time at that position, while the bases guanine, cytosine, and thymine were each present 10% of the time. Similarly, the number "6" refers to guanine, "7' to cytosine, and "8" to thymine, wherein in each case, each of the other three bases was present only 10% of the time. The oligonucleotide sequence used to mutagenize apu3.16 HVR-H1 was:
GCAGCTTCTGGCTTCAACNTC556577668788ATSCACTGGGTGCGTCAGG (SEQ ID NO: 785).

HVR-H2 was also modified to include a stop codon in the Kunkel template, followed by a mutagenesis utilizing three mutagenic oligonucleotides. The stop codon-encoding oligonucleotide in all cases was GGCCTGGAATGGGTTGCATAATAATATGCCGATAGCGTCAAGG (SEQ ID NO: 373). The three mutagenic oligonucleotides were two permutations of a first desired sequence, and one second desired sequence. The first desired sequence included: one fixed and one randomized tyrosine residue at either of positions 50 and 54 using the NNS mixed codon set (described above); fixed residues at positions 51 (isoleucine), 52a (proline), 53 (tyrosine), 55 (glycine), and 57 (threonine); and soft randomization of positions S52, S56, and S58 (according to the soft randomization scheme described above). The second desired sequence included: fixed residues at positions 51 (isoleucine), 52a (proline), 53 (tyrosine), 55 (glycine), and 57 (threonine); hard randomization of the tyrosines at positions 50 and 54 using the NNS mixed codon set (described above), and soft randomization of positions S52, S56, and S58 (according to the soft randomization scheme described above.) The oligonucleotides used to mutagenize apu2.16 HVR-H2 were GGCCTGGAATGGGTTGCANNSATC567CCGTACTACGGT567ACC56 7TATGCCGATAGCGT CAAGG (SEQ ID NO: 786), GGCCTGGAATGGGTTGCATACATC567CCGTACNNSGGT567 ACC567TATGCCGATAGCGTCAAGG (SEQ ID NO: 787), and GGCCTGGAATGGGTTGCANNS ATC567CCGTACNNSGGT567ACC567TATGCCGATAGCGTCAAGG (SEQ ID NO: 788).

In the second apu2.16 library, HVR-H2 and HVR-H3 were mutagenized. HVR-H2 was mutagenized identically to the modifications made to HVR-H2 in the first apu2.16 library, using the same stop codon-containing oligonucleotide and same three mutagenic oligonucleotides. HVR-H3 was mutagenized identically to the modifications made to HVR-H3 in the first apu18 library (described in Example 2), using the same stop-codon-containing oligonucleotide and same six mutagenic oligonucleotides.

In the third apu2.16 library, HVR-H1 and HVR-H3 were mutagenized. HVR-H1 was mutagenized identically to the modifications made to HVR-H1 in the first apu2.16 library, using the same stop-codon-containing oligonucleotide and mutagenic oligonucleotide. HVR-H3 was mutagenized identically to the modifications made to HVR-H3 in the first apu18 library (described in Example 2), using the same stop-codon-containing oligonucleotide and same six mutagenic oligonucleotides.

Mutagenesis reactions for each of the three apu2.16-derived libraries were transformed into electrocompetent *E. coli* XL-1 by electroporation. Cells were allowed to recover for 30 minutes at 37° C. with agitation in SOC medium. Twenty microliters of the cell-containing SOC medium was reserved to determine the number of transformants, and the remainder was then transferred to 500 ml 2YT containing carbenicillin and $10^{10}$ M13K07 helper phage per milliliter. After 45 minutes incubation at 37° C. with agitation, the broth was supplemented with kanamycin and grown overnight at 37° C. with agitation. The number of transformants for each library was $>10^9$. Phage were harvested and concentrated from the broth by centrifugation and PEG precipitation, and used in subsequent rounds of selection.

The three third-generation libraries were each sorted separately against K63-linked polyubiquitin immobilized on Maxisorp plates (NUNC) as described above in Example 1(A). Stringency was modulated in three ways: by the concentration of biotinylated polyubiquitin; by the addition of excess unbiotinylated polyubiquitin to compete for binding before capture on neutravidin-coated wells; and by the duration of the competition. Each round of solution sorting included 3 μM monoubiquitin and 30 μg/mL K48-linked polyubiquitin in the sorting buffer during the incubation step. The eluted phage were amplified and pooled for further rounds of sorting. Subsequent selection rounds were solution-phase sorted. The first round of solution sorting included 100 nM biotinylated (Sulfo-NHS-biotin, Pierce) polyubiquitin incubated with the phage pools for one hour at room temperature. The mixture was then diluted tenfold in solution-sorting buffer (PBST with 0.5% Superblock (Pierce)), and captured using neutravidin-coated wells for five minutes. A reaction containing unbiotinylated polyubiquitin chains served as a control to monitor background phage binding. The plates were washed with PBST and eluted with 0.1 M HCl for 10 minutes. For the second solution-sorted round, phage was equilibrated with 30 nM biotinylated polyubiquitin, as in round one, but was diluted tenfold in solution-sorting buffer containing 30 µg/mL of unbiotinylated polyubiquitin (K63-linked) for five minutes of off-rate selection followed by capture on neutravidin-coated wells.

After the first round of solution sorting, 6.5 times enrichment was observed for the combined libraries based on apu2.16 (see Table E). An additional 10-fold enrichment was obtained after the second solution sort for slow off rate (see Table E).

TABLE E

Results from Third Generation Anti-Polyubiquitin Antibody Library Solution Sorting

| Library | Plate Sort | | Solution Sort | | | |
|---|---|---|---|---|---|---|
| | Round 1 | | Round 2 (100 nM) | | Round 3 (30 nM) | |
| | Library size | Enrichment | Library size | Enrichment | Library size | Enrichment |
| 16-1 | 1.06e+06 | ND | 1.04e+05 | 6.5 | 1.00e+05 | 10 |
| 16-2 | 5.98e+05 | ND | | | | |
| 16-3 | 1.76e+05 | ND | | | | |

After one round of plate sorting and two rounds of solution sorting, individual clones selected from the third generation were grown in a 96-well format and screened by phage ELISA as described above in Example 2. Seventy-two unique clones were identified by sequencing. Of those clones, twelve demonstrated the greatest degree of specificity for K63-linked polyubiquitin in the phage ELISA assay (FIG. 22). Those twelve were designated apu3.01-3.12, and their HVR-H1, HVR-H2, and HVR-H3 sequences appear in FIGS. 23A and 23B. The light chain HVR for each of the K63-linked polyubiquitin-specific clones were not sequenced, but the sequences of HVR-L1 and HVR-L2 were expected to be invariant, while the HVR-L3 sequence was expected to identical to that for apu2.16. The HVR-L1 sequence was RASQSVSSAVA (SEQ ID NO: 79) and the HVR-L2 sequence was SASSLYS (SEQ ID NO: 80), according to the library design. All clones had the same heavy chain and light chain framework sequences (see FIG. 6).

Apu2.07 (see Example 2 and FIGS. 16A and 16B)) and apu3.07 (see above and FIGS. 23A and 23B) were expressed in either CHO or 293 cells as human IgGs. Expression constructs were made by Kunkel mutagenesis of appropriate pRK mammalian expression vectors encoding the heavy and light chains of human IgG (Gorman et al., DNA Prot. Eng. Tech. 2:3-10 (1990)). IgGs were purified by affinity chromatography using standard methodologies.

The ability of each IgG to specifically bind to polyubiquitin of the appropriate linkage immobilized to a nitrocellulose membrane was assessed by Western blot. K48- or K63-linked polyubiquitins and monoubiquitin (Boston Biochem) were run 4-20% Tris-glycine polyacrylamide gels (Invitrogen). The contents of the gels were transferred to nitrocellulose by electroblotting. Non-specific binding sites on the nitrocellulose membrane were blocked for 1 hour in 5% non-fat skim milk powder dissolved in Tris-buffered saline containing 0.1% Tween-20 (TBST). The K48-specific or K63-specific antibodies were then added to the blot at a concentration of 2 µg/mL (apu 2.07 IgG) or 1 µg/mL (apu3.07 IgG) and incubated for one hour to allow binding to occur. As a positive control, one blot was incubated with rabbit anti-ubiquitin antibodies (Sigma). Blots were washed in TBST and bound antibodies detected by peroxidase-conjugated goat anti-human Ig Fc (ICN) or peroxidase-conjugated anti-rabbit Ig (Amersham) diluted 1:10,000 in TBST containing 5% non-fat milk powder. After one hour, blots were washed in TBST and developed using Super Signal West Dura reagent (Pierce) to reveal peroxidase activity. The results are shown in FIGS. 24A-24D.

As expected, the apu2.07 IgG specifically recognized immobilized K48-linked tetraubiquitin and K48-linked tri- to heptaubiquitin (FIG. 24A), but did not bind to any of the immobilized K63-linked polyubiquitin samples. Similarly, the apu3.07 IgG specifically recognized immobilized K63-linked tetraubiquitin and K63-linked tri- to heptaubiquitin (FIG. 24B), but did not bind to any of the immobilized K48-linked polyubiquitin samples. Neither IgG bound to immobilized monoubiquitin. To assess the sensitivity of each IgG, additional western blot analysis was performed with varied concentrations of immobilized K48-linked and K63-linked tetraubiquitin (25-1000 ng/lane) (FIGS. 24C and 24D). Apu2.07 IgG detected as little as 50 ng immobilized K48-linked tetraubiquitin, and again did not specifically bind to immobilized K63-linked tetraubiquitin (FIG. 24C). Apu3.07 IgG detected as little as 50 ng immobilized K63-linked tetraubiquitin, and again did not specifically bind to immobilized K48-linked tetraubiquitin (FIG. 24D). In both cases, increased amounts of immobilized tetraubiquitin resulted in increased observed binding.

To determine whether the IgG were able to detect endogenously polyubiquitinylated proteins, protein lysates were prepared from the human embryonic kidney cell line 293T treated with or without 20 µM of the proteasome inhibitor Velcade® (bortezomib) for four hours. Lysates were resolved by SDS-PAGE in a 4-20% Tris-glycine polyacrylamide gel (Invitrogen), and western blotting was performed as described above. The results are shown in FIG. 25. A polyclonal anti-ubiquitin antibody (Sigma) detected a large number of high molecular weight proteins (leftmost lanes) both in the presence and absence of Velcade® treatment. The apu2.07 IgG bound to numerous proteins of varied molecular weights (rightmost lanes), and the observed binding was heavier to the immobilized velcade-treated lysates than to the immobilized untreated lysates. Significantly less binding overall was observed with the apu3.07 IgG (center lanes), which was expected to bind to K63-polyubiquitinylated proteins, and there was no apparent difference in binding between the velcade-treated and untreated lanes. K48-linked polyubiquitinylation is known to target intracellular proteins for proteolytic degradation (Chau et al., Science 243: 1576-1583 (1989); Finley et al., Mol. Cell. Biol. 14: 5501-5509 (1994); Flick et al., Nat. Cell. Biol. 6:634-641 (2004)). Thus, one explanation for the apu2.07 IgG results was that when proteolytic processing was prevented, an increased amount of K48-polyubiquitinylated proteins remained in the lysate, resulting in increased binding by the apu2.07 IgG over the untreated sample. K63-linked polyubiquitinylation is not known to target proteins for degradation (Pickart and Fushman, Curr. Opin. Chem. Biol. 8: 610-616 (2004); Hicke and Dunn, Annu. Rev. Cell Dev. Biol. 19: 141-172 (2003); Spece et al., Mol. Cell. Biol. 15: 1265-1273 (1995); Ulrich, Eukaryot. Cell 1:1-10 (2002); Spence et al., Cell 102: 67-76 (2000); Seibenhener et al., Mol. Cell. Biol. 24(18): 8055-8068 (2004)). Thus, one explanation for the apu 3.07 IgG results was that inhibition of proteasomes did not result in an accumulation of K63-polyubiquitinylated proteins.

Example 5

Structural Analysis of Fab Binding to Anti-K63-Linked Polyubiquitin

To better understand the interaction of the anti-K63-linked polyubiquitin fab with polyubiquitin, the anti-K63-linked polyubiquitin fab apu2.16 was co-crystallized with K63-linked diubiquitin. Crystals were grown in hanging drops using 1 µL of an apu2.16 solution (15 mg/mL in 10 mM Tris, 75 mM NaCl pH 8.0) and 1 µL of well solution (0.1M LiCl, 0.1 M Tris pH 8.2, 1 M citrate). To each drop was added 0.5 µL of 0.1 M cupric chloride, and each drop was streak seeded. Crystal clusters grew over the course of several days and could be manipulated to obtain a single, diffracting crystal. The structure was determined by molecular replacement. Native data were collected at 100K and were processed with HKL2000. Crystals belonged to the C2 space group with cell dimensions a=177.7 Å, b=94.9 Å, c=97.9 Å and β=107, with two complexes in the asymmetric unit. The structure was solved by molecular replacement using the program Phaser and the coordinates of a variant of the humanized 4d5 fab fragment (PDB for 4d5: PDB code 1FVE). Model building was carried out in program Coot and the structure was refined with Refmac5. The resolution of the structure is 3.1 Å. The complex has been refined to an R of 24.5% and an $R_{free}$ of 30.4%.

The interaction between apu2.16 and K63-linked diubiquitin is shown in FIGS. 26A-26C. The structural epitope is a combination of residues which bury at least 25% of their solvent accessible surface area upon binding fab and/or have more than one atom within 4.5 Å of either the heavy or light chain of the fab. The ubiquitin chain which donates K63 is chain A, and the ubiquitin chain which donates the C-terminus is chain B. Fab light chain residues belong to chain L, and fab heavy chain residues belong to chain H. Chain number preceeds residue number in the table below, and fab residues are numbered sequentially.

TABLE F

| Residues located in the apu2.16-K63-linked diubiquitin binding interface | |
|---|---|
| Ubiquitin Residues | Fab Residues |
| A 18 Glu | L 31 Ser |
| A 19 Pro | L 49 Tyr |
| A 20 Ser | L 50 Ser |
| A 21 Asp | L 51 Ala |
| A 55 Thr | L 52 Ser |
| A 56 Leu | L 53 Ser |
| A 57 Ser | L 66 Arg |
| A 58 Asp | L 98 Phe |
| A 60 Asn | H 30 Lys |
| A 61 Ile | H 31 Thr |
| A 62 Gln | H 32 Gly |
| B 8 Leu | H 33 Leu |
| B 9 Thr | H 50 Tyr |
| B 34 Glu | H 52 Ser |
| B 35 Gly | H 54 Tyr |
| B 36 Ile | H 55 Tyr |
| B 37 Pro | H 99 Glu |
| B 39 Asp | H 100 Tyr |
| B 40 Gln | H 101 Tyr |
| B 71 Leu | H 102 Arg |
| B 72 Arg | H 104 Tyr |
| B 73 Leu | H 105 Thr |
| B 74 Arg | |
| B 75 Gly | |

As shown in Table F, and as indicated in FIG. 26B in dark grey, there were eleven residues in the K63-diubiquitin A chain and thirteen residues in the K63-diubiquitin B chain that were located within 4.5 Å of apu2.16 when bound to apu2.16. As shown in Table F, and as indicated in FIG. 26C in dark grey, there were eight residues in the apu2.16 light chain and fourteen residues in the apu2.16 heavy chain that were located within 3.5 Å of K63-linked diubiquitin when bound to that molecule. Based on this data, residues likely to mediate the interaction between the two on K63-linked diubiquitin include Glu-18, Ser-20, Leu-57, and Asp-58 in the A chain and Pro-37, Arg-74, and Gly-75 in the B chain. Interestingly, the antibody does not interact intimately with the K63-Gly 76 linkage but instead derives specificity via interactions the surface of the di-ubiquitin complex adjoining the linkage.

We claim:

1. A nucleic acid molecule that encodes an antibody that specifically binds lysine-48-linked polyubiquitin, wherein the antibody comprises a hypervariable (HVR)-H1, a HVR-H2, a HVR-H3, a HVR-L1, a HVR-L2, and a HVR-L3, wherein the HVR-H1 sequence is selected from SEQ ID NOs: 265 to 280; wherein the HVR-H2 sequence is selected from SEQ ID NOs: 281 to 296; wherein the HVR-H3 sequence is selected from SEQ ID NOs: 297 to 312; wherein the HVR-L1 sequence is SEQ ID NO: 79; wherein the HVR-L2 sequence is SEQ ID NO: 80; and wherein the HVR-L3 sequence is selected from SEQ ID NOs: 313 to 328.

2. The nucleic acid molecule of claim 1, wherein the antibody comprises HVR-H1, HVR-H2, and HVR-H3 sequences selected from the following groups of HVR-H1, HVR-H2, and HVR-H3 sequences: SEQ ID NO: 265, SEQ ID NO: 281, and SEQ ID NO: 297; SEQ ID NO. 266, SEQ ID NO: 282, and SEQ ID NO: 298; SEQ ID NO: 267, SEQ ID NO: 283, and SEQ ID NO: 299; SEQ ID NO: 268, SEQ ID NO: 284, and SEQ ID NO: 300; SEQ ID NO: 269, SEQ ID NO: 285, and SEQ ID NO: 301; SEQ ID NO: 270, SEQ ID NO: 286, and SEQ ID NO: 302; SEQ ID NO: 271, SEQ ID NO: 287, and SEQ ID NO: 303; SEQ ID NO: 272, SEQ ID NO: 288, and SEQ ID NO: 304; SEQ ID NO: 273, SEQ ID NO: 289, and SEQ ID NO: 305; SEQ ID NO: 274, SEQ ID NO: 290, and SEQ ID NO: 306; SEQ ID NO: 275, SEQ ID NO: 291, and SEQ ID NO: 307; SEQ ID NO: 276, SEQ ID NO: 292, and SEQ ID NO: 308; SEQ ID NO: 277, SEQ ID NO: 293, and SEQ ID NO: 309; SEQ ID NO: 278, SEQ ID NO: 294, and SEQ ID NO: 310; and SEQ ID NO: 279, SEQ ID NO: 295, and SEQ ID NO: 311.

3. The nucleic acid molecule of claim 1, wherein the antibody comprises an HVR-H1 sequence of SEQ ID NO: 269, an HVR-H2 sequence of SEQ ID NO: 285, an HVR-H3 sequence of SEQ ID NO: 301, an HVR-L1 sequence of SEQ ID NO: 79, an HVR-L2 sequence of SEQ ID NO: 80, and an HVR-L3 sequence of SEQ ID NO: 317.

4. A nucleic acid molecule that encodes an antibody that specifically binds to lysine-63-linked polyubiquitin, wherein the antibody comprises a hypervariable (HVR)-H1, a HVR-H2, a HVR-H3, a HVR-L1, a HVR-L2, and a HVR-L3, wherein the HVR-H1 sequence is selected from SEQ ID NOs: 695 to 705; wherein the HVR-H2 sequence is selected from SEQ ID NOs: 706 to 716; wherein the HVR-H3 sequence is selected from SEQ ID NOs: 717 to 727; wherein the HVR-L1 sequence is SEQ ID NO: 79; wherein the HVR-L2 sequence is SEQ ID NO: 80; and wherein the HVR-L3 sequence is selected from SEQ ID NOs: 728 to 738.

5. The nucleic acid molecule of claim 4, wherein the antibody comprises HVR-H1, HVR-H2, and HVR-H3 sequences selected from the following groups of HVR-H1, HVR-H2, and HVR-H3 sequences: SEQ ID NO: 695, SEQ ID NO: 706, and SEQ ID NO: 717; SEQ ID NO: 696, SEQ ID NO: 707, and SEQ ID NO: 718; SEQ ID NO: 697, SEQ ID NO: 708, and SEQ ID NO: 719; SEQ ID NO: 698, SEQ ID NO: 709, and SEQ ID NO: 720; SEQ ID NO: 699, SEQ ID NO: 710, and SEQ ID NO: 721; SEQ ID NO: 700, SEQ ID NO: 711, and SEQ ID NO: 722; SEQ ID NO: 701, SEQ ID NO: 712, and SEQ ID NO: 723; SEQ ID NO: 702, SEQ ID NO: 713, and SEQ ID NO: 724; SEQ ID NO: 703, SEQ ID NO: 714, and SEQ ID NO: 725; and SEQ ID NO: 704, SEQ ID NO: 715, and SEQ ID NO: 726.

6. The nucleic acid molecule of claim 4, wherein the antibody comprises an HVR-H1 sequence of SEQ ID NO: 701, an HVR-H2 sequence of SEQ ID NO: 712, an HVR-H3 sequence of SEQ ID NO; 723, an HVR-L1 sequence of SEQ ID NO: 79, an HVR-L2 sequence of SEQ ID NO: 80, and an HVR-L3 sequence of SEQ ID NO: 734.

7. A vector comprising the nucleic acid molecule of claim 1.

8. A host cell comprising the vector of claim 7.

9. A nucleic acid molecule that encodes an antibody that specifically binds to lysine-63-linked polyubiquitin, wherein the antibody comprises a hypervariable (HVR)-H1, a HVR-H2, a HVR-H3, a HVR-L1, a HVR-L2, and a HVR-L3, wherein the HVR-H1 sequence is selected from SEQ ID NOs: 329 to 337; wherein the HVR-H2 sequence is selected from SEQ ID NOs: 338 to 346; wherein the HVR-H3 sequence is selected from SEQ ID NOs: 347 to 355; wherein the HVR-L1 sequence is SEQ ID NO: 79; wherein the HVR-L2 sequence is SEQ ID NO: 80; and wherein the HVR-L3 sequence is selected from SEQ ID NOs: 356 to 364.

10. The nucleic acid molecule of claim 9, wherein the antibody comprises HVR-H1, HVR-H2, and HVR-H3 sequences selected from the following groups of HVR-H1, HVR-H2, and HVR-H3 sequences: SEQ ID NO: 329, SEQ ID NO: 338, and SEQ ID NO: 347; SEQ ID NO: 330, SEQ ID NO: 339, and SEQ ID NO: 348; SEQ ID NO: 331, SEQ ID NO: 340, and SEQ ID NO: 349; SEQ ID NO: 332, SEQ ID NO: 341, and SEQ ID NO: 350; SEQ ID NO: 333, SEQ ID NO: 342, and SEQ ID NO: 351; SEQ ID NO: 334, SEQ ID NO: 343, and SEQ ID NO: 352; SEQ ID NO: 335, SEQ ID NO: 344, and SEQ ID NO: 353; and SEQ ID NO: 336, SEQ ID NO: 345, and SEQ ID NO: 354.

11. The nucleic acid molecule of claim 9, wherein the antibody comprises an HVR-H1 sequence of SEQ ID NO: 330, an HVR-H2 sequence of SEQ ID NO: 339, an HVR-H3 sequence of SEQ ID NO: 348, an HVR-L1 sequence of SEQ ID NO: 79, an HVR-L2 sequence of SEQ ID NO: 80, and an HVR-L3 sequence of SEQ ID NO: 357.

12. A nucleic acid molecule that encodes an antibody that specifically binds to lysine-63-linked polyubiquitin wherein the antibody comprises a hypervariable (HVR)-H1, a HVR-H2, a HVR-H3, a HVR-L1, a HVR-L2, and a HVR-L3, wherein the HVR-H1 sequence is selected from SEQ ID NOs: 739 to 749; wherein the HVR-H2 sequence is selected from SEQ ID NOs: 750 to 760; wherein the HVR-H3 sequence is selected from SEQ ID NOs: 761 to 771; wherein the HVR-L1 sequence is SEQ ID NO: 79; wherein the HVR-L2 sequence is SEQ ID NO: 80; and wherein the HVR-L3 sequence is selected from SEQ ID NOs: 772 to 782.

13. The nucleic acid molecule of claim 12, wherein the antibody comprises HVR-H1, HVR-H2, and HVR-H3 sequences selected from the following groups of HVR-H1, HVR-H2, and HVR-H3 sequences: SEQ ID NO: 739, SEQ ID NO: 750, and SEQ ID NO: 761; SEQ ID NO: 740, SEQ ID NO: 751, and SEQ ID NO: 762; SEQ ID NO: 741, SEQ ID NO: 752, and SEQ ID NO: 763; SEQ ID NO: 742, SEQ ID NO: 753, and SEQ ID NO: 764; SEQ ID NO: 743, SEQ ID NO: 754, and SEQ ID NO: 765; SEQ ID NO: 744, SEQ ID NO: 755, and SEQ ID NO: 766; SEQ ID NO: 745, SEQ ID NO: 756, and SEQ ID NO: 767; SEQ ID NO: 746, SEQ ID NO: 757, and SEQ ID NO: 768; SEQ ID NO: 747, SEQ ID NO: 758, and SEQ ID NO: 769; and SEQ ID NO:748, SEQ ID NO: 759, and SEQ ID NO: 770.

14. The nucleic acid molecule of claim 12, wherein the antibody comprises an HVR-H1 sequence of SEQ ID NO: 739, an HVR-H2 sequence of SEQ ID NO: 750, an HVR-H3 sequence of SEQ ID NO: 761, an HVR-L1 sequence of SEQ ID NO: 79, an HVR-L2 sequence of SEQ ID NO: 80, and an HVR-L3 sequence of SEQ ID NO: 772.

15. The nucleic acid molecule of claim 12, wherein the antibody comprises an HVR-H1 sequence of SEQ ID NO: 740, an HVR-H2 sequence of SEQ ID NO: 751, an HVR-H3 sequence of SEQ ID NO: 762, an HVR-L1 sequence of SEQ ID NO: 79, an HVR-L2 sequence of SEQ ID NO: 80, and an HVR-L3 sequence of SEQ ID NO: 773.

16. The nucleic acid molecule of claim 12, wherein the antibody comprises an HVR-H1 sequence of SEQ ID NO: 744, an HVR-H2 sequence of SEQ ID NO: 755, an HVR-H3 sequence of SEQ ID NO: 766, an HVR-L1 sequence of SEQ ID NO: 79, an HVR-L2 sequence of SEQ ID NO: 80, and an HVR-L3 sequence of SEQ ID NO: 777.

17. A nucleic acid molecule that encodes an antibody that specifically binds to lysine-63-linked polyubiquitin, wherein the antibody comprises a hypervariable (HVR)-H1, a HVR-H2, a HVR-H3, a HVR-L1, a HVR-L2, and a HVR-L3, wherein the HVR-H1 sequence is selected from SEQ ID NOs: 789 to 800; wherein the HVR-H2 sequence is selected from SEQ ID NOs: 801 to 812; wherein the HVR-H3 sequence is selected from SEQ ID NOs: 813 to 824; wherein the HVR-L1 sequence is SEQ ID NO: 79; wherein the HVR-L2 sequence is SEQ ID NO: 80; and wherein the HVR-L3 sequence is SEQ ID NO: 777.

18. The nucleic acid of claim 17, wherein the antibody comprises HVR-H1, HVR-H2, and HVR-H3 sequences selected from the following groups of HVR-H1, HVR-H2, and HVR-H3 sequences: SEQ ID NO: 789, SEQ ID NO: 801, and SEQ ID NO: 813; SEQ ID NO: 790, SEQ ID NO: 802, and SEQ ID NO: 814; SEQ ID NO: 791, SEQ ID NO: 803, and SEQ ID NO: 815; SEQ ID NO: 792, SEQ ID NO: 804, and SEQ ID NO: 816; SEQ ID NO: 793, SEQ ID NO: 805, and SEQ ID NO: 817; SEQ ID NO: 794, SEQ ID NO: 806, and SEQ ID NO: 818; SEQ ID NO: 795, SEQ ID NO: 807, and SEQ ID NO: 819; SEQ ID NO: 796, SEQ ID NO: 808, and SEQ ID NO: 820; SEQ ID NO: 797, SEQ ID NO: 809, and SEQ ID NO: 821; SEQ ID NO: 798, SEQ ID NO: 810, and SEQ ID NO: 822; and SEQ ID NO: 799, SEQ ID NO: 811, and SEQ ID NO: 823.

19. The nucleic acid of claim 17, wherein the antibody comprises an HVR-H1 sequence of SEQ ID NO: 795, an HVR-H2 sequence of SEQ ID NO: 807, an HVR-H3 sequence of SEQ ID NO: 819, an HVR-L1 sequence of SEQ ID NO: 79, an HVR-L2 sequence of SEQ ID NO: 80, and an HVR-L3 sequence of SEQ ID NO: 777.

20. A vector comprising the nucleic acid molecule of claim 9.

21. A host cell comprising the vector of claim 20.

* * * * *